(12) United States Patent
Mun et al.

(10) Patent No.: US 10,934,308 B2
(45) Date of Patent: Mar. 2, 2021

(54) COMPOUND FOR ORGANIC ELECTRONIC ELEMENT, ORGANIC ELECTRONIC ELEMENT USING SAME, AND ELECTRONIC DEVICE COMPRISING SAME

(71) Applicant: DUK SAN NEOLUX CO., LTD., Cheonan-si (KR)

(72) Inventors: Soung Yun Mun, Cheonan-si (KR); Seul Gi Kim, Daejeon (KR); Sun Hee Lee, Hwaseong-si (KR); Yeon Hee Choi, Cheonan-si (KR); Sun Pil Hwang, Ansan-si (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 297 days.

(21) Appl. No.: 15/760,004

(22) PCT Filed: Sep. 12, 2016

(86) PCT No.: PCT/KR2016/010284
§ 371 (c)(1),
(2) Date: Mar. 14, 2018

(87) PCT Pub. No.: WO2017/048025
PCT Pub. Date: Mar. 23, 2017

(65) Prior Publication Data
US 2018/0251473 A1 Sep. 6, 2018

(30) Foreign Application Priority Data

Sep. 18, 2015 (KR) .................... 10-2015-0132231
Nov. 26, 2015 (KR) .................... 10-2015-0166385

(51) Int. Cl.
*H01L 51/00* (2006.01)
*C07D 495/04* (2006.01)
(Continued)

(52) U.S. Cl.
CPC ......... *C07D 495/04* (2013.01); *C07D 209/88* (2013.01); *C07D 405/12* (2013.01);
(Continued)

(58) Field of Classification Search
None
See application file for complete search history.

(56) References Cited

U.S. PATENT DOCUMENTS

2008/0157657 A1* 7/2008 Matsunami ........... H01L 51/006
313/504
2009/0128011 A1* 5/2009 Miyazaki ............... C09K 11/06
313/504
(Continued)

FOREIGN PATENT DOCUMENTS

KR 10-2010-0094414 A 8/2010
KR 10-2011-0041726 A 4/2011
(Continued)

OTHER PUBLICATIONS

Saint-Ruf, G., Ng Ph Buu-Hoï, and P. Jacquignon. "657. Cyclodehydration of arylidene-α-tetralones derived from fluorene, dibenzofuran, and dibenzothiophen." Journal of the Chemical Society (Resumed), 1959, 3237-3241. (Year: 1959).*

*Primary Examiner* — Robert S Loewe
(74) *Attorney, Agent, or Firm* — Vorys, Sater, Seymour & Pease LLP; Mih Suhn Koh

(57) ABSTRACT

The present invention provides a novel compound capable of improving the light emitting efficiency, stability and life span of a device, and an organic electric element and an electronic device using the same.

17 Claims, 1 Drawing Sheet

(51) Int. Cl.

| | |
|---|---|
| *C07D 405/12* | (2006.01) |
| *C07D 409/12* | (2006.01) |
| *C07D 491/04* | (2006.01) |
| *C07D 209/88* | (2006.01) |
| *H01L 51/52* | (2006.01) |
| *H01L 51/50* | (2006.01) |

(52) U.S. Cl.
 CPC ......... *C07D 409/12* (2013.01); *C07D 491/04* (2013.01); *H01L 51/006* (2013.01); *H01L 51/0052* (2013.01); *H01L 51/0059* (2013.01); *H01L 51/0061* (2013.01); *H01L 51/0071* (2013.01); *H01L 51/0072* (2013.01); *H01L 51/0074* (2013.01); *H01L 51/5072* (2013.01); *H01L 51/5092* (2013.01); *H01L 51/5206* (2013.01); *H01L 51/5221* (2013.01); *H01L 51/0081* (2013.01); *H01L 51/0085* (2013.01); *H01L 51/5016* (2013.01); *H01L 51/5056* (2013.01)

(56) References Cited

U.S. PATENT DOCUMENTS

| | | | |
|---|---|---|---|
| 2014/0034915 A1* | 2/2014 | Lee | H01L 51/0074 257/40 |
| 2016/0225992 A1* | 8/2016 | Ito | C09B 23/148 |
| 2017/0162797 A1* | 6/2017 | Lee | C07D 403/04 |

FOREIGN PATENT DOCUMENTS

| | | | |
|---|---|---|---|
| KR | 10-2014-0120090 A | 10/2014 | |
| KR | 20140120090 A * | 10/2014 | ............ C09K 11/06 |
| KR | 10-2016-0089033 A | 7/2016 | |
| KR | 10-2016-0090058 A | 7/2016 | |

* cited by examiner

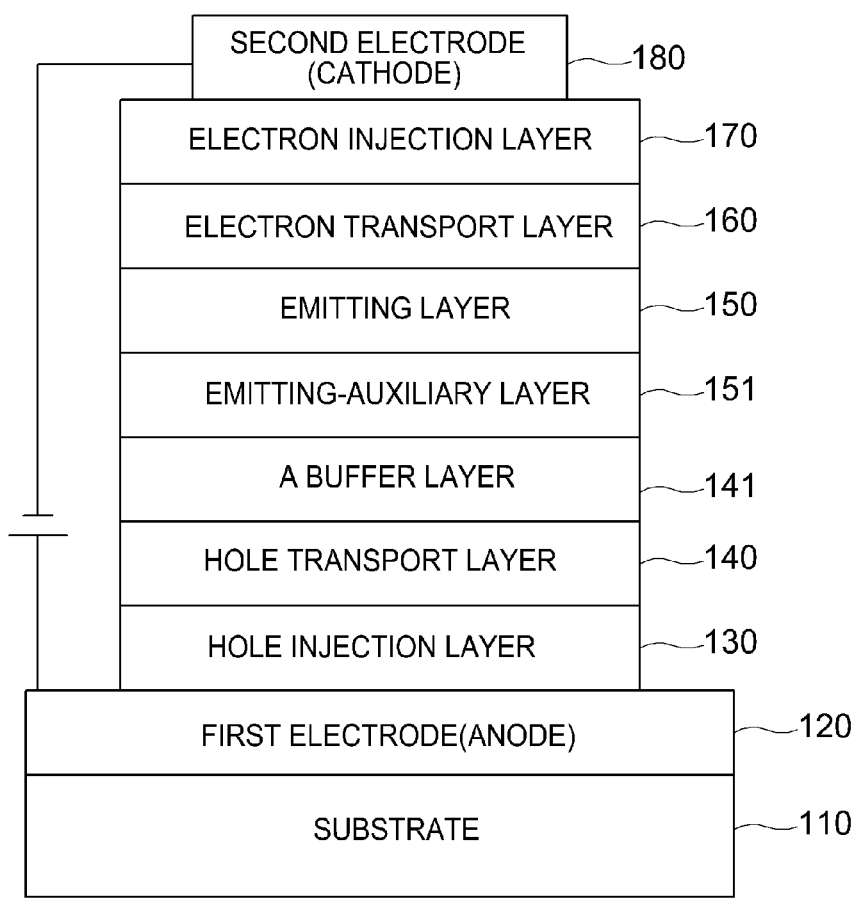

COMPOUND FOR ORGANIC ELECTRONIC ELEMENT, ORGANIC ELECTRONIC ELEMENT USING SAME, AND ELECTRONIC DEVICE COMPRISING SAME

BACKGROUND

Technical Field

The present invention relates to compound for organic electric element, organic electric element using the same, and an electronic device thereof.

Background Art

In general, organic light emitting phenomenon refers to a phenomenon that converts electric energy into light energy by using an organic material. An organic electric element using an organic light emitting phenomenon usually has a structure including an anode, a cathode, and an organic material layer interposed therebetween. Here, in order to increase the efficiency and stability of the organic electronic element, the organic material layer is often composed of a multi-layered structure composed of different materials, and for example, may include a hole injection layer, a hole transport layer, an emitting layer, an electron transport layer, an electron injection layer and the like.

A material used as an organic material layer in an organic electric element may be classified into a light emitting material and a charge transport material, such as a hole injection material, a hole transport material, an electron transport material, an electron injection material and the like depending on its function.

And the light emitting material may be classified into a polymer type and a low molecular type depending on the molecular weight, and into a fluorescent material derived from the singlet excited state of electrons and a phosphorescent material derived from the triplet excited state of electrons depending on the light emitting mechanism. Further, the light emitting material can be classified into blue, green, and red light emitting materials and yellow and orange light emitting materials necessary for realizing better natural color depending on the luminescent color.

Meanwhile, when only one material is used as a light emitting material, there arises a problem that the maximum light emission wavelength shifts to a long wavelength due to intermolecular interaction, the color purity drops, or the efficiency of the device decreases due to the light emission attenuation effect, therefore a host/dopant system can be used as a light emitting material in order to increase luminous efficiency through increase of color purity and energy transfer. When the small amount of dopant having a smaller energy band gap than the host forming the emitting layer is mixed on the emitting layer, the excitons generated in the emitting layer are transported to the dopant to emit light with high efficiency. At this time, since the wavelength of the host is shifted to the wavelength band of the dopant, light of a desired wavelength can be obtained depending on the type of the dopant used.

Currently, the portable display market is growing in size as a large-area display, which requires more power than the power consumption required by existing portable displays. Therefore, power consumption is a very important factor for portable displays, which have a limited power source, such as a battery, and efficiency and lifetime issues must be solved.

Efficiency, life span, driving voltage and the like are related to each other. As the efficiency is increased, the driving voltage is relatively decreased, and as the driving voltage drops, the crystallization of the organic material due to joule heating generated during driving is reduced, and as a result, the life span tends to increase. However, simply improving the organic material layer cannot maximize the efficiency. This is because, when the optimal combination of the energy level and T1 value between each organic material layer and the intrinsic properties (mobility, interface characteristics, etc.) of the material are achieved, long life and high efficiency can be achieved at the same time. Therefore, it is necessary to develop a light emitting material having a high thermal stability and achieving a charge balance in the emitting layer efficiently.

That is, in order to sufficiently exhibit the excellent characteristics of the organic electric element, a material for forming an organic material layer in an element such as a hole injection material, a hole transport material, a light emitting material, an electron transport material, an electron injection material, an emitting-auxiliary layer material, and the like should be supported by stable and efficient materials. However, such a stable and efficient organic material layer material for an organic electric element has not been sufficiently developed yet. Therefore, development of new materials is continuously required, and especially development of host materials for the emitting layer is urgently required.

Otherwise, in the case of a polycyclic compound containing a heteroatom, the difference in properties according to the material structure is so large that it is applied to various layers as OLED material. In particular, it has characteristics of different band gaps (HOMO, LUMO), electrical characteristics, chemical properties, and physical properties depending on the number of rings, fused positions and the type and arrangement of heteroatoms, therefore application development for various OLED layers using the same has been progressed. Recently, development of OLED material for heteroatom type, number and position of pentacyclic compounds has been actively developed.

DETAILED DESCRIPTION OF THE INVENTION

Summary

Using the characteristics of the polycyclic compound, the present invention provides a compound capable of maximizing the effect of improving luminous efficiency and long life, while maintaining or slightly reducing the driving voltage of the device, and an organic electric element using the same and an electronic device thereof.

Technical Solution

The present invention provides compounds represented by Formula (1), organic electric elements comprising the same and electronic devices thereof.

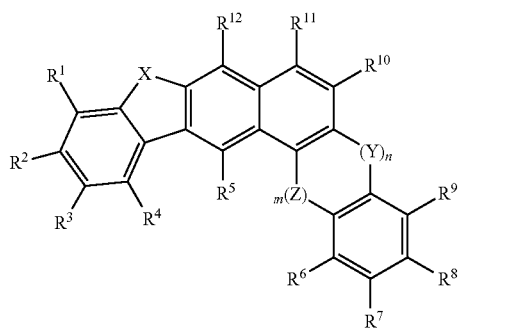

Formula (1)

Effects of the Invention

By using the compound according to the present invention, it is possible to achieve a high luminous efficiency, a low driving voltage, and a high heat resistance of the element, and can greatly improve the color purity and lifetime of the element.

BRIEF DESCRIPTION OF THE DRAWINGS

The FIGURE illustrates an example of an organic electric element according to the present invention.
100: organic electric element,
110: substrate
120: the first electrode(anode),
130: the hole injection layer
140: the hole transport layer,
141: a buffer layer
150: the emitting layer,
151: the emitting auxiliary layer
160: the electron transport layer,
170: the electron injection layer
180: the second electrode(cathode)

DETAILED DESCRIPTION

Hereinafter, some embodiments of the present invention will be described in detail. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if a component is described as being "connected", "coupled", or "connected" to another component, the component may be directly connected or connected to the other component, but another component may be "connected", "coupled" or "connected" between each component.

As used in the specification and the accompanying claims, unless otherwise stated, the following is the meaning of the term as follows.

Unless otherwise stated, the term "halo" or "halogen", as used herein, includes fluorine, bromine, chlorine, or iodine.

Unless otherwise stated, the term "alkyl" or "alkyl group", as used herein, has a single bond of 1 to 60 carbon atoms, and means saturated aliphatic functional radicals including a linear alkyl group, a branched chain alkyl group, a cycloalkyl group (alicyclic), an cycloalkyl group substituted with a alkyl or an alkyl group substituted with a cycloalkyl.

Unless otherwise stated, the term "haloalkyl" or "halogen alkyl", as used herein, includes an alkyl group substituted with a halogen.

Unless otherwise stated, the term "heteroalkyl", as used herein, means alkyl substituted one or more of carbon atoms consisting of an alkyl with hetero atom.

Unless otherwise stated, the term "alkenyl" or "alkynyl", as used herein, has double or triple bonds of 2 to 60 carbon atoms, but is not limited thereto, and includes a linear or a branched chain group.

Unless otherwise stated, the term "cycloalkyl", as used herein, means alkyl forming a ring having 3 to 60 carbon atoms, but is not limited thereto.

Unless otherwise stated, the term "alkoxyl group", "alkoxy group" or "alkyloxy group", as used herein, means an oxygen radical attached to an alkyl group, but is not limited thereto, and has 1 to 60 carbon atoms.

Unless otherwise stated, the term "alkenoxyl group", "alkenoxy group", "alkenyloxyl group" or "alkenyloxy group", as used herein, means an oxygen radical attached to an alkenyl group, but is not limited thereto, and has 2 to 60 carbon atoms.

Unless otherwise stated, the term "aryloxyl group" or "aryloxy group", as used herein, means an oxygen radical attached to an aryl group, but is not limited thereto, and has 6 to 60 carbon atoms.

Unless otherwise stated, the term "aryl group" or "arylene group", as used herein, has 6 to 60 carbon atoms, but is not limited thereto. Herein, the aryl group or arylene group means a monocyclic and polycyclic aromatic group, and may also be formed in conjunction with an adjacent group. Examples of "aryl group" may include a phenyl group, a biphenyl group, a fluorene group, or a spirofluorene group.

The prefix "aryl" or "ar" means a radical substituted with an aryl group. For example, an arylalkyl may be an alkyl substituted with an aryl, and an arylalenyl may be an alkenyl substituted with aryl, and a radical substituted with an aryl has a number of carbon atoms as defined herein.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substituted with an arylcarbonyl, wherein the arylcarbonyl may be a carbonyl substituted with an aryl.

Unless otherwise stated, the term "heteroalkyl", as used herein, means alkyl containing one or more of hetero atoms.

Unless otherwise stated, the term "heteroaryl group" or "heteroarylene group", as used herein, means a C2 to C60 aryl containing one or more of hetero atoms or arylene group, but is not limited thereto, and includes at least one of monocyclic and polycyclic rings, and may also be formed in conjunction with an adjacent group.

Unless otherwise stated, the term "heterocyclic group", as used herein, contains one or more heteroatoms, but is not limited thereto, has 2 to 60 carbon atoms, includes any one of monocyclic and polycyclic rings, and may include heteroaliphadic ring and/or heteroaromatic ring. Also, the heterocyclic group may also be formed in conjunction with an adjacent group.

Unless otherwise stated, the term "heteroatom", as used herein, represents at least one of N, O, S, P, or Si.

Also, the term "heterocyclic group" may include a ring containing SO₂ instead of carbon consisting of cycle. For example, "heterocyclic group" includes compound below.

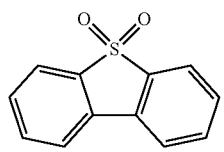 [SMILES: O=S1(=O)c2ccccc2-c2ccccc21]

Unless otherwise stated, the term "aliphatic", as used herein, means an aliphatic hydrocarbon having 1 to 60 carbon atoms, and the term "aliphatic ring", as used herein, means an aliphatic hydrocarbon ring having 3 to 60 carbon atoms.

Unless otherwise stated, the term "ring", as used herein, means an aliphatic ring having 3 to 60 carbon atoms, or an aromatic ring having 6 to 60 carbon atoms, or a hetero ring having 2 to 60 carbon atoms, or a fused ring formed by the combination of them, and includes a saturated or unsaturated ring.

Other hetero compounds or hetero radicals other than the above-mentioned hetero compounds include, but are not limited thereto, one or more heteroatoms.

Unless otherwise stated, the term "carbonyl", as used herein, is represented by —COW, wherein R' may be hydrogen, an alkyl having 1 to 20 carbon atoms, an aryl having 6 to 30 carbon atoms, a cycloalkyl having 3 to 30 carbon atoms, an alkenyl having 2 to 20 carbon atoms, an alkynyl having 2 to 20 carbon atoms, or the combination of these.

Unless otherwise stated, the term "ether", as used herein, is represented by —R—O—R', wherein R or R' may be independently hydrogen, an alkyl having 1 to 20 carbon atoms, an aryl having 6 to 30 carbon atoms, a cycloalkyl having 3 to 30 carbon atoms, an alkenyl having 2 to 20 carbon atoms, an alkynyl having 2 to 20 carbon atoms, or the combination of these.

Unless otherwise stated, the term "substituted or unsubstituted", as used herein, means that substitution is substituted by at least one substituent selected from the group consisting of, but is not limited thereto, deuterium, halogen, an amino group, a nitrile group, a nitro group, a $C_1$-$C_{20}$ alkyl group, a $C_1$-$C_{20}$ alkoxyl group, a $C_1$-$C_{20}$ alkylamine group, a $C_1$-$C_{20}$ alkylthiopen group, a $C_6$-$C_{20}$ arylthiopen group, a $C_2$-$C_{20}$ alkenyl group, a $C_2$-$C_{20}$ alkynyl group, a $C_3$-$C_{20}$ cycloalkyl group, a $C_6$-$C_{20}$ aryl group, a $C_6$-$C_{20}$ aryl group substituted by deuterium, a $C_8$-$C_{20}$ arylalkenyl group, a silane group, a boron group, a germanium group, and a $C_2$-$C_{20}$ heterocyclic group.

Unless otherwise expressly stated, the Formula used in the present invention, as used herein, is applied in the same manner as the substituent definition according to the definition of the exponent of the following Formula.

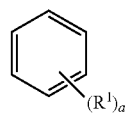

Wherein, when a is an integer of zero, the substituent $R^1$ is absent, when a is an integer of 1, the sole substituent $R^1$ is linked to any one of the carbon constituting the benzene ring, when a is an integer of 2 or 3, they are respectively combined as follows, in which $R^1$ may be the same as or different from each other, and when a is an integer of 4 to 6, and it is bonded to the carbon of the benzene ring in a similar manner, whereas the indication of hydrogen bonded to the carbon forming the benzene ring is omitted.

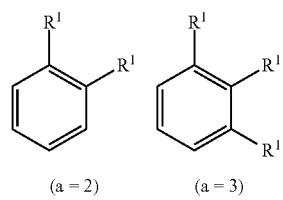

Hereinafter, a compound according to an aspect of the present invention and an organic electric element comprising the same will be described.

According to a specific example of the present invention, there is provided a compound represented by Formula (1).

Formula (1)

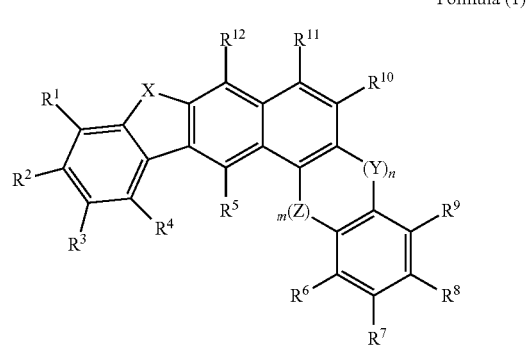

{In Formula (1),

1) X, Y and Z are each independently selected from the group consisting of N-$L^1$-$Ar^1$, O, S, $CR^{13}R^{14}$, $SiR^{15}R^{16}$ (Provided that both X and Y, or both of X and Z are not N-$L^1$-$Ar^1$).

2) m and n are each independently 0 or 1, and m+n is 1 or more, and when m or n is 0, it is a single bond, 3) $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ and $R^{16}$ are each independently selected from the group consisting of hydrogen; deuterium; halogen; a $C_6$-$C_{60}$ aryl group; a fluorenyl group; a $C_2$-$C_{60}$ heterocyclic group including at least one heteroatom of O, N, S, Si or P; a $C_1$-$C_{50}$ alkyl group; a fused ring group of a $C_3$-$C_{60}$ aliphatic ring and a $C_6$-$C_{60}$ aromatic ring; a $C_2$-$C_{20}$ alkenyl group; a $C_1$-$C_{30}$ alkoxyl group; a $C_6$-$C_{30}$ aryloxy group; and -L'-N($R^a$)($R^b$); $R^1$, $R^2$, $R^3$, $R^4$, $R^5$, $R^6$, $R^7$, $R^8$, $R^9$, $R^{10}$, $R^{11}$, and $R^{12}$ may form a ring together with neighboring groups and $R^{13}$, $R^{14}$, $R^{15}$, and $R^{16}$ may be bonded to each other to form a spiro compound together with C or Si to which they are bonded, 4) $L^1$ may be selected from the group consisting of a single bond, a $C_6$-$C_{60}$ arylene group, and a fluorenylene group; a $C_2$-$C_{60}$ heteroarylene group including at least one heteroatom selected from O, N, S, Si or P;

5) Ar¹ may be selected from the group consisting of a $C_6$-$C_{60}$ aryl group; a fluorenyl group; a fused ring group of a $C_3$-$C_{60}$ aliphatic ring and a $C_6$-$C_{60}$ aromatic ring; a $C_2$-$C_{60}$ heterocyclic group including at least one heteroatom of O, N, S, Si or P;

6) L¹ may be selected from the group consisting of a single bond; a $C_6$-$C_{60}$ arylene group; a fluorenylene group; a fused ring group of a $C_3$-$C_{60}$ aliphatic ring and a $C_6$-$C_{60}$ aromatic ring; a $C_2$-$C_{60}$ heterocyclic group including at least one heteroatom selected from O, N, S, Si or P;

7) $R^a$ and $R^b$ are independently selected from the group consisting of a $C_6$-$C_{60}$ aryl group; a fluorenyl group; a fused ring group of a $C_3$-$C_{60}$ aliphatic ring and a $C_6$-$C_{60}$ aromatic ring; and a $C_2$-$C_{60}$ heterocyclic group containing at least one hetero atom of O, N, S, Si, or P;

wherein, the aryl group, heteroaryl group, fluorenyl group, arylene group, heterocyclic group, fused ring group may be substituted with one or more substituents selected from the group consisting of deuterium; halogen; silane group; siloxane group; boron group; germanium group; cyano group; nitro group; -L'-N($R^a$)($R^b$); $C_1$-$C_{20}$ alkylthio group; $C_1$-$C_{20}$ alkoxyl group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$-$C_{20}$ heterocyclic group; $C_3$-$C_{20}$ cycloalkyl group; $C_7$-$C_{20}$ arylalkyl group and $C_8$-$C_{20}$ arylalkenyl group, wherein the substituents may combine each other and form a ring, wherein the term 'ring' means a $C_3$-$C_{60}$ aliphatic ring or a $C_6$-$C_{60}$ aromatic ring or a $C_2$-$C_{60}$ heterocyclic ring or a fused ring formed by the combination thereof and comprises a saturated or unsaturated ring.}

In a specific aspect of the invention, the compound represented by Formula 1 includes a compound represented by Formula 2 to Formula 5 below, and provides a compound included therein.

<Formula (2)>

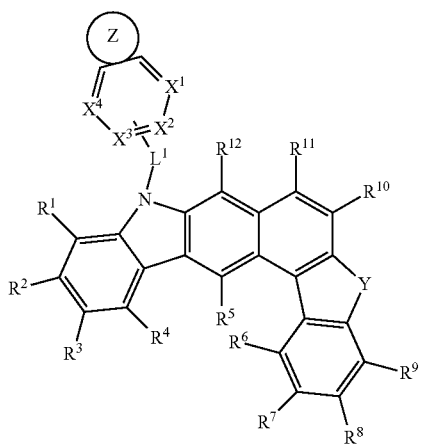

<Formula (3)>

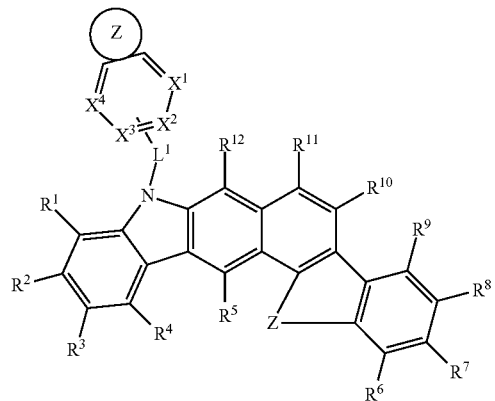

<Formula (4)>

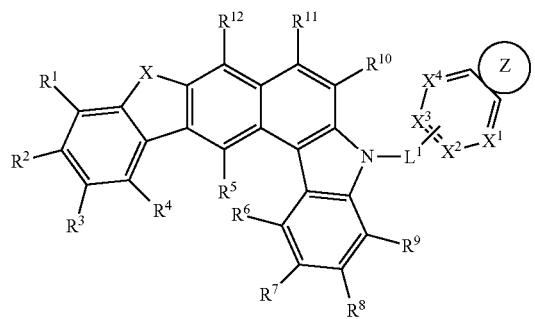

<Formula (5)>

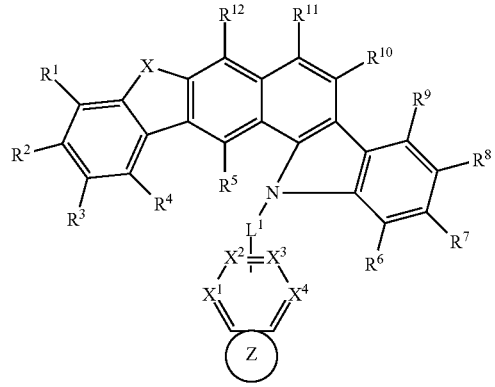

{In Formula (2) to Formula (5),

1)

is independently selected from a single or a double aromatic ring of $C_6$ to $C_{60}$; and the group consisting of a $C_2$-$C_{60}$ heterocyclic group containing at least one hetero atom of O, N, S, Si, or P.

2) $X^1$, $X^2$, $X^3$, and $X^4$ are carbons independently bonded to $CR^{17}$, N or L¹, and at least one of $X^1$, $X^2$, $X^3$, and $X^4$ contains N, and one of the remaining $X^1$, $X^2$, $X^3$, and $X^4$ must be a carbon bonded to L¹, 3) $R^{17}$ is the same as $R^1$ to $R^{16}$ defined above and plurality of $R^{17}$ may be bonded to each other to form a ring, except that in Formulas 2 and 3, Y or Z is $N-L^1-Ar^1$ and in Formulas 4 and 5, X is $N-L^1-Ar^1$.}

Also, the compound represented by Formula 1 comprises compounds represented by Formula (6) to (9).

<Formula (6)>

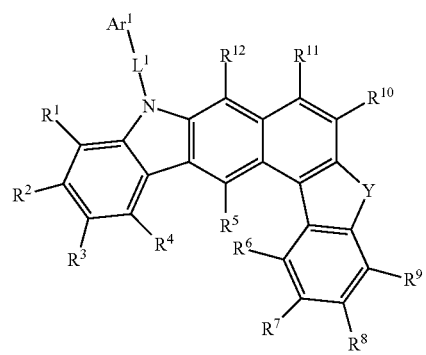

<Formula (7)>

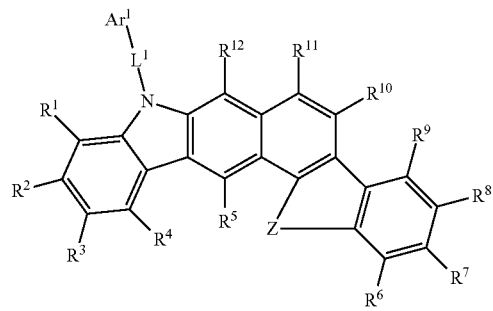

<Formula (8)>

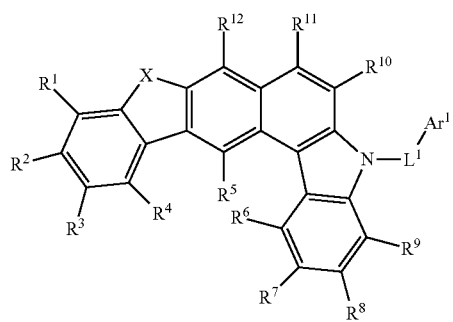

<Formula (9)>

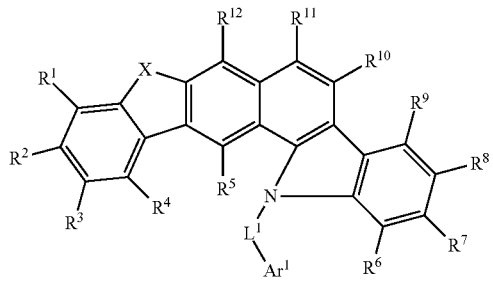

The present invention also provides a compound wherein

is represented by any one of the following Formulas Z-1 to Z-9 in the compounds represented by Formulas (2) to (5).

<Z-1>

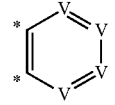

<Z-2>

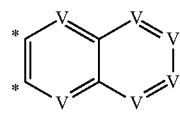

<Z-3>

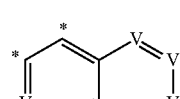

<Z-4>

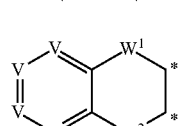

<Z-5>

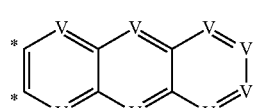

<Z-6>

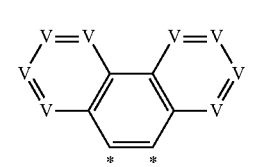

<Z-7>

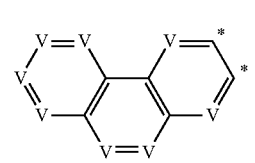

-continued

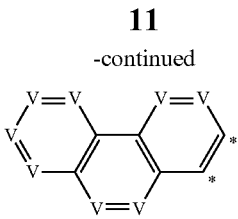
<Z-8>

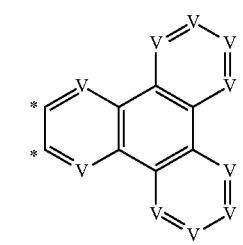
<Z-9>

{In Formulas Z-1 to Z-9,
1) * represents the corresponding adjacent group in Formulas (2) to (3),
2) V is $CR^{18}$ or N,
3) $W^1$ and $W^2$ are each independently single bond, $CR^{19}R^{20}$, $NAr^4$, O, S or $SiR^{21}R^{22}$
4) $R^{18}$, $R^{19}$, $R^{20}$, $R^{21}$, and $R^{22}$ are the same as $R^1$ to $R^{12}$ defined above,
5) $Ar^4$ is the same as $Ar^1$ defined above,
6) Plurality of $R^{18}$ may be bonded to each other to form a ring, and $R^{19}$, $R^{20}$, $R^{21}$, and $R^{22}$ may be bonded to each other to form a spiro bonded with C or Si to be bonded.}

The structure

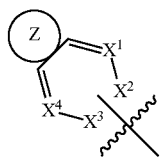

including the Z ring provides a compound represented by any one of the following Formulas Z-10 to Z-31.

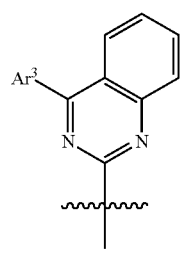
<Z-10>

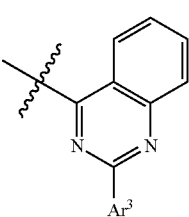
<Z-11>

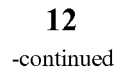
<Z-12>

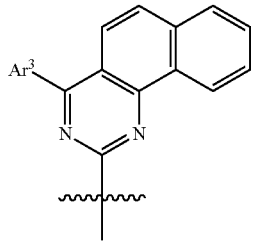
<Z-13>

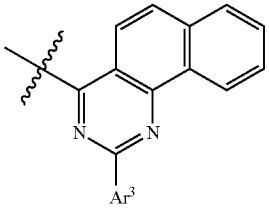
<Z-14>

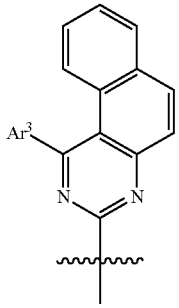
<Z-15>

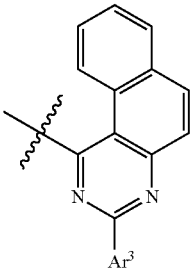
<Z-16>

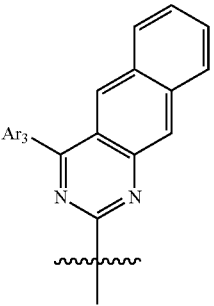

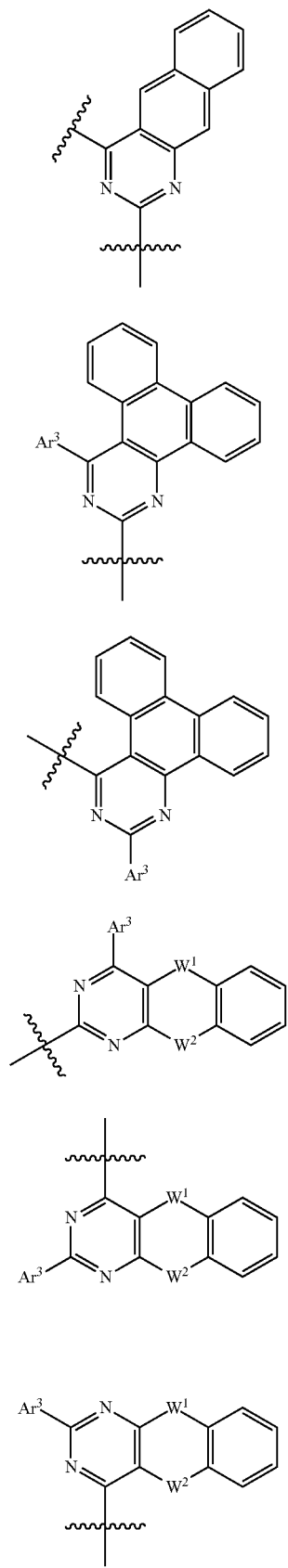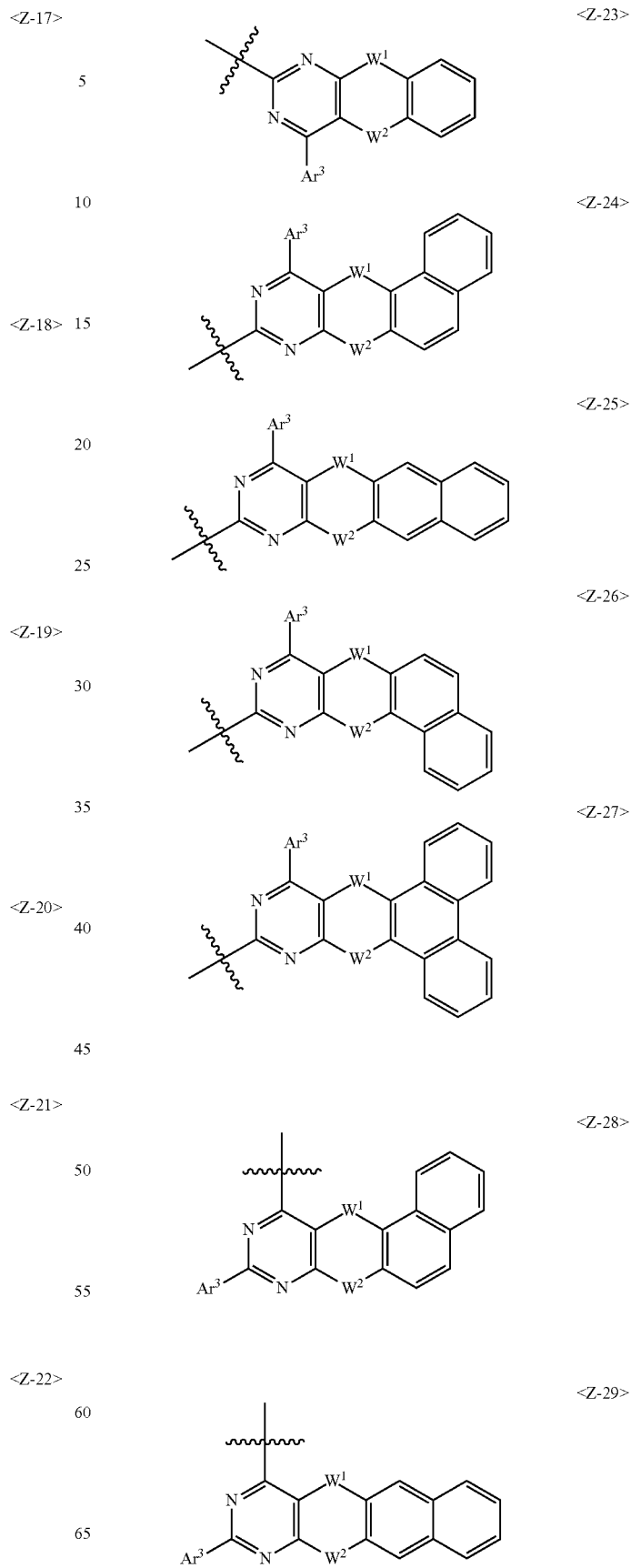

-continued
<Z-30>
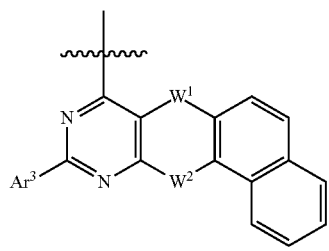
<Z-31>
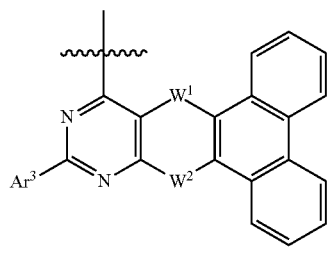
{In Formulas Z-10 to Z-31,
1) Ar³ is the same as Ar¹ defined in Formula (1)
Specifically, Formula (1) of the present invention comprises a compound represented by the following Formulas (1-1-1) to (8-2-3) and provides the compound.
1-1-1
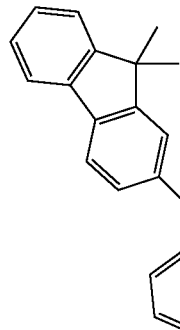
1-1-2
1-1-3
-continued
1-1-4
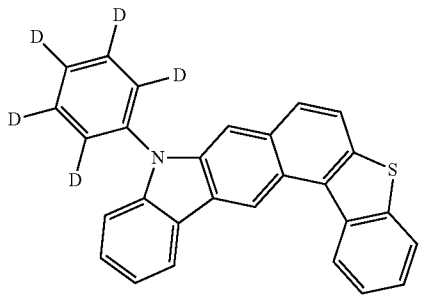
1-1-5
1-1-6
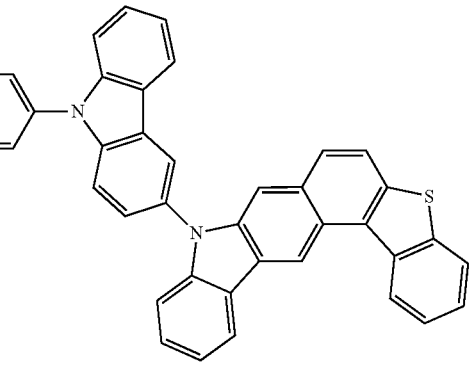
1-1-7
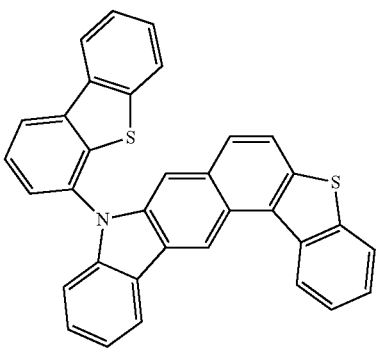

-continued
1-1-8
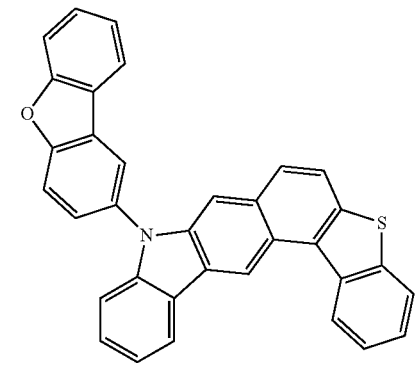
1-1-9
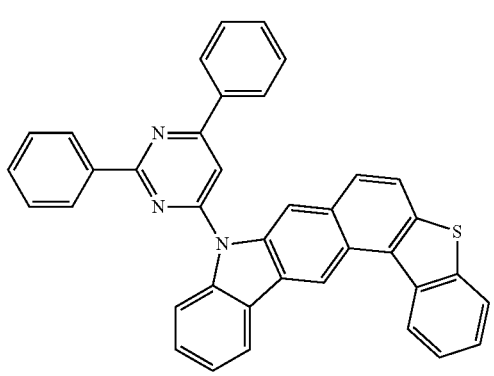
1-1-10

1-1-11

-continued
1-1-12
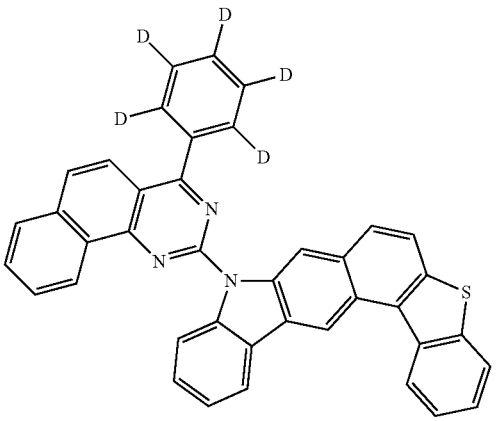
1-1-13
1-1-14

-continued
1-1-15
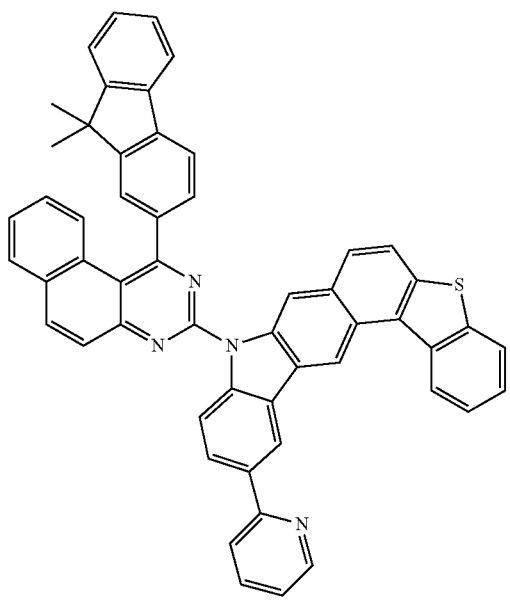
1-1-16
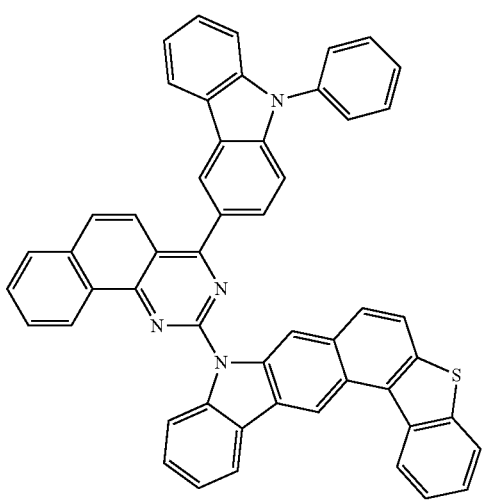
1-1-17
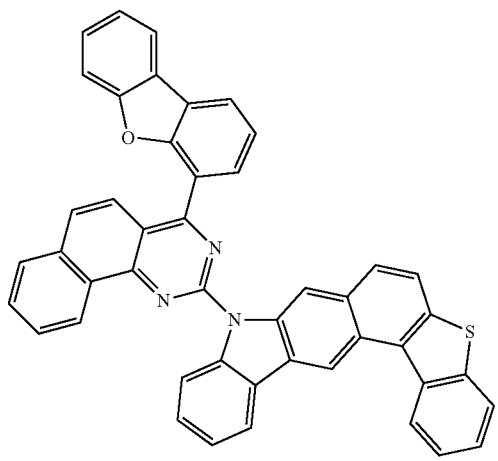
1-1-18
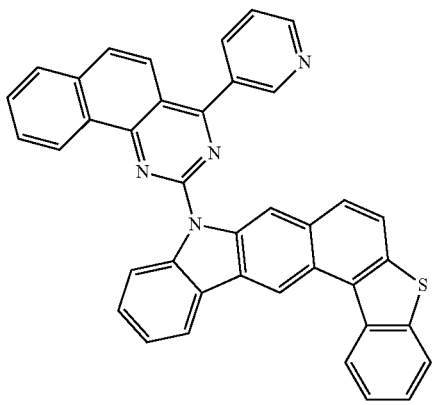
1-1-19
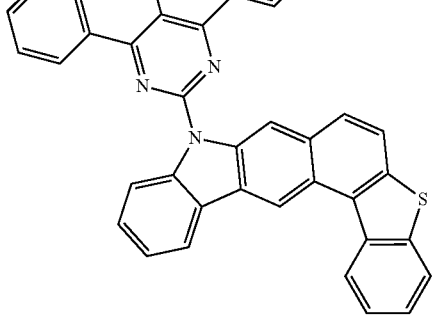
1-1-20
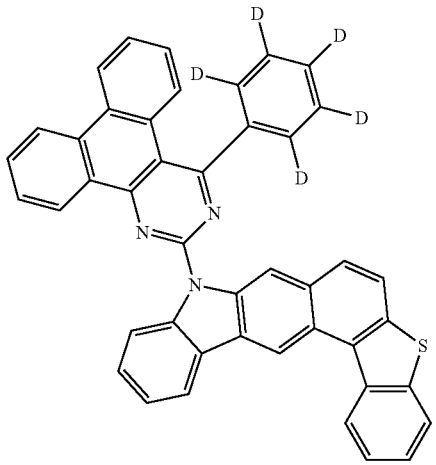

1-1-21
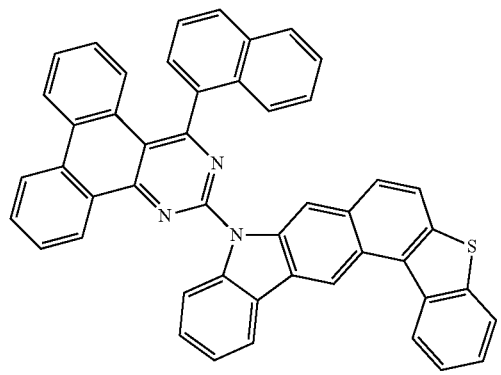
1-1-22
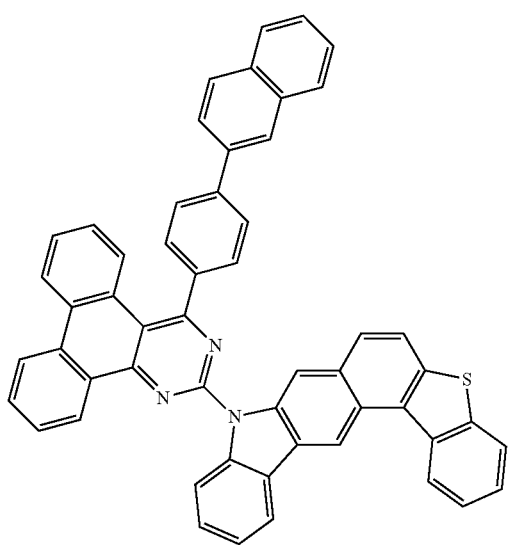
1-1-23
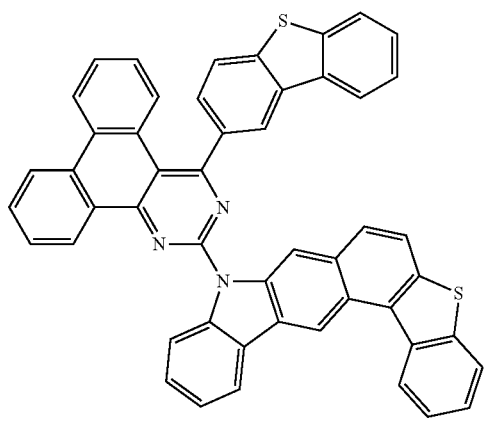
1-1-24
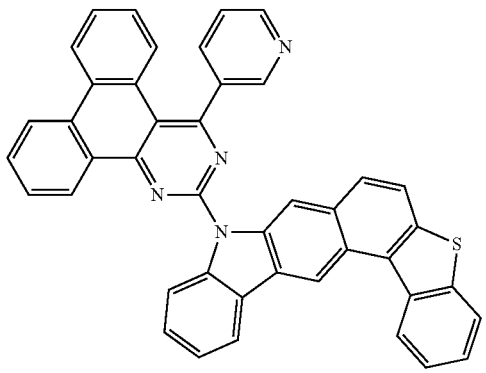
1-1-25
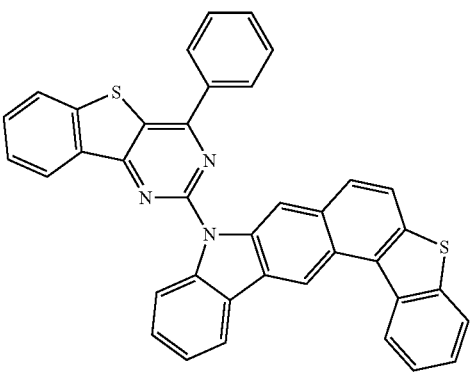
1-1-26

-continued
1-1-27
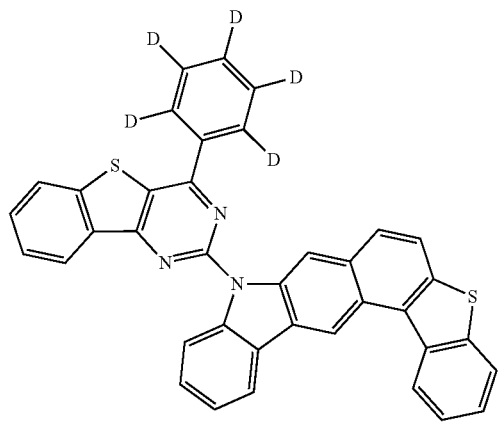
1-1-28
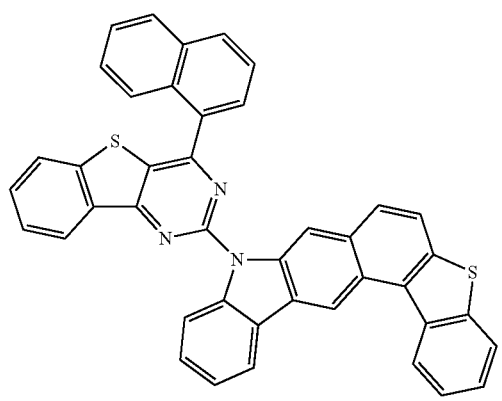
1-1-29
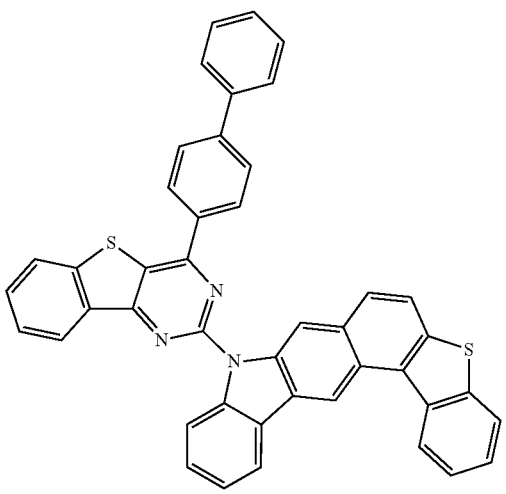
-continued
1-1-30
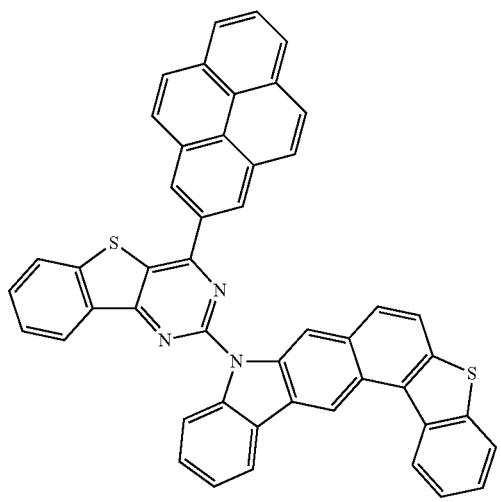
1-1-31
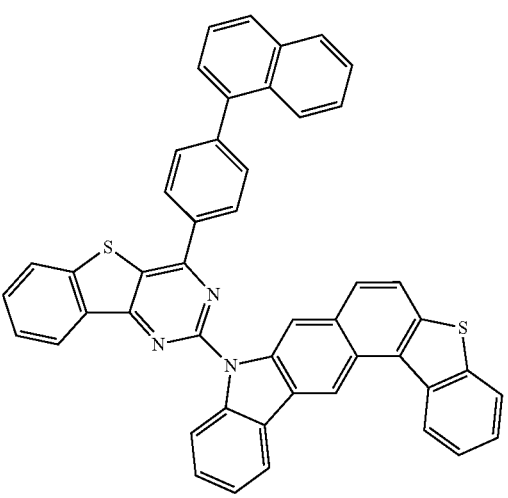
1-1-32
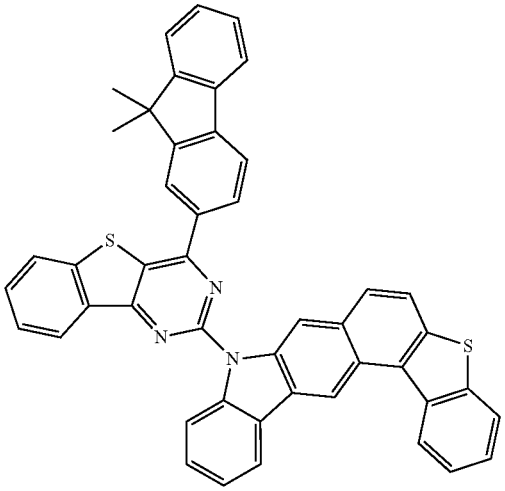

1-1-33
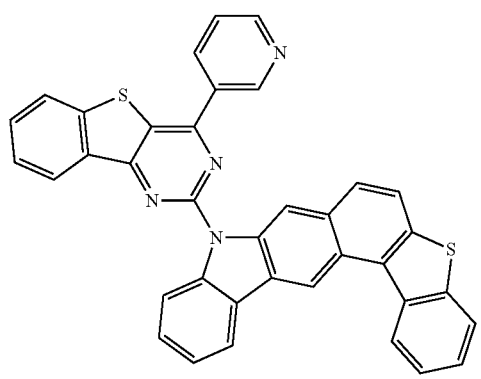
1-1-34
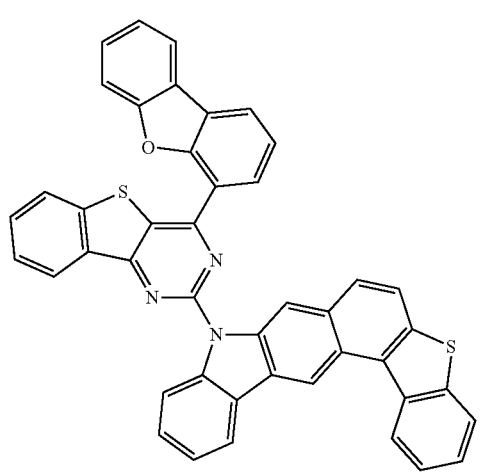
1-1-35
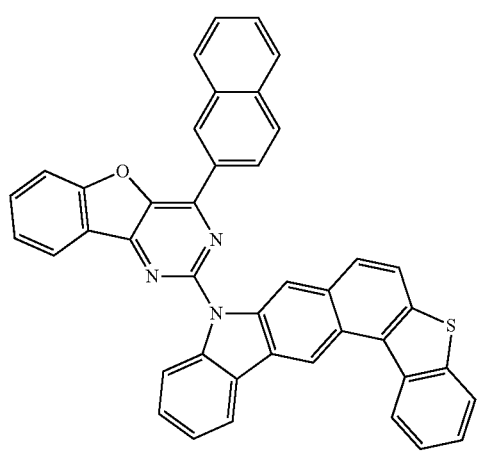
1-1-36
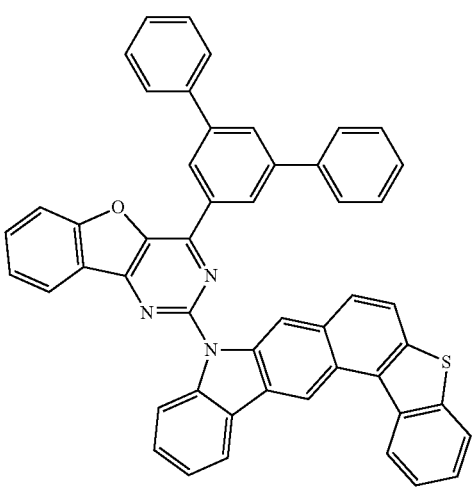
1-1-37
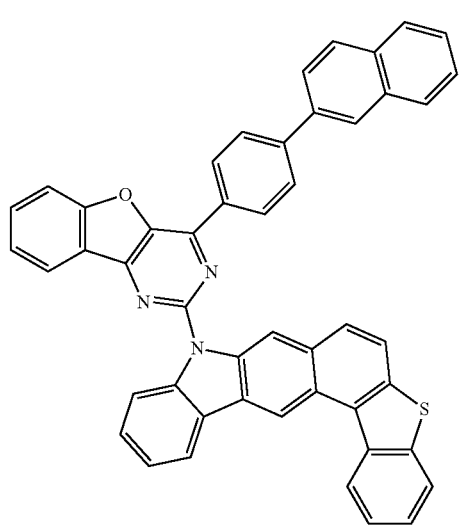
1-1-38
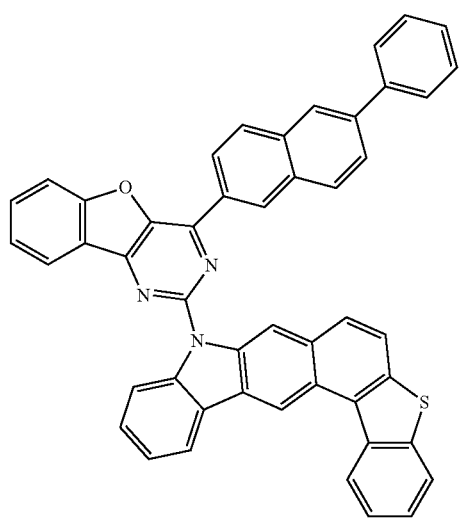

-continued
1-1-40
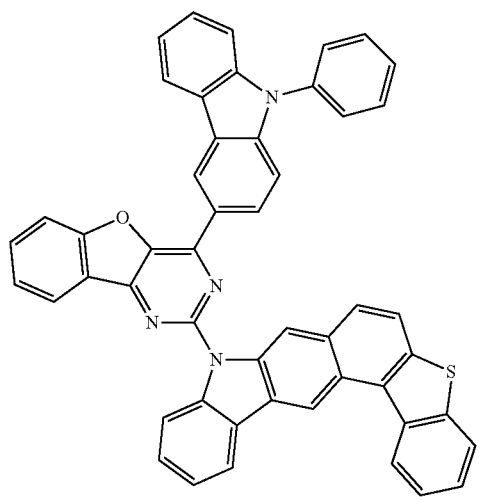
1-1-41
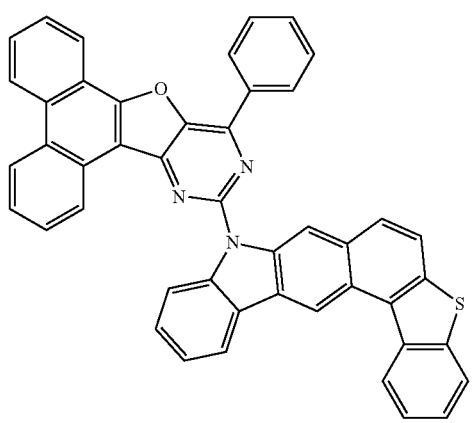
1-1-42
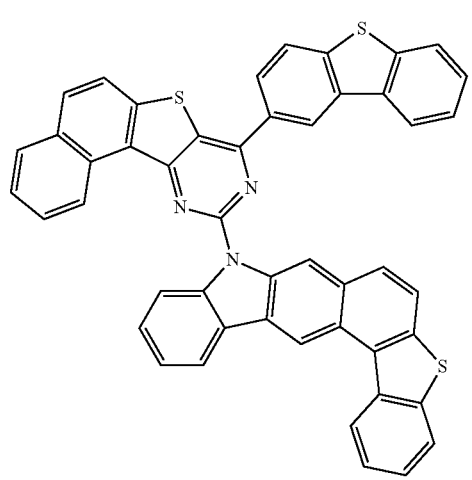
-continued
1-1-43
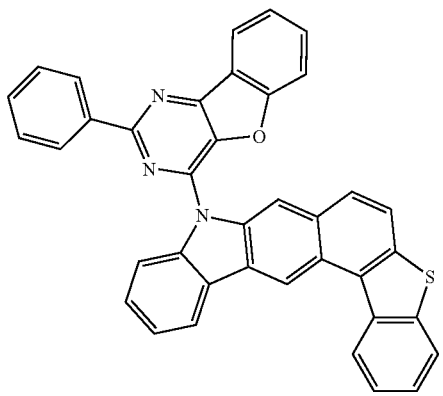
1-1-44
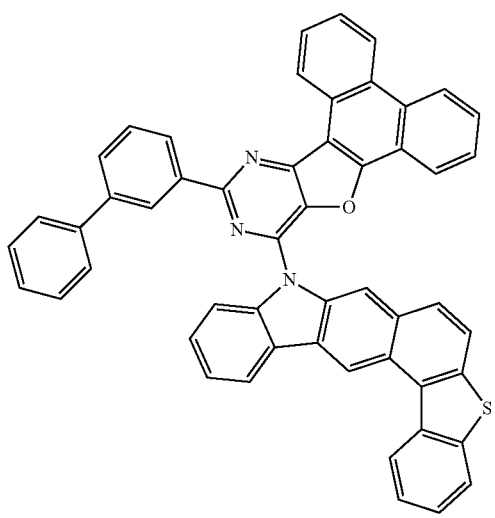
1-1-45
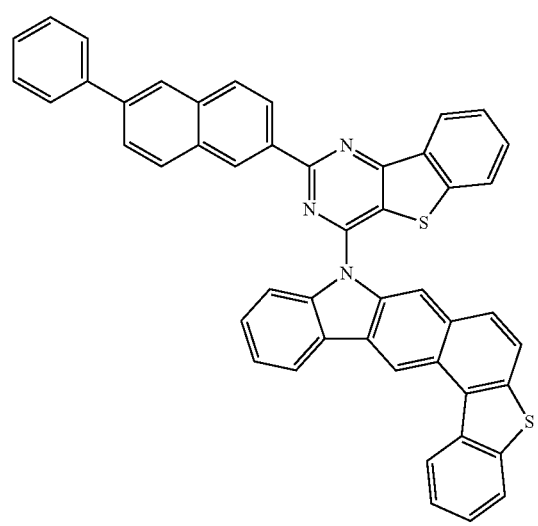

1-1-46
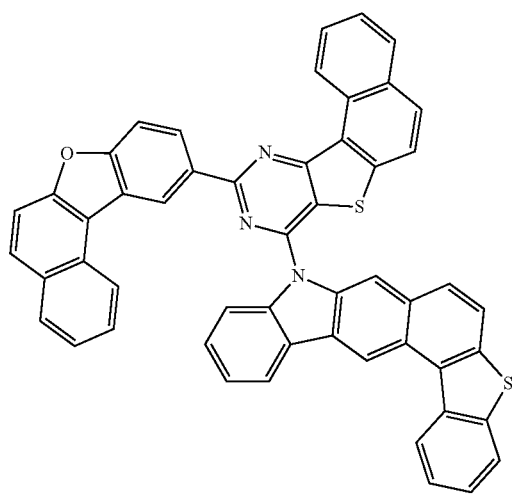
1-1-47
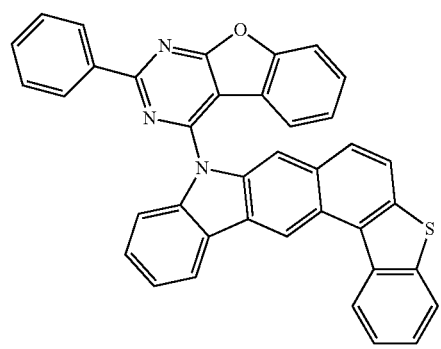
1-1-48
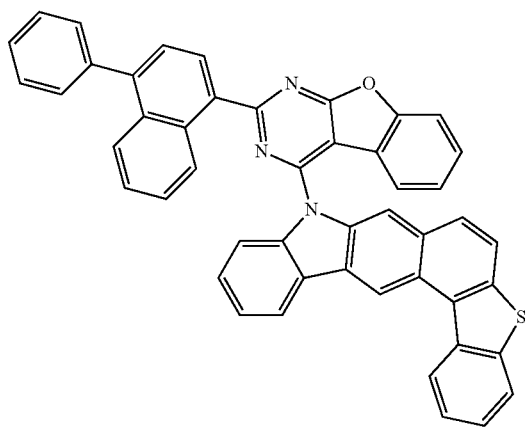
1-1-49
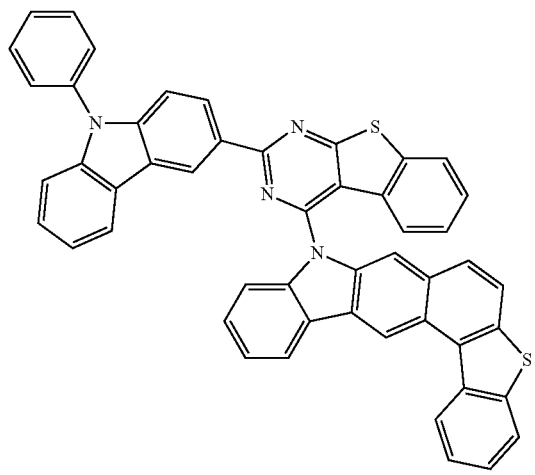
1-1-50
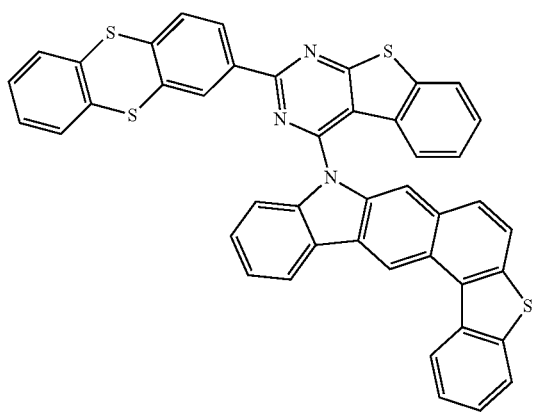
1-1-51
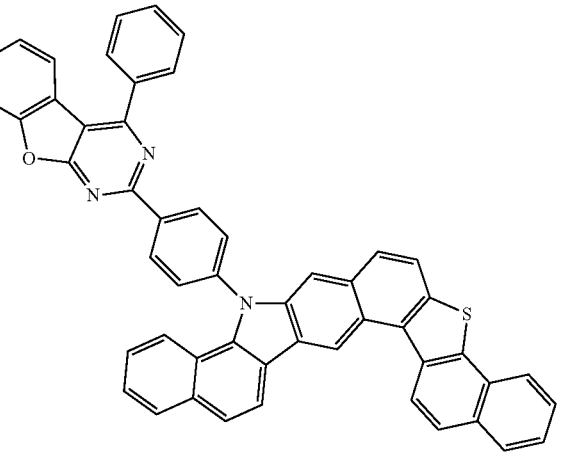

1-1-52
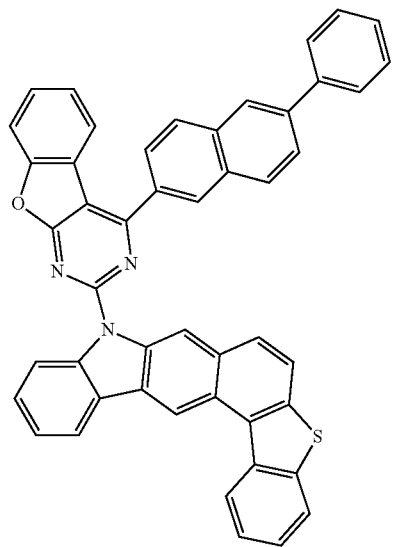
1-1-53
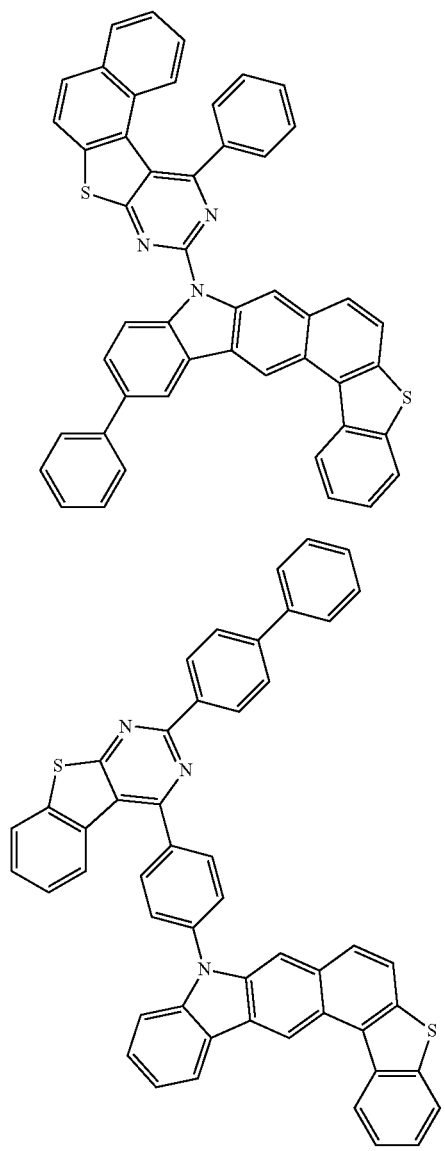
1-1-54
1-1-55
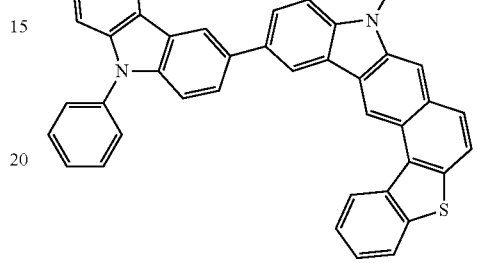
1-1-56
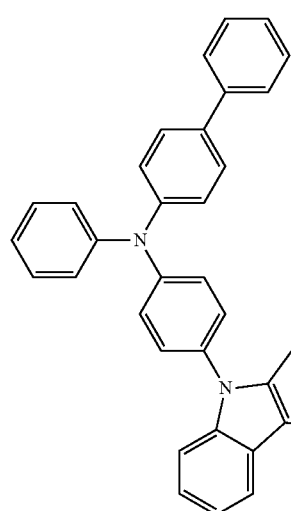
1-1-57
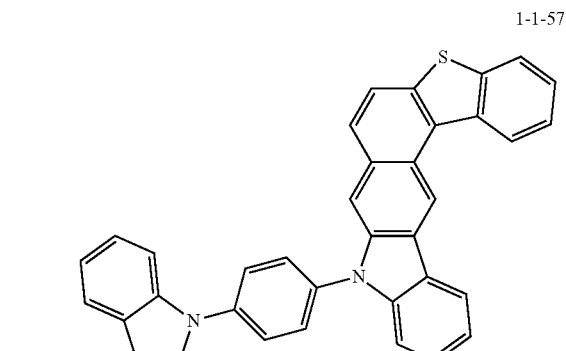
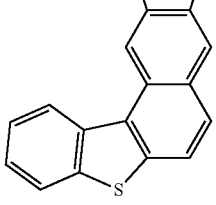

33
-continued
1-1-58
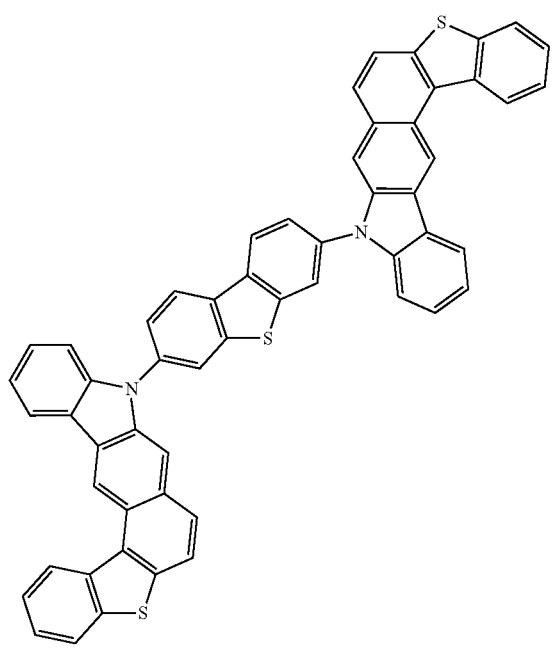
1-1-59
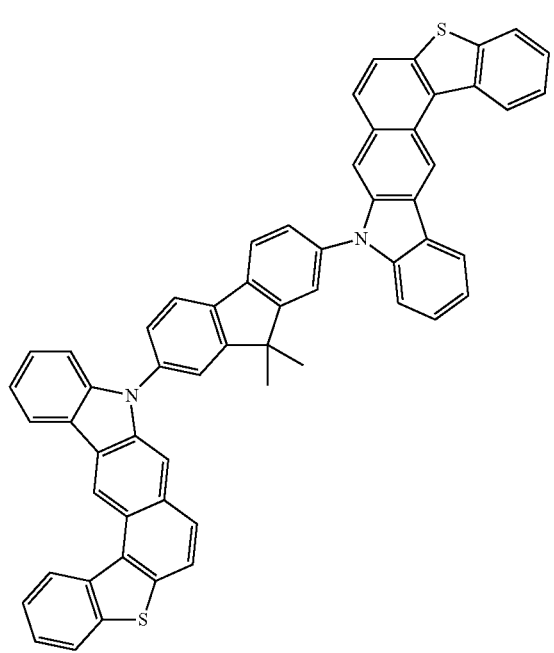
34
-continued
1-1-60
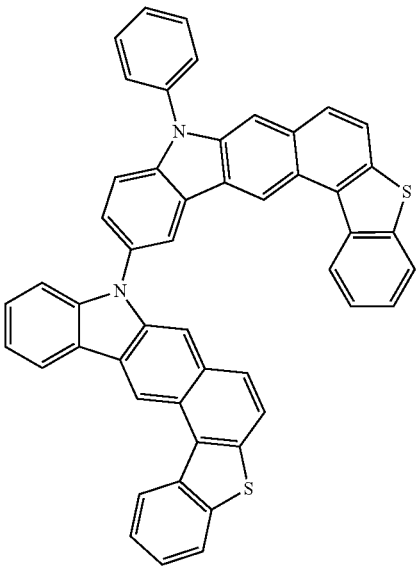
1-1-61
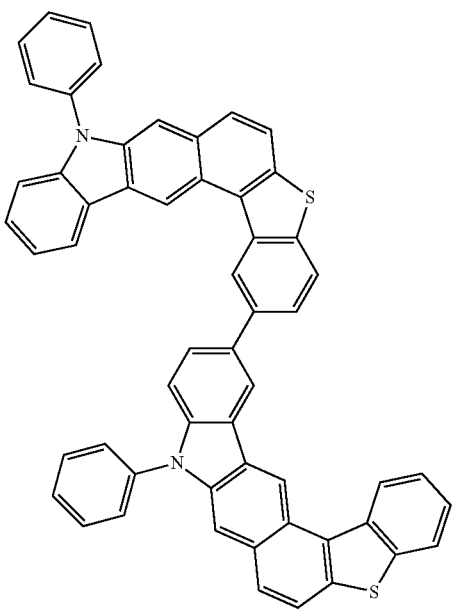
1-2-1
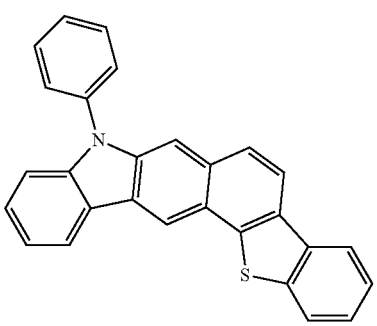

35
-continued
1-2-2
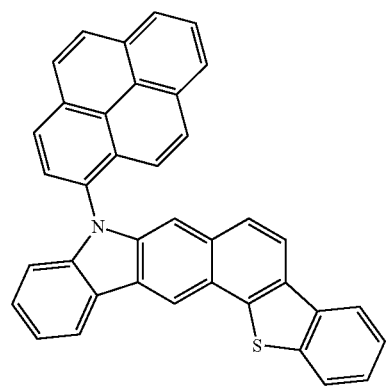
1-2-3
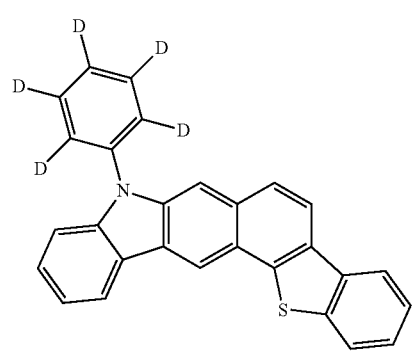
1-2-4
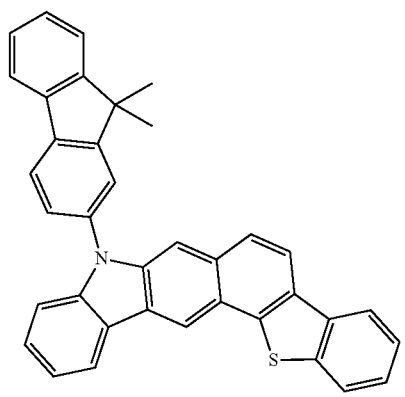
1-2-5
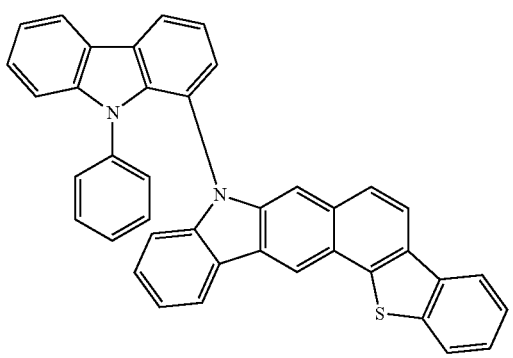
36
-continued
1-2-6
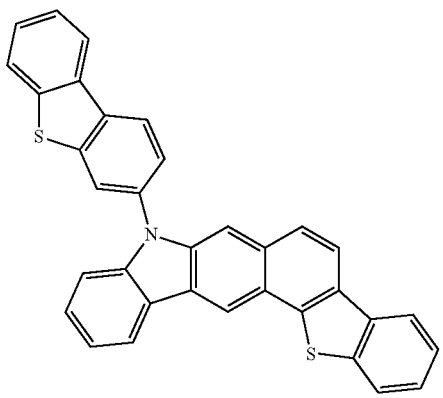
1-2-7
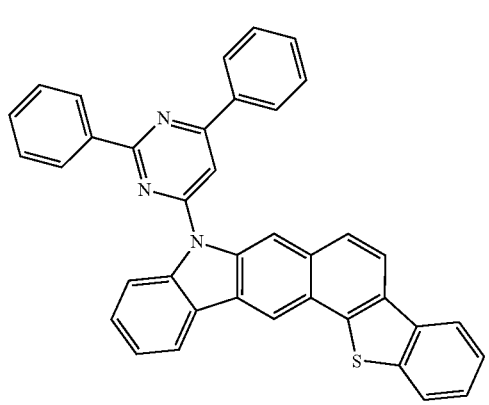
1-2-8
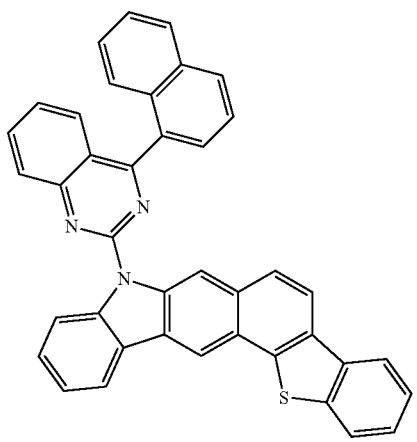
1-2-9
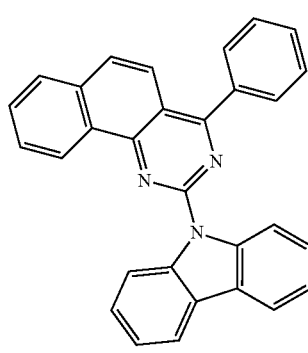

1-2-10
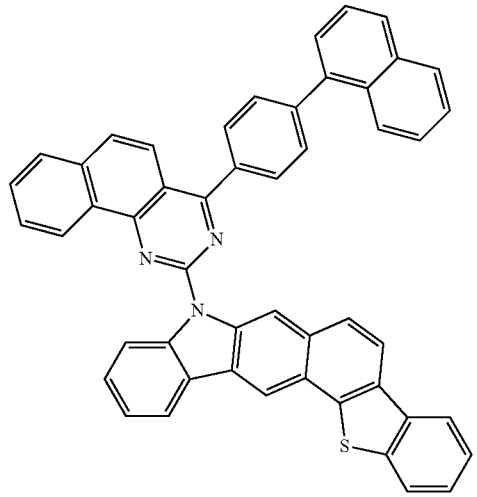
1-2-11
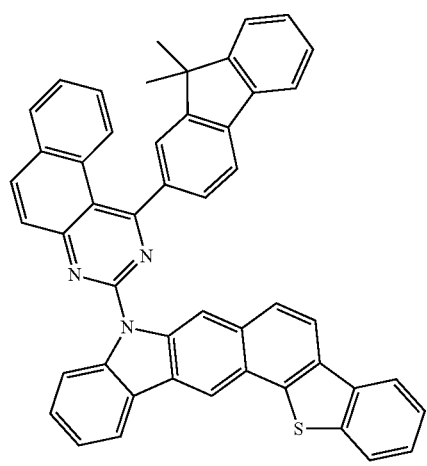
1-2-12
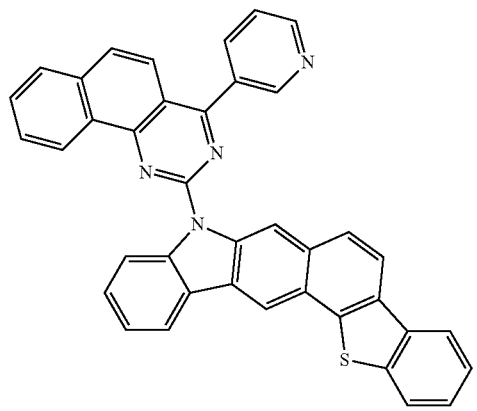
1-2-13
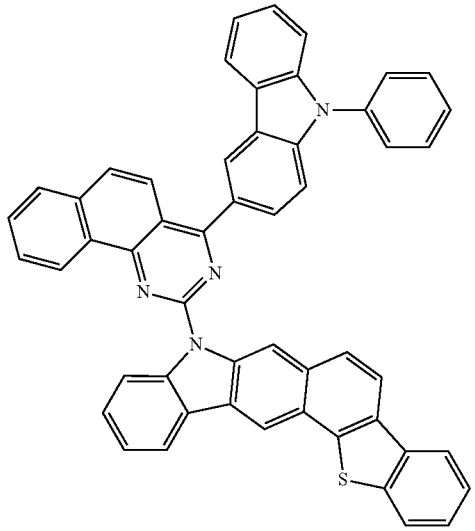
1-2-14
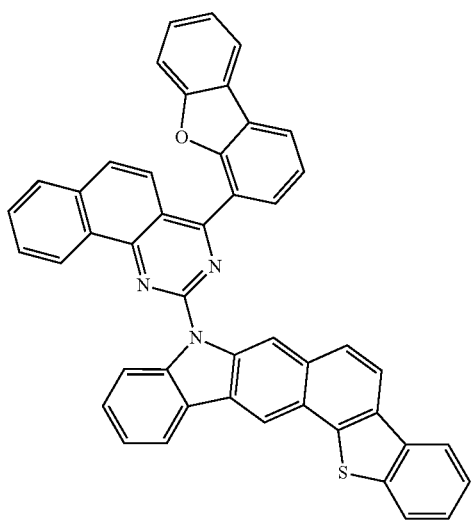
1-2-15
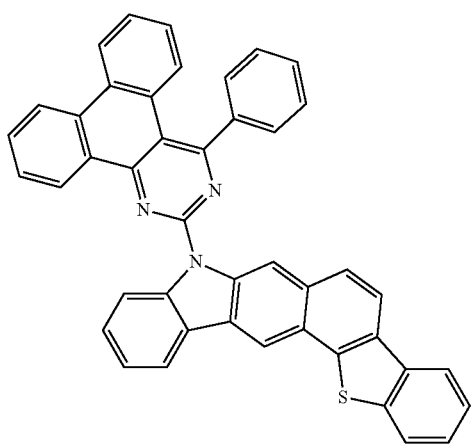

1-2-16
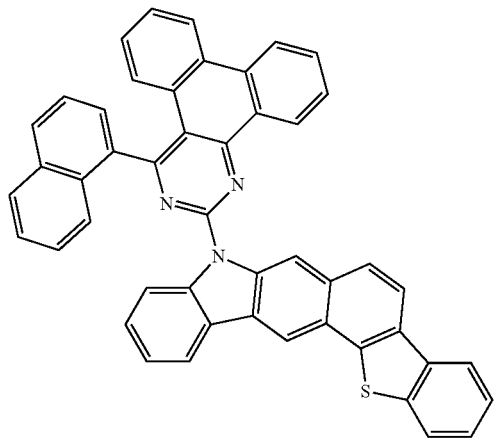
1-2-17
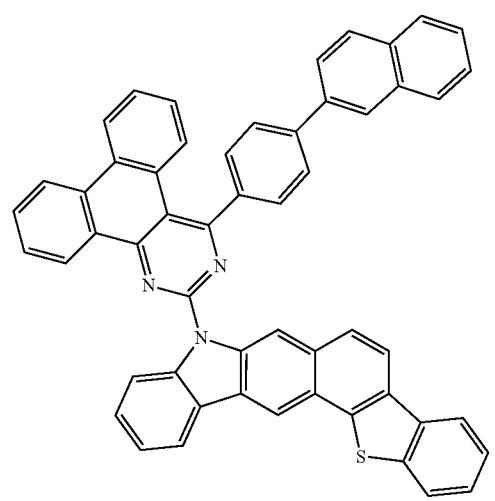
1-2-18
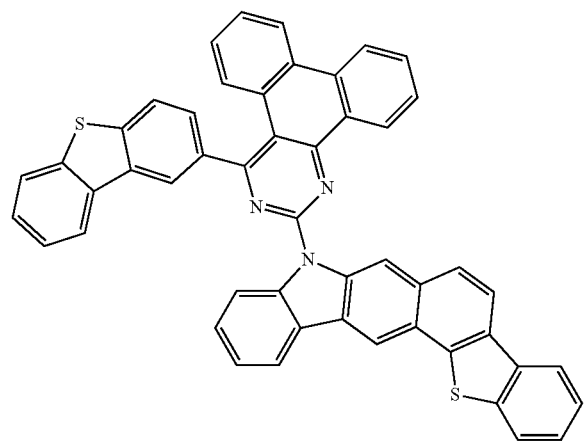
1-2-19
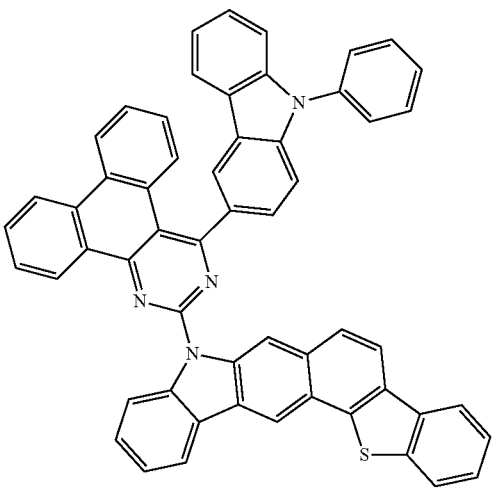
1-2-20
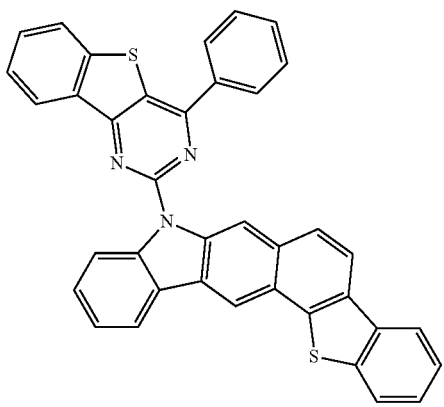
1-2-21
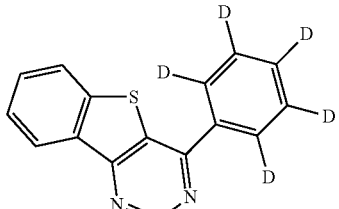

1-2-22
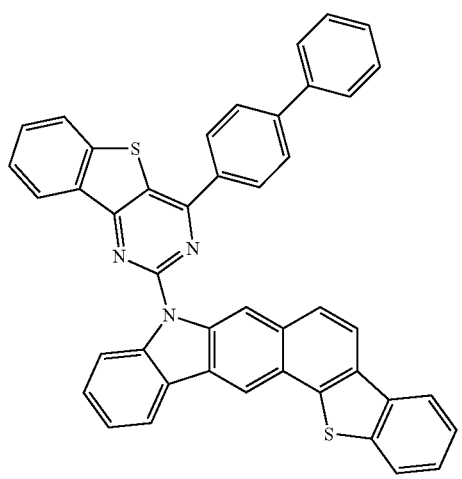
1-2-23
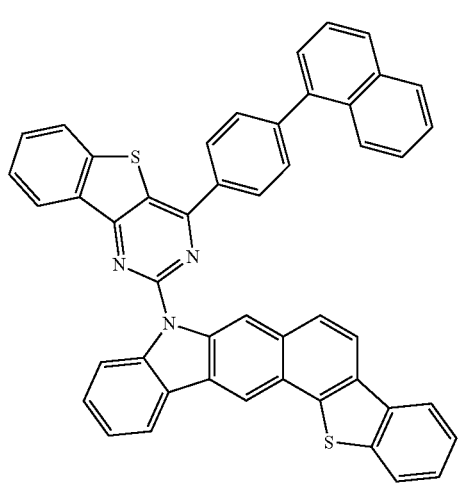
1-2-24
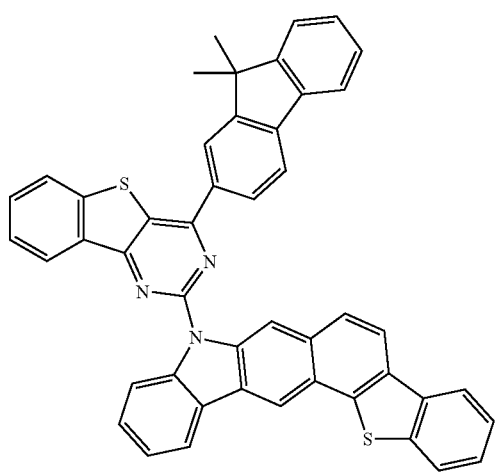
1-2-25
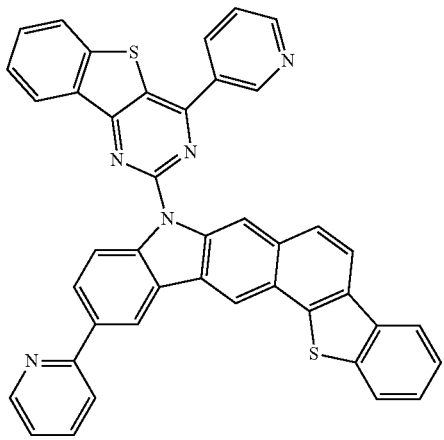
1-2-26
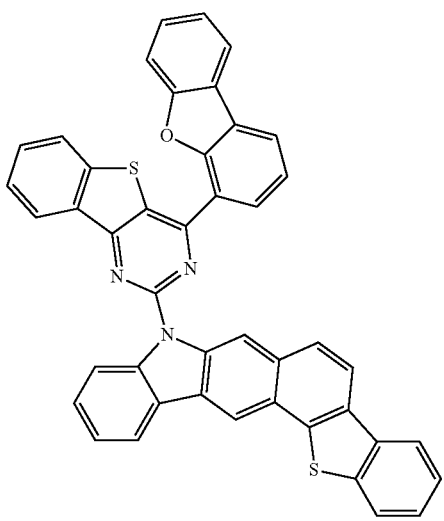
1-2-27
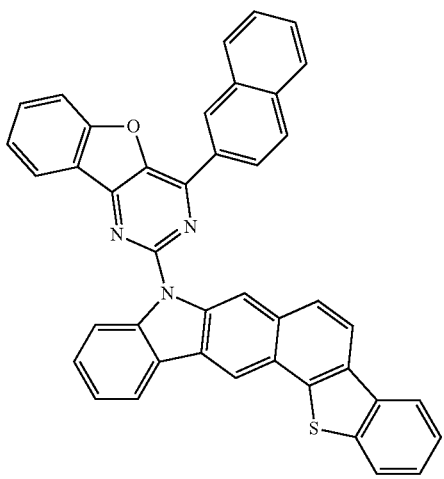

1-2-28
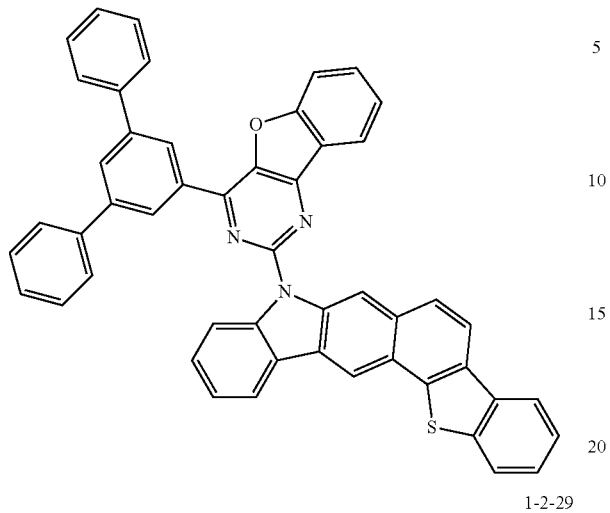
1-2-31
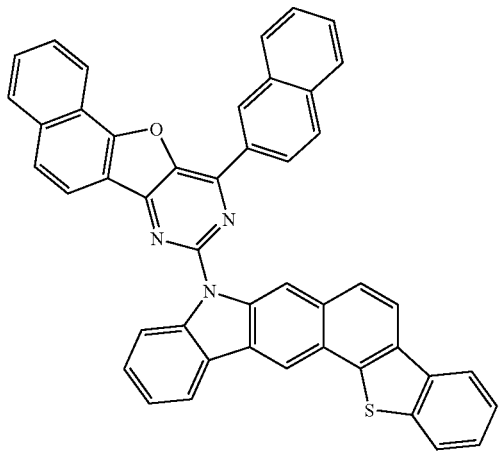
1-2-29
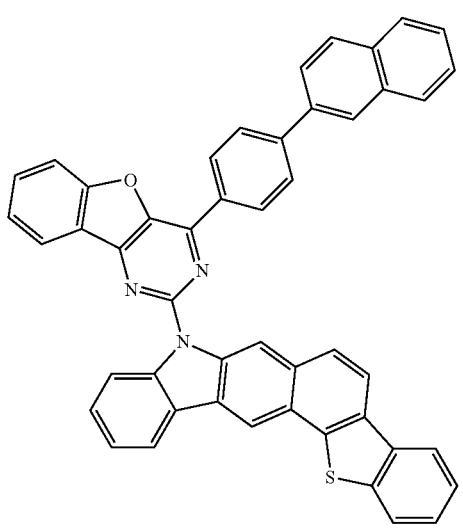
1-2-32
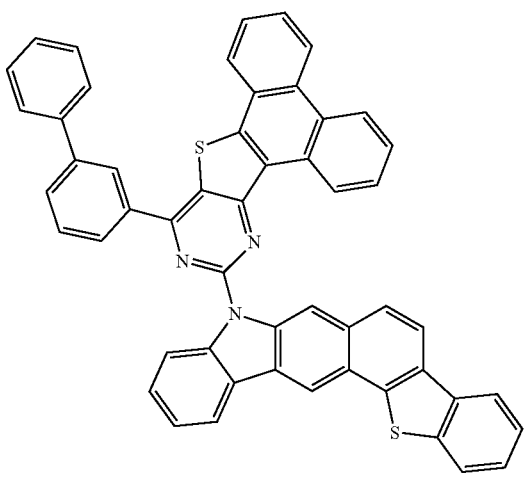
1-2-30
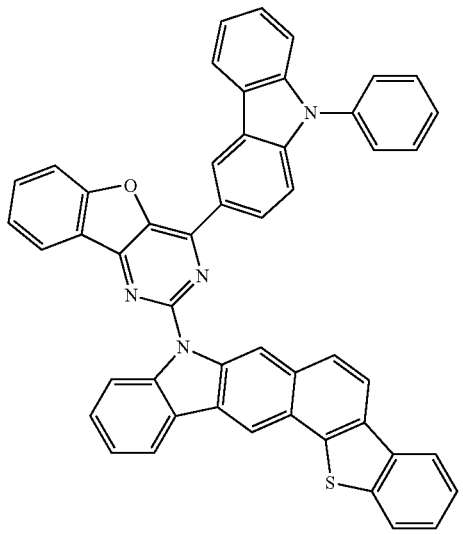
1-2-33
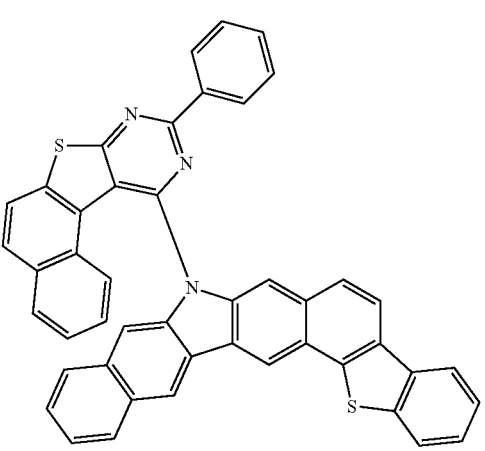

-continued
1-2-34
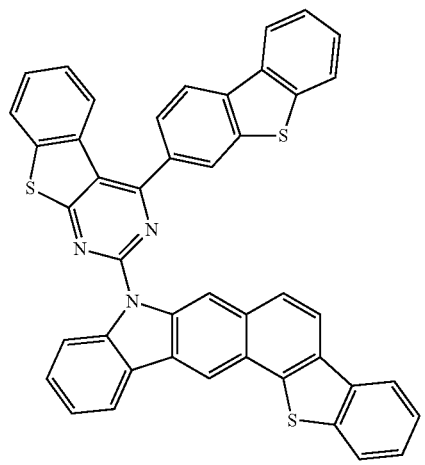
1-2-35
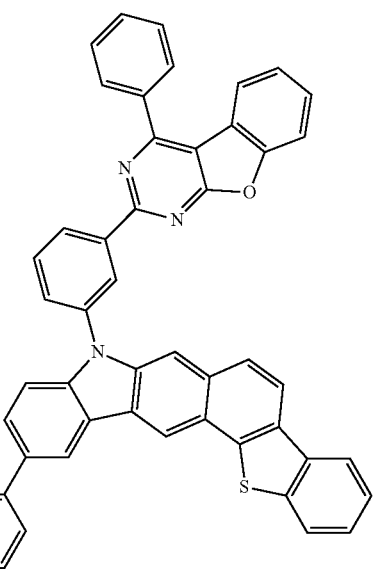
1-2-36
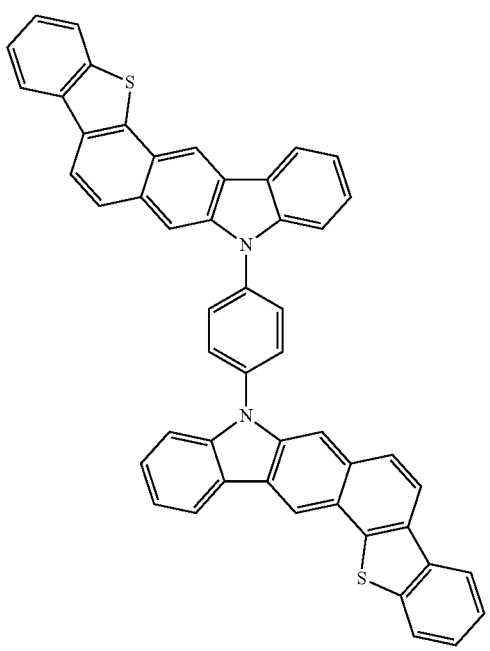
1-2-37
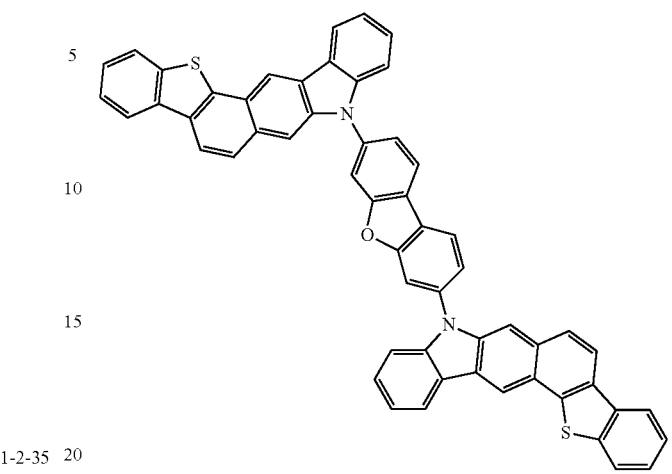
1-2-38
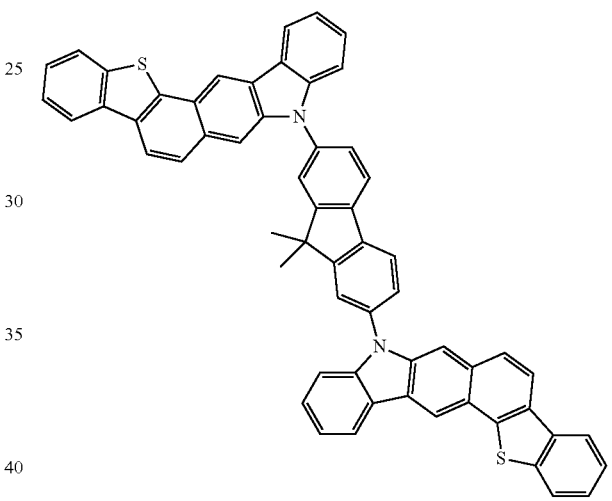
1-2-39
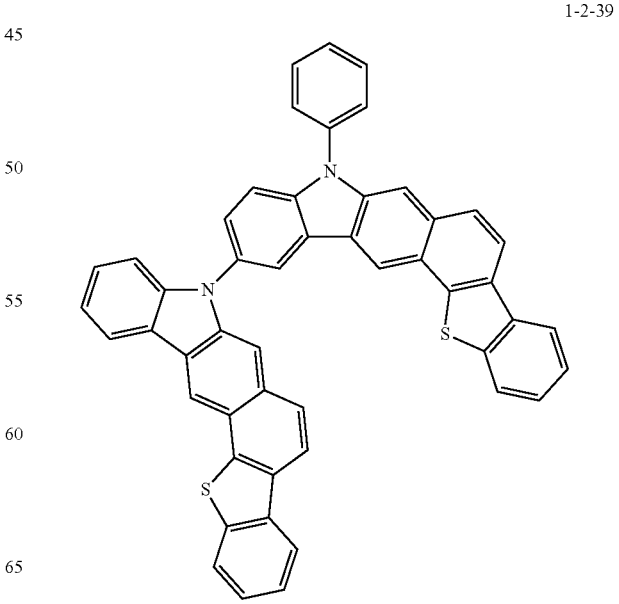

1-2-40
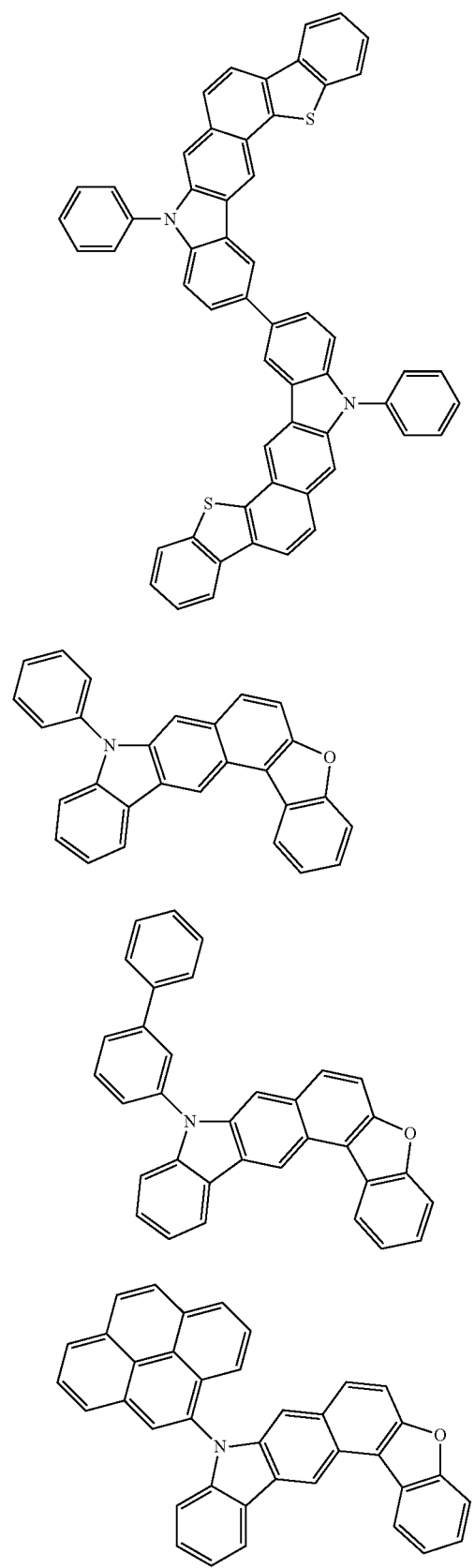
2-1-1
2-1-2
2-1-3
2-1-4
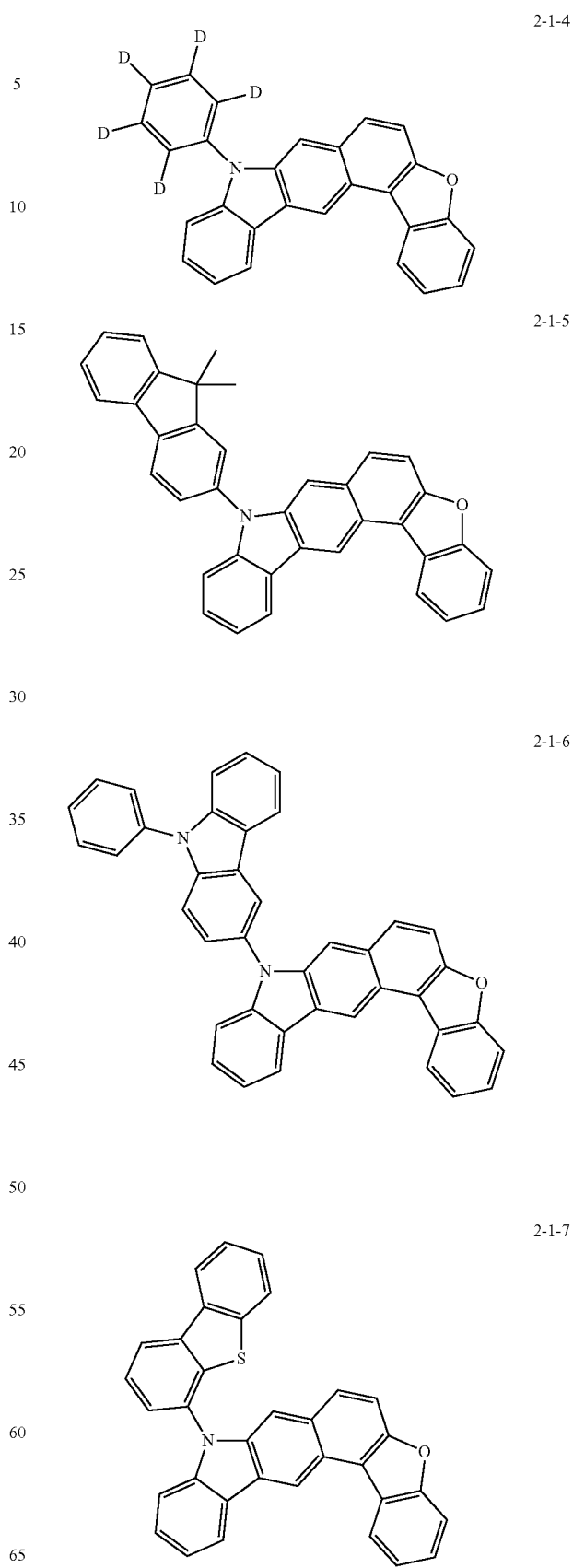
2-1-5
2-1-6
2-1-7

2-1-8
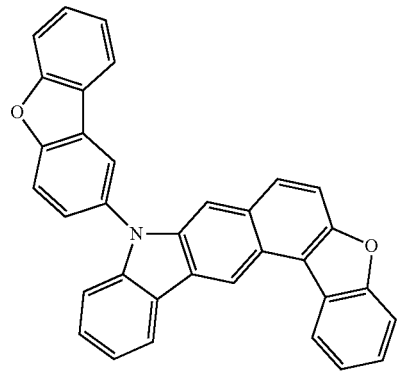
2-1-9
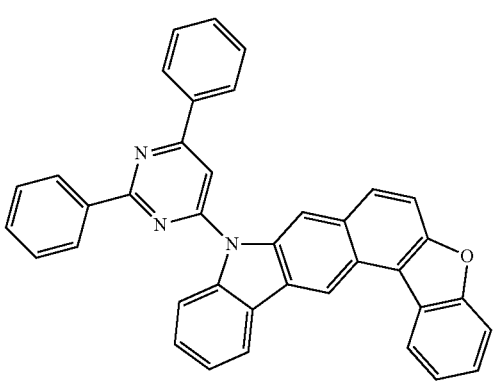
2-1-10
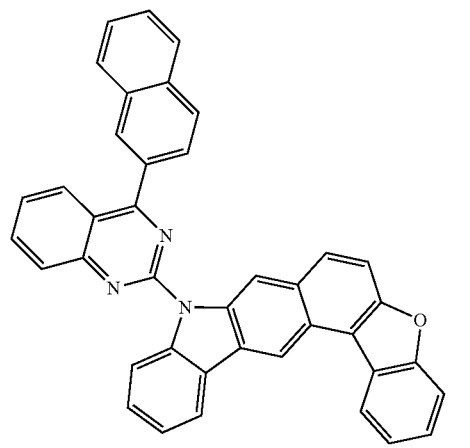
2-1-11
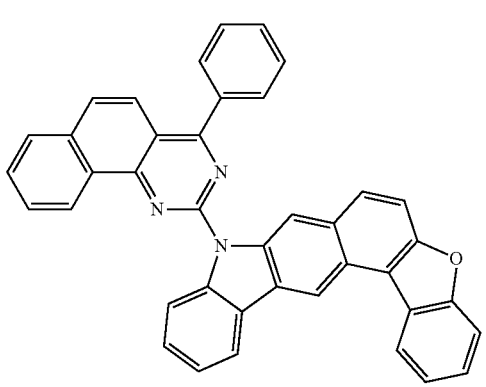
2-1-12
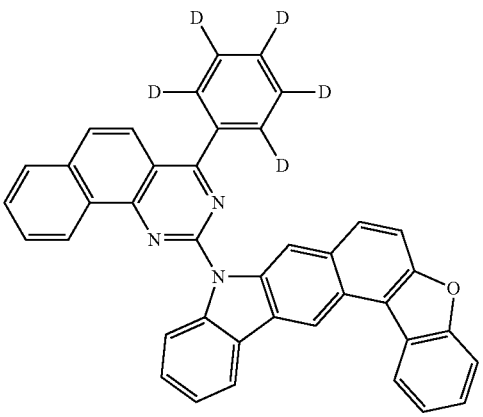
2-1-13
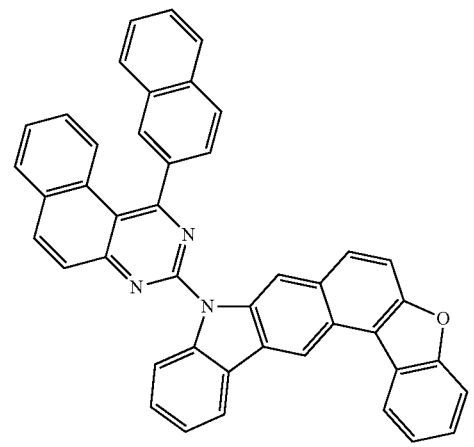
2-1-14
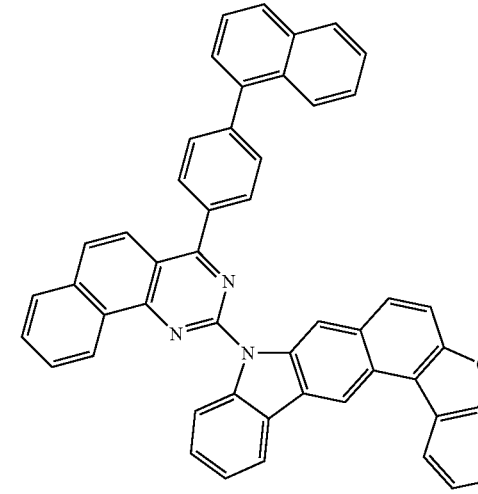

-continued
2-1-15
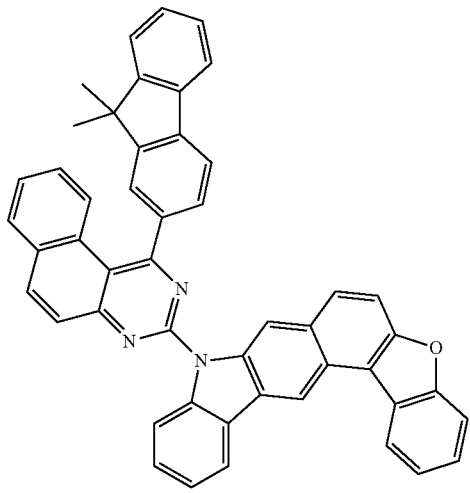
2-1-16
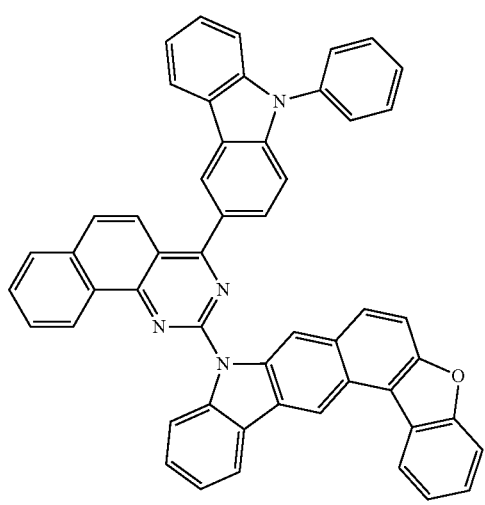
2-1-17
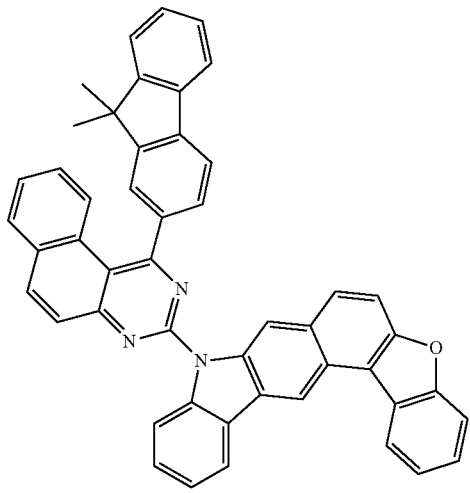
2-1-18
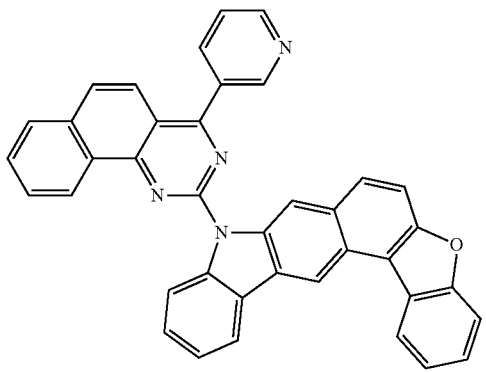
2-1-19
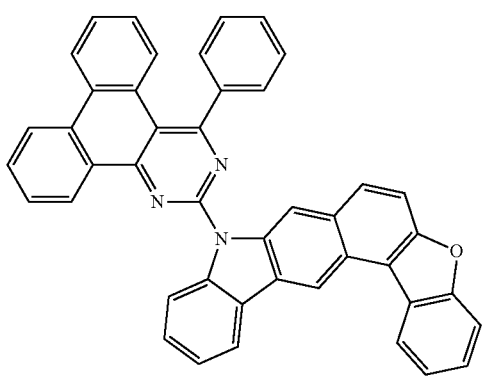
2-1-20
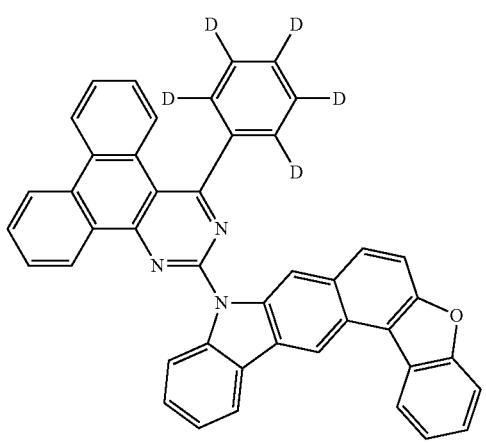
2-1-21
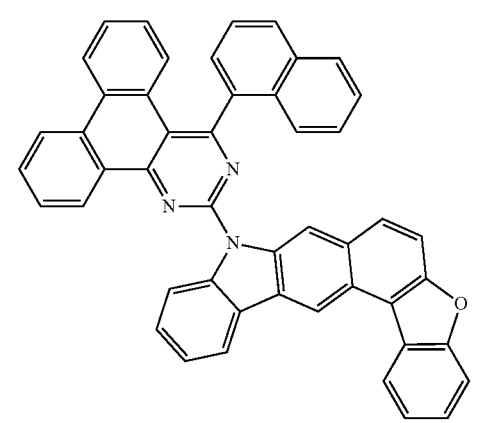

2-1-22
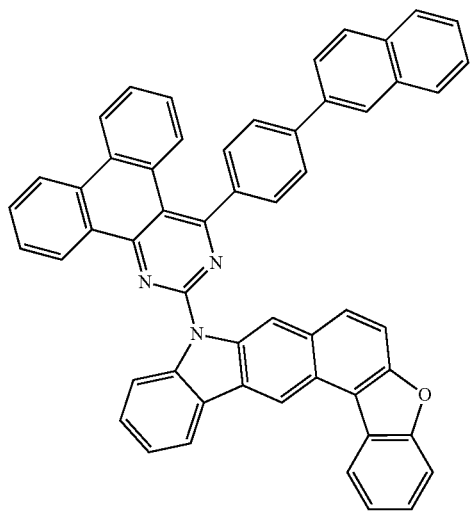
2-1-23
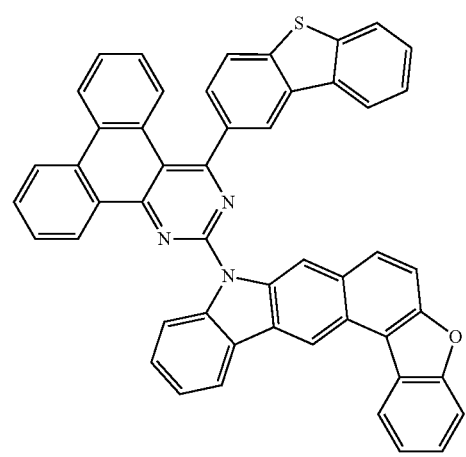
2-1-24
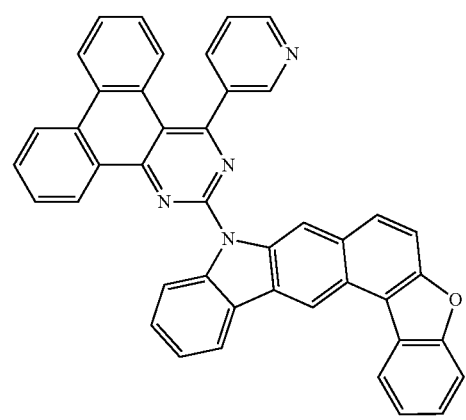
2-1-25
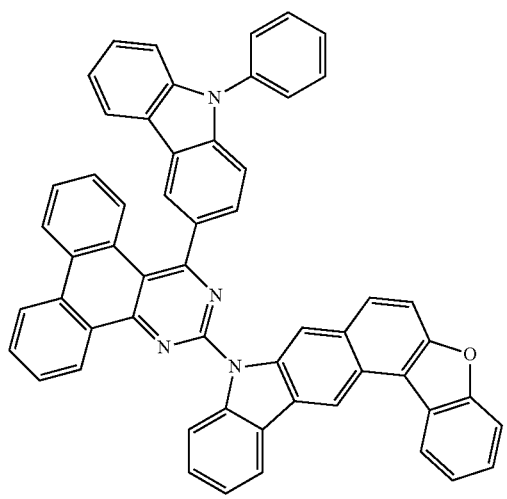
2-1-26
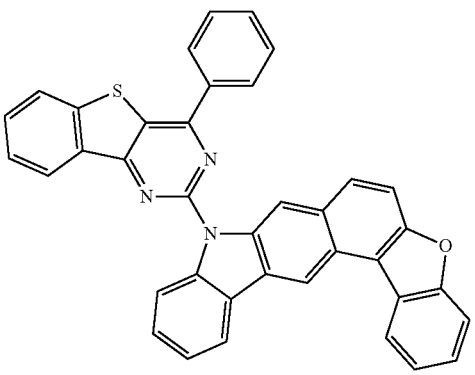
2-1-27
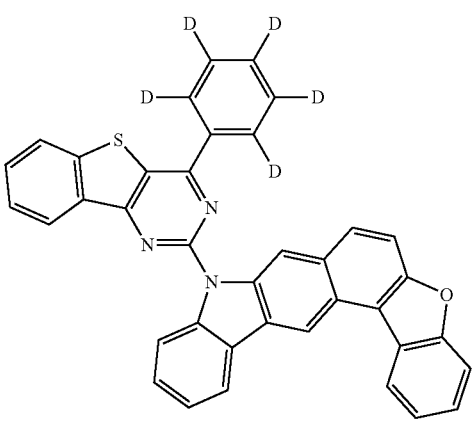

2-1-28
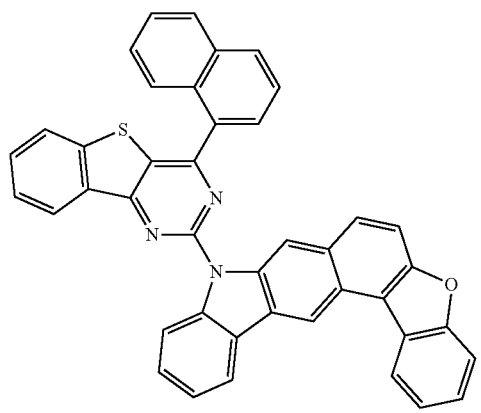
2-1-29
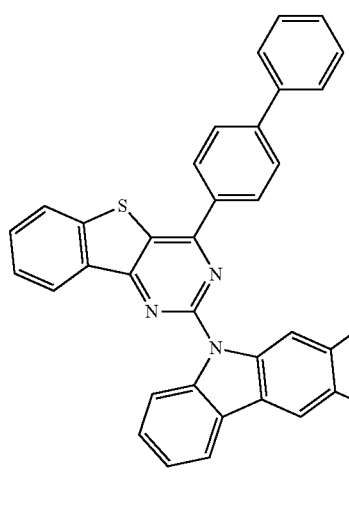
2-1-30
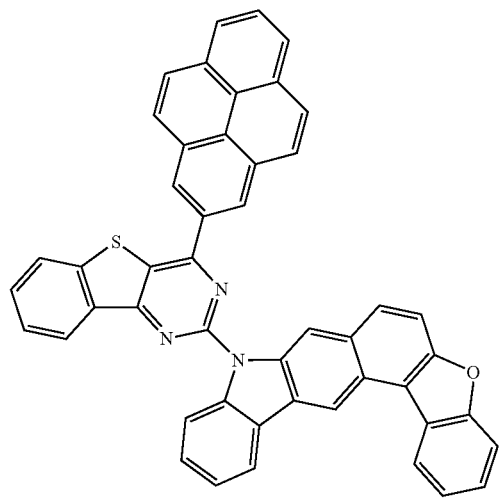
2-1-31
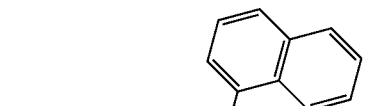
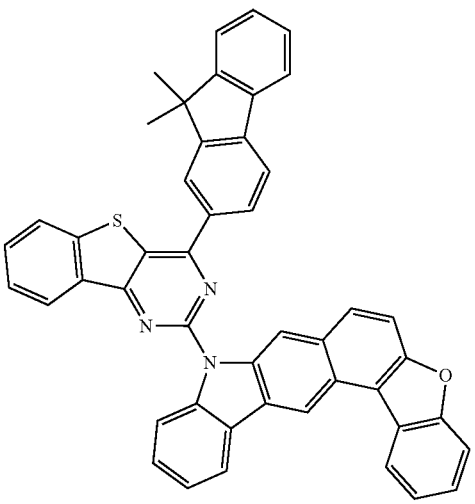
2-1-32
2-1-33
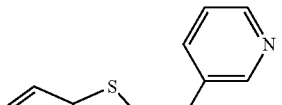
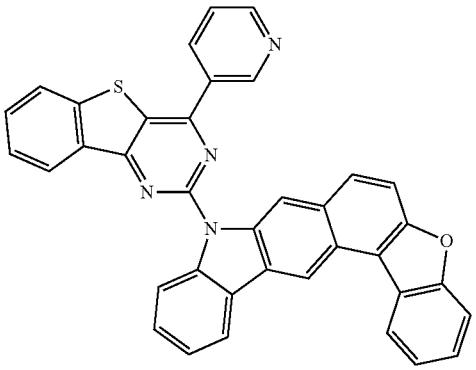

2-1-34
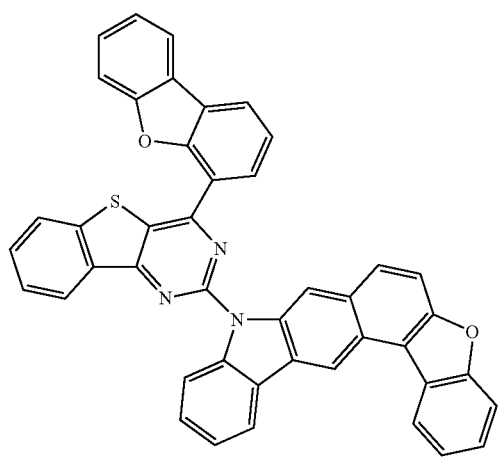
2-1-35
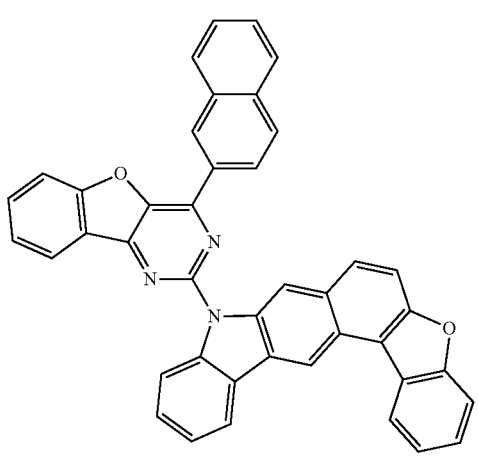
2-1-36
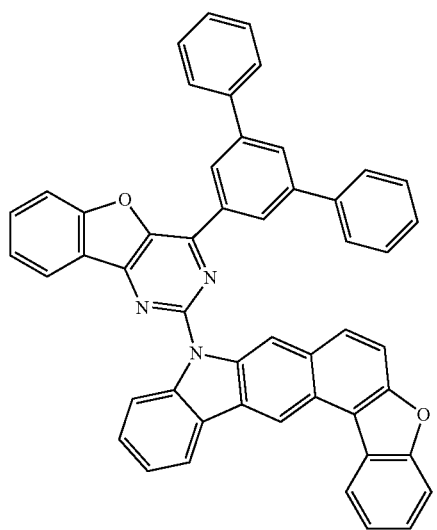
2-1-37
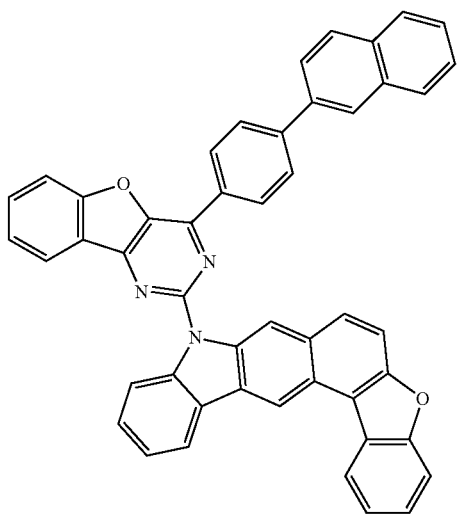
2-1-38
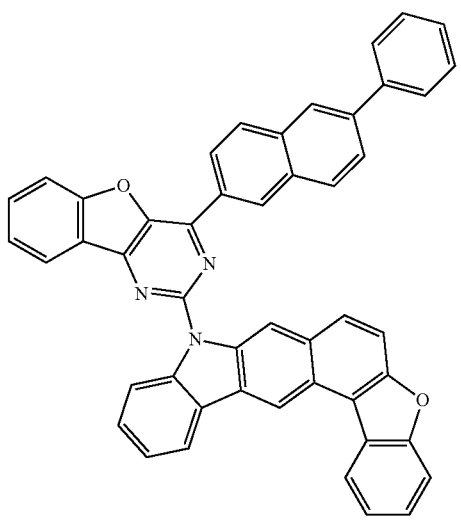
2-1-39
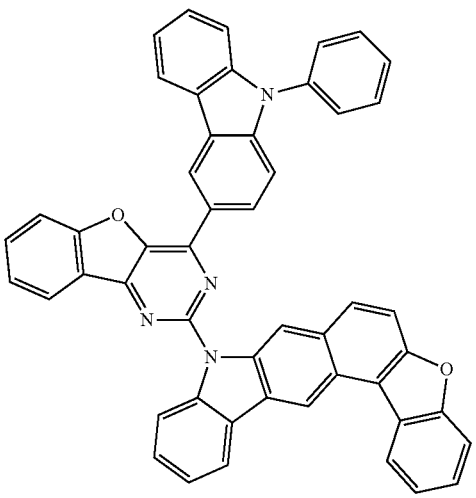

2-1-40
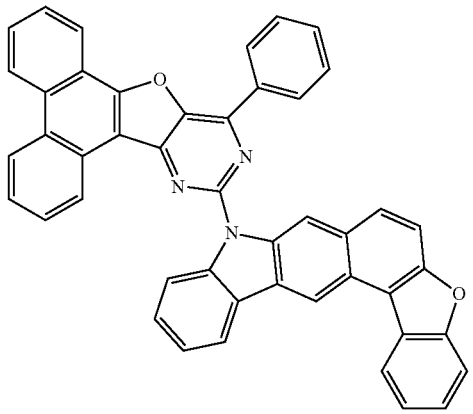
2-1-41
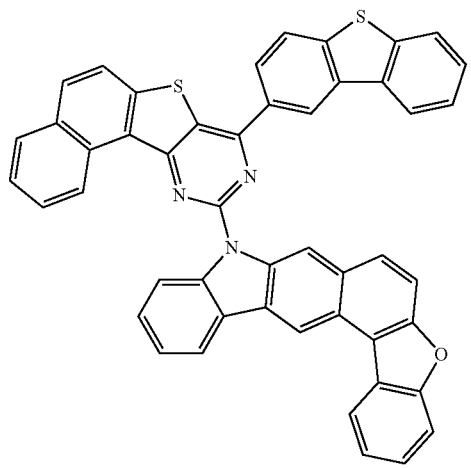
2-1-42
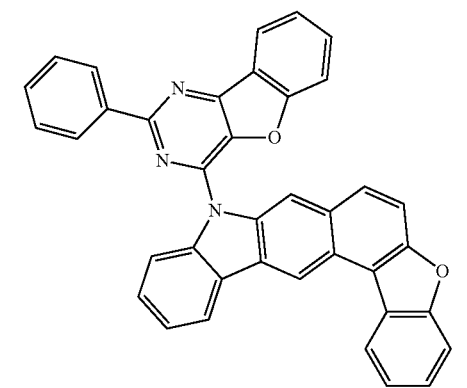
2-1-43
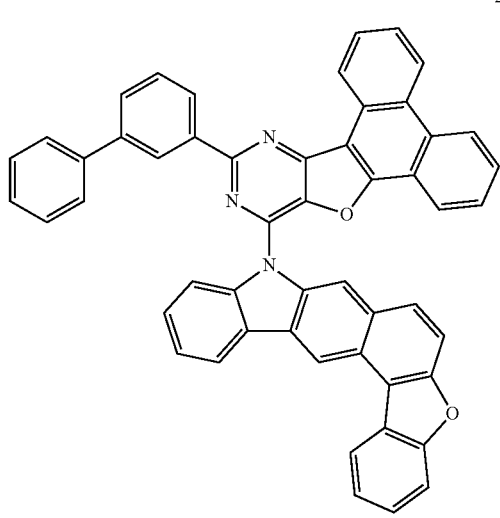
2-1-44
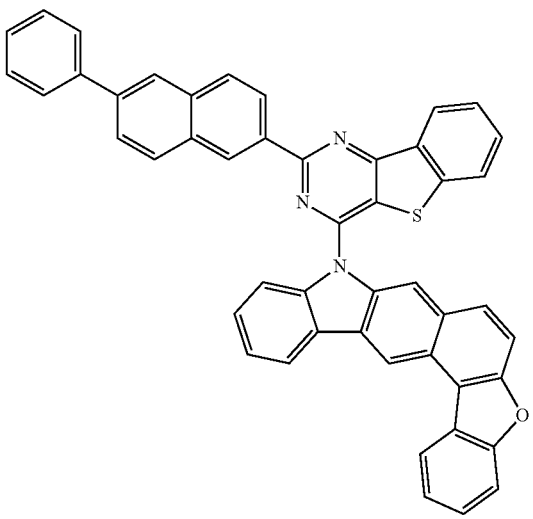
2-1-45
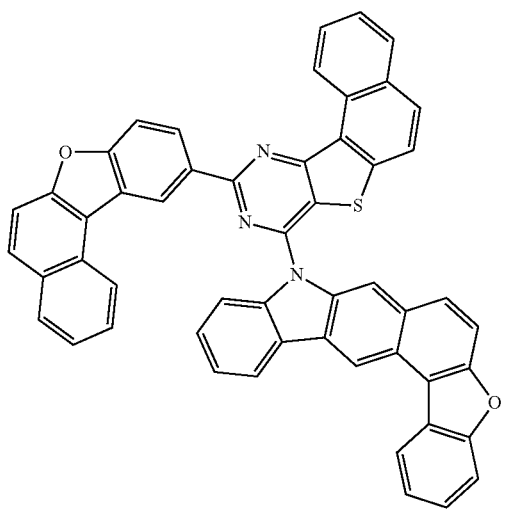

2-1-46
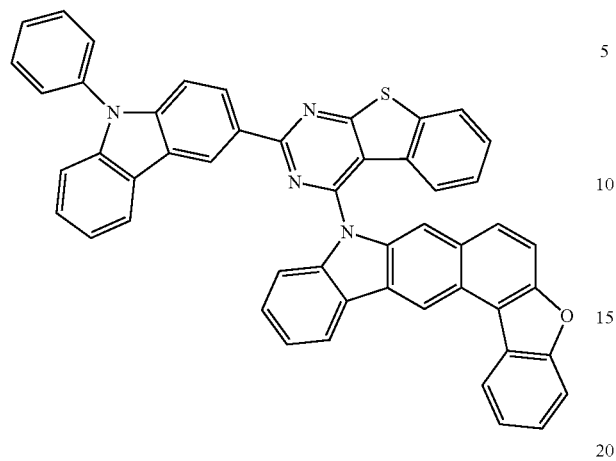
2-1-47
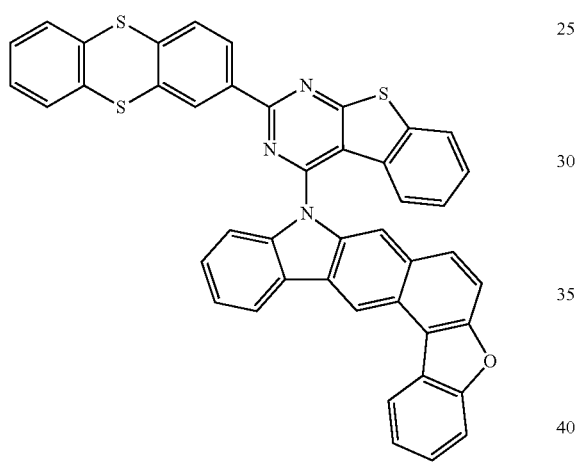
2-1-48
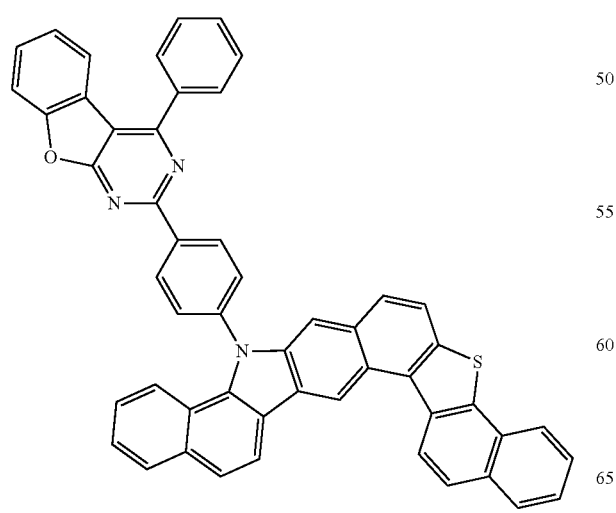
2-1-49
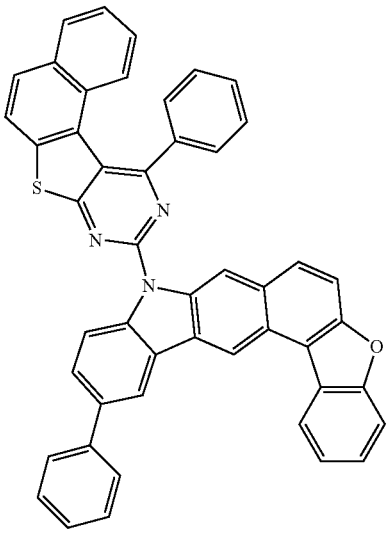
2-1-50
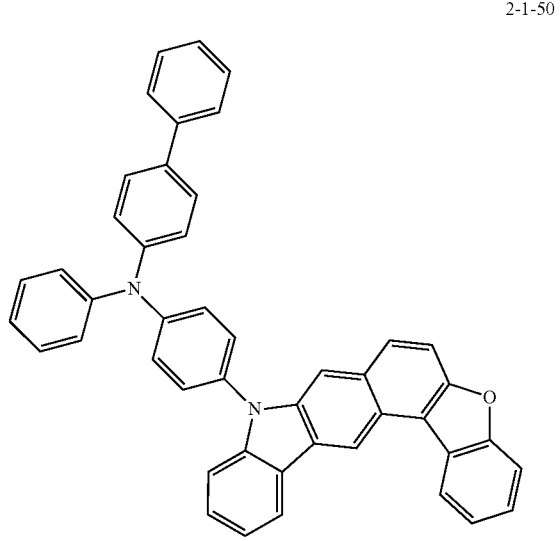
2-2-1
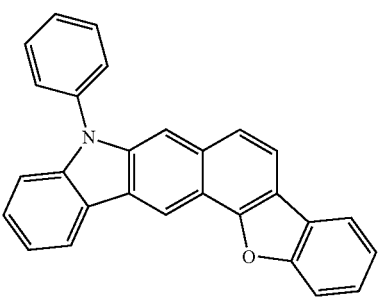

2-2-2
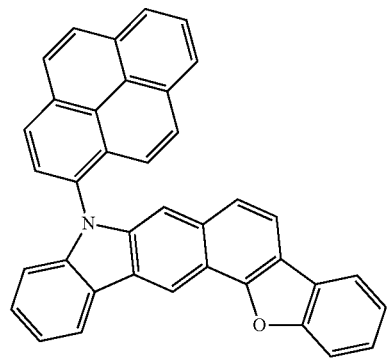
2-2-3
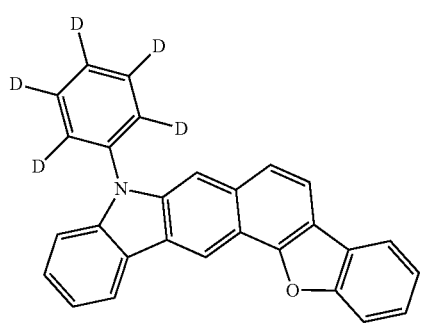
2-2-4
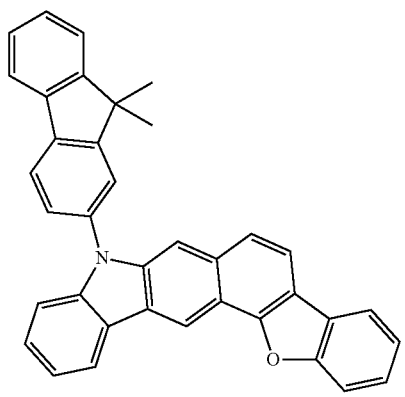
2-2-5
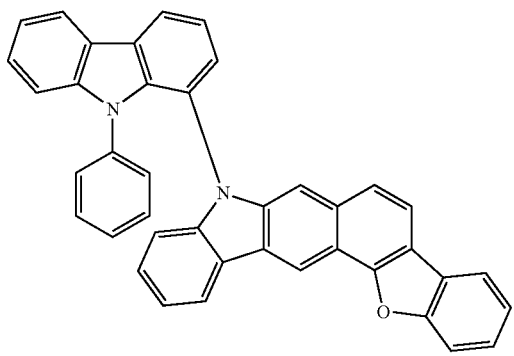
2-2-6
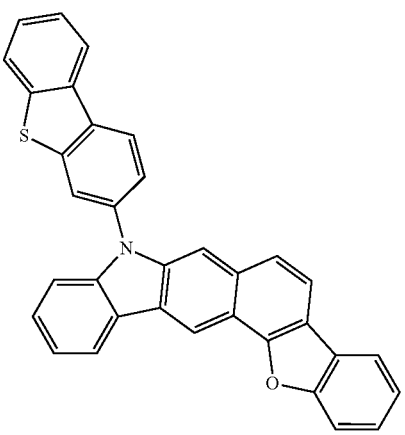
2-2-7
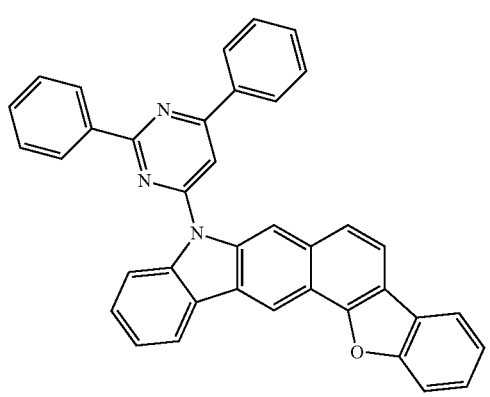
2-2-8
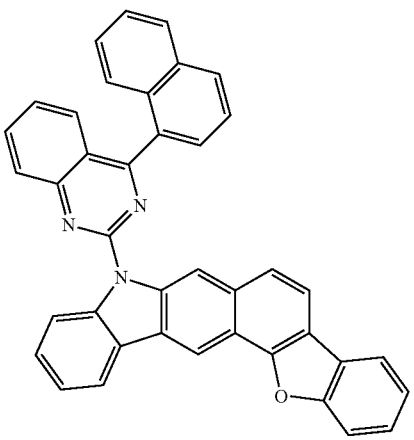
2-2-9
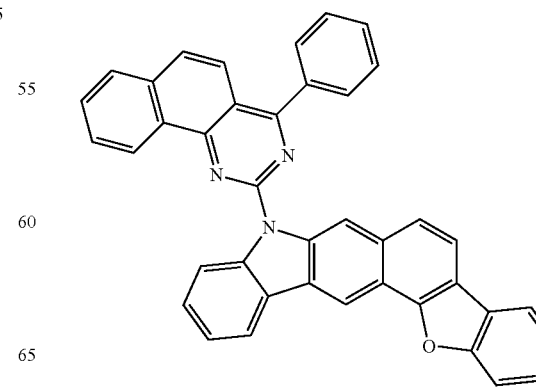

-continued
2-2-10
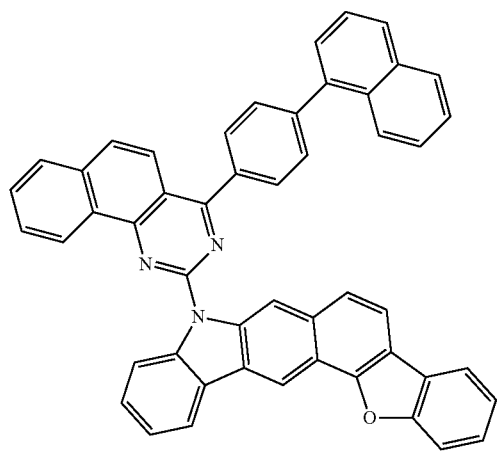
2-2-11
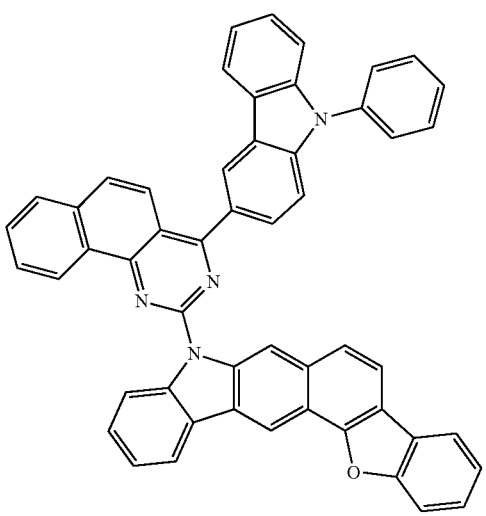
2-2-12
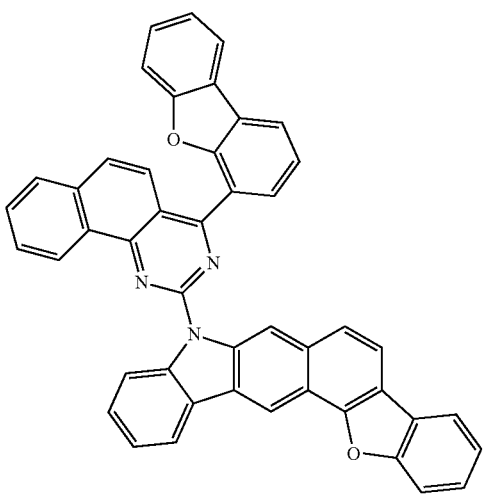
2-2-13
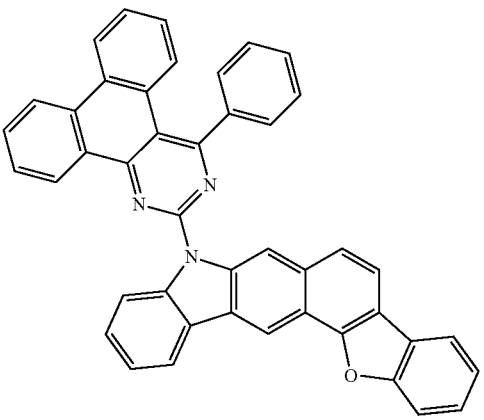
2-2-14
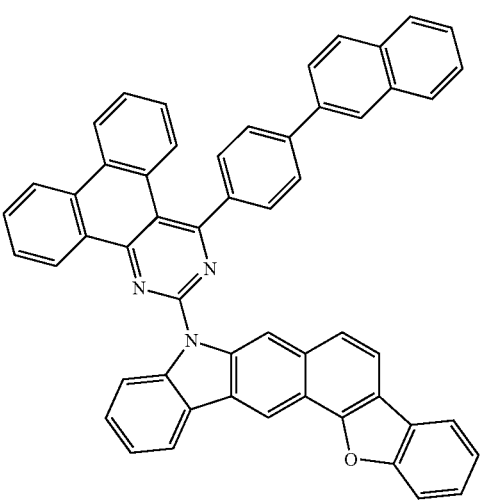
2-2-15
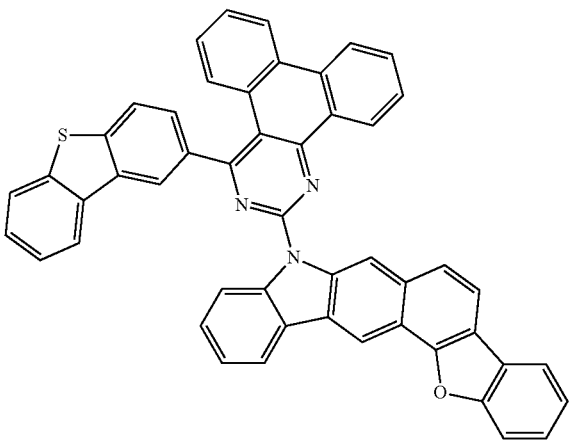

-continued
2-2-16
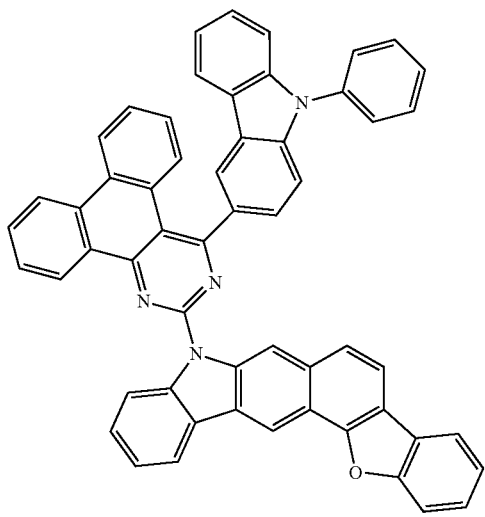
2-2-17
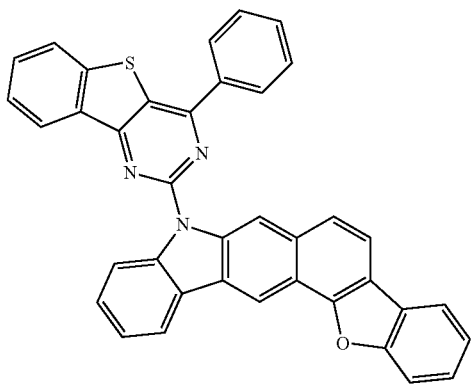
2-2-18
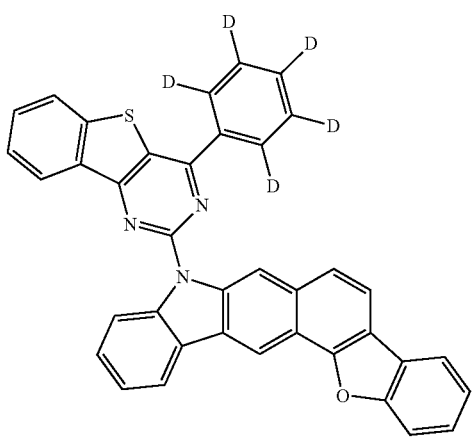
-continued
2-2-19
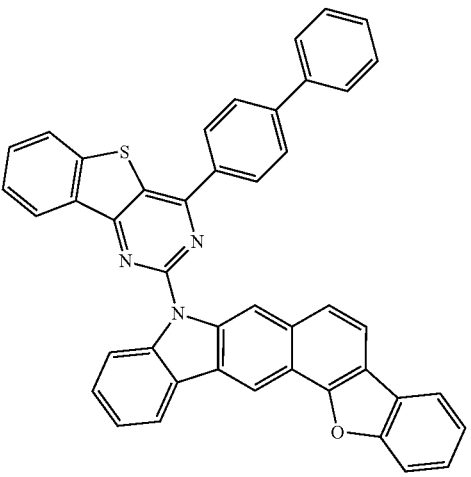
2-2-20
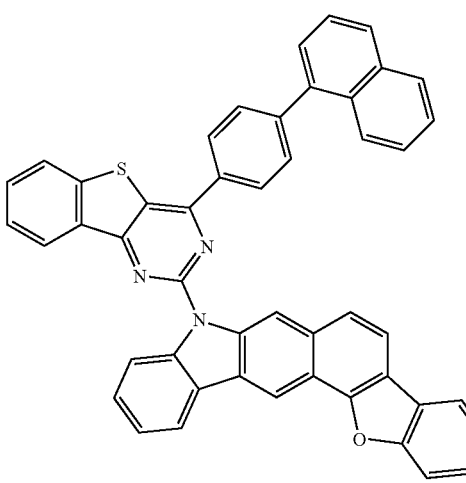
2-2-21
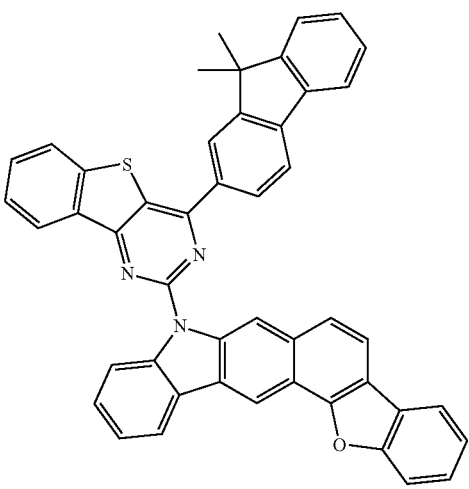

2-2-22
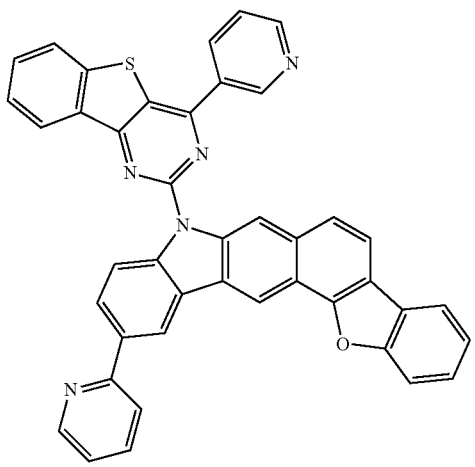
2-2-23
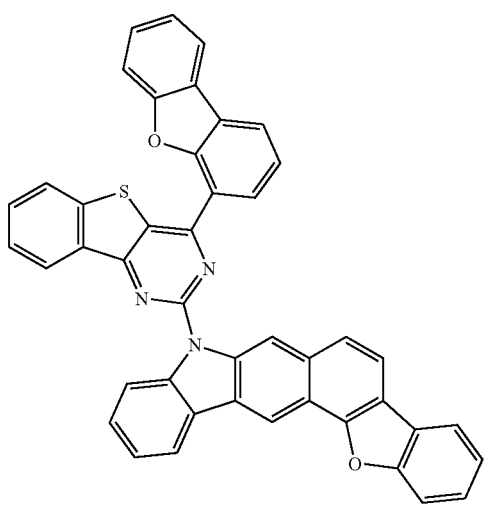
2-2-24
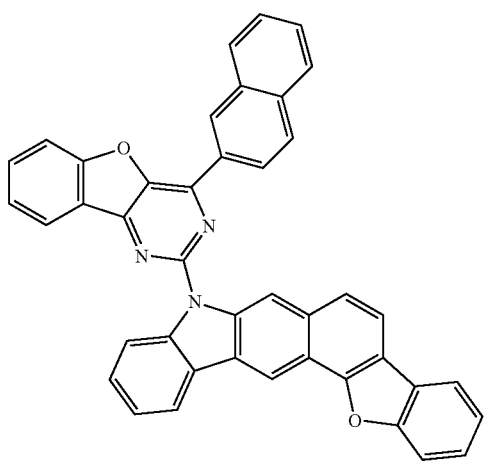
2-2-25
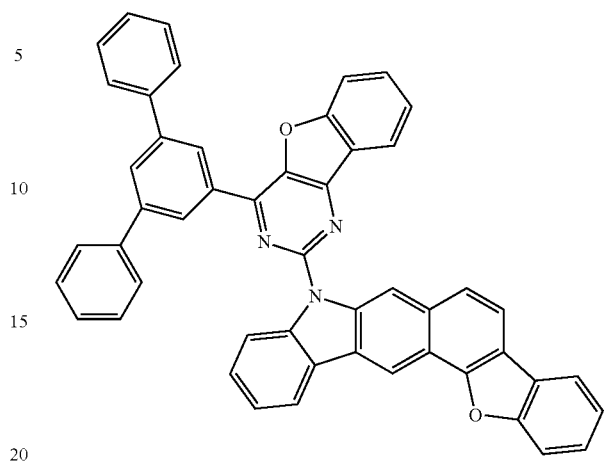
2-2-26
2-2-27
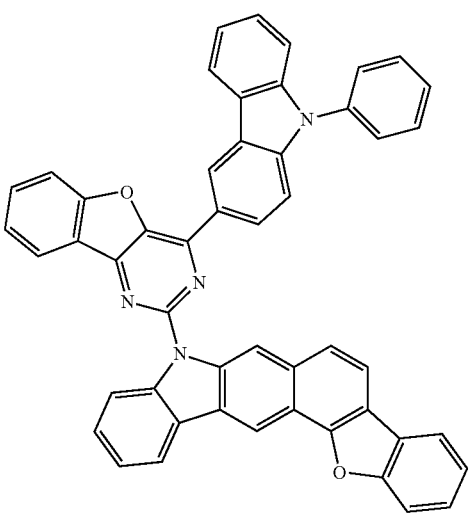

2-2-28
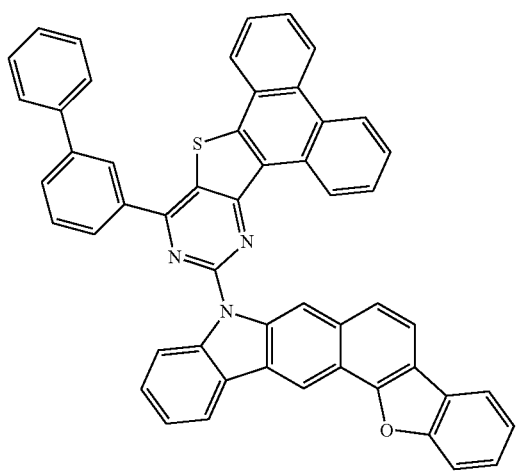
2-2-29
2-2-30
3-1-1
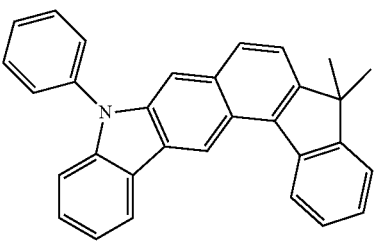
3-1-2
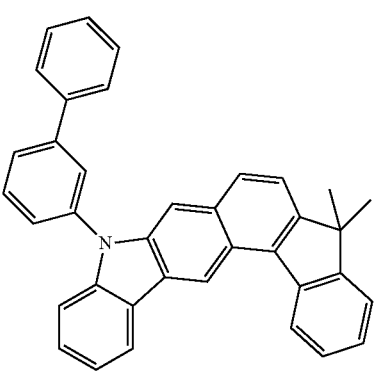
3-1-3
3-1-4
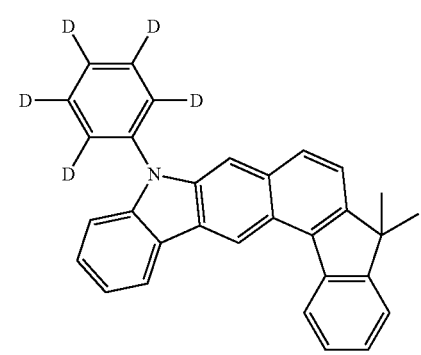

3-1-5
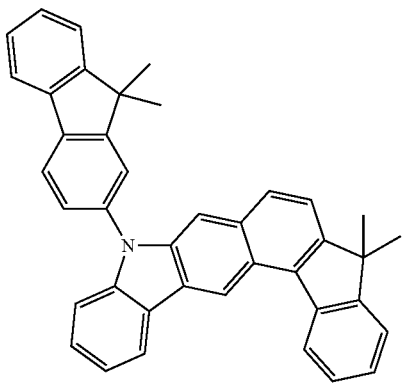
3-1-6
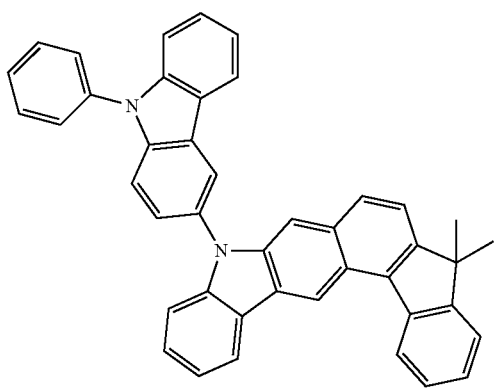
3-1-7
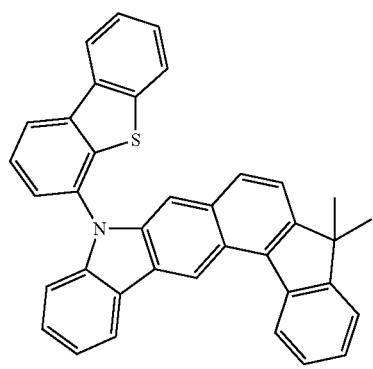
3-1-8
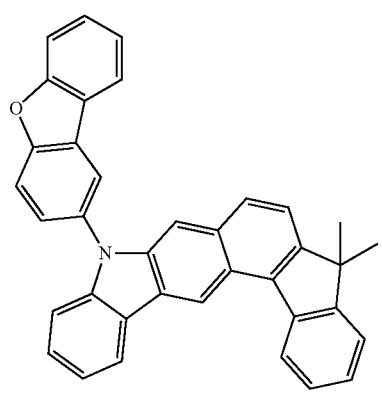
3-1-9
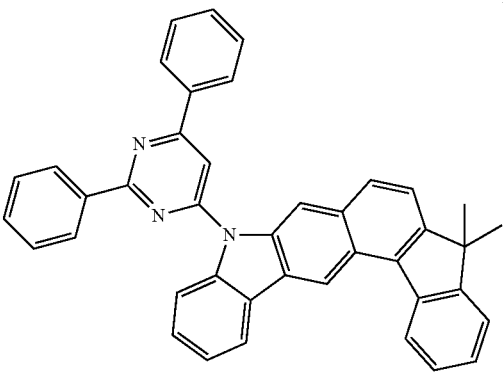
3-1-10
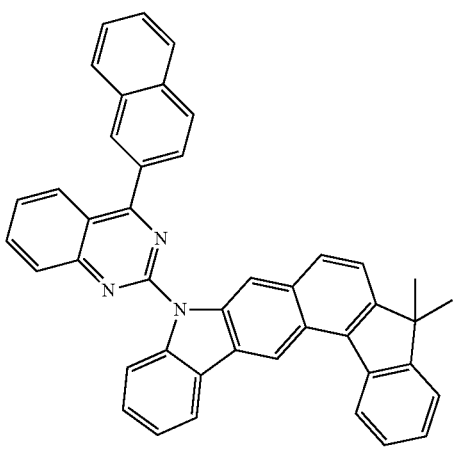
3-1-11
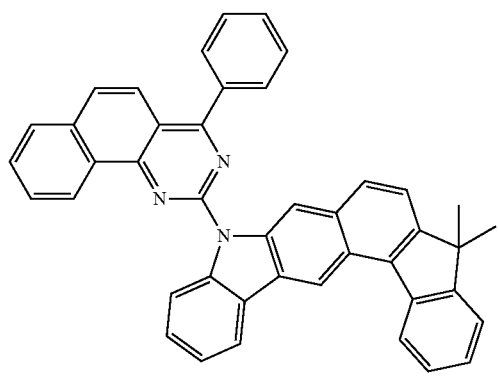
3-1-12
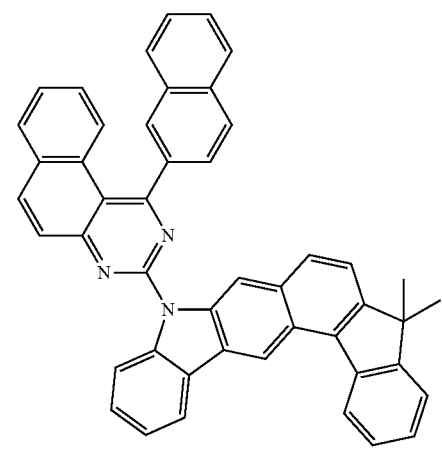

3-1-13
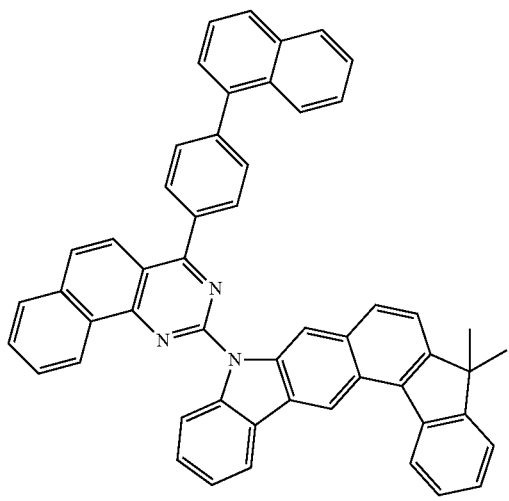
3-1-14
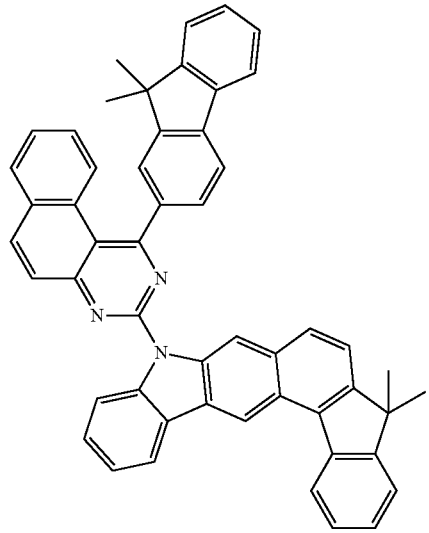
3-1-15
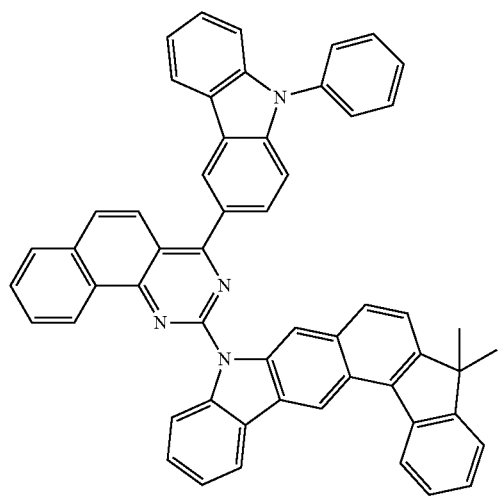
3-1-16
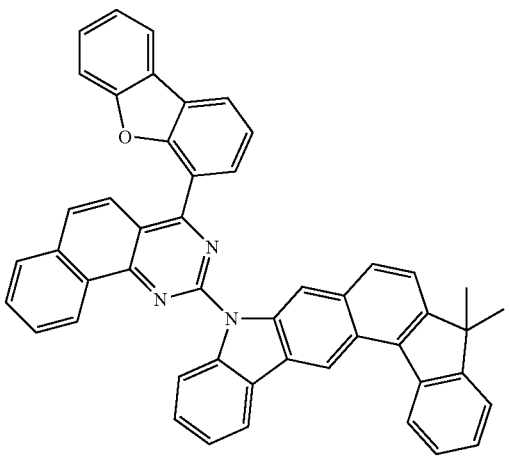
3-1-17
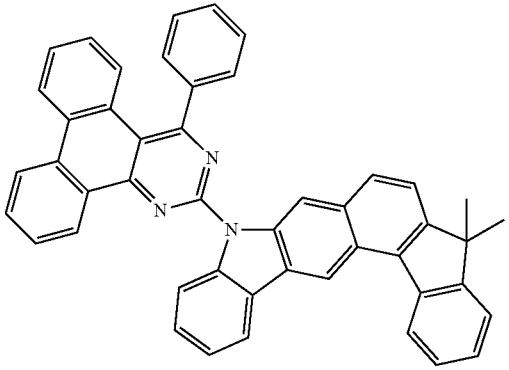
3-1-18
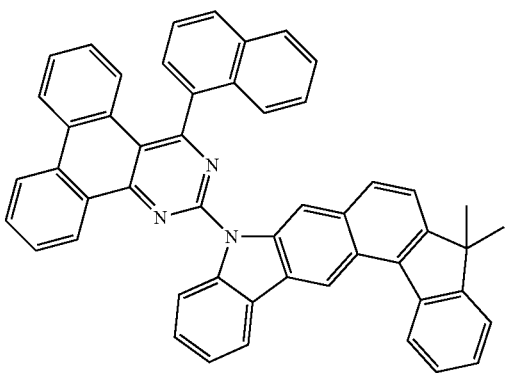

3-1-19
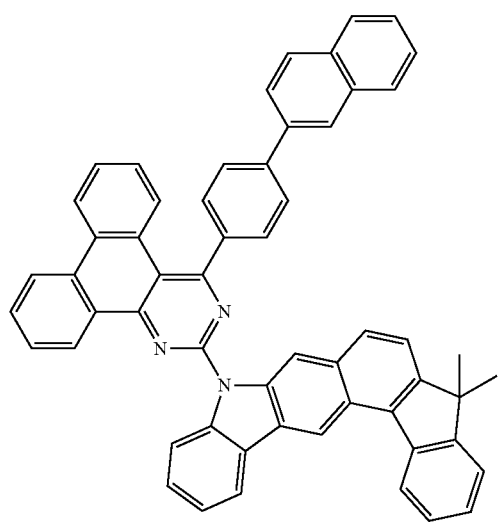
3-1-22
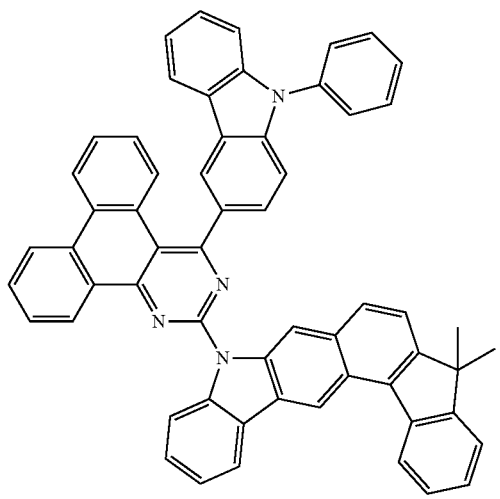
3-1-20
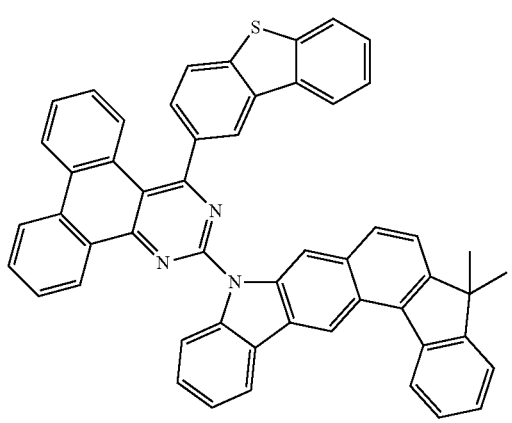
3-1-23
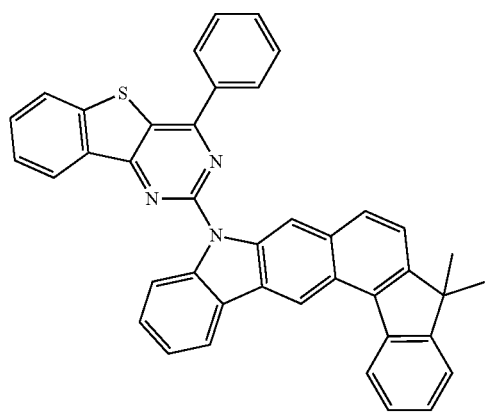
3-1-21
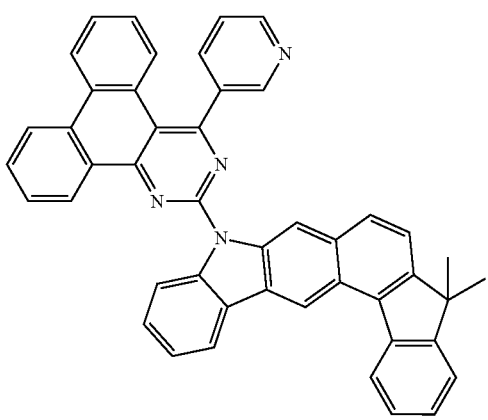
3-1-24
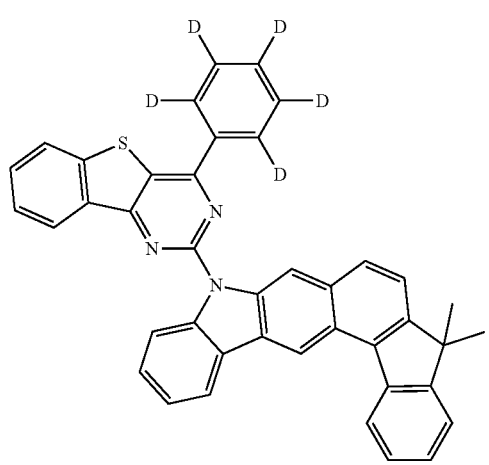

3-1-25
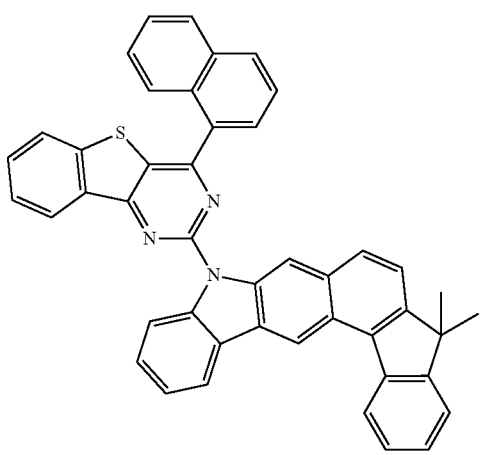
3-1-26
3-1-27
3-1-28
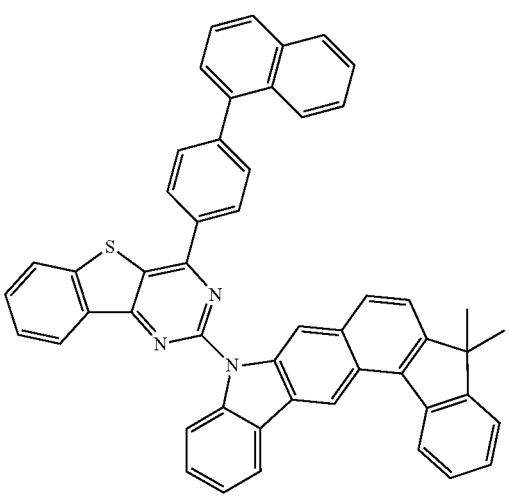
3-1-29
3-1-30

-continued
3-1-31
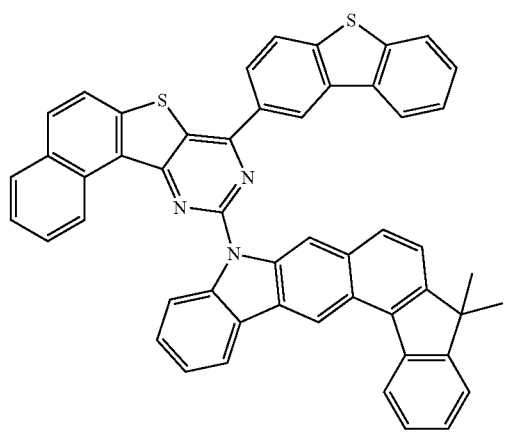
3-1-32
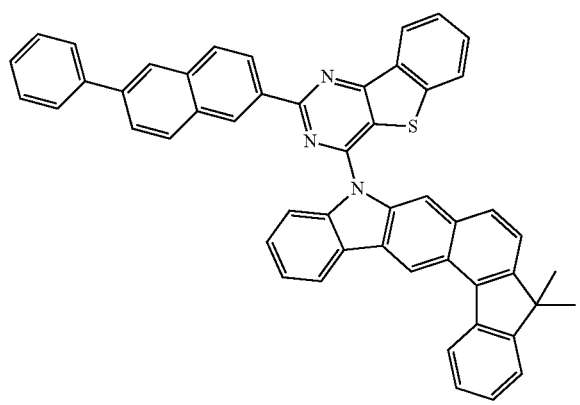
3-1-33
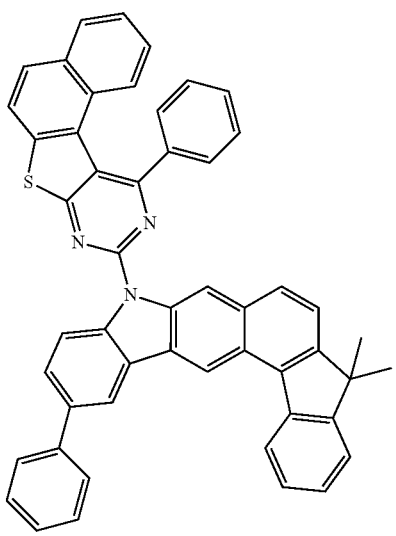
3-1-34
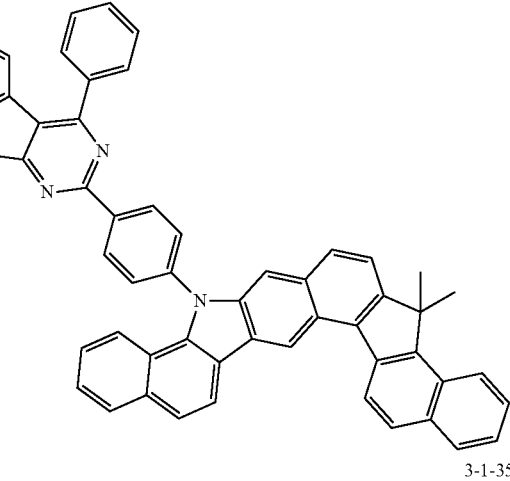
3-1-35
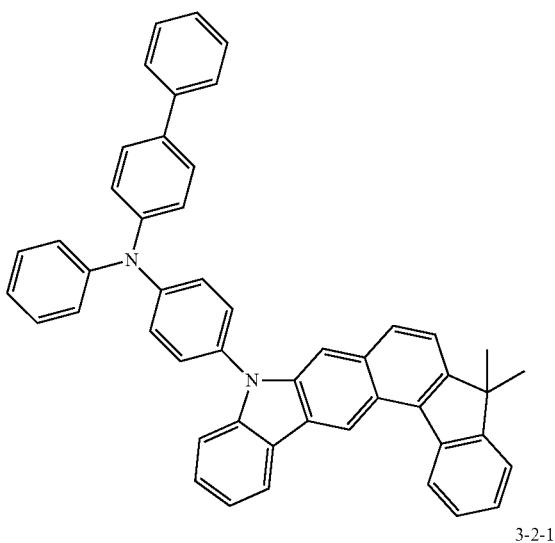
3-2-1
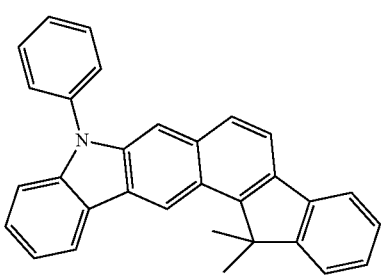
3-2-2
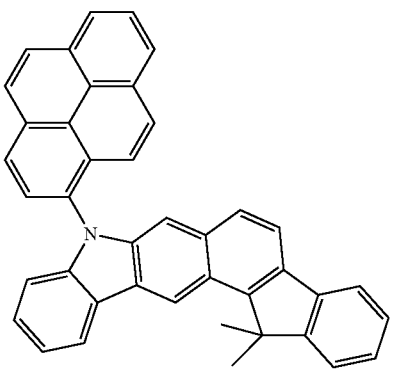

3-2-3
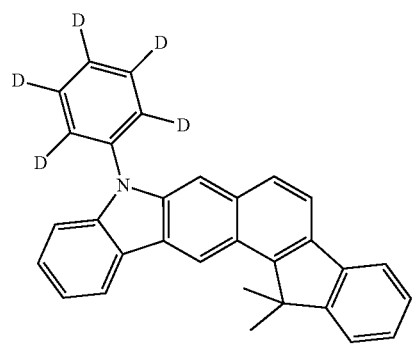
3-2-4
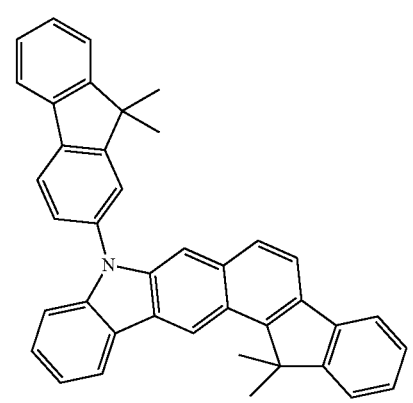
3-2-5
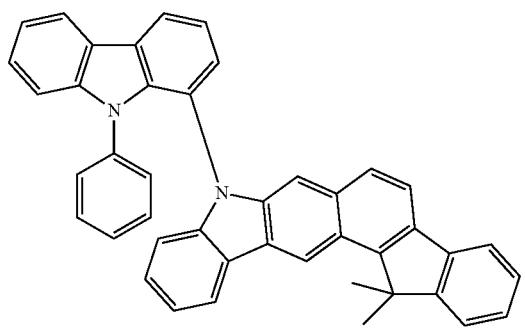
3-2-6
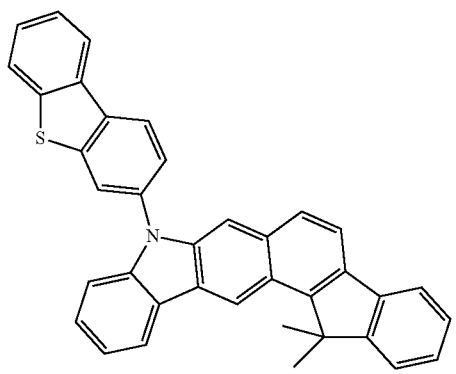
3-2-7
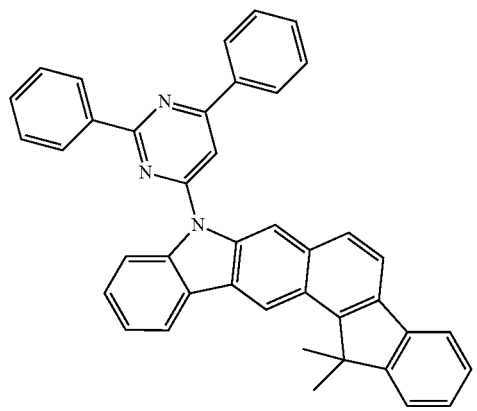
3-2-8
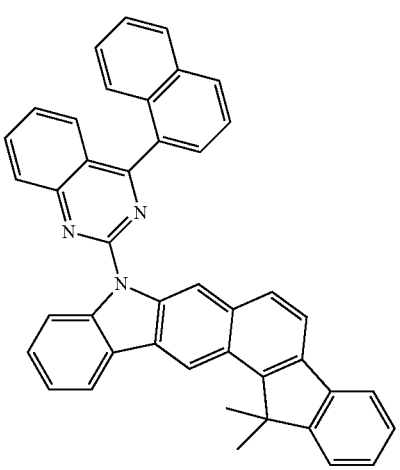
3-2-9
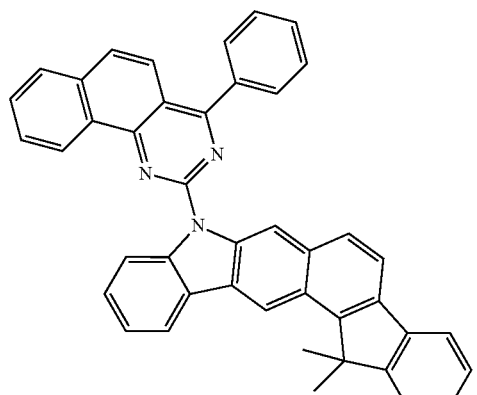

3-2-10
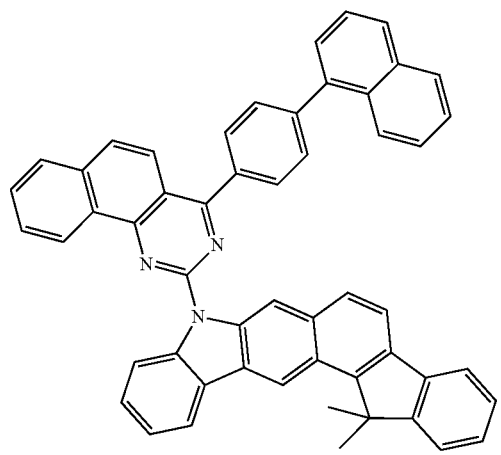
3-2-13
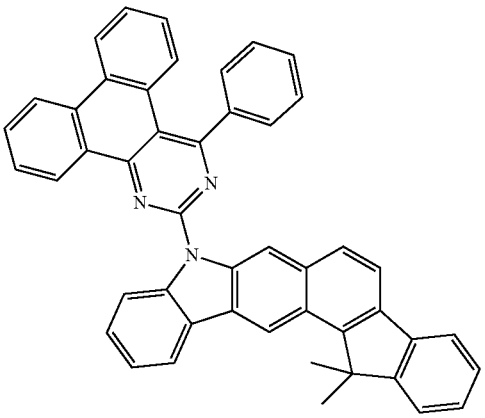
3-2-11
3-2-14
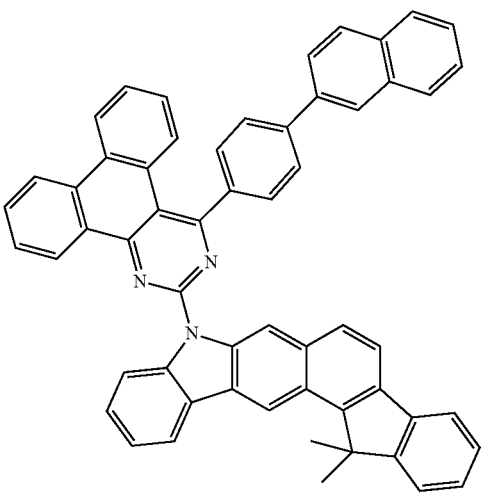
3-2-12
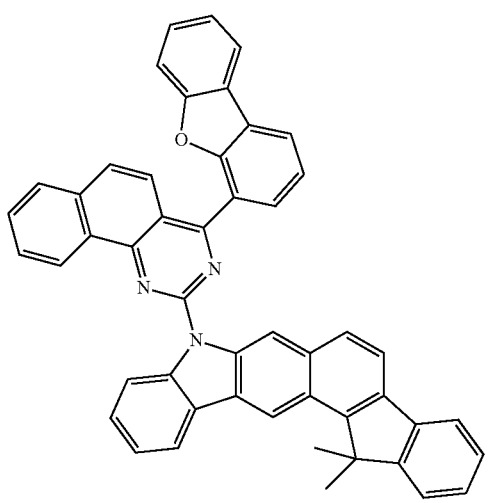
3-2-15
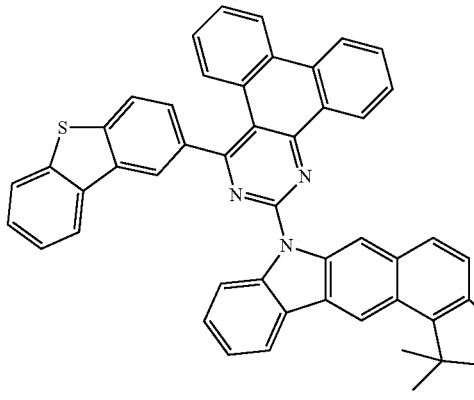

3-2-16
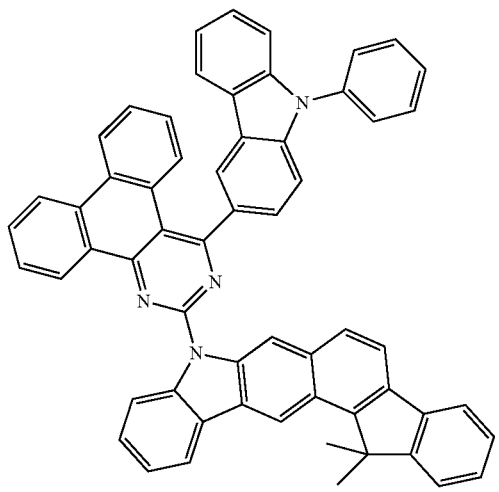
3-2-17
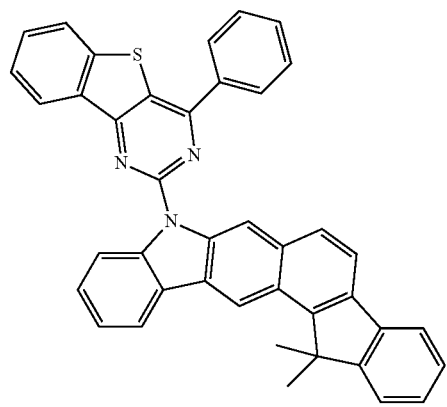
3-2-18
3-2-19
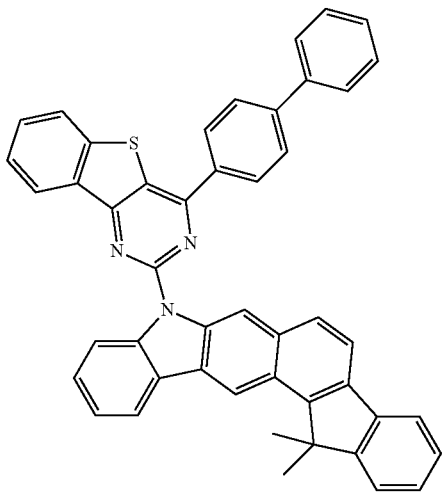
3-2-20
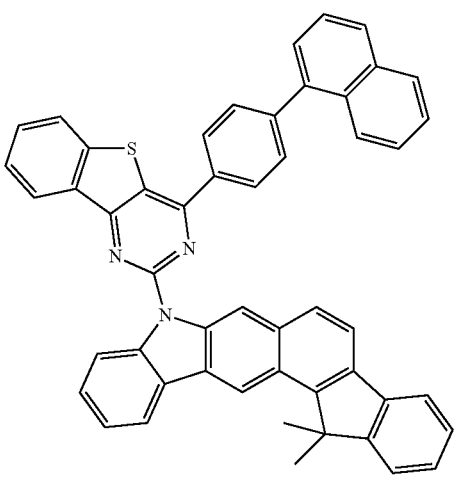
3-2-21
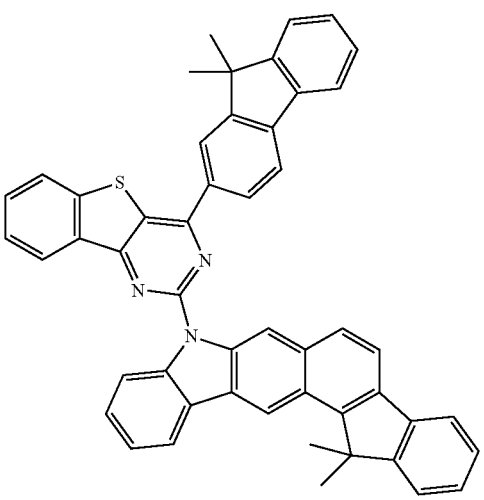

89
-continued
3-2-22
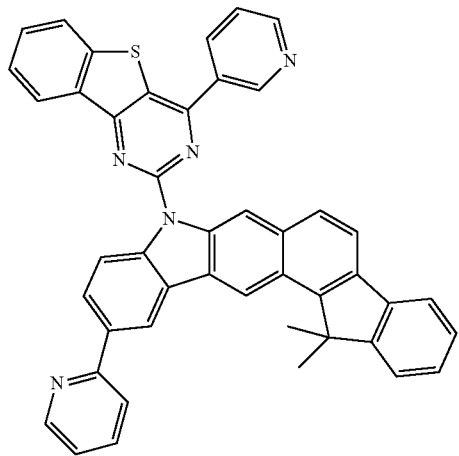
3-2-23
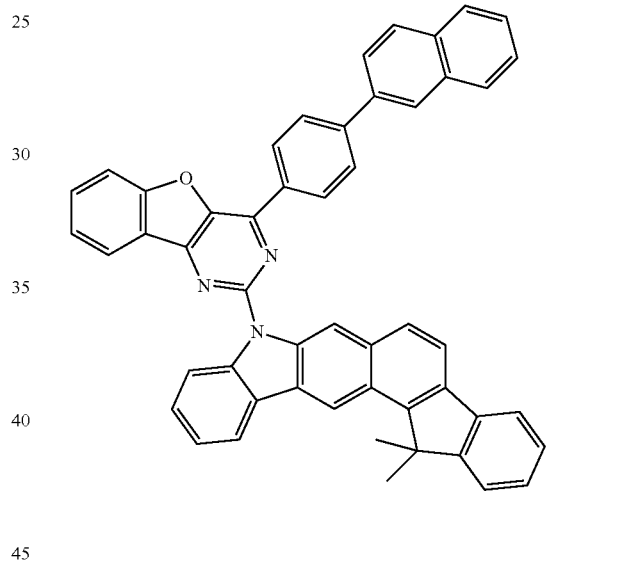
3-2-24
90
-continued
3-2-25
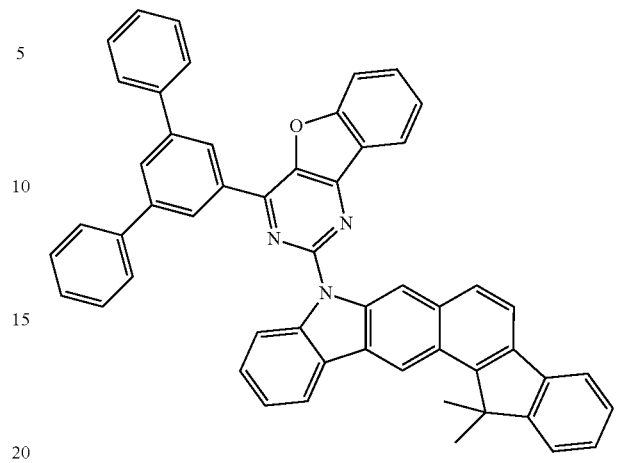
3-2-26
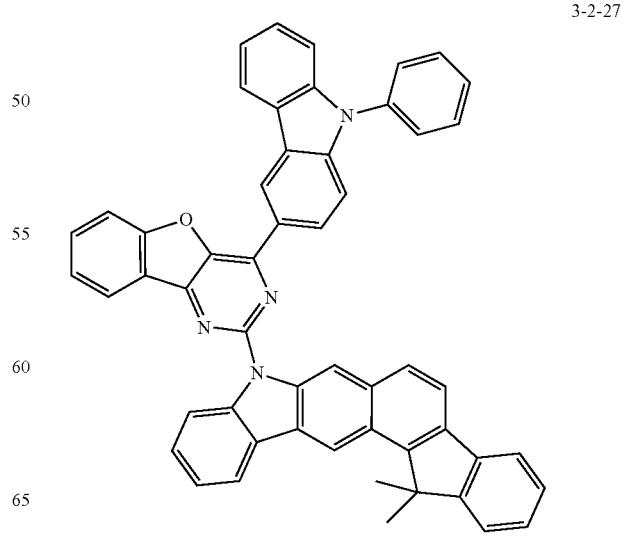
3-2-27

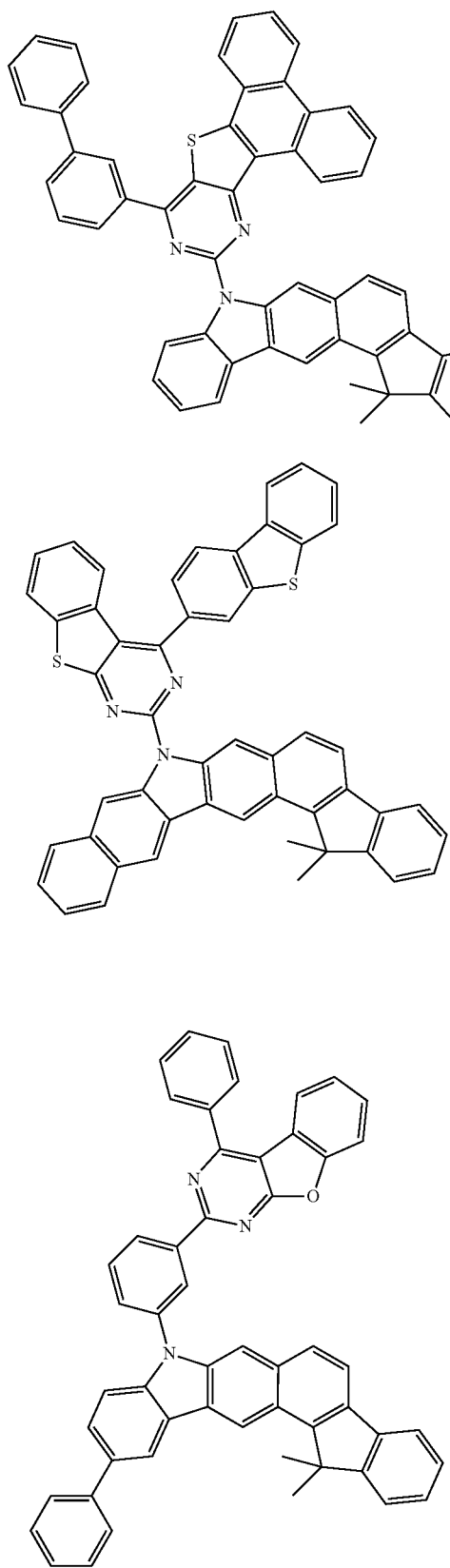
3-2-28
3-2-29
3-2-30
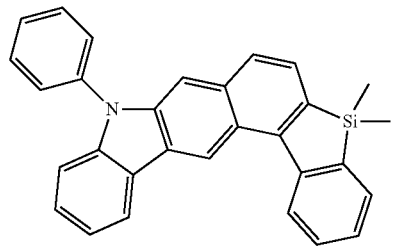
4-1-1
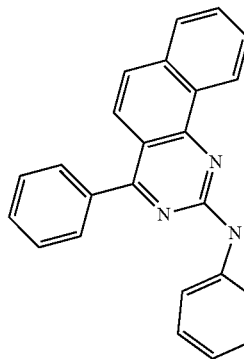
4-1-2
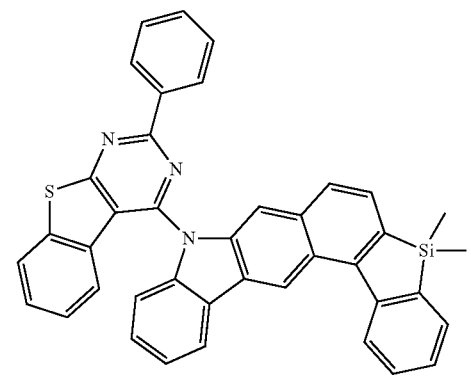
4-1-3
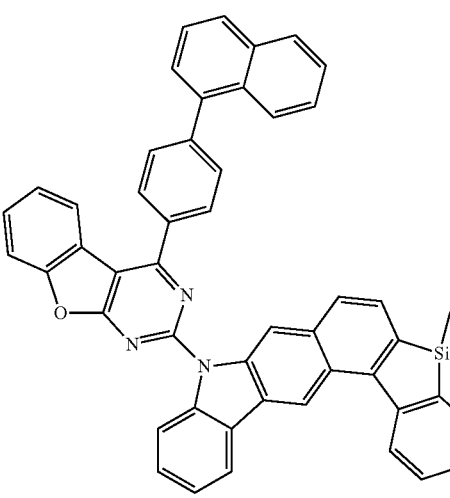
4-1-4

4-1-5
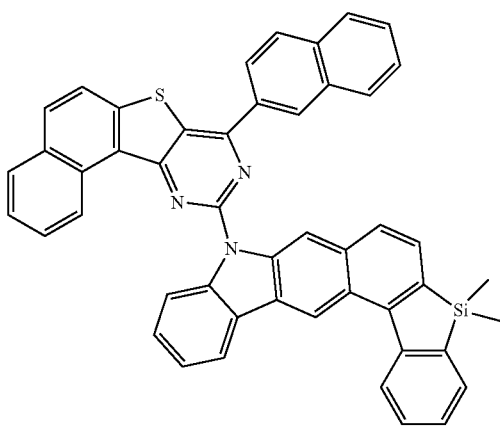
4-2-1
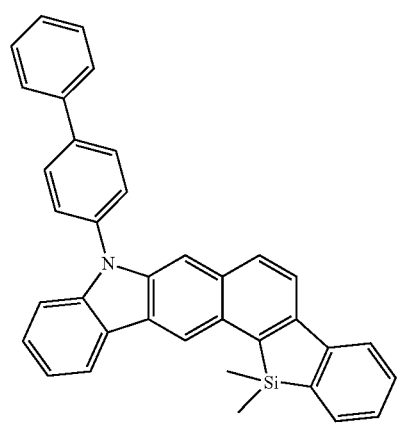
4-2-2
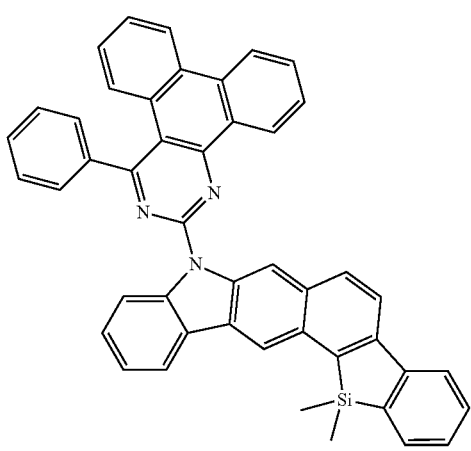
4-2-3
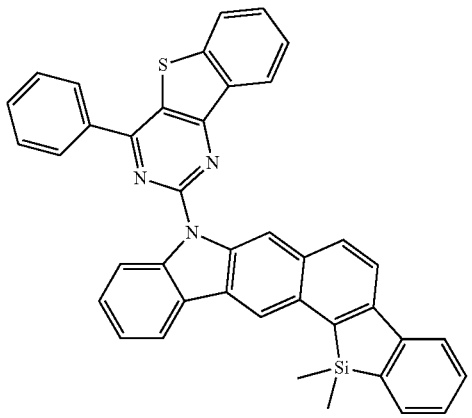
4-2-4
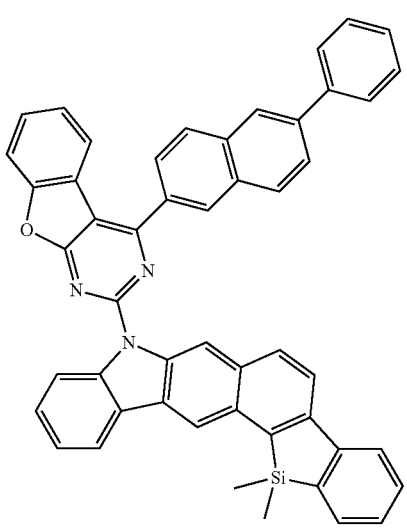
4-2-5
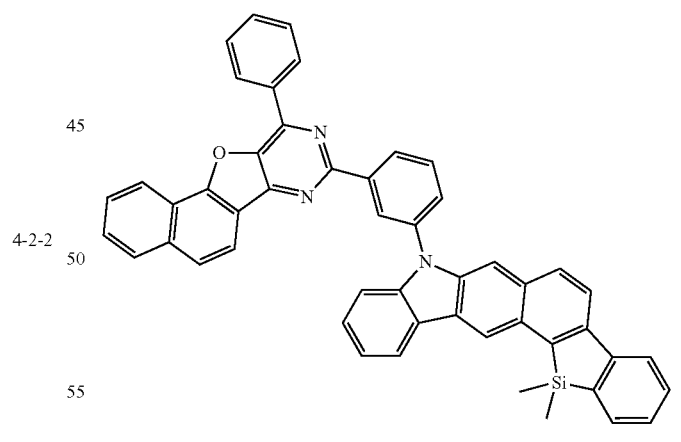
5-1-1
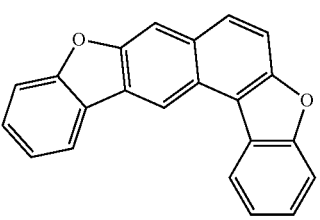

5-1-2 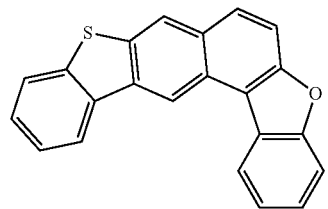
5-1-3 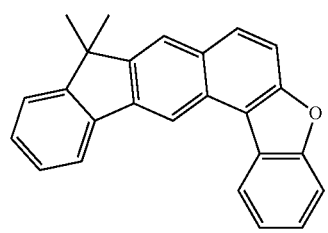
5-1-4 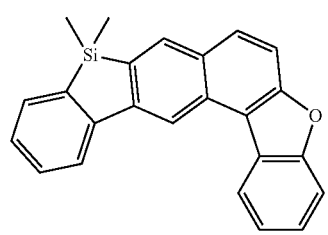
5-1-5 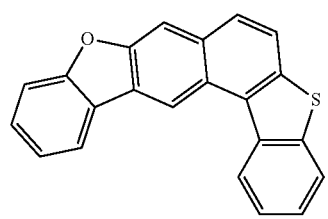
5-1-6 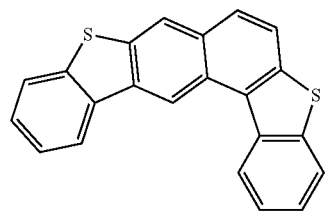
5-1-7 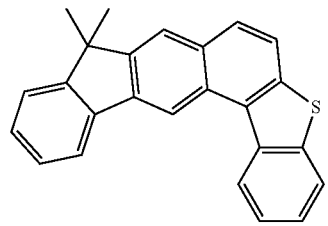
5-1-8 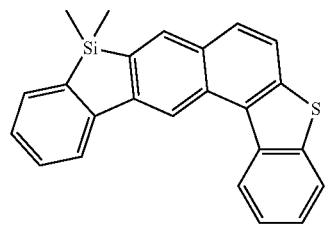
5-1-9 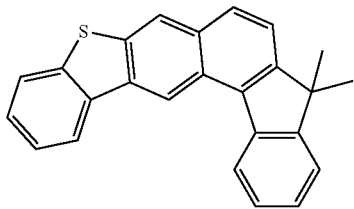
5-1-10 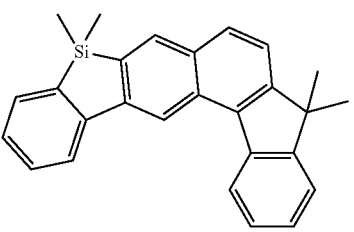
5-1-11 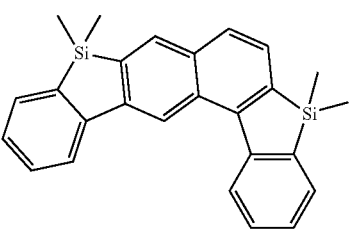
5-1-12 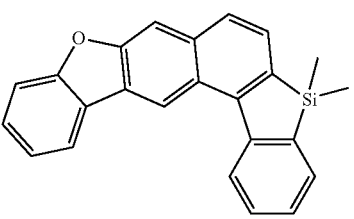
5-1-13 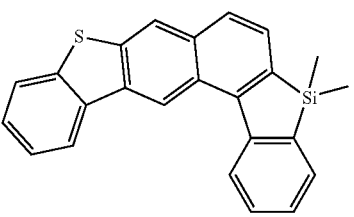
5-1-14 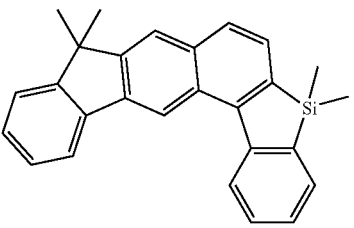
5-1-15 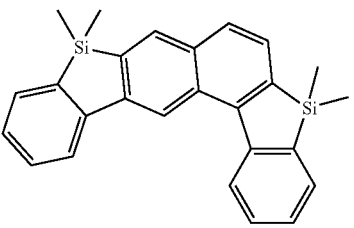

5-1-16
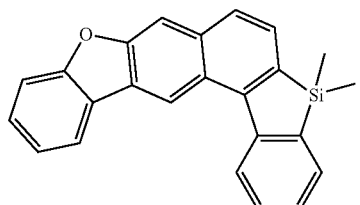
5-1-17
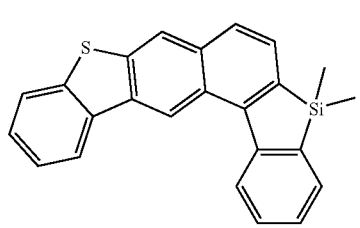
5-1-18
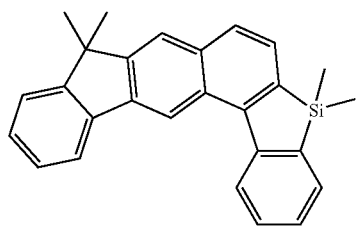
5-2-1
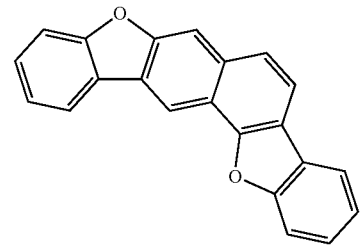
5-2-2
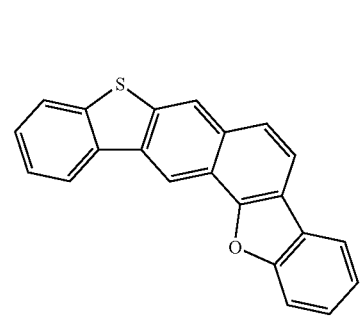
5-2-3
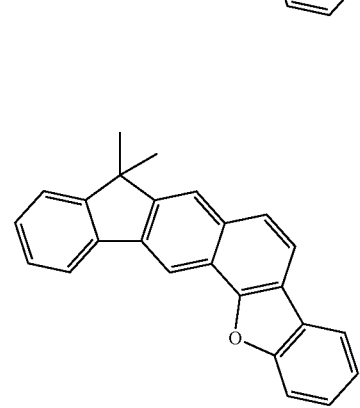
5-2-4
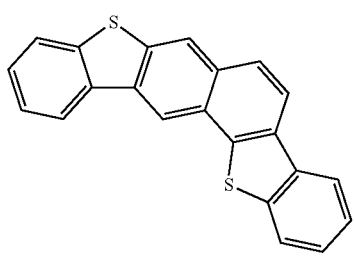
5-2-5
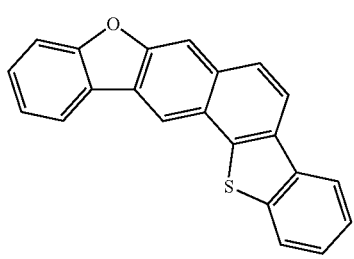
5-2-6
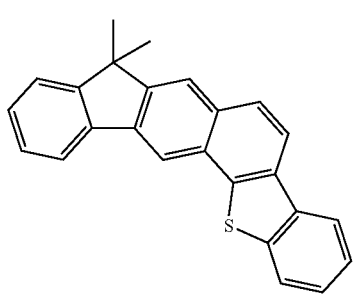
5-2-7
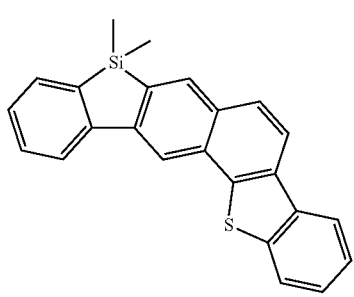
5-2-8
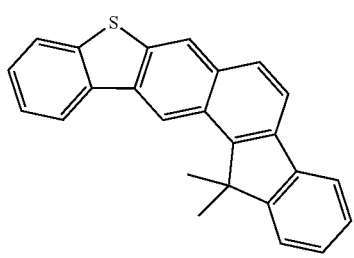
5-2-9
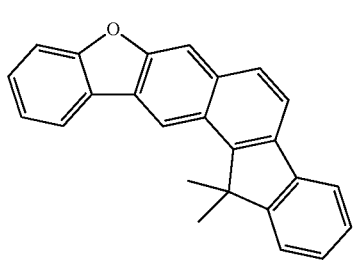

-continued
5-2-10
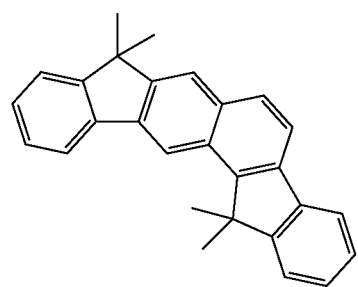
5-2-11
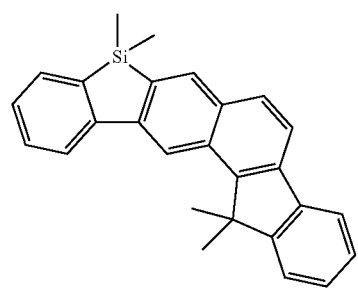
5-2-12
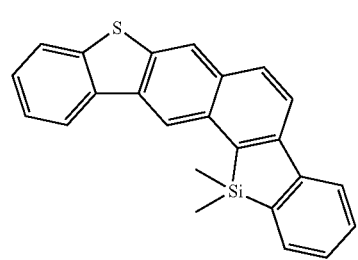
5-2-13
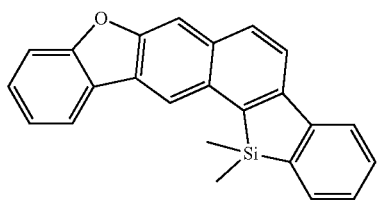
5-2-14
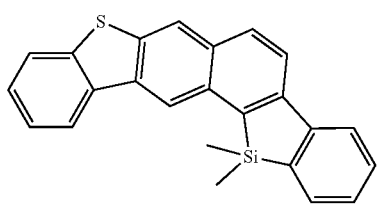
5-2-15
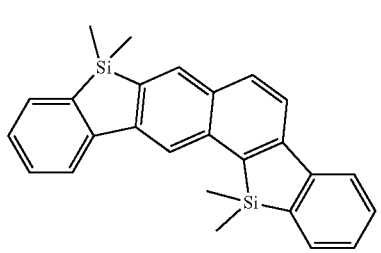
-continued
6-1-1
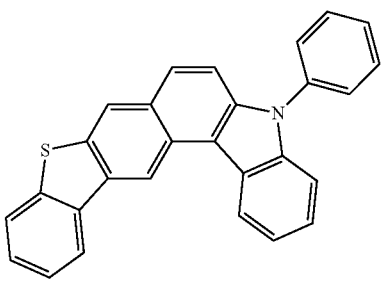
6-1-2
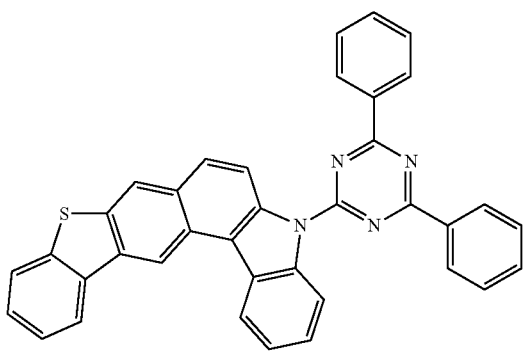
6-1-3
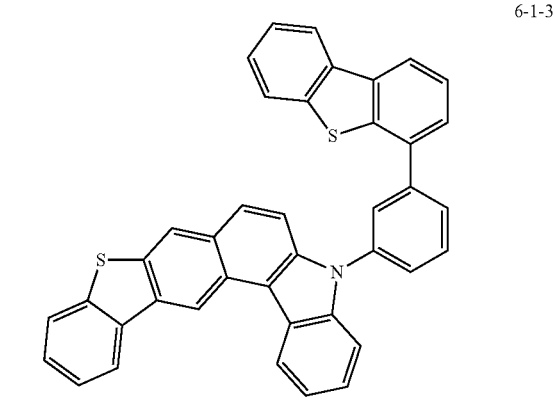
6-1-4
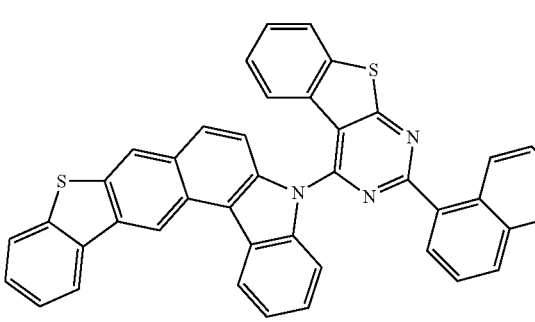

101
-continued
6-1-5
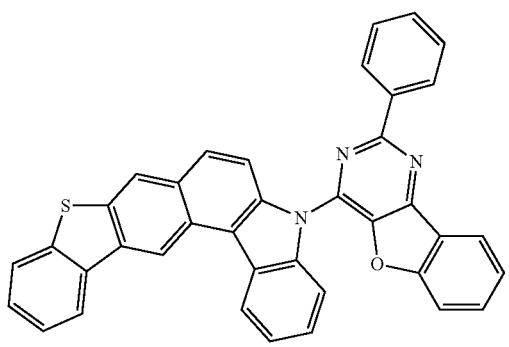
6-2-1
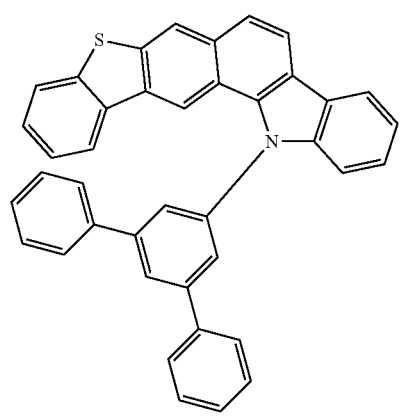
6-2-2
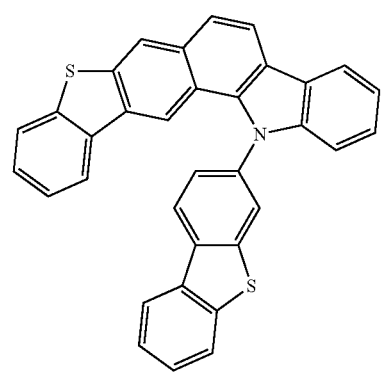
6-2-3
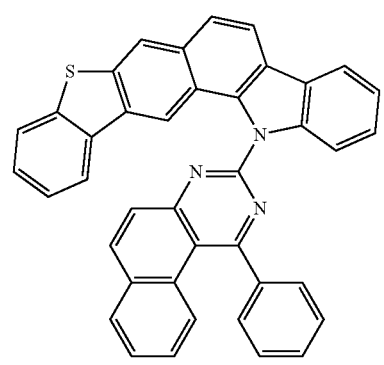
102
-continued
6-2-4
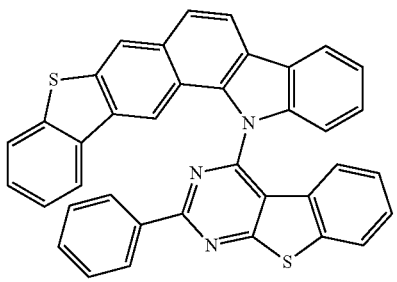
6-2-5
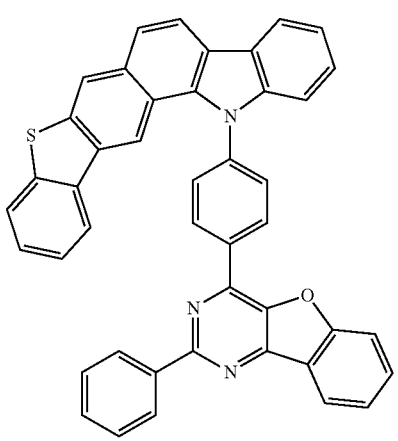
7-1-1
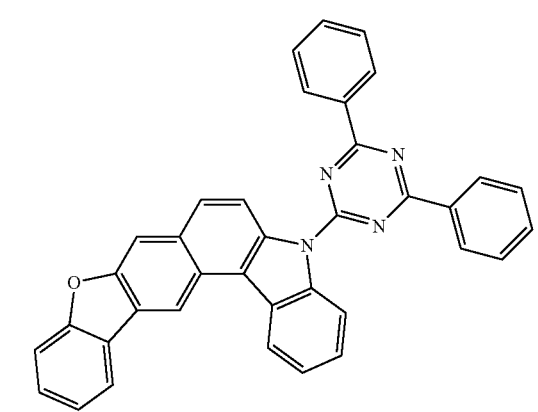
7-1-2
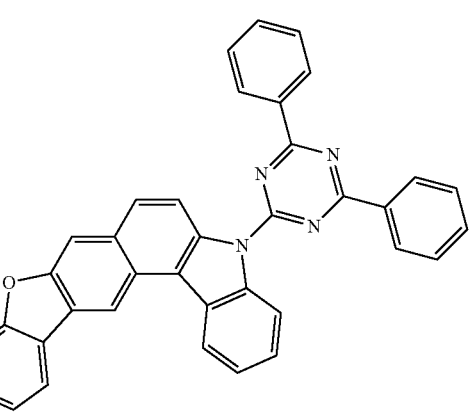

7-1-3
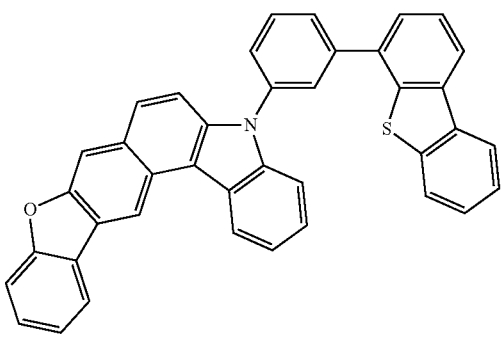
7-1-4
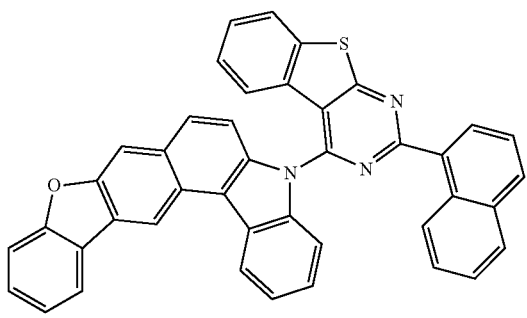
7-1-5
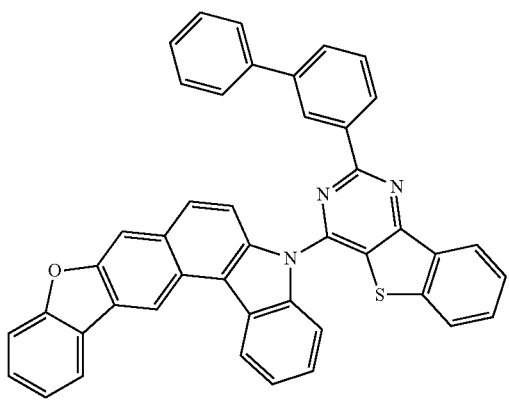
7-2-1
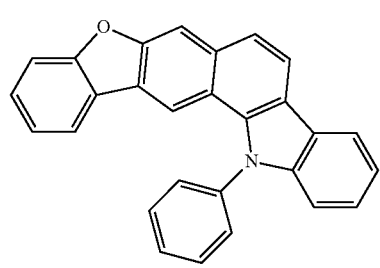
7-2-2
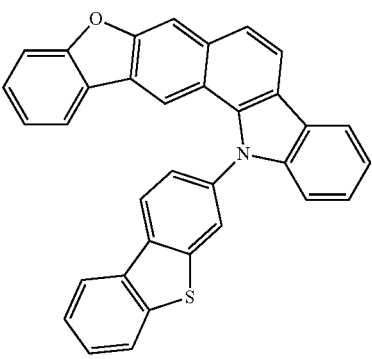
7-2-3
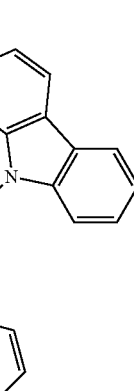
7-2-4
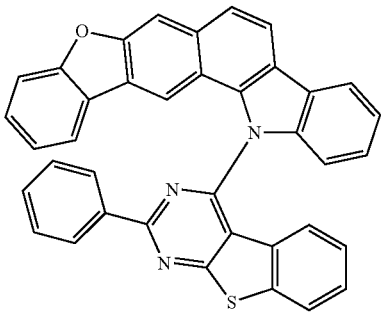
7-2-5
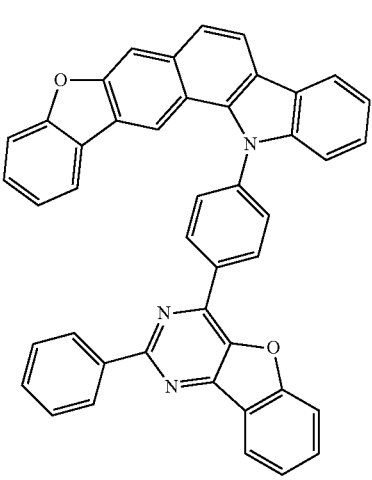

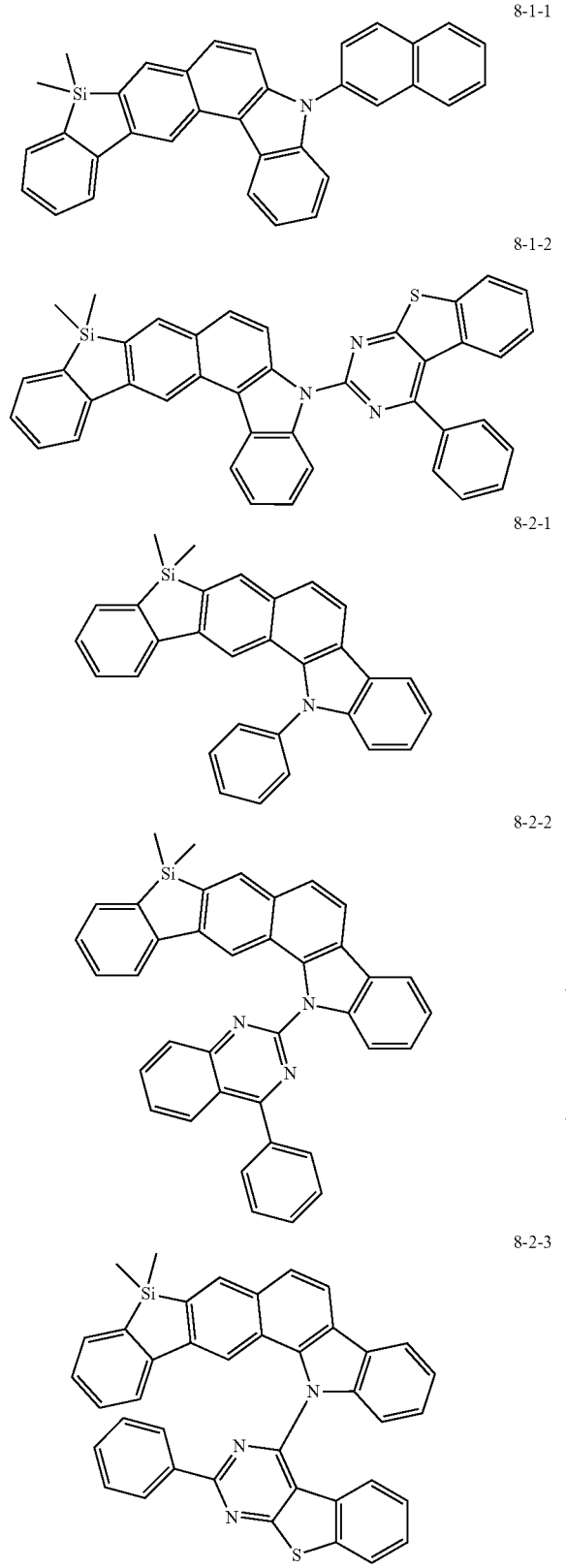

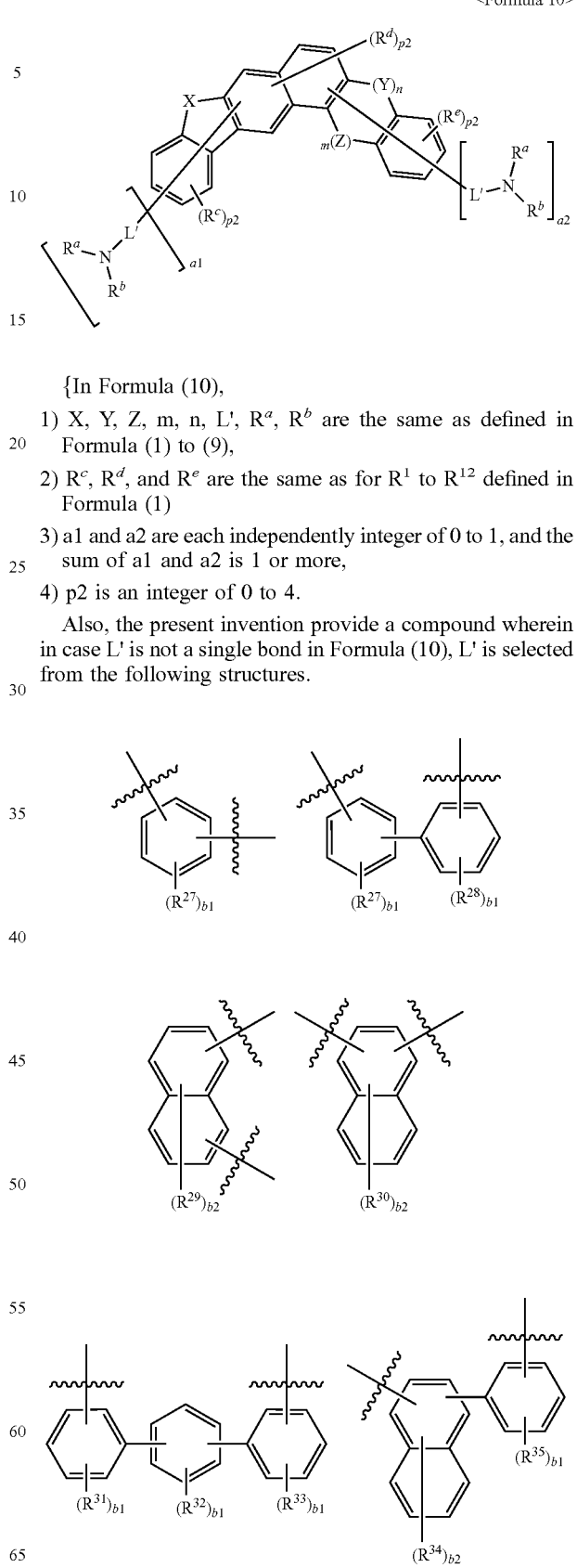

{In Formula (10),
1) X, Y, Z, m, n, L', $R^a$, $R^b$ are the same as defined in Formula (1) to (9),
2) $R^c$, $R^d$, and $R^e$ are the same as for $R^1$ to $R^{12}$ defined in Formula (1)
3) a1 and a2 are each independently integer of 0 to 1, and the sum of a1 and a2 is 1 or more,
4) p2 is an integer of 0 to 4.

Also, the present invention provide a compound wherein in case L' is not a single bond in Formula (10), L' is selected from the following structures.

Also, the compound represented by Formula (1) includes a compound represented by Formula (10) and the present invention provides a compound contained therein.

107

-continued

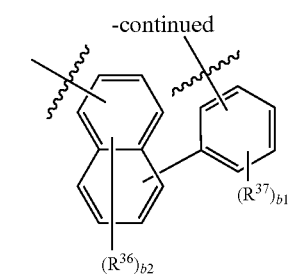

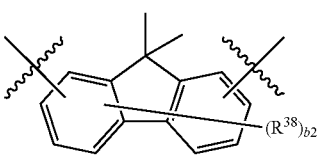

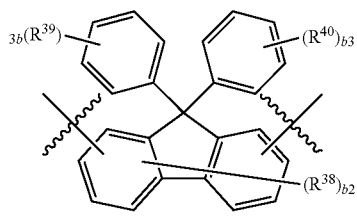

108

-continued

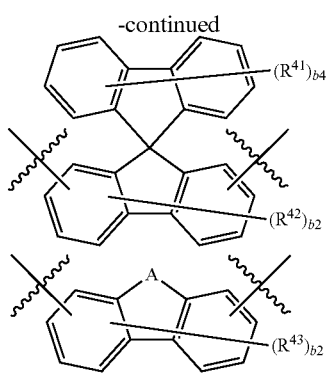

{In the above formula representing L',
1) A represents $NAr^2$, O, S, $CR^{23}R^{24}$ or $SiR^{25}R^{26}$
2) $Ar^2$ is selected from a $C_6$-$C_{60}$ aryl group; a fluorenyl group; a fused ring group of a $C_3$-$C_{60}$ aliphatic ring and a $C_6$-$C_{60}$ aromatic ring; a $C_2$-$C_{60}$ heterocyclic group including at least one heteroatom of O, N, S, Si or P; and -L'-N($R^a$)($R^b$);
3) $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, and $R^{43}$ are each independently selected from a $C_6$-$C_{60}$ aryl group; a $C_2$-$C_{60}$ heterocyclic group including at least one heteroatom of O, N, S, Si or P; a fluorenyl group; a $C_1$-$C_{50}$ alkyl group; and -L'-N($R^a$)($R^b$); or a plurality of $R^{27}$ to $R^{43}$ may be bonded to each other to form a ring, and a plurality of $R^{23}$, $R^{24}$, and $R^{25}$ may be bonded to each other to form a spiro compound with C or Si to which they are bonded
4) b1 is an integer of 0 to 4, b2 is an integer of 0 to 6, b3 is an integer of 0 to 5, b4 is an integer of 0 to 8.}

Accordingly, the present invention provides the compounds represented by the following Formulas A 1-1-1 to A 6-2-7.

A 1-1-1

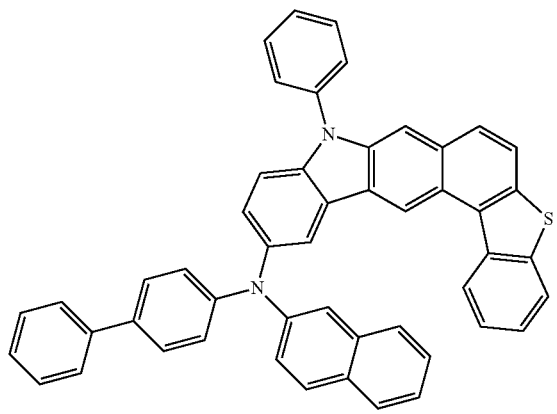

A 1-1-2

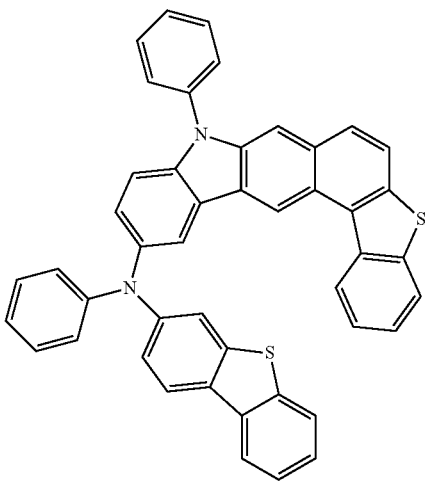

-continued
A 1-1-3
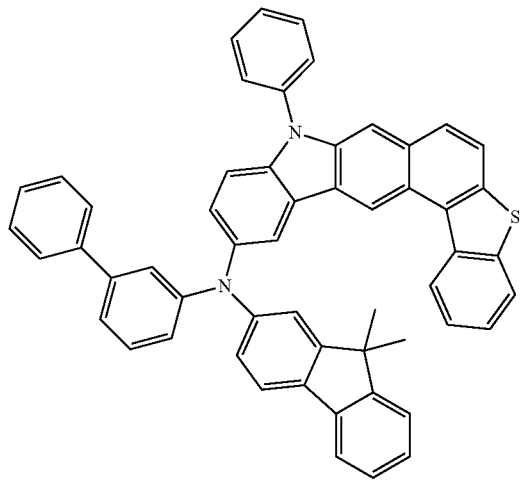
A-1-1-4
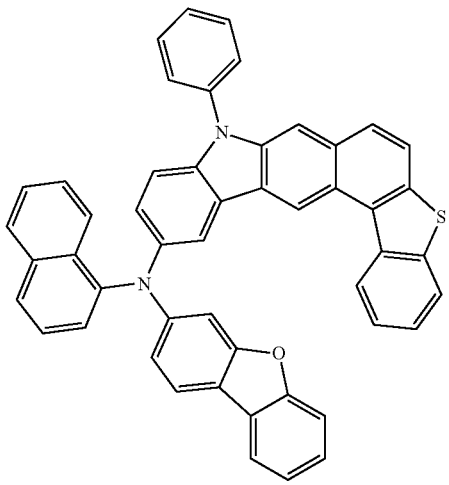
A 1-1-5
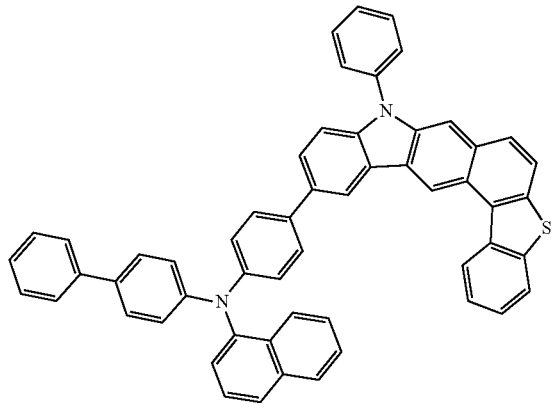
A 1-1-6
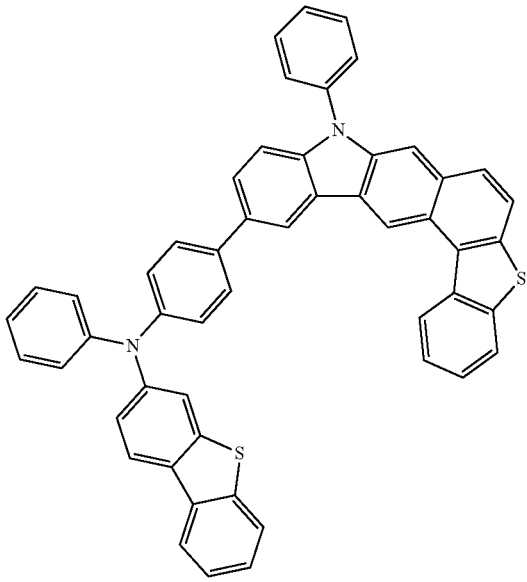
A 1-1-7
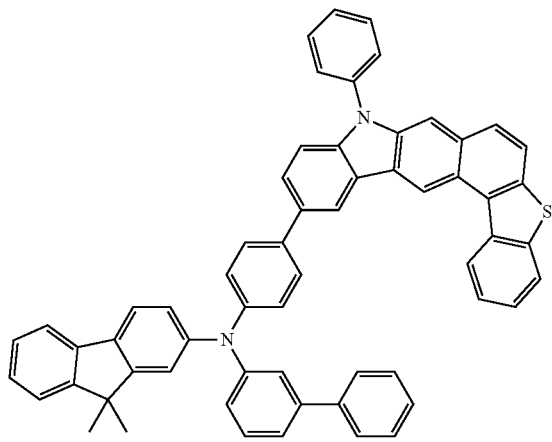
A 1-1-8
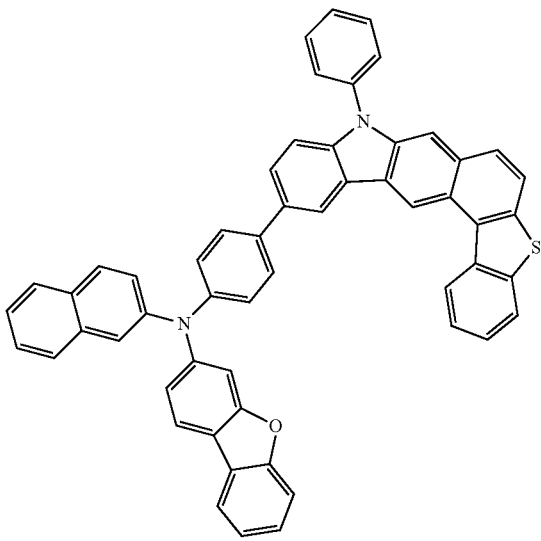

A 1-1-9
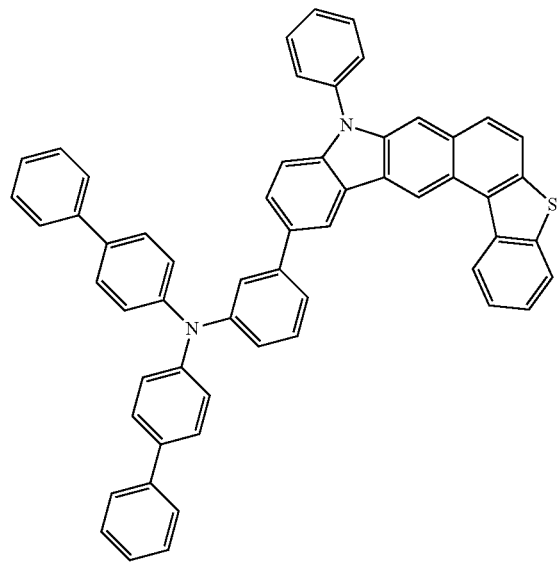
A 1-1-10
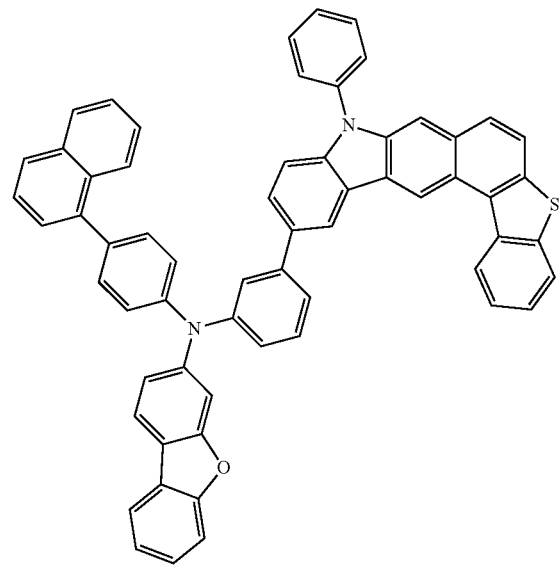
A 1-1-11
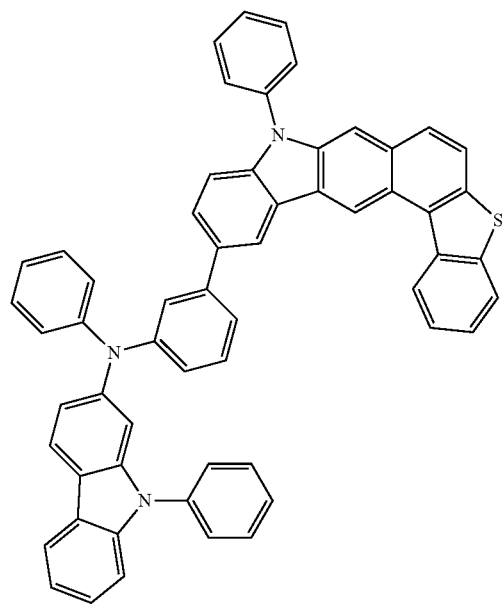
A 1-1-12
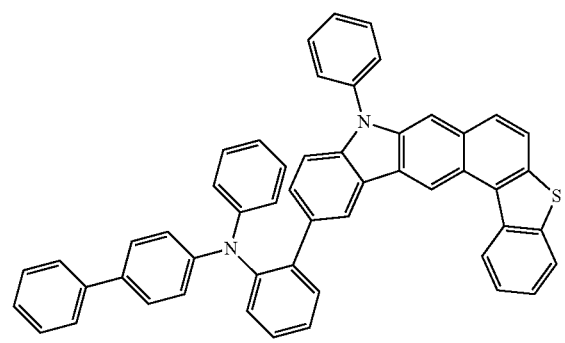

-continued
A 1-1-13
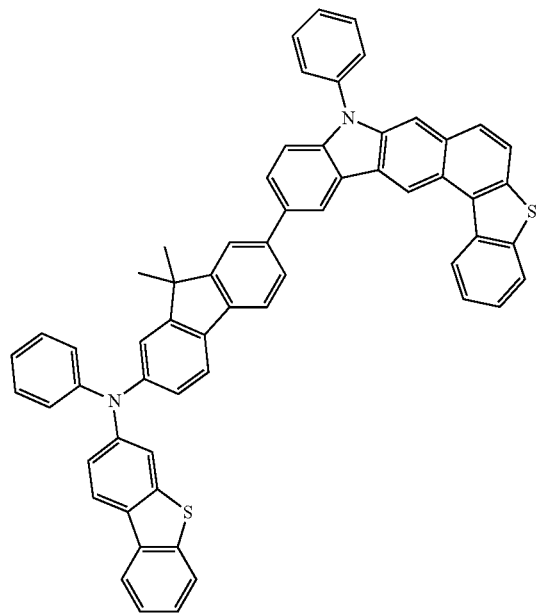
A 1-1-14
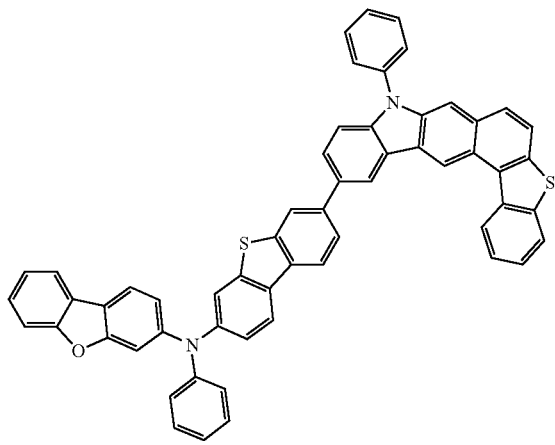
A 1-1-15
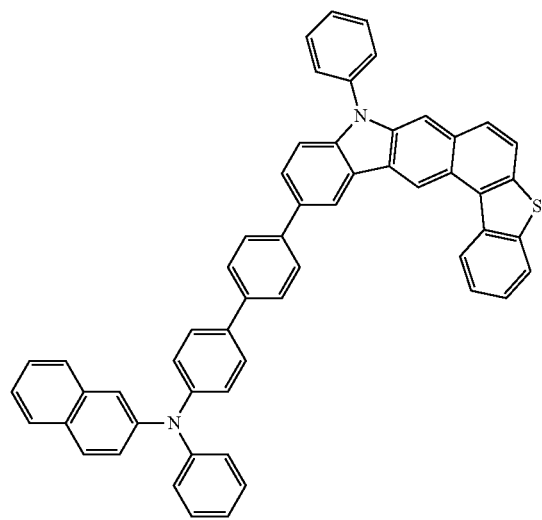
A 1-1-16
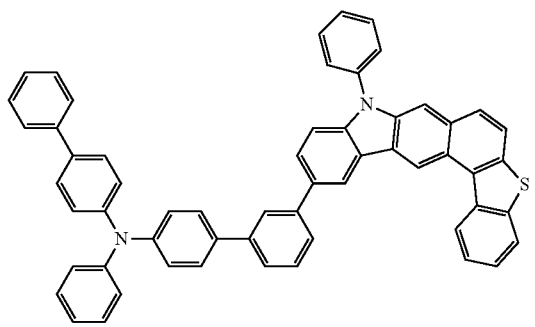

A 1-1-17
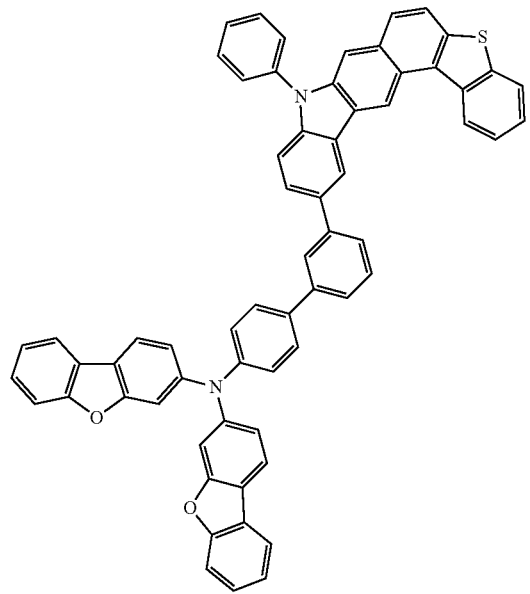
A 1-1-18
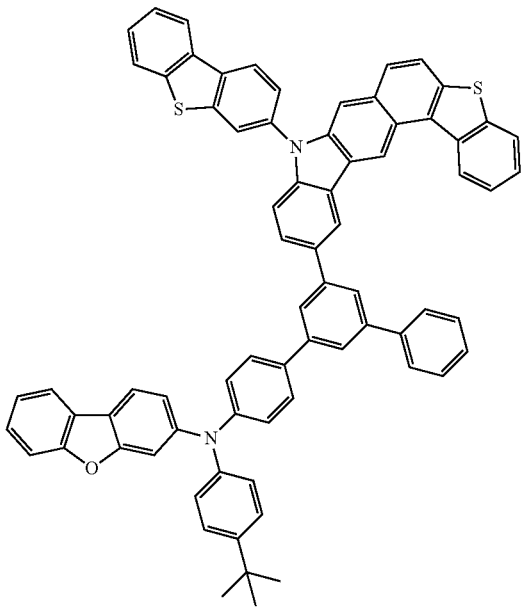
A 1-1-19
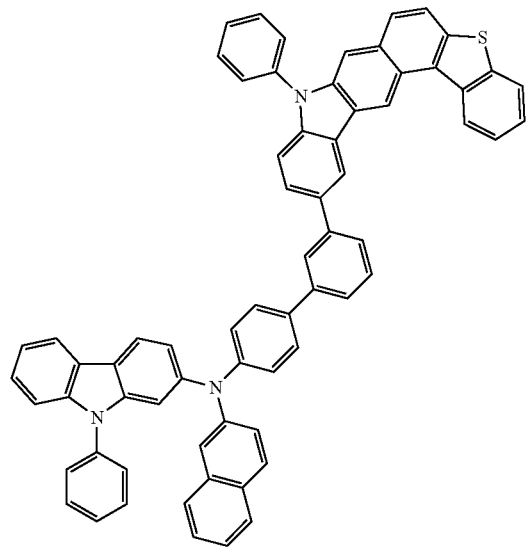
A 1-1-20
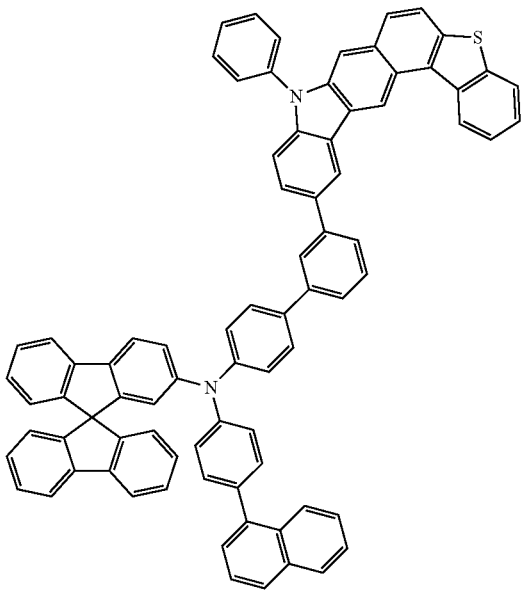

-continued
A 1-1-21
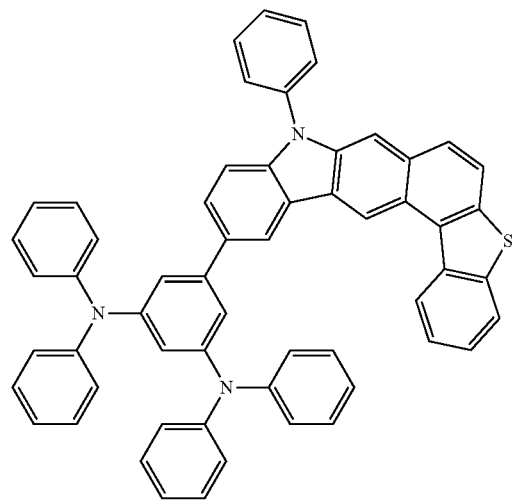
A 1-1-22
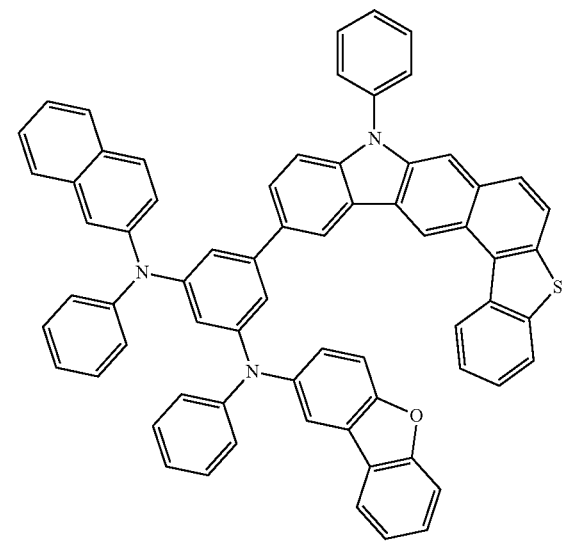
A 1-1-23
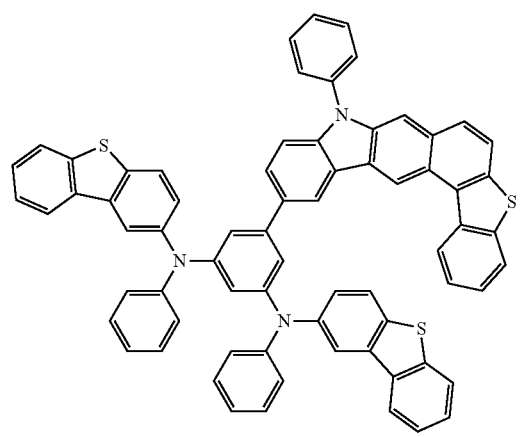
A 1-1-24
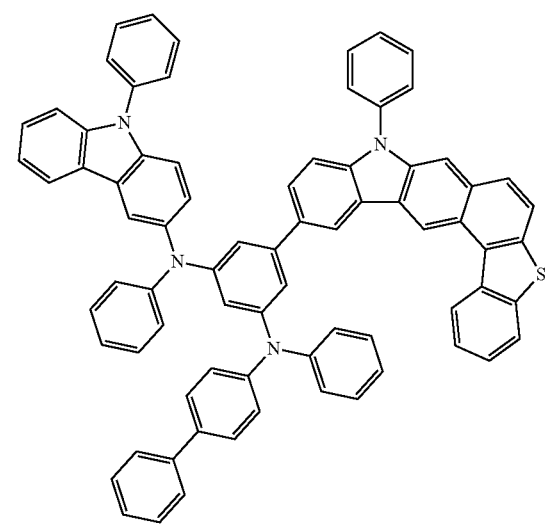
A 1-1-25
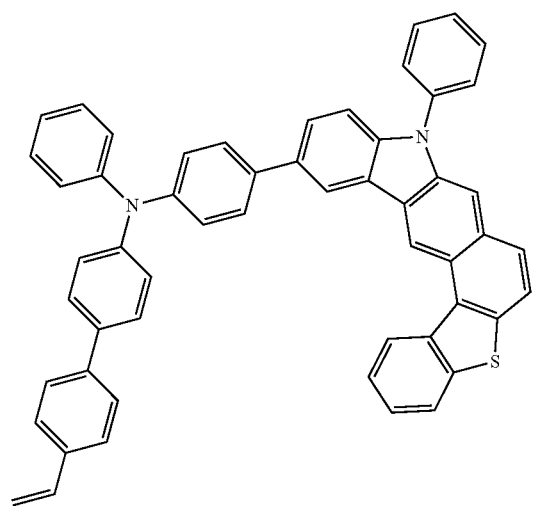
A 1-1-26
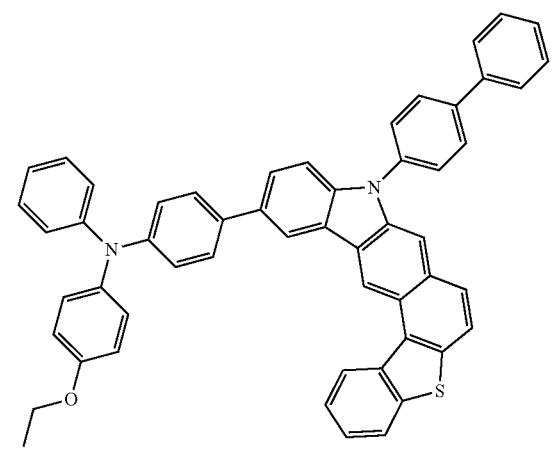

-continued
A 1-1-27
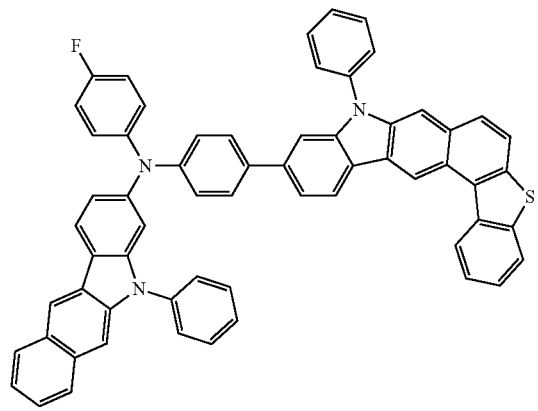
A 1-1-28
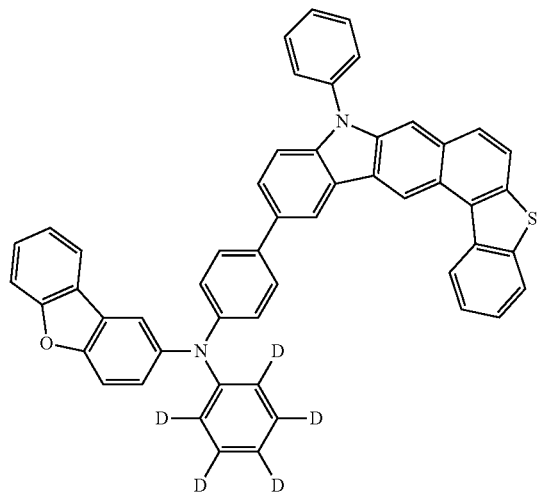
A 1-1-29
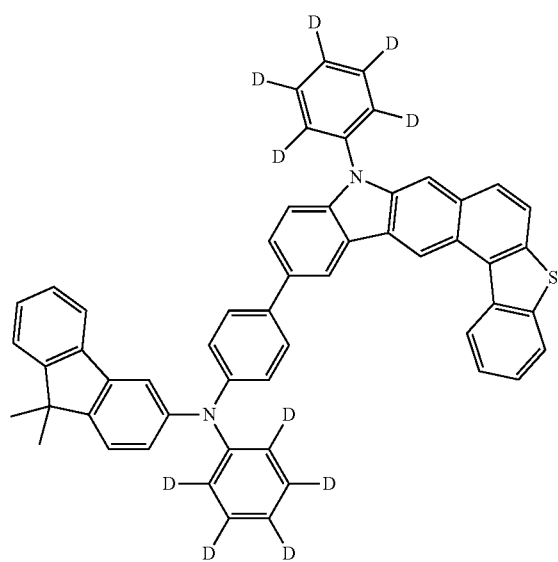
A 1-1-30
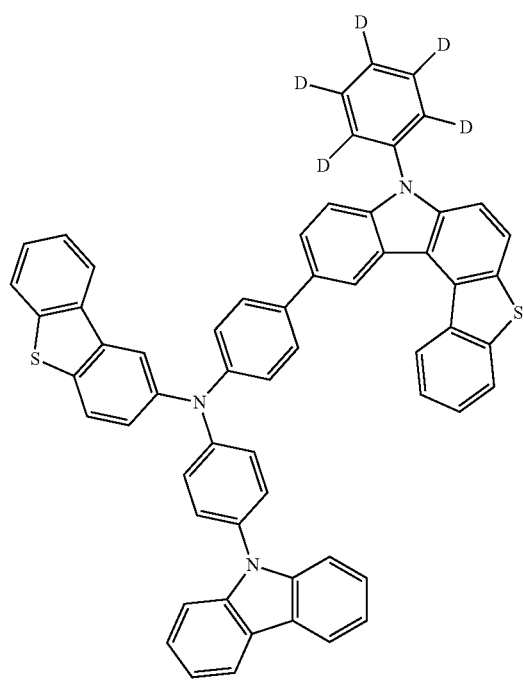

-continued
A 1-1-31
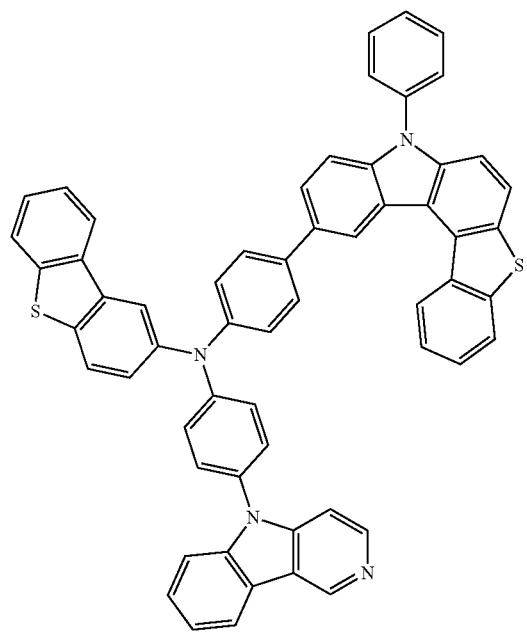
A 1-1-32
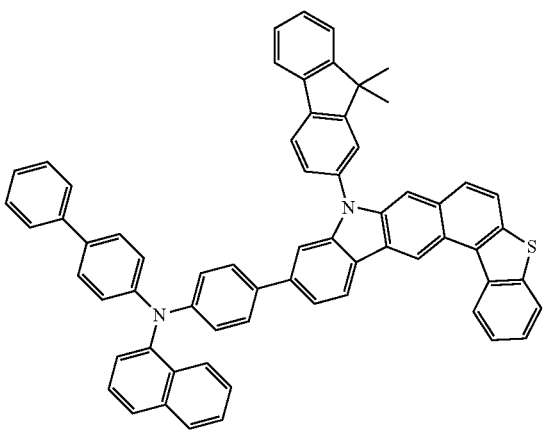
A 1-1-33
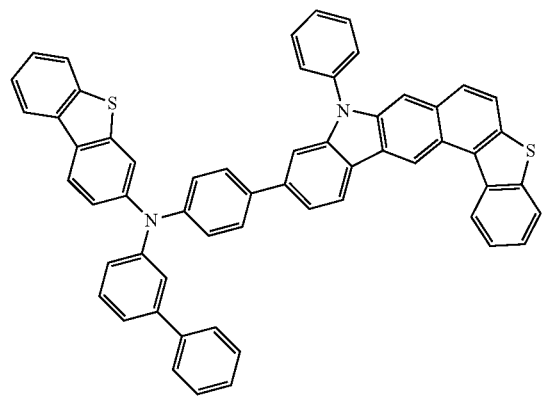
A 1-1-34
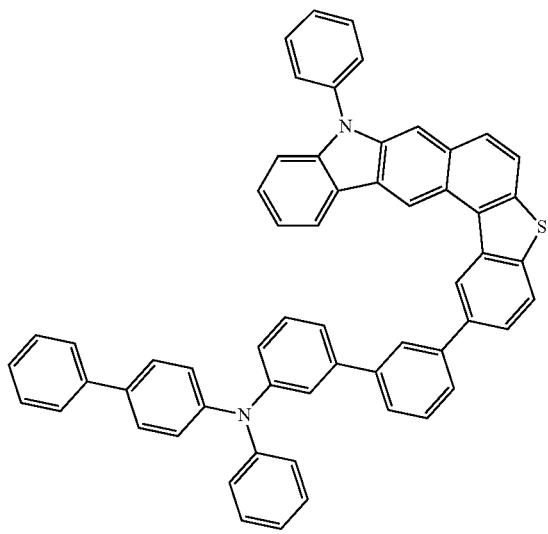

-continued
A 1-2-1
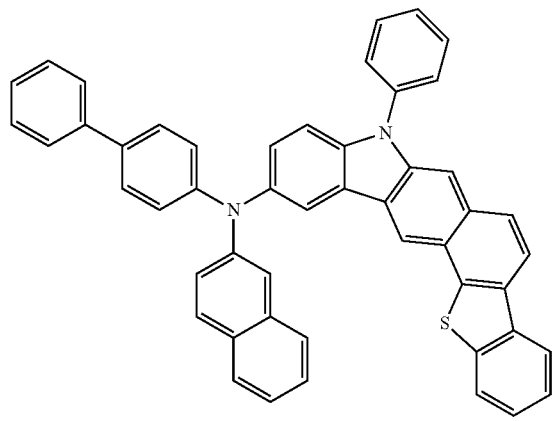
A 1-2-2
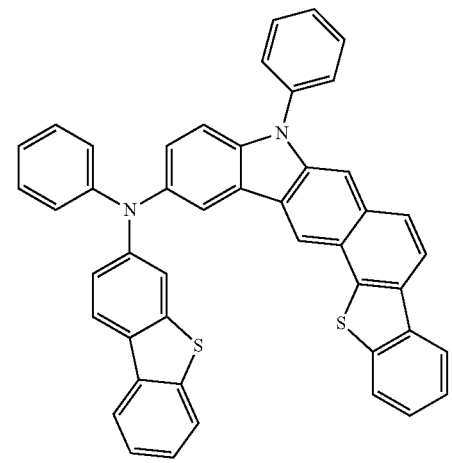
A 1-2-3
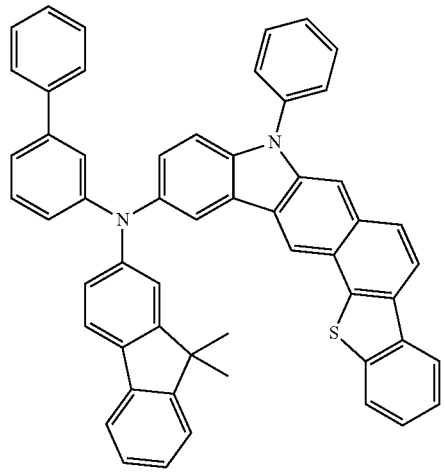
A 1-2-4
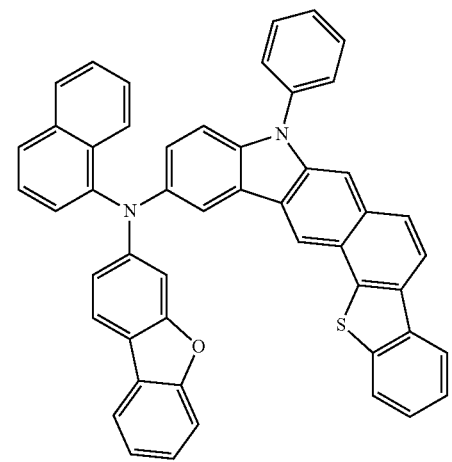
A 1-2-5
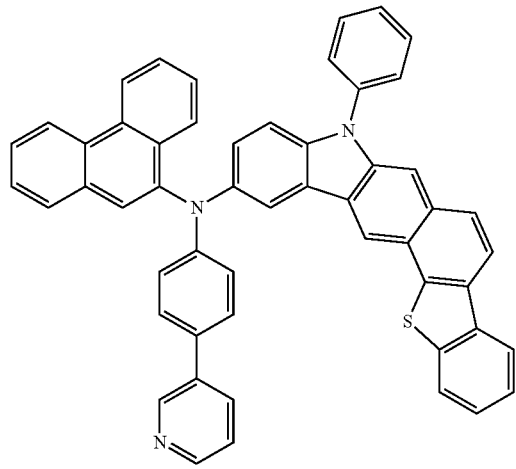
A 1-2-6
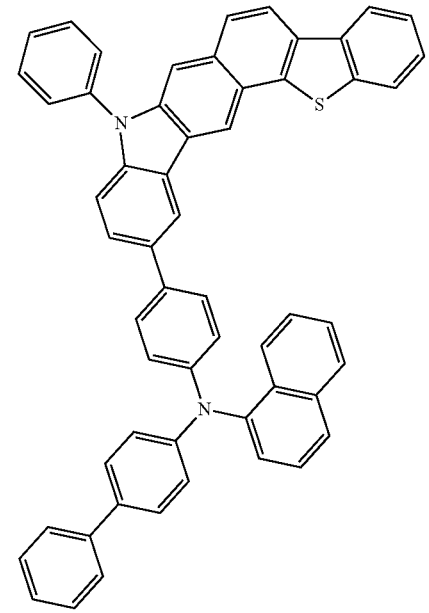

-continued
A 1-2-7
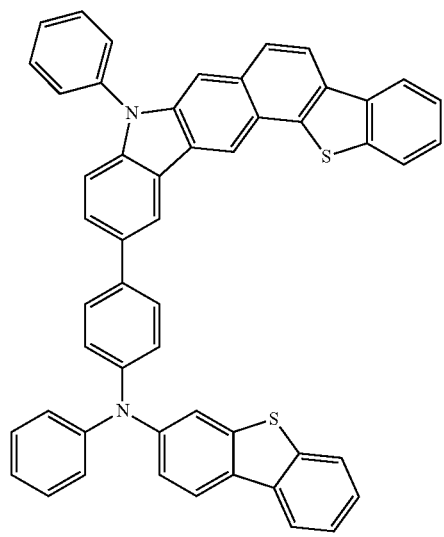
A 1-2-8
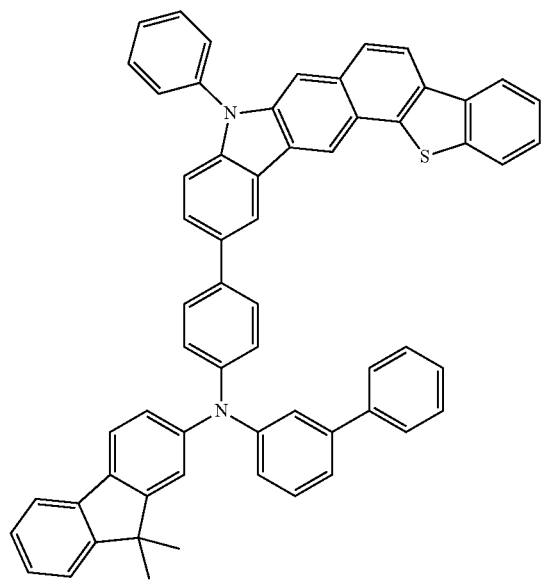
A 1-2-9
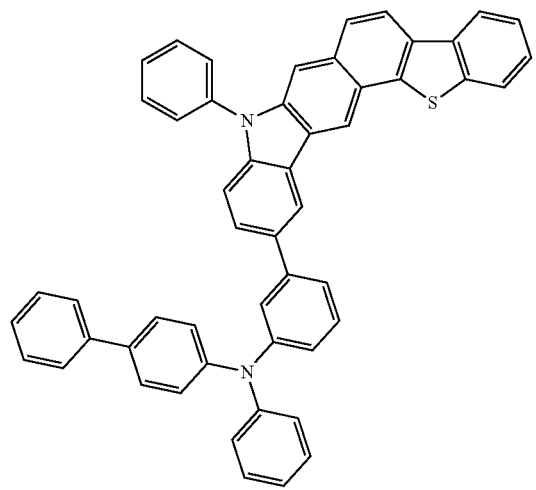
A 1-2-10
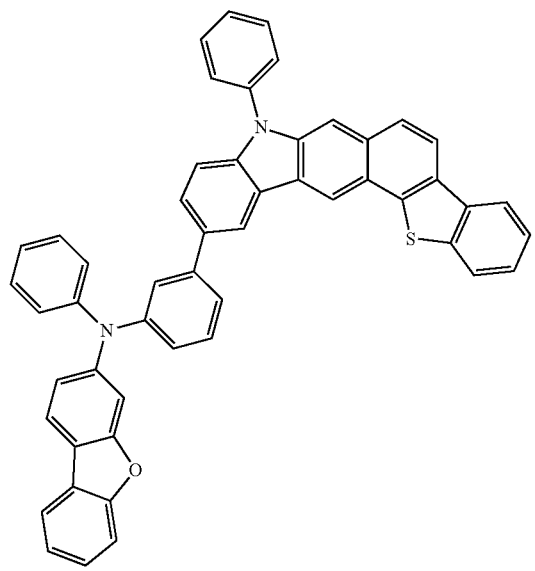

-continued
A 1-2-11
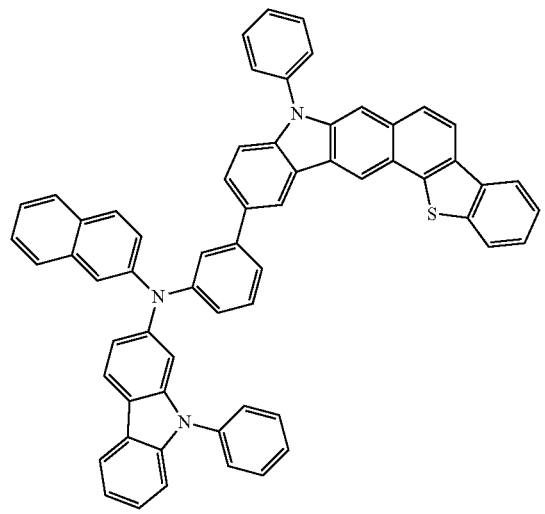
A 1-2-12
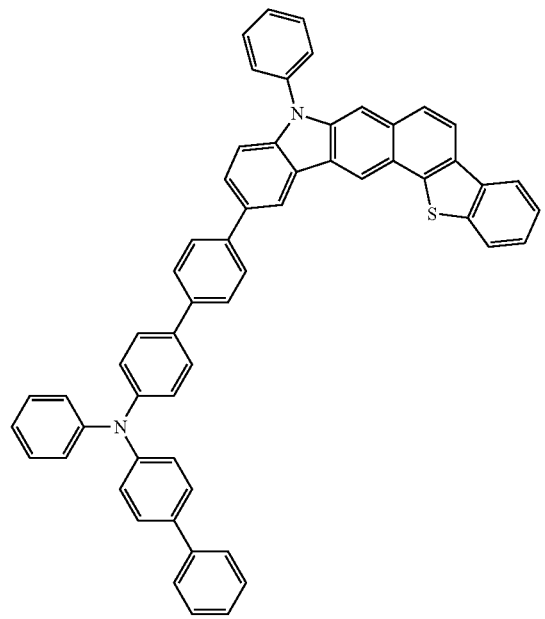
A 1-2-13
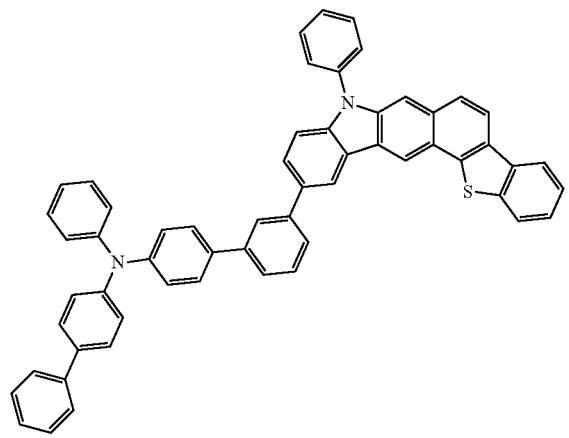
A 1-2-14
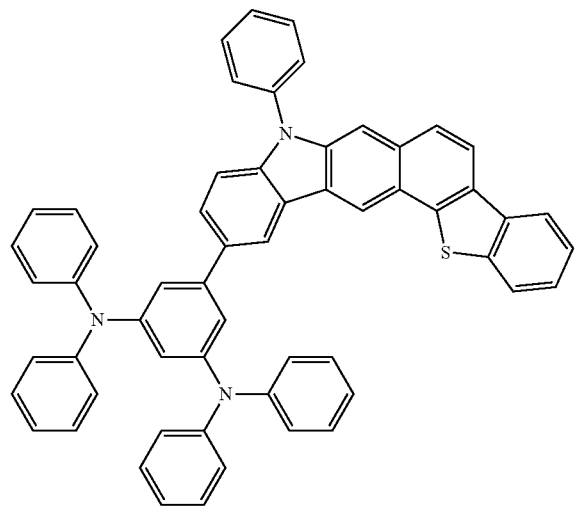

-continued
A 1-2-15
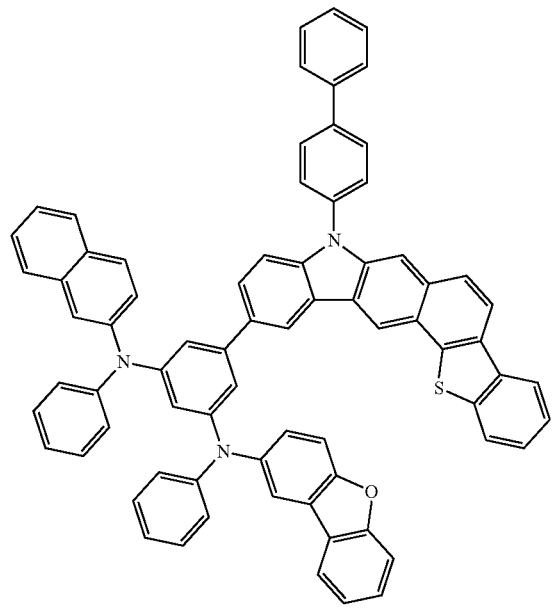
A 1-2-16
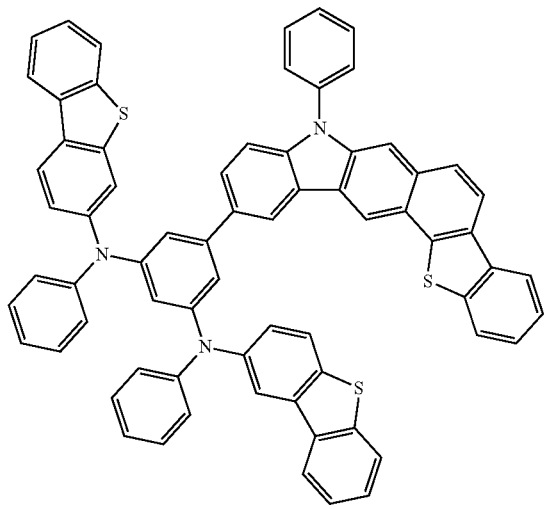
A 1-2-17
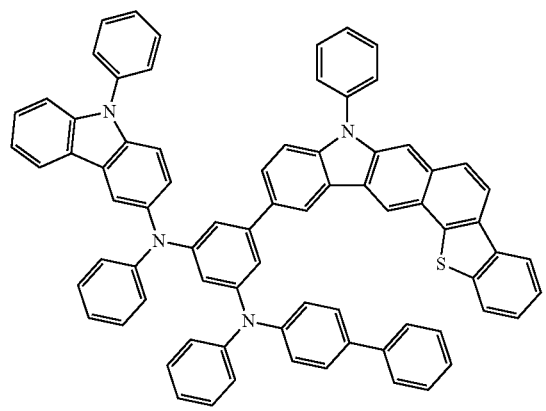
A 1-2-18
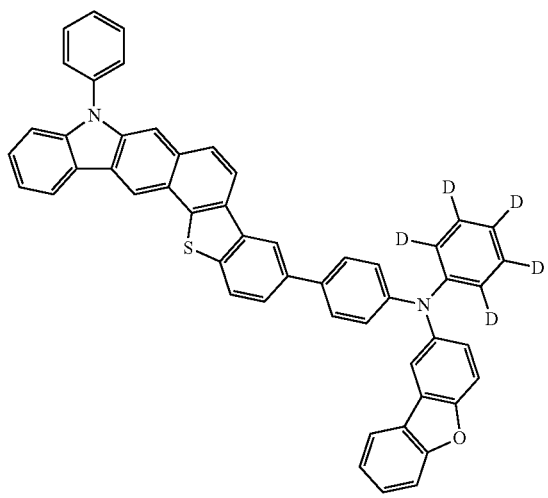
A 2-1-1
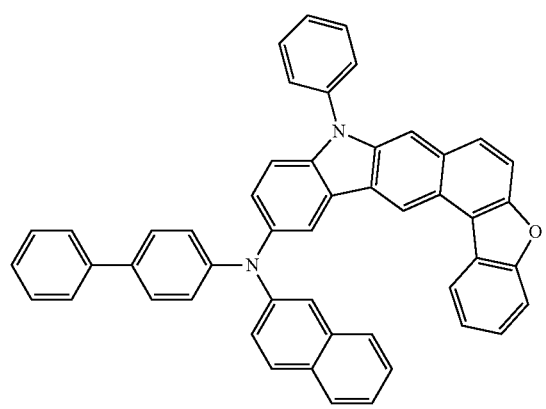
A 2-1-2
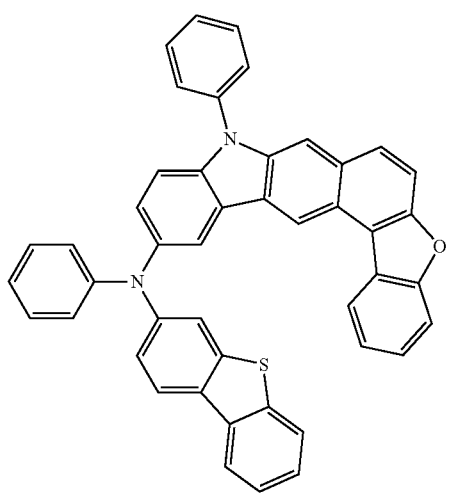

-continued
A 2-1-3
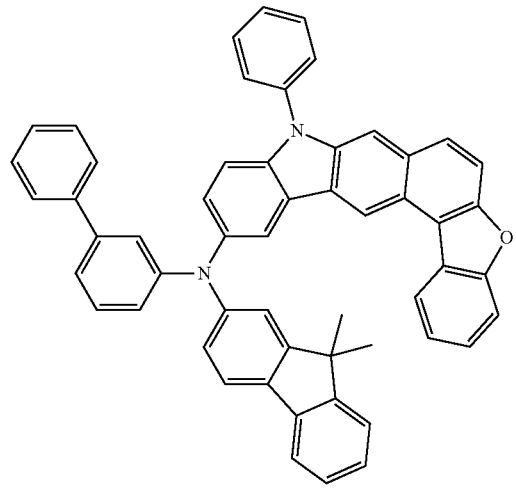
A 2-1-4
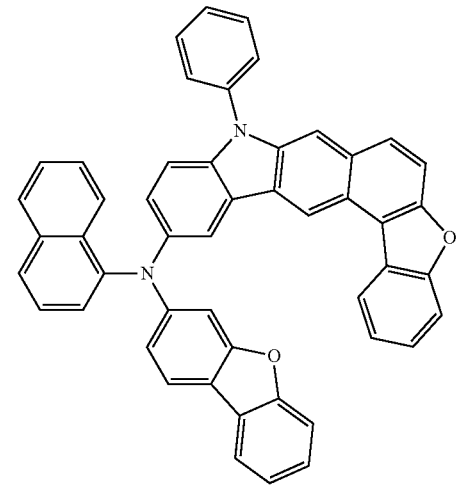
A 2-1-5
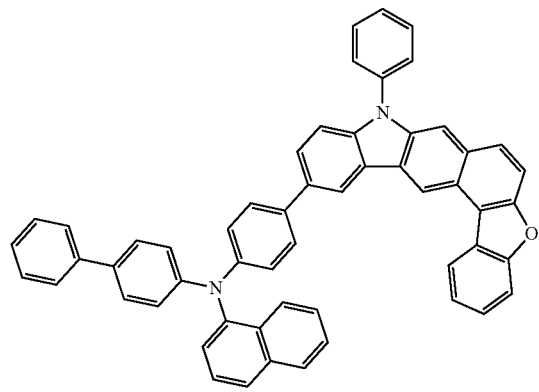
A 2-1-6
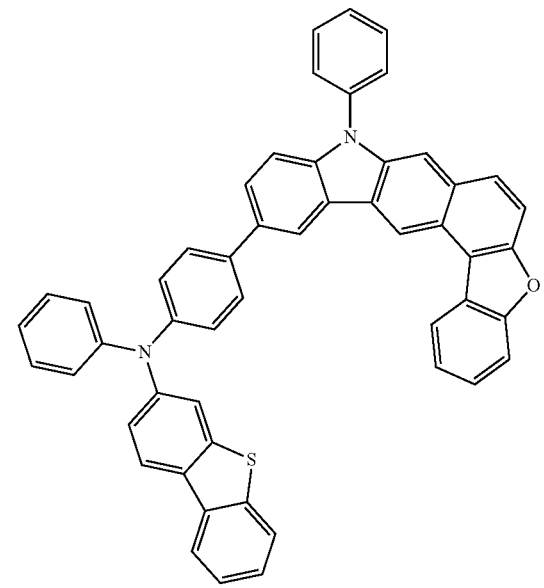
A 2-1-7
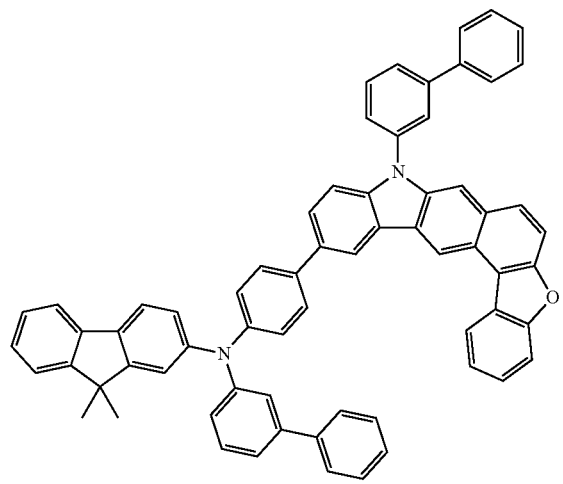
A 2-1-8
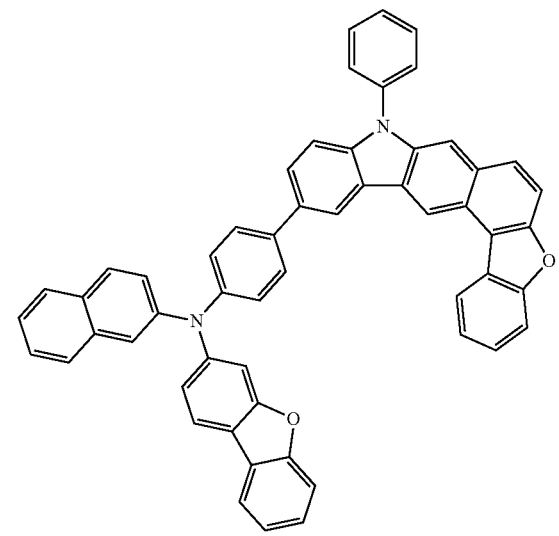

-continued
A 2-1-9
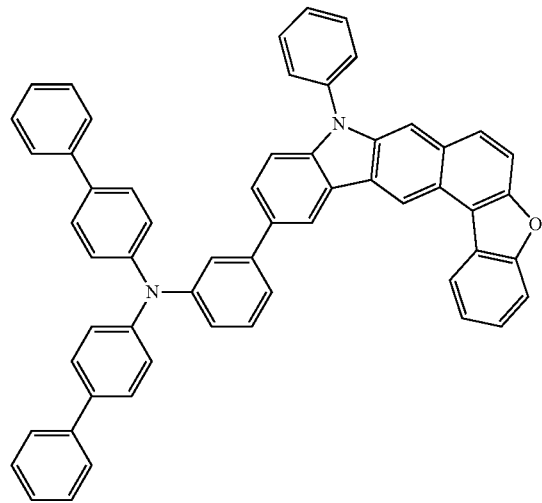
A 2-1-10
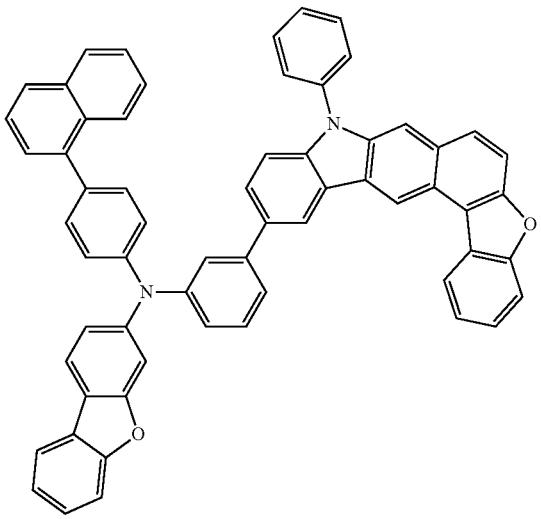
A 2-1-11
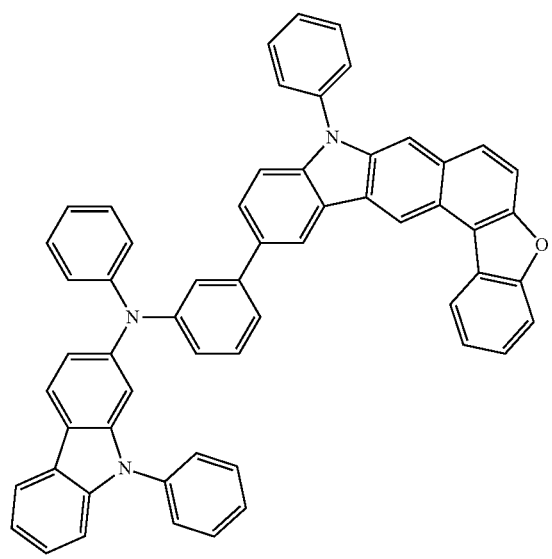
A 2-1-12
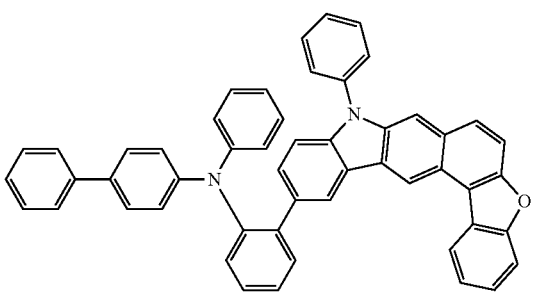

A 2-1-13
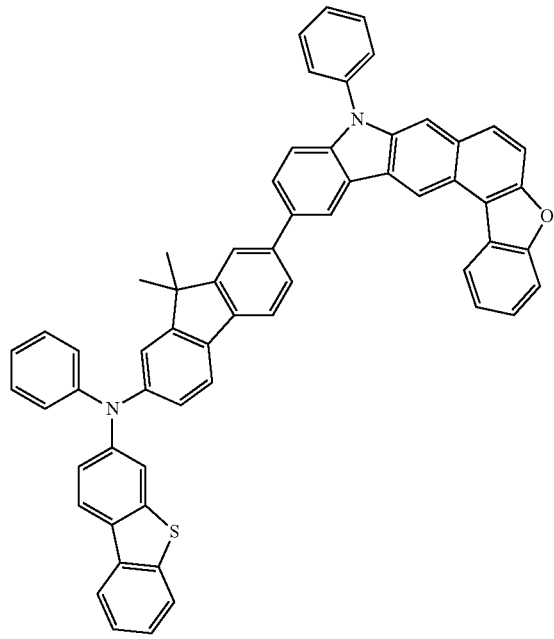
A 2-1-14
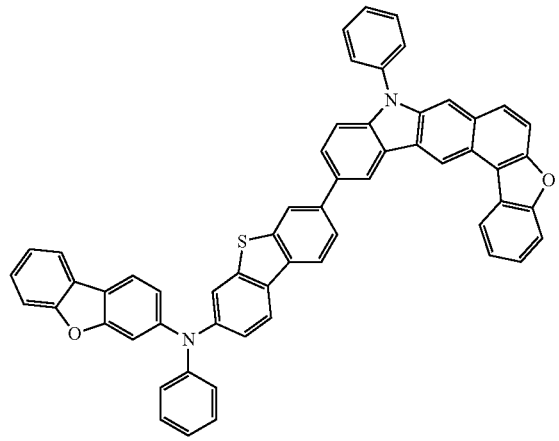
A 2-1-15
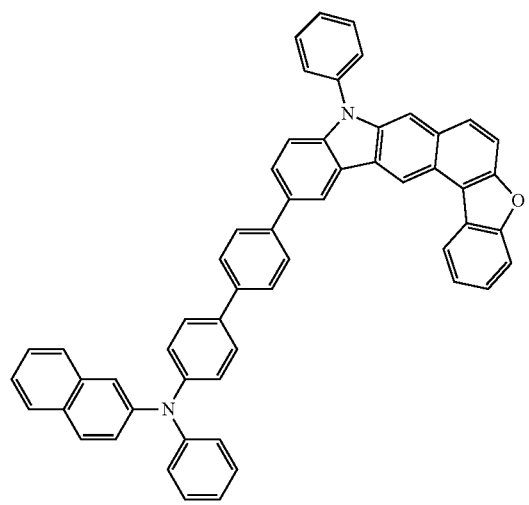
A 2-1-16
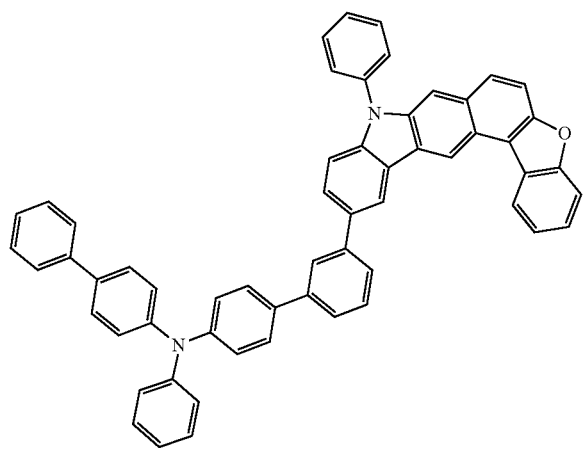

A 2-1-17
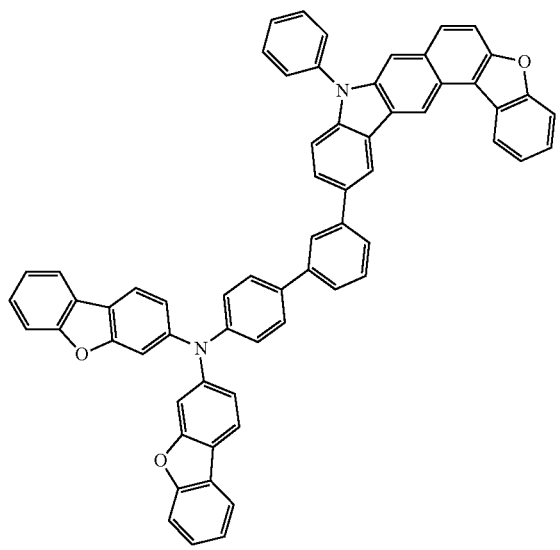
A 2-1-18
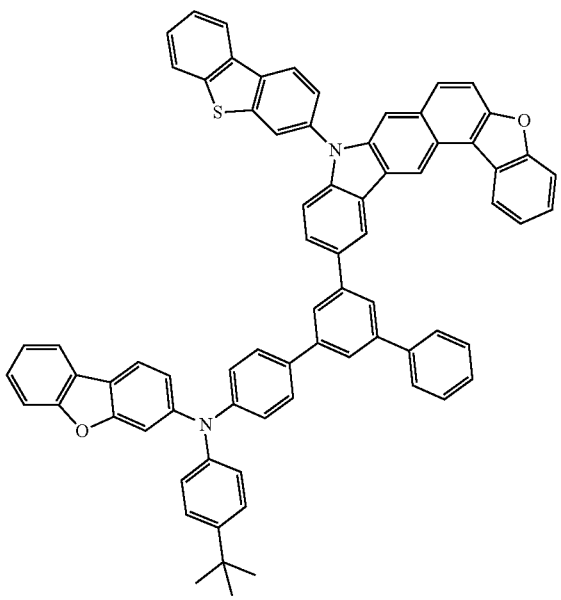
A 2-1-19
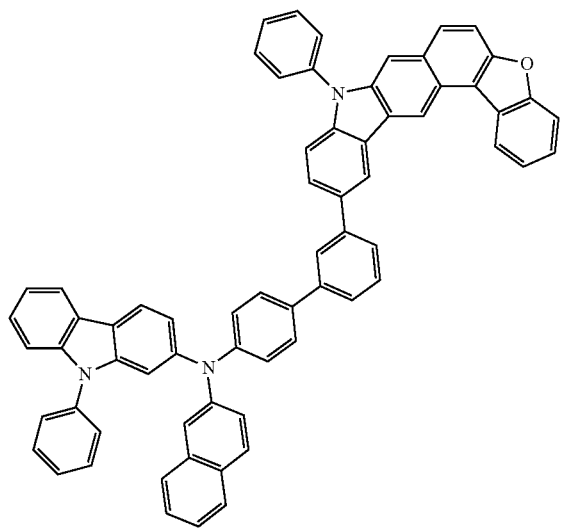
A 2-1-20
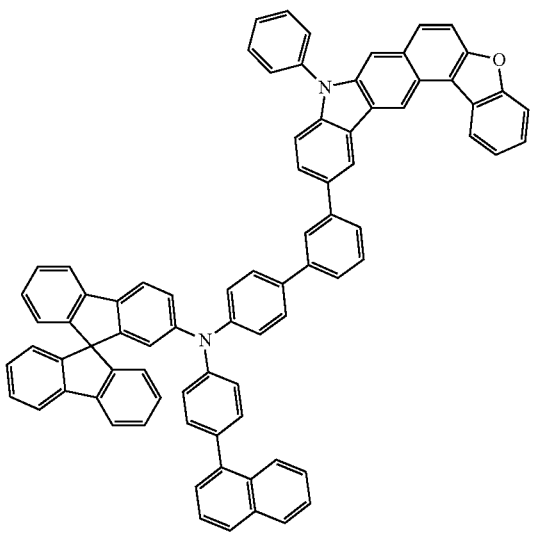

-continued
A 2-1-21
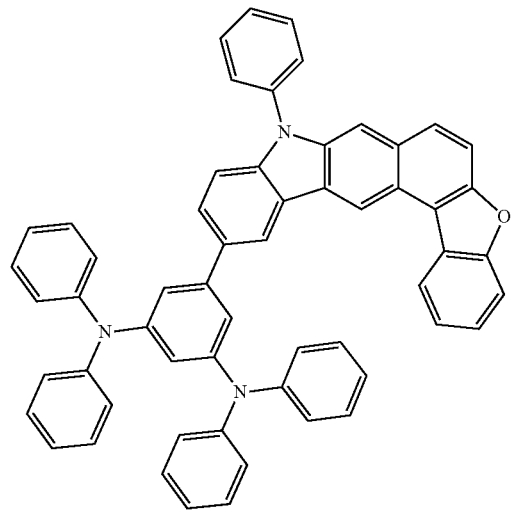
A 2-1-22
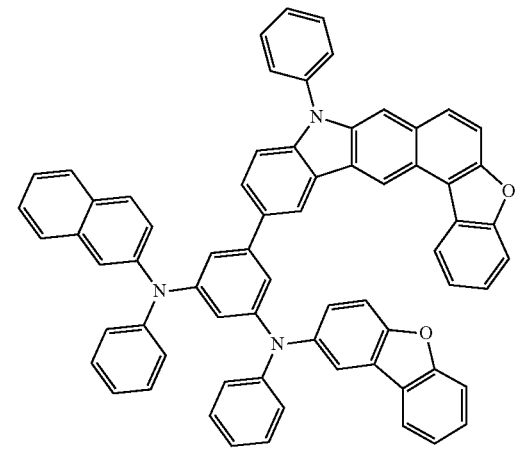
A 2-1-23
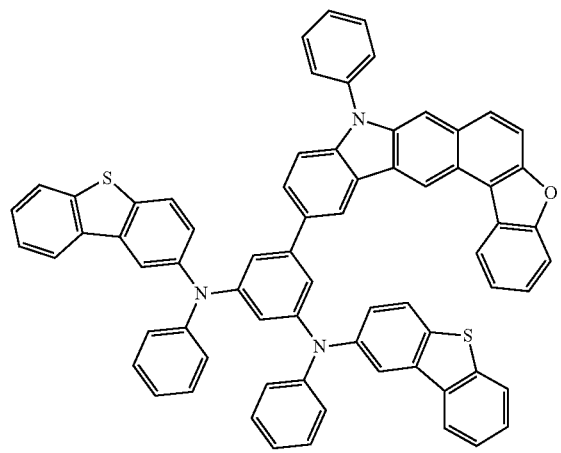
A 2-1-24
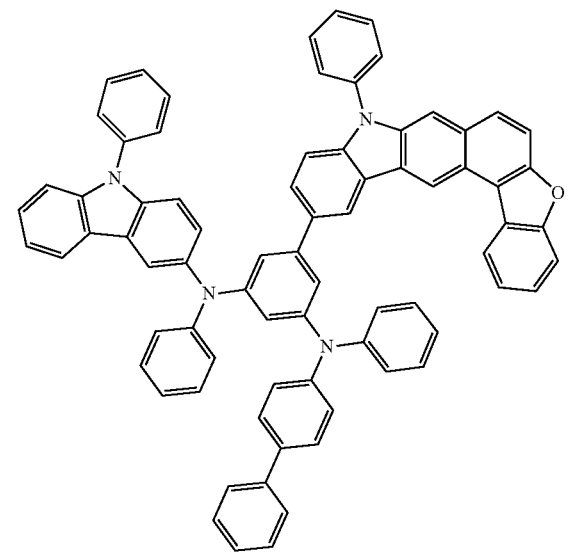
A 2-1-25
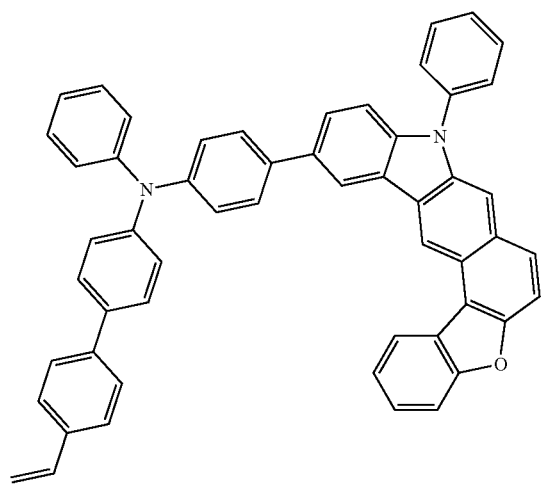
A 2-1-26
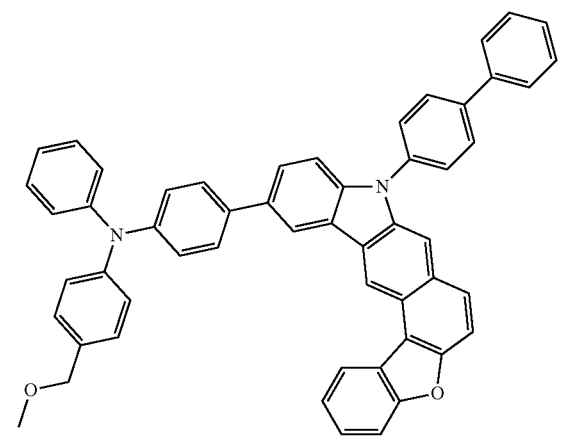

A 2-1-27
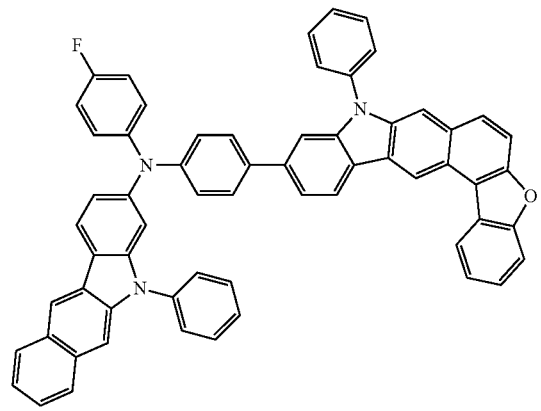
A 2-1-28
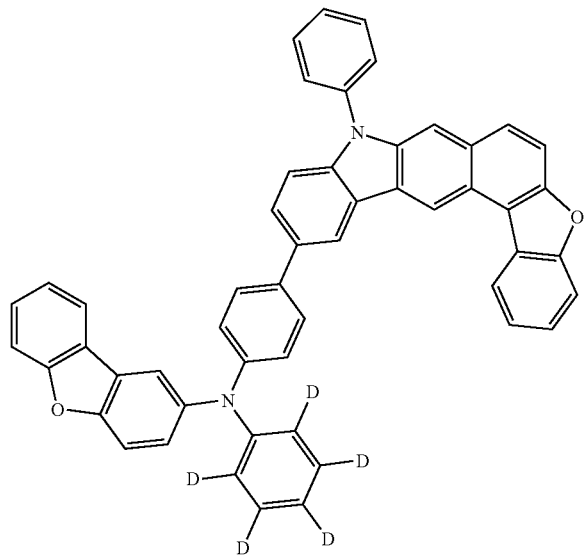
A 2-1-29
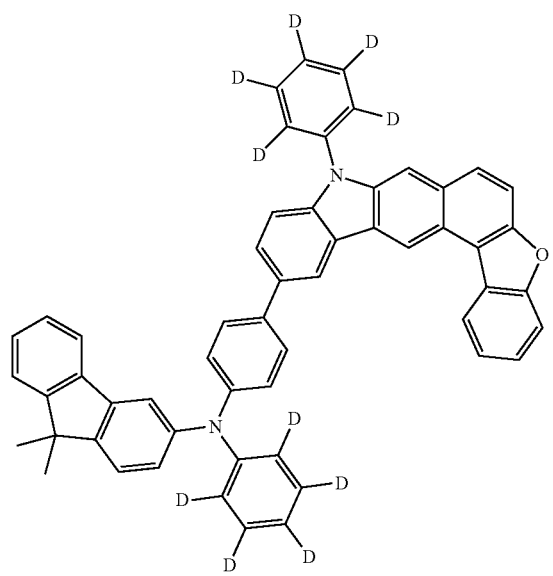
A 2-1-30
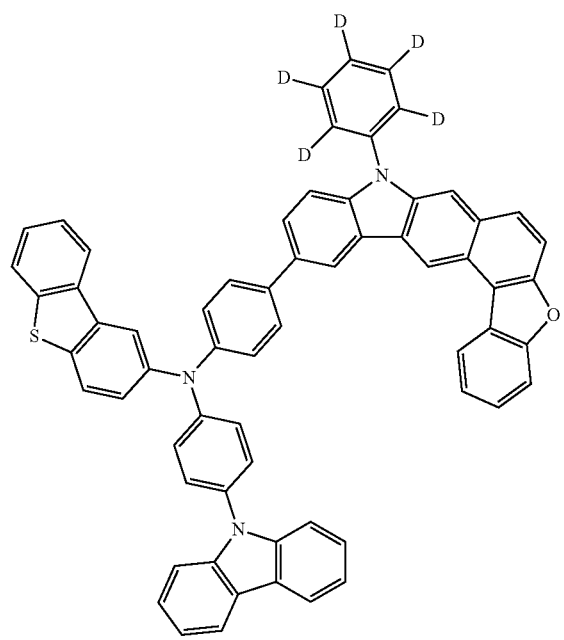

-continued
A 2-1-31
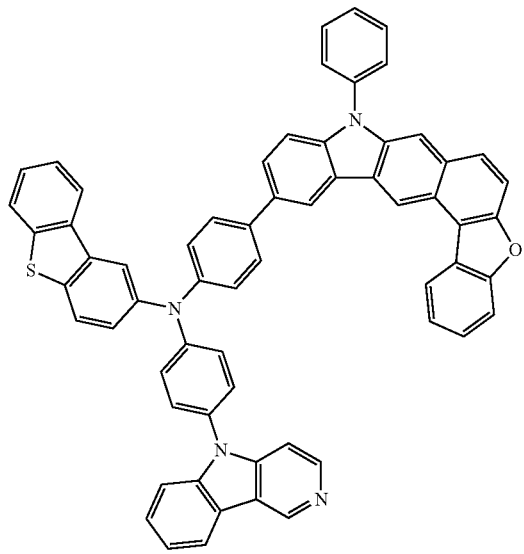
A 2-2-1
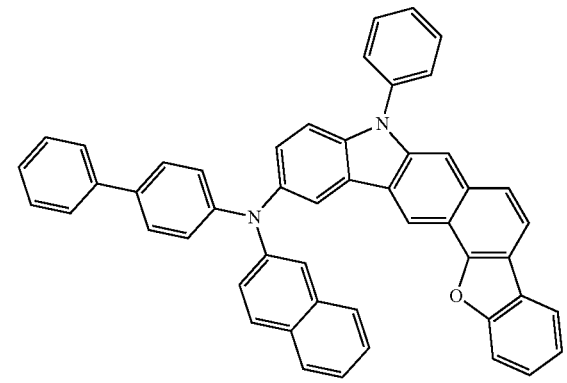
A 2-2-2
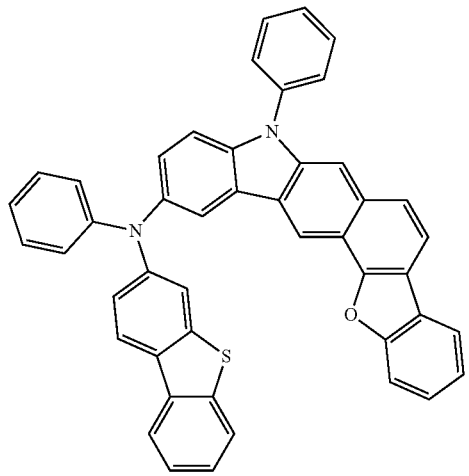
A 2-2-3
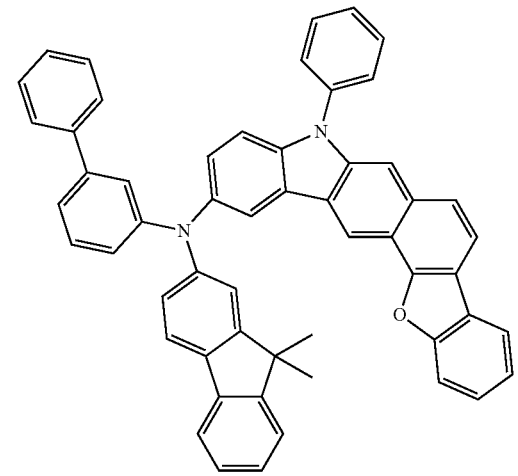
A 2-2-4
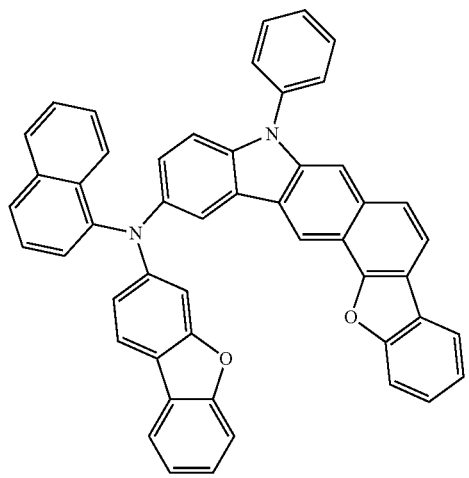
A 2-2-5
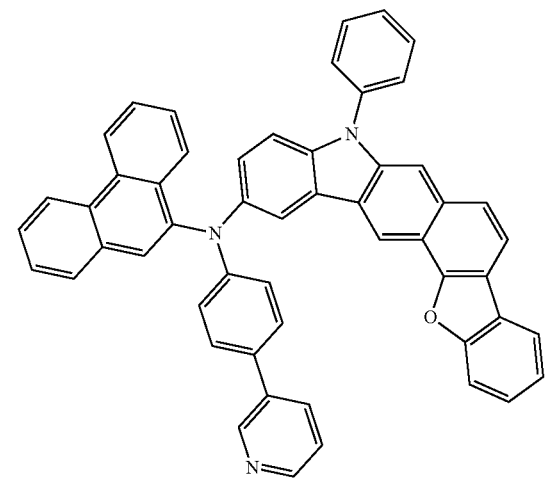

-continued
A 2-2-6
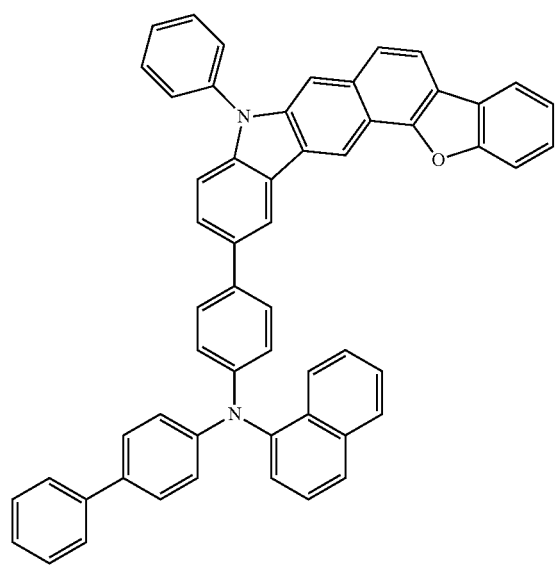
A 2-2-7
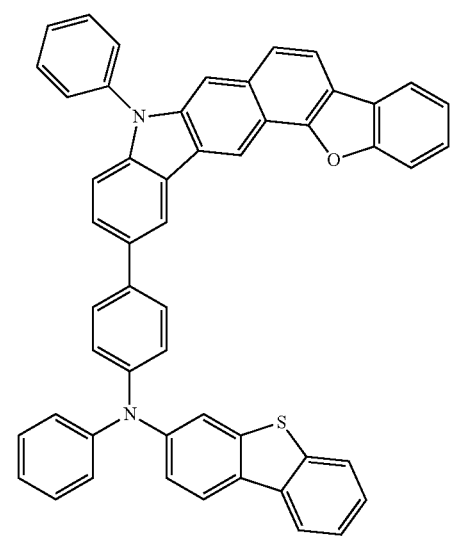
A 2-2-8
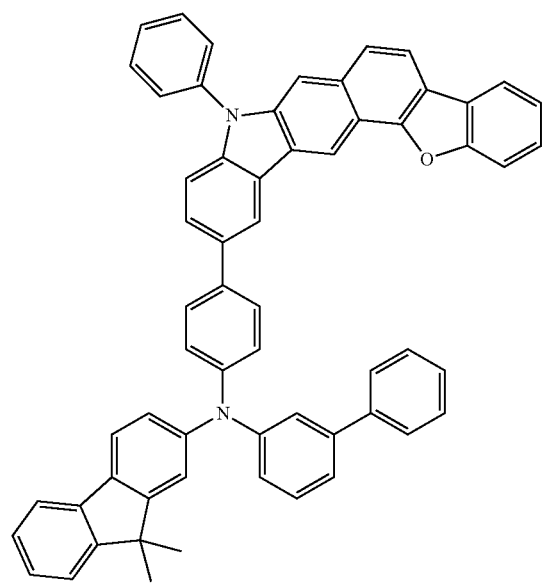
A 2-2-9
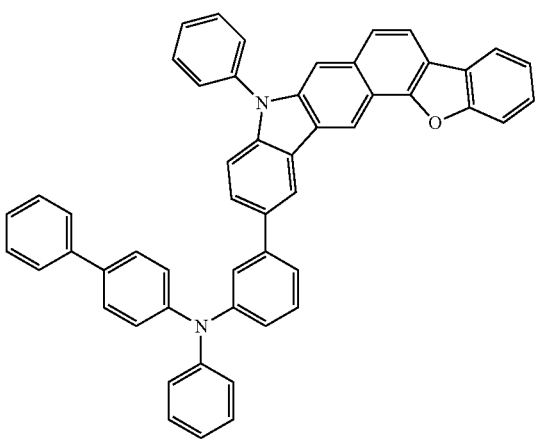

-continued
A 2-2-10
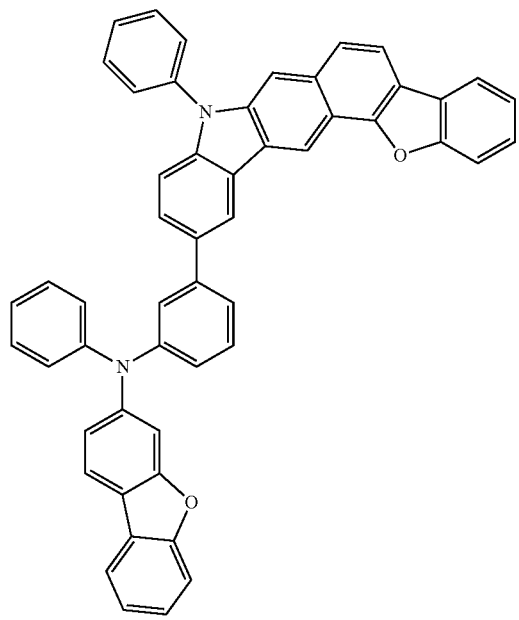
A 2-2-11
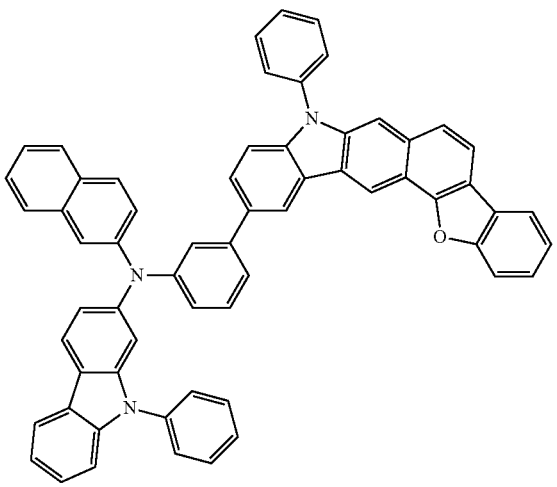
A 2-2-12
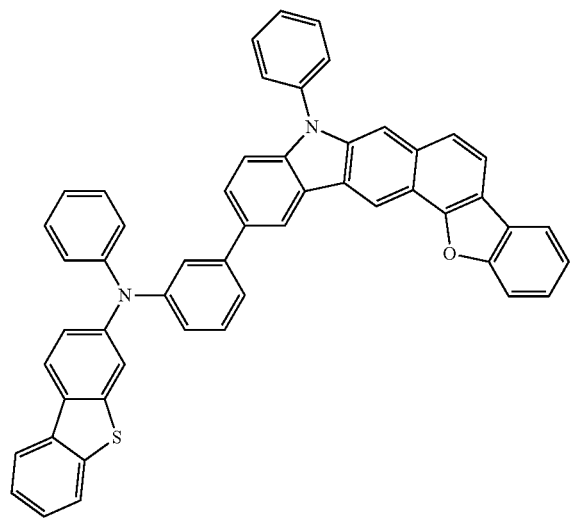
A 2-2-13
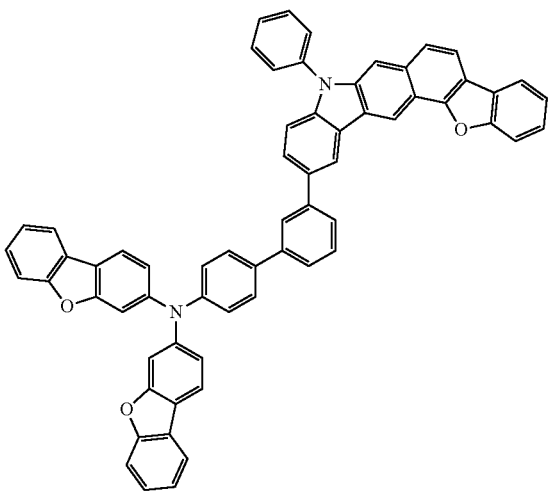
A 2-2-14
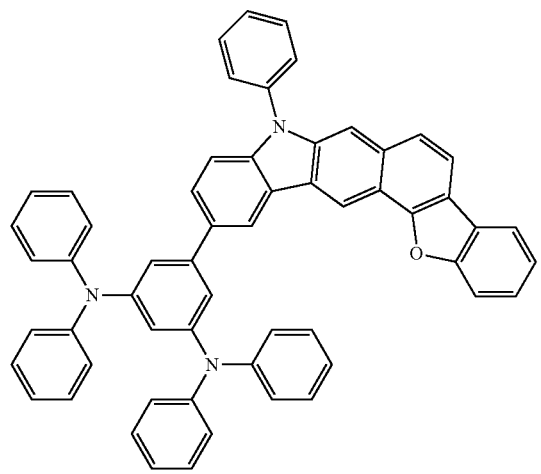
A 2-2-15
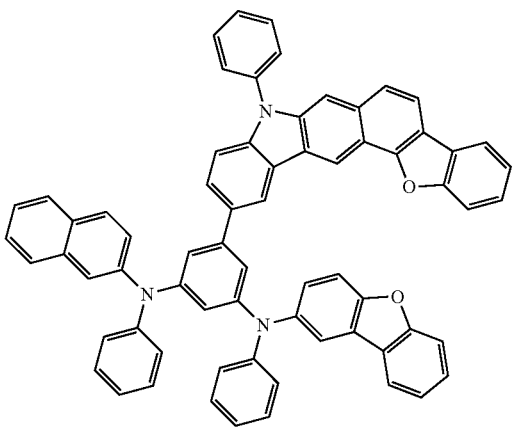

-continued
A 2-2-16
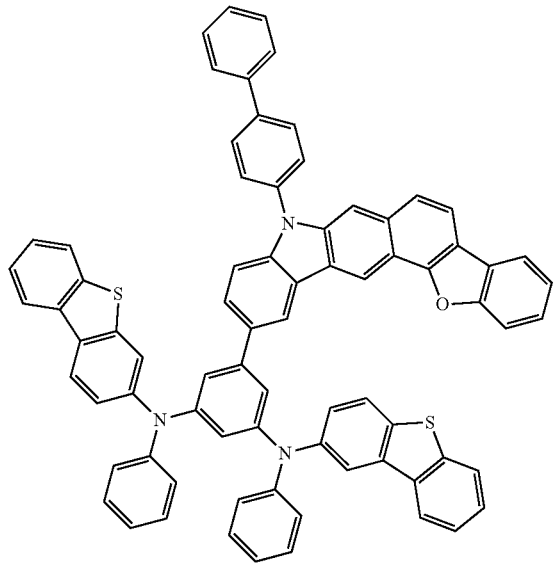
A 2-2-17
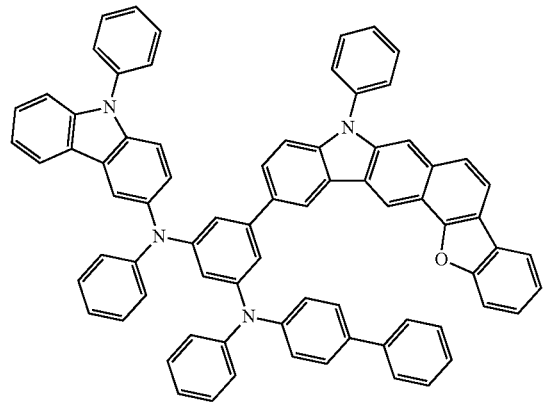
A 2-2-18
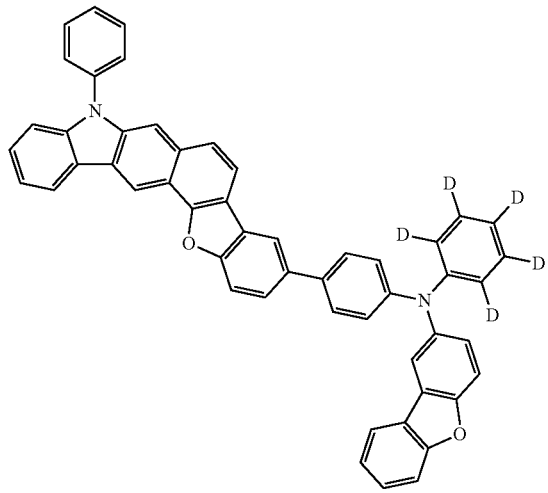
A 3-1-1
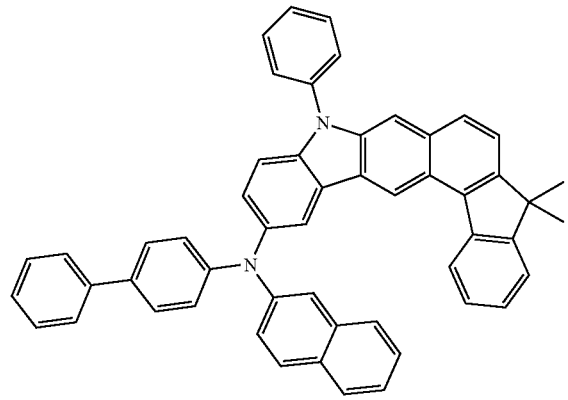
A 3-1-2
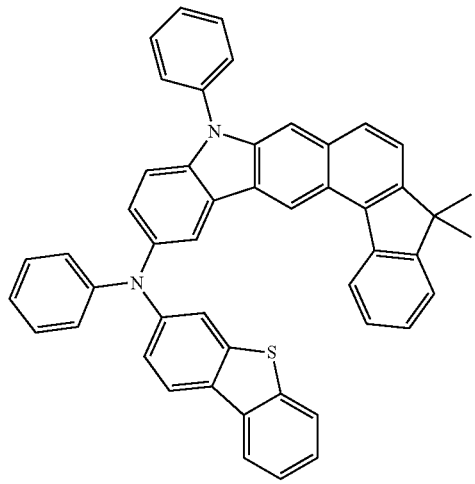
A 3-1-3
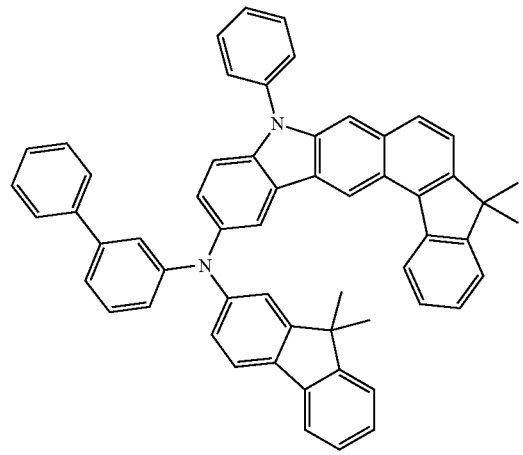

-continued
A 3-1-4
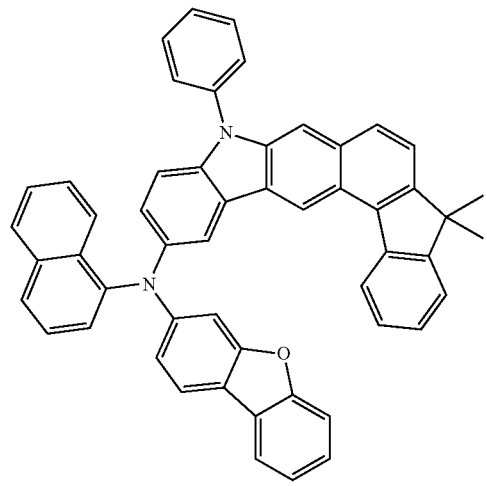
A 3-1-5
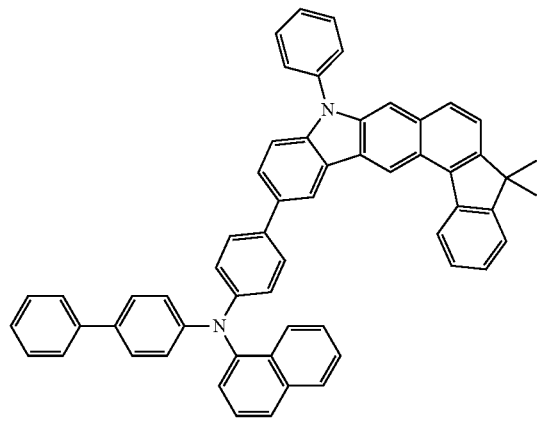
A 3-1-6
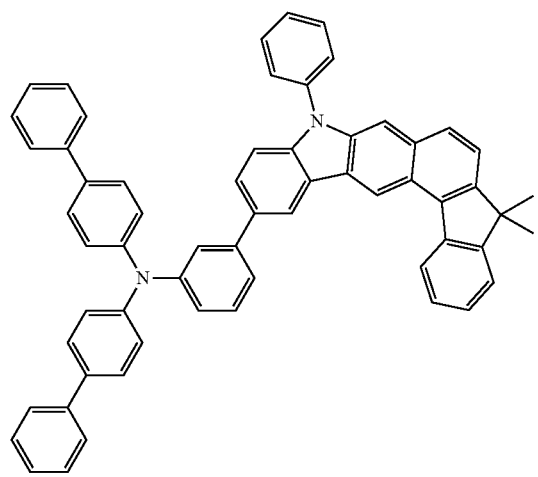
A 3-1-7
A 3-1-8
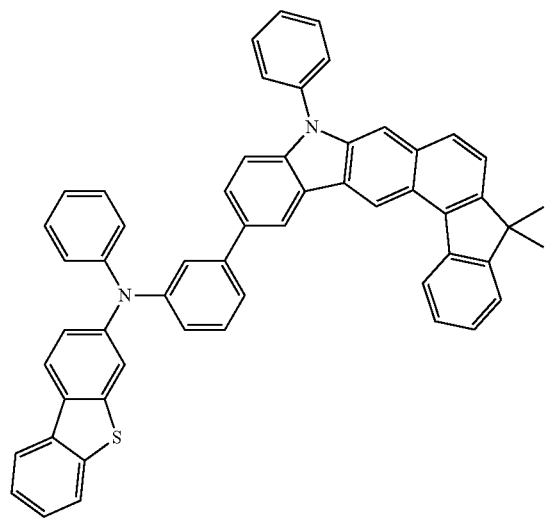
A 3-1-9

-continued
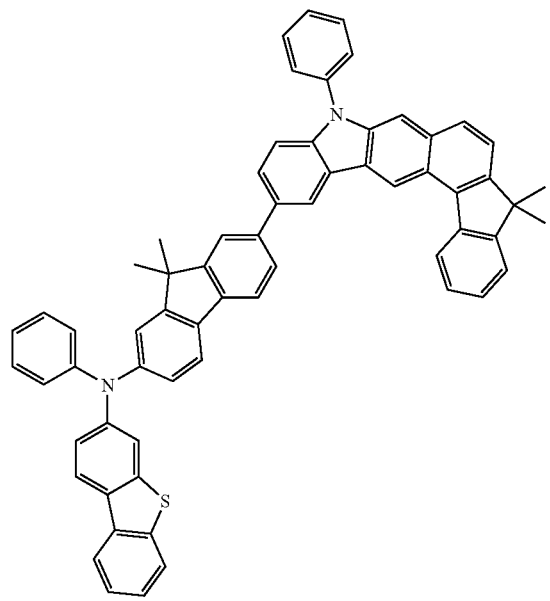
A 3-1-10
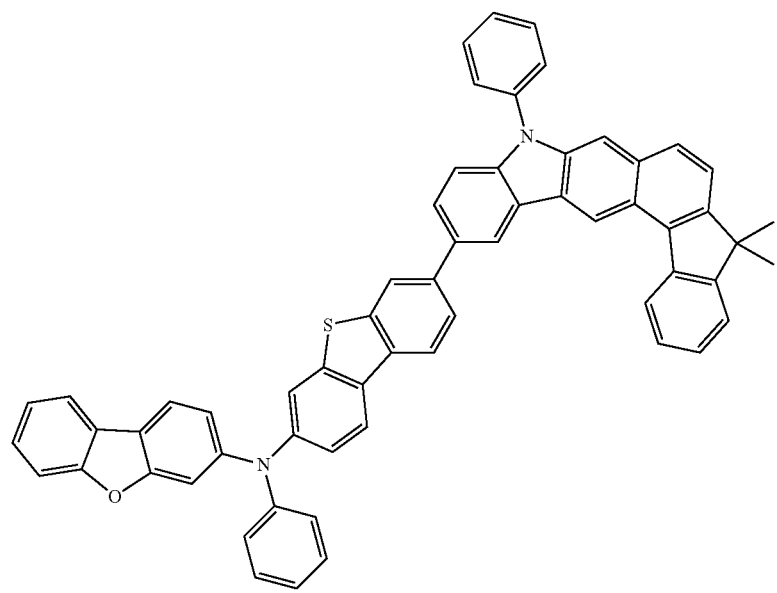
A 3-1-11

-continued
A 3-1-12
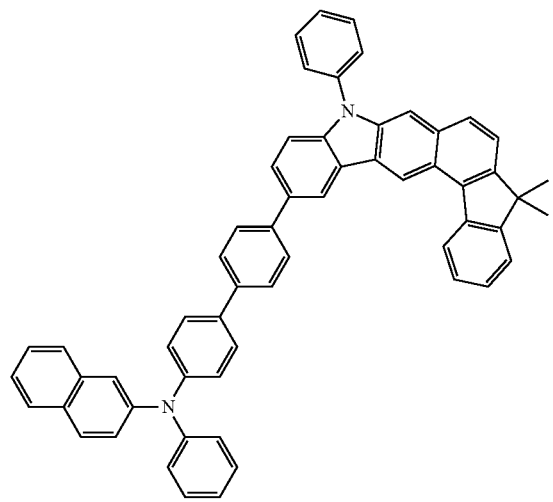
A 3-1-13
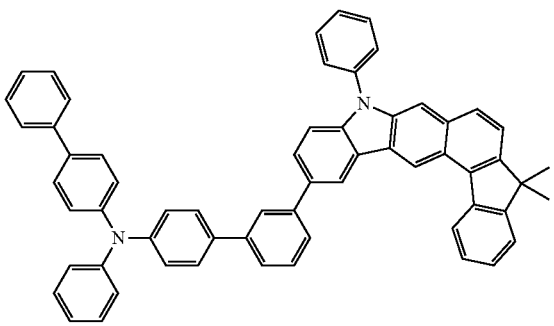
A 3-1-14
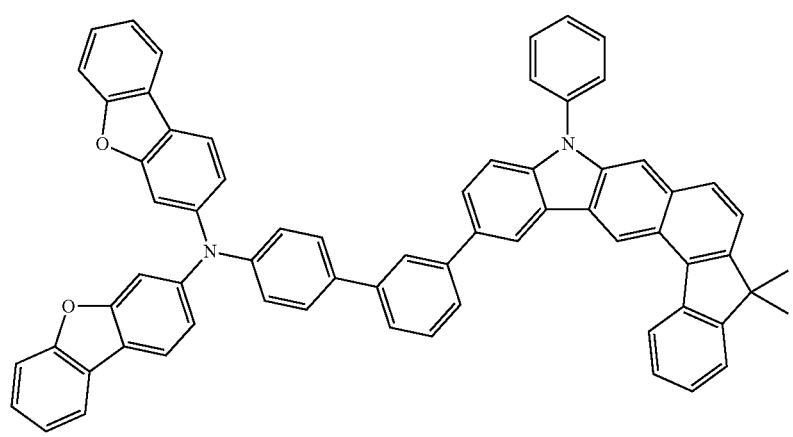
A 3-1-15
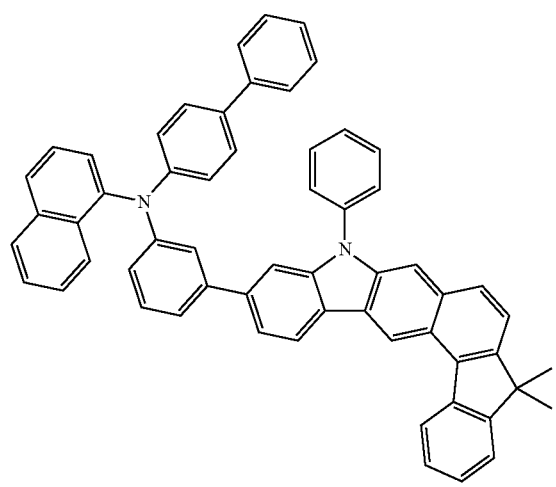
A 3-2-1
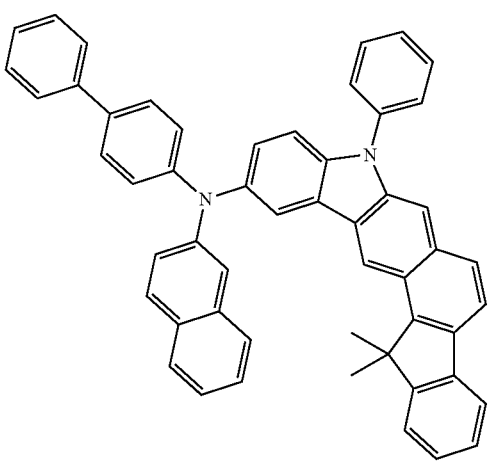

-continued
A 3-2-2
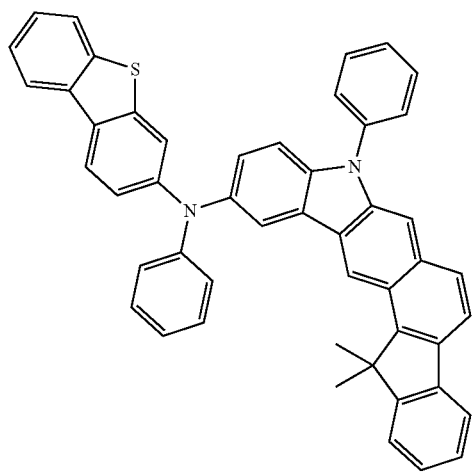
A 3-2-3
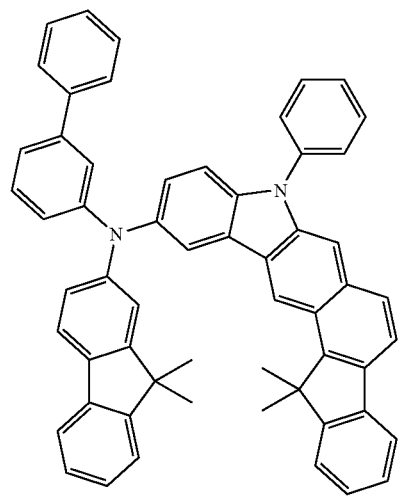
A 3-2-4
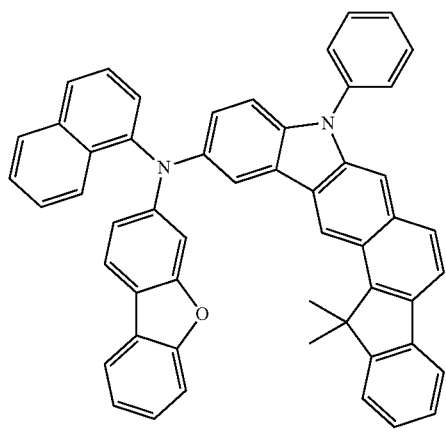
A 3-2-5
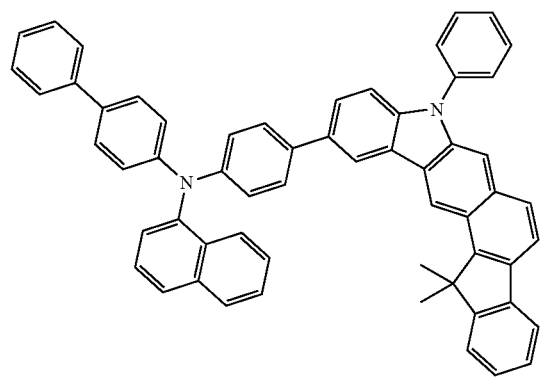
A 3-2-6
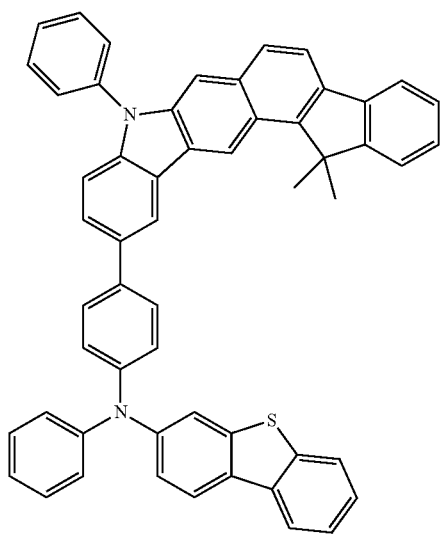
A 3-2-7
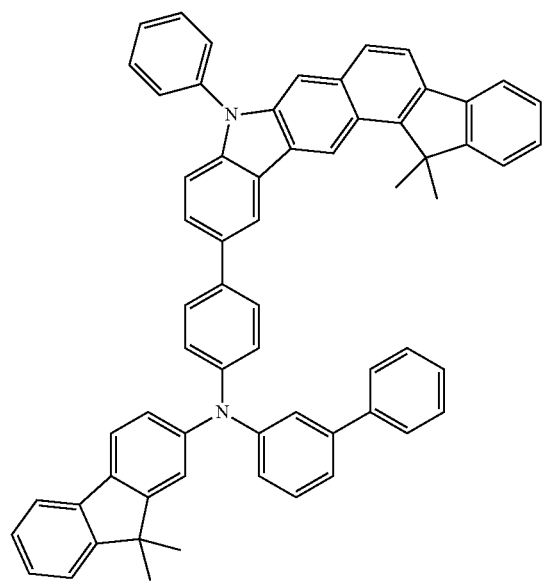

A 3-2-8
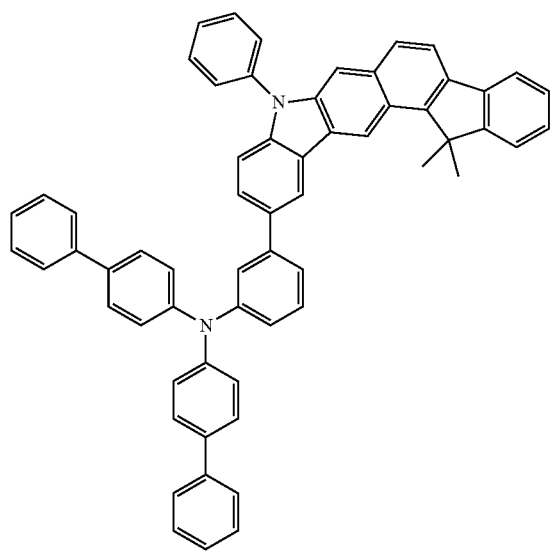
A 3-2-9
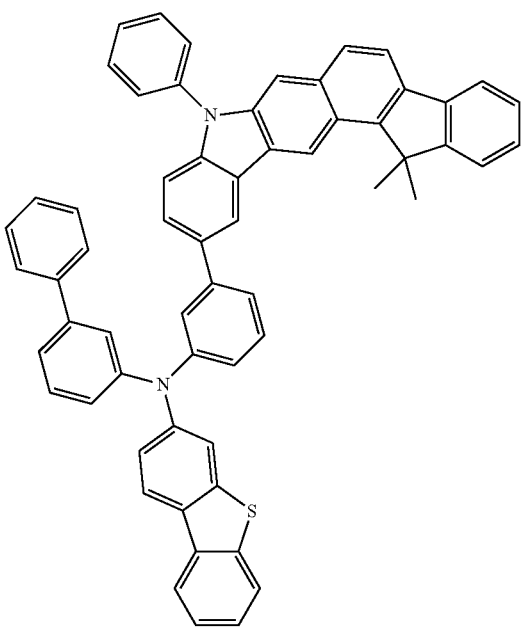
A 3-2-10
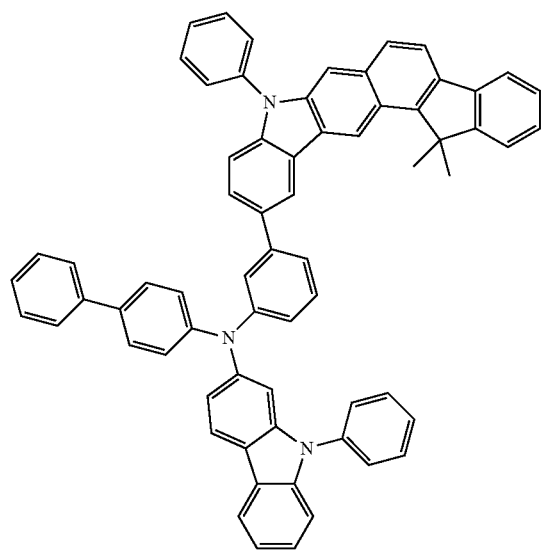
A 3-2-11
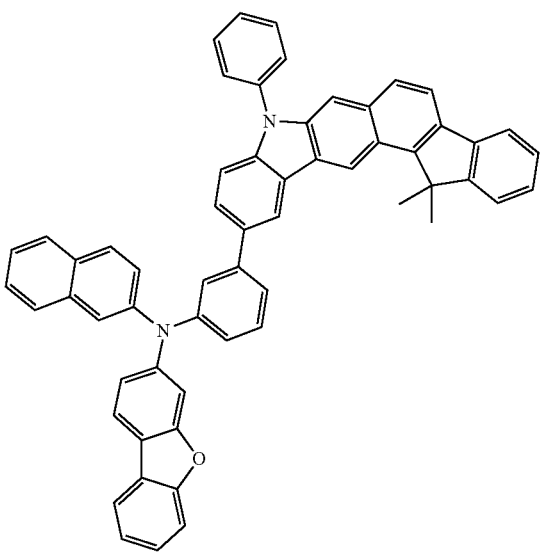

-continued
A 3-2-12
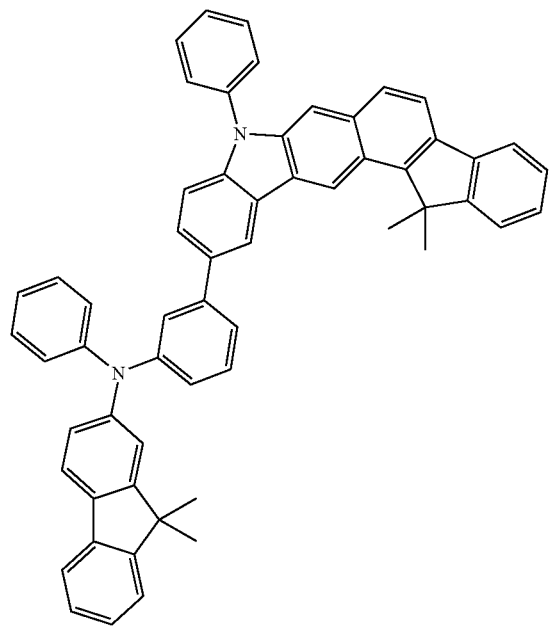
A 3-2-13
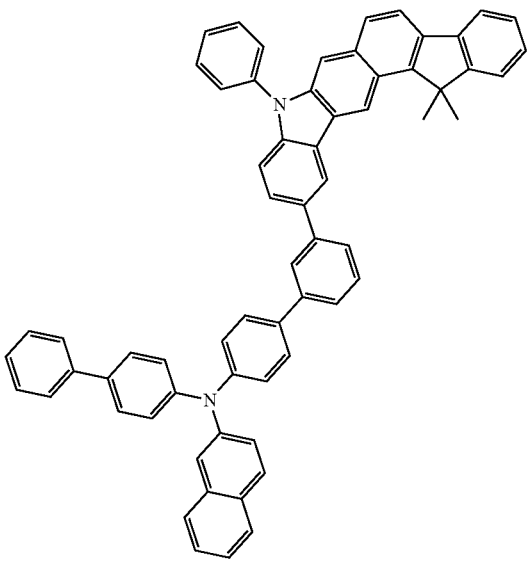
A 3-2-14
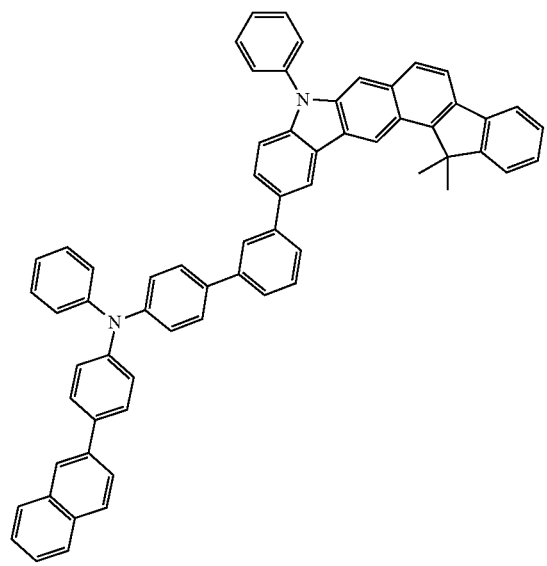
A 4-1-1
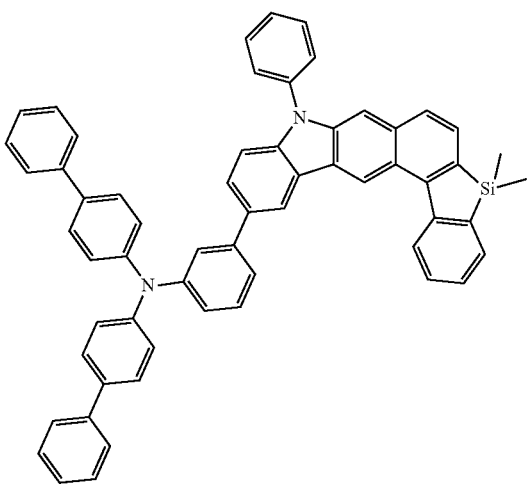

-continued
A 4-1-2
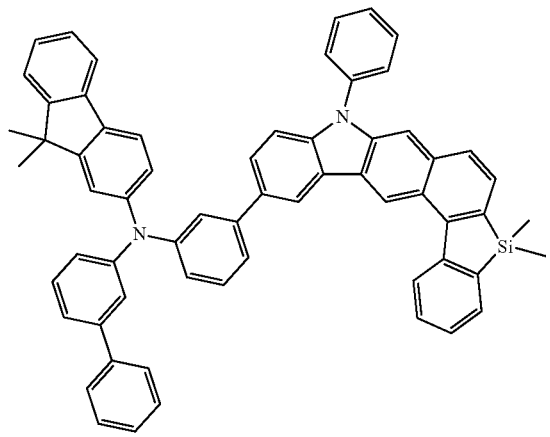
A 4-1-3
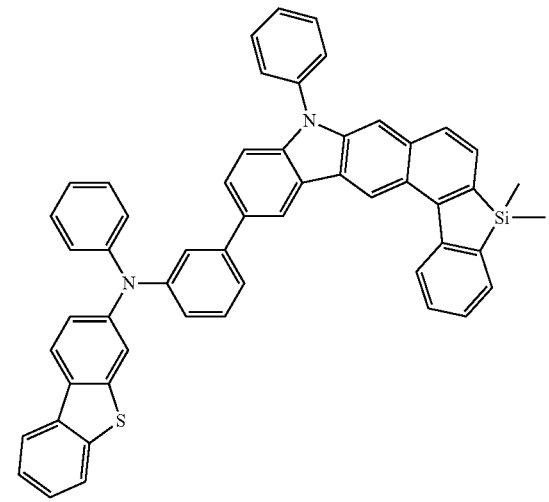
A 4-1-4
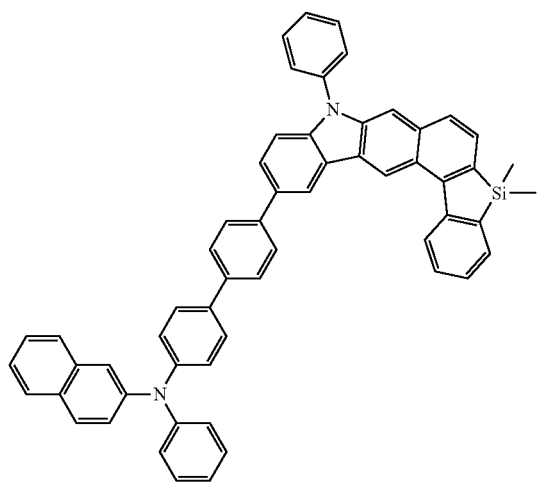
A 4-2-1
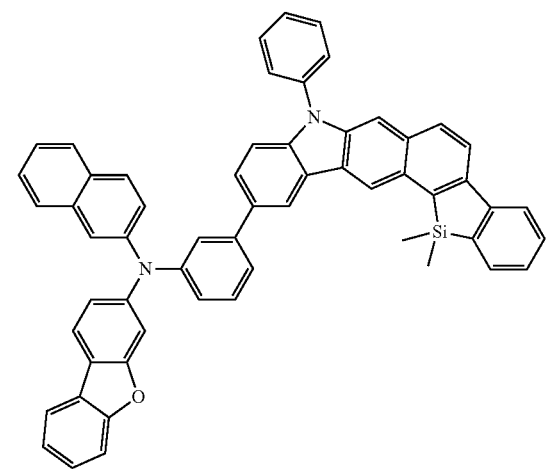
A 4-2-2
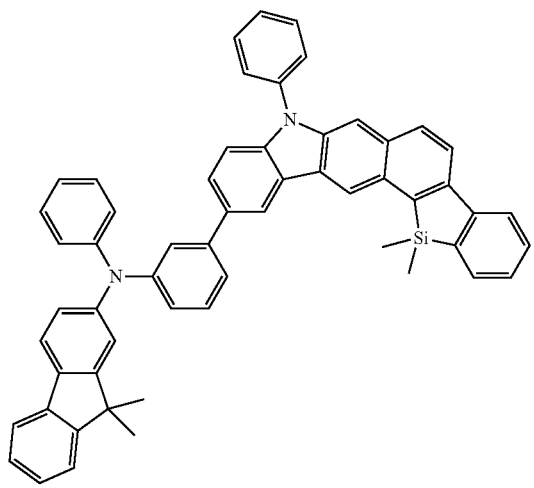
A 4-2-3
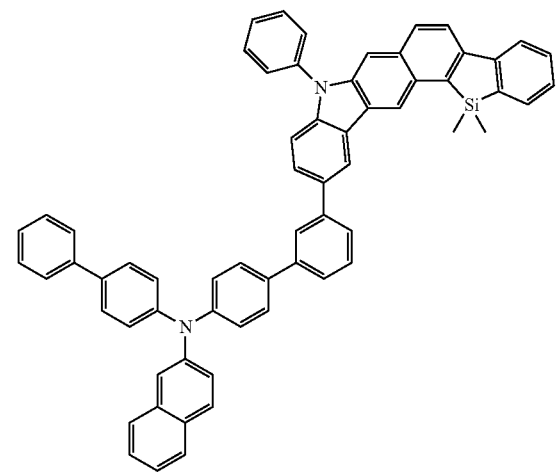

-continued
A 4-2-4
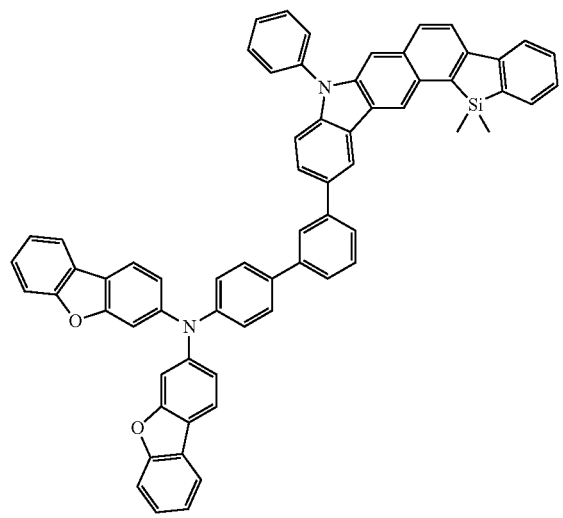
A 5-1-1
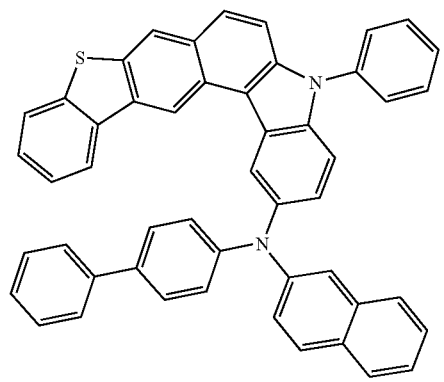
A 5-1-2
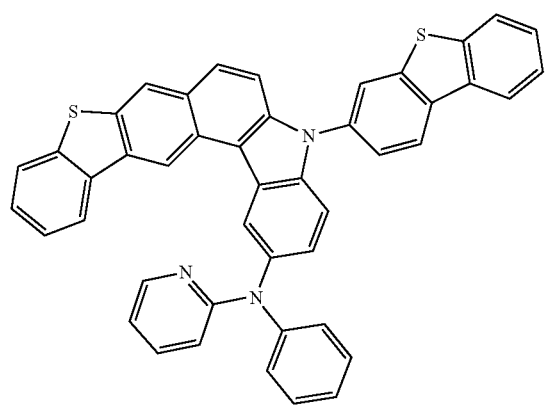
A 5-1-3
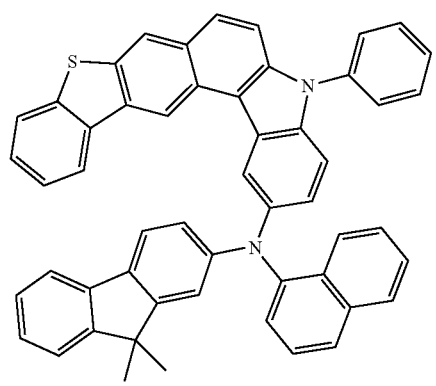
A 5-1-4
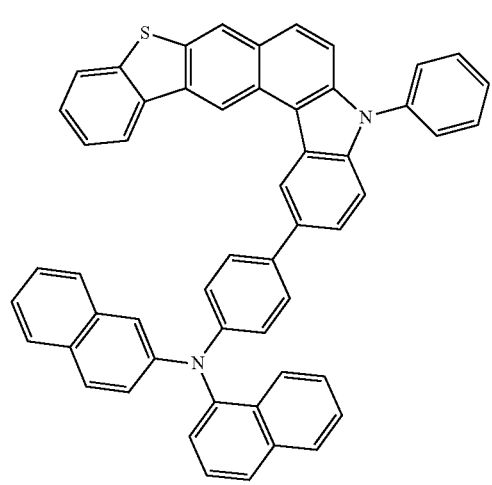
A 5-1-5
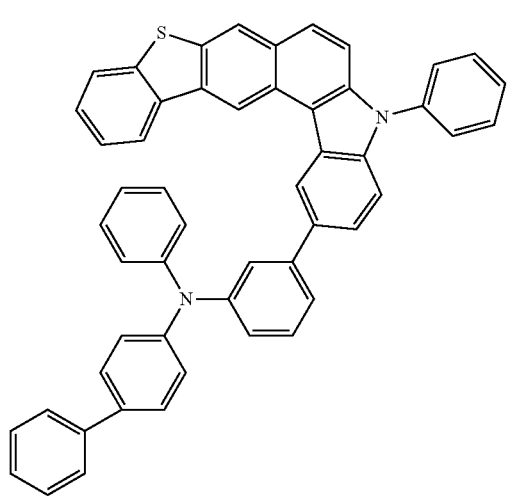

-continued
A 5-1-6
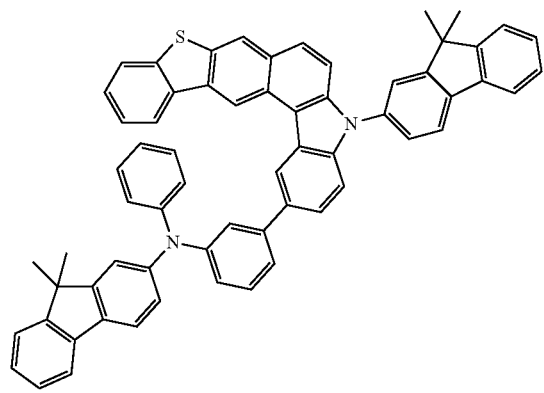
A 5-1-7
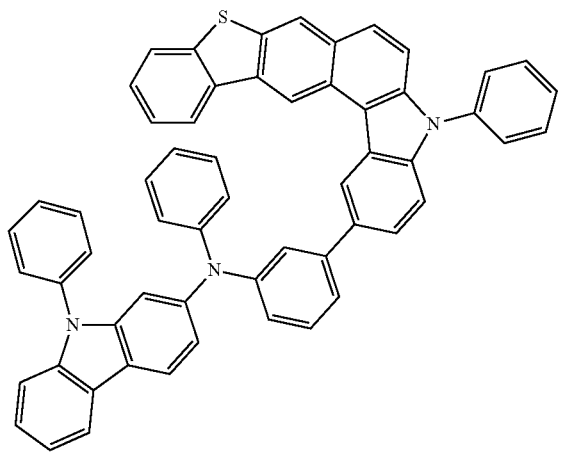
A 5-1-8
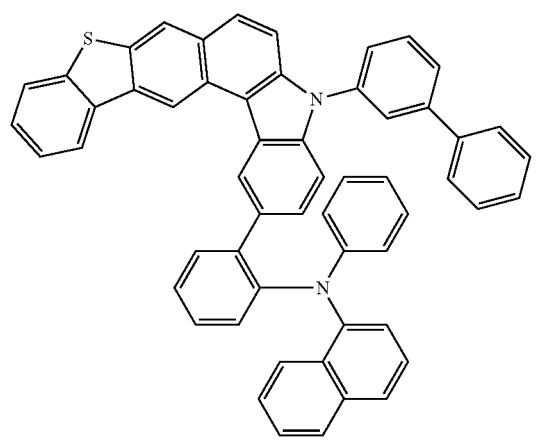
A 5-1-9
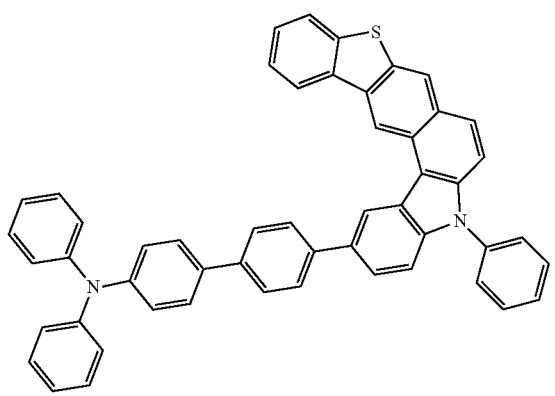
A 5-1-10
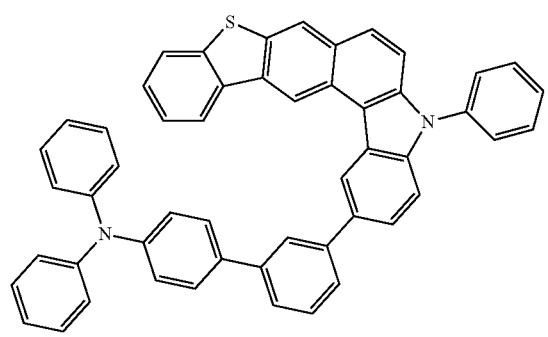
A 5-1-11
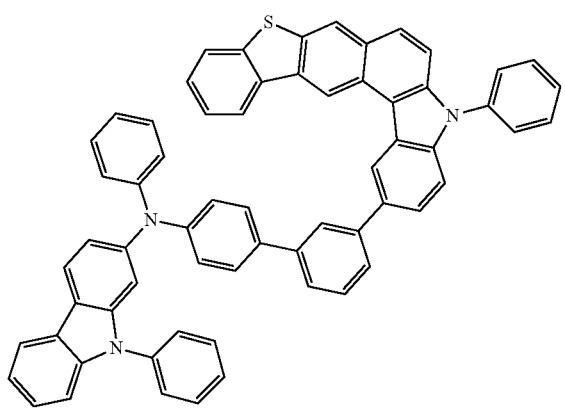

-continued
A 5-1-12
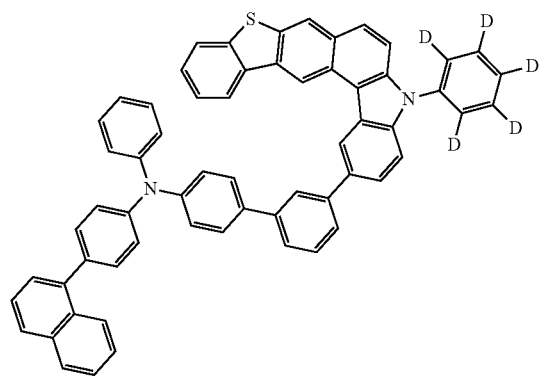
A 5-1-13
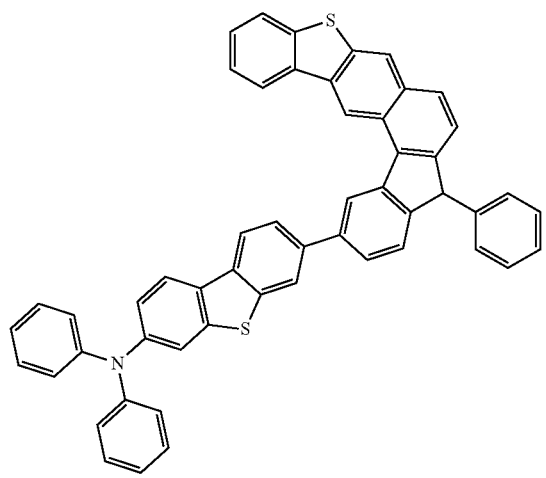
A 5-2-1
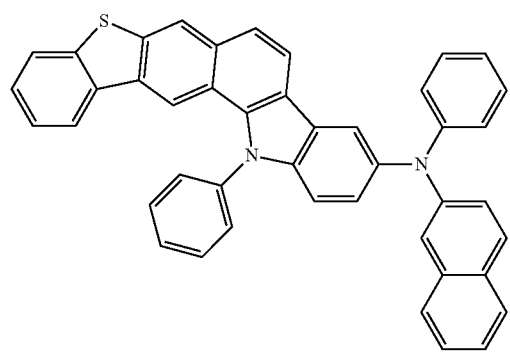
A 5-2-2
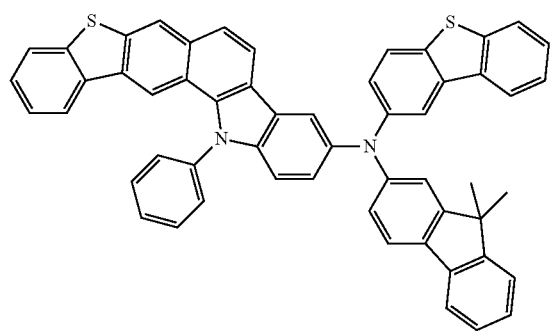
A 5-2-3
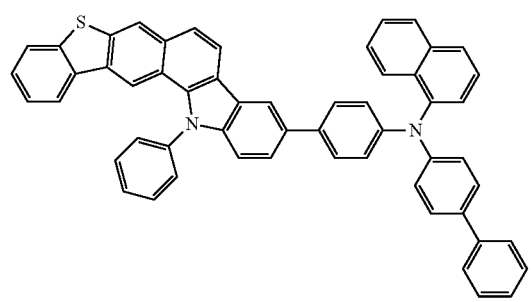
A 5-2-4
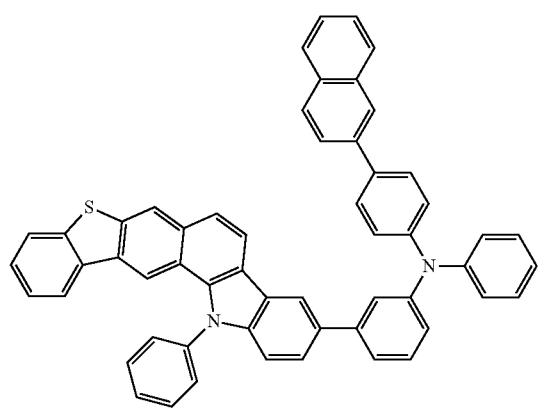

A 5-2-5
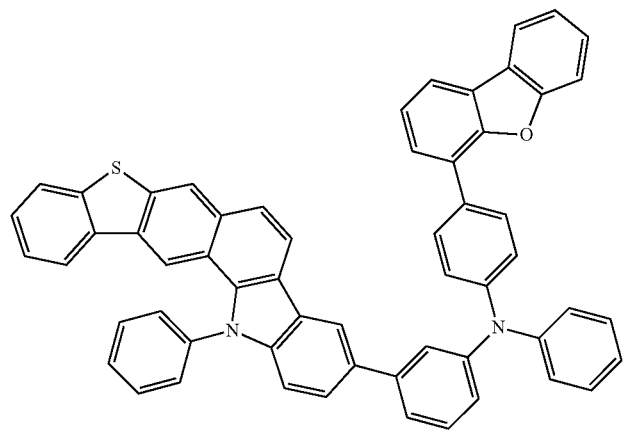
A 5-2-6
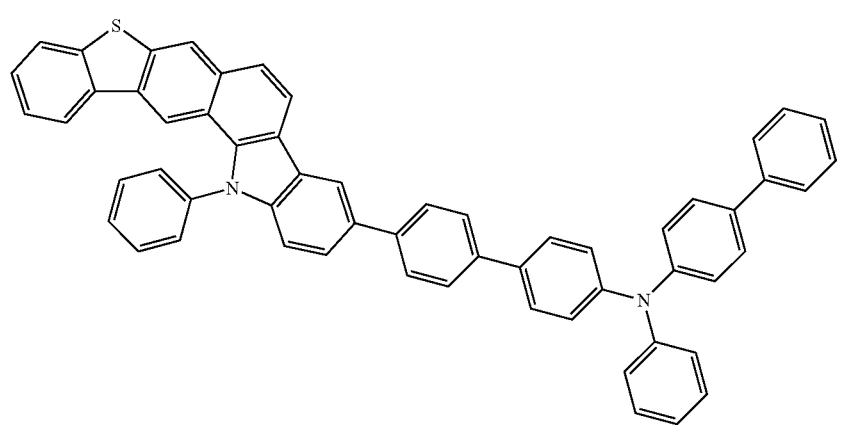
A 5-2-7
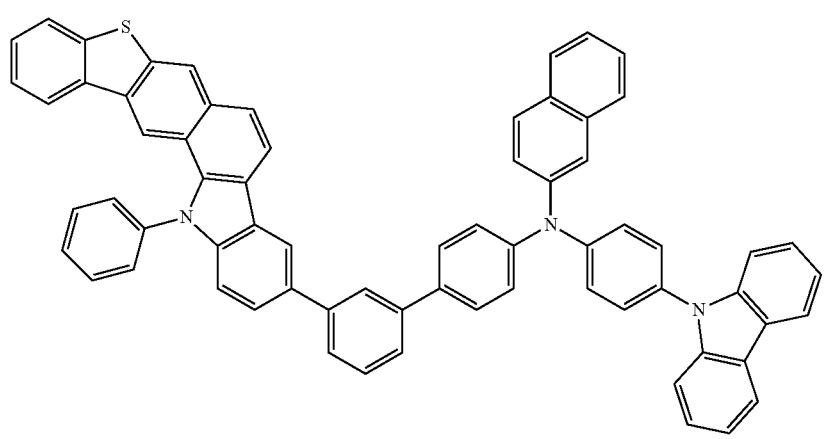

-continued
A 6-1-1
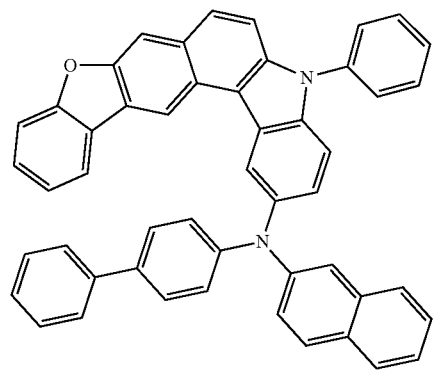
A 6-1-2
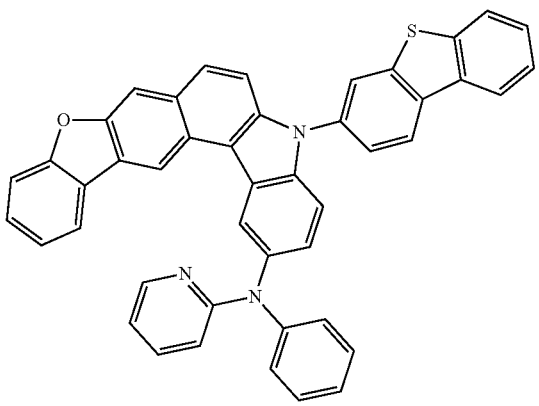
A 6-1-3
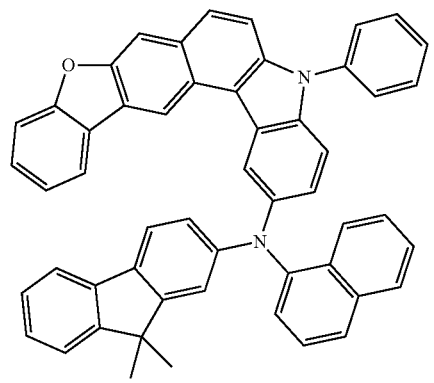
A 6-1-4
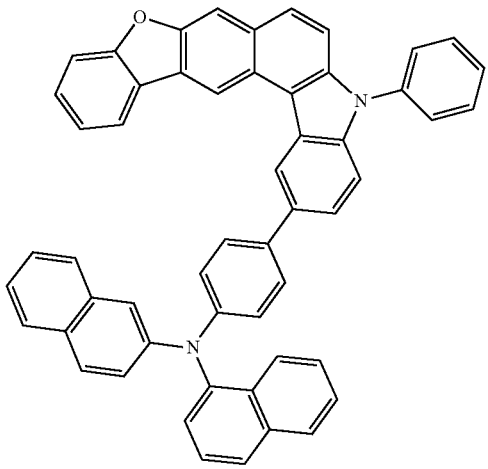
A 6-1-5
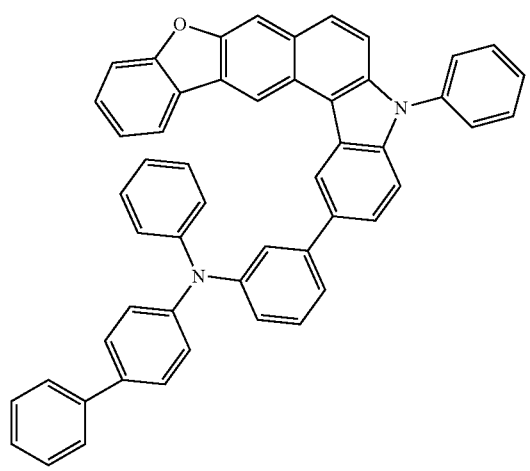
A 6-1-6
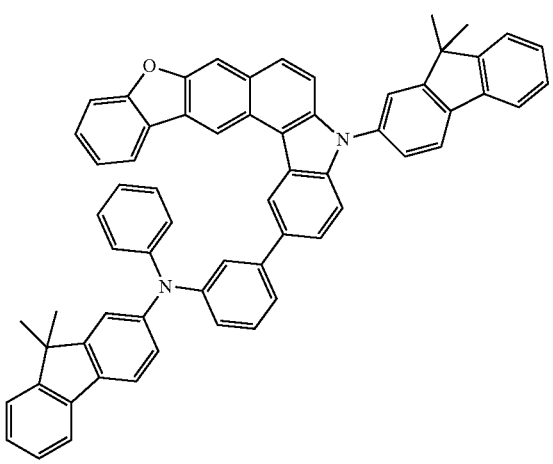

-continued
A 6-1-7
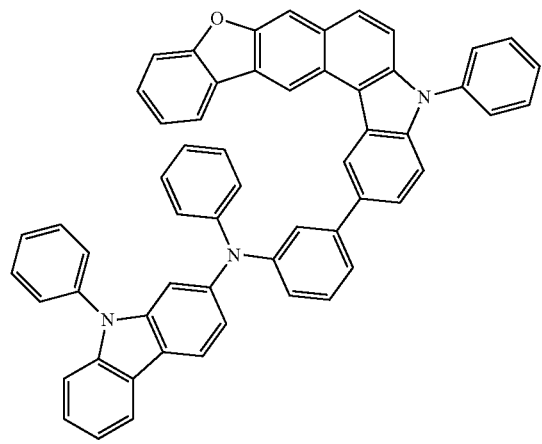
A 6-1-8
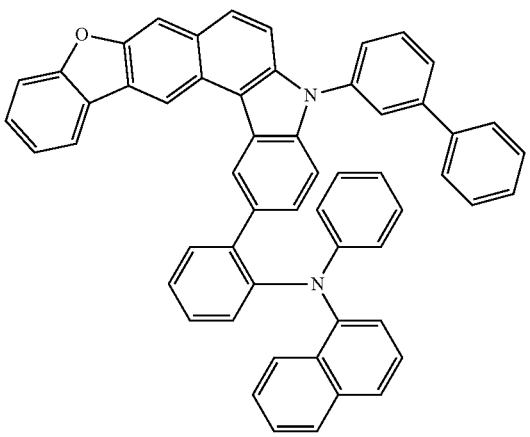
A 6-1-9
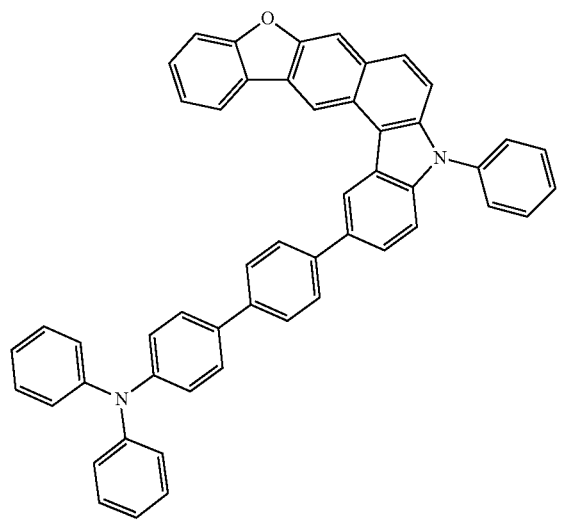
A 6-1-10
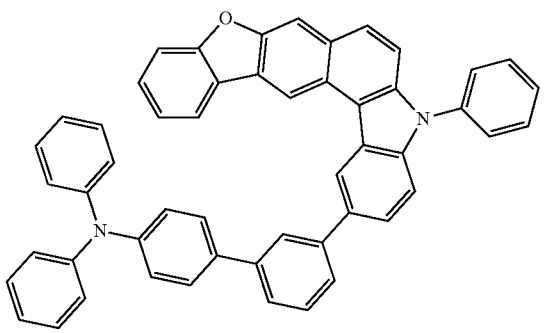
A 6-1-11
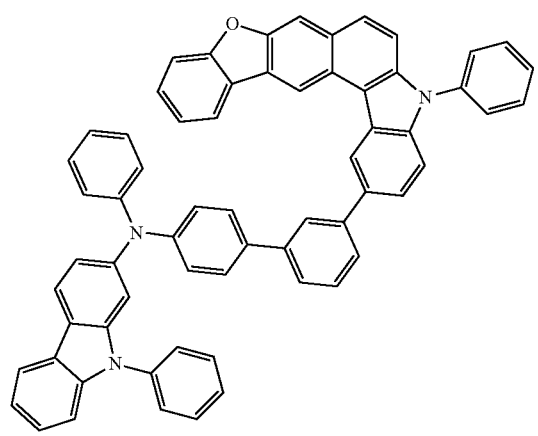
A 6-1-12
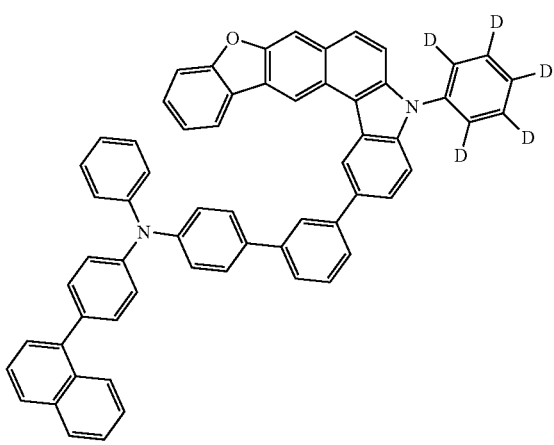

A 6-1-13
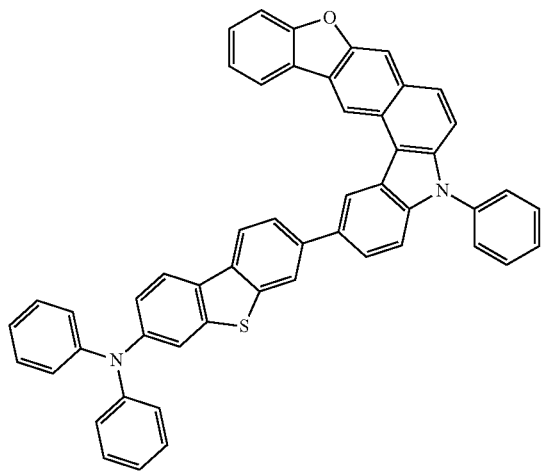
A 6-2-1
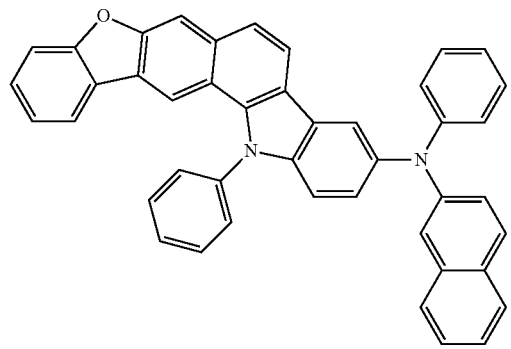
A 6-2-2
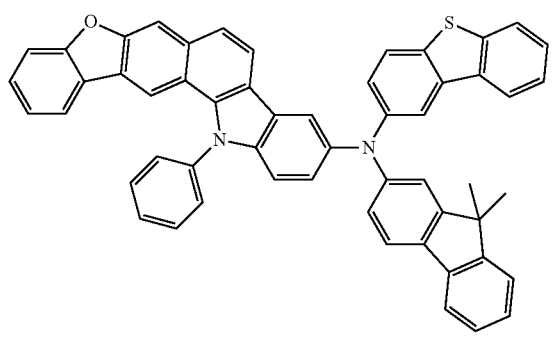
A 6-2-3
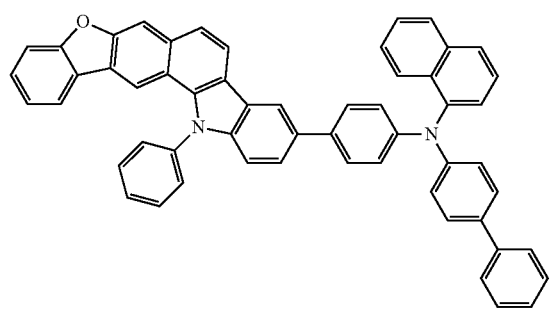
A 6-2-4
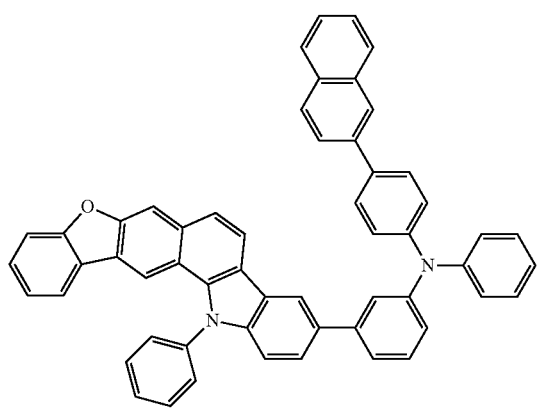
A 6-2-5
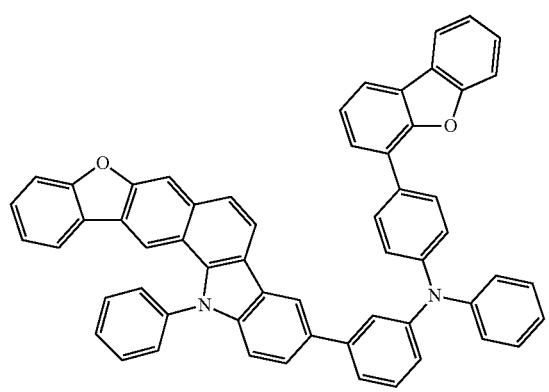

A 6-2-6

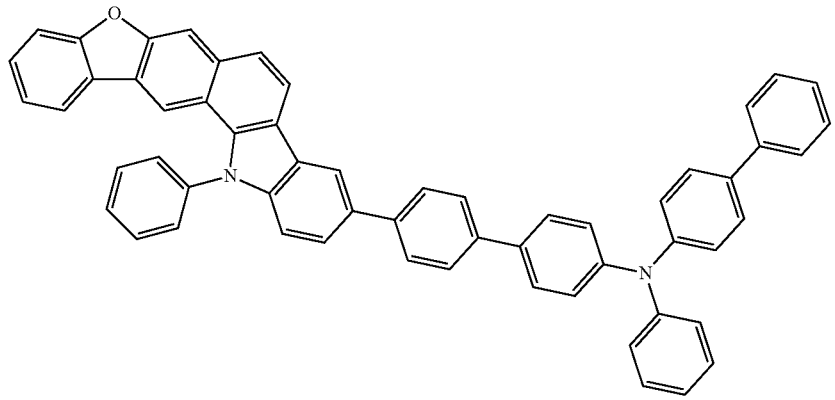

A 6-2-7

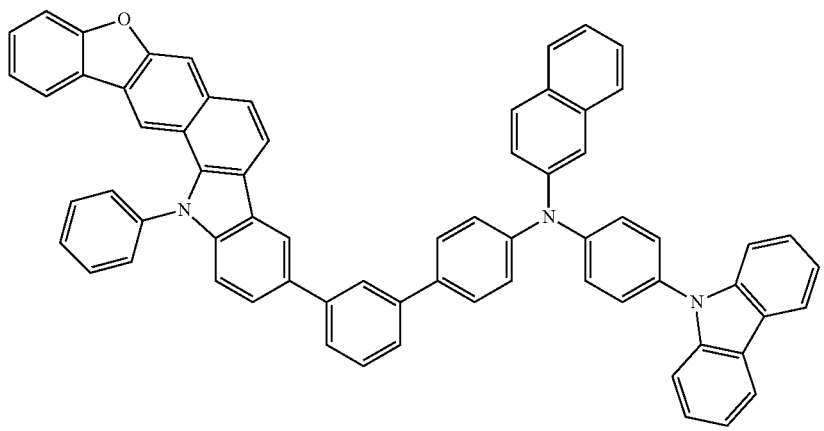

Referring to the FIGURE, the organic electric element (100) according to the present invention includes a first electrode (120) formed on a substrate (110), a second electrode (180), and an organic material layer including the compound represented by Formula 1 between the first electrode (120) and the second electrode (180). Here, the first electrode (120) may be an anode (positive electrode), and the second electrode (180) may be a cathode (negative electrode). In the case of an inverted organic electric element, the first electrode may be a cathode, and the second electrode may be an anode.

The organic material layer may include a hole injection layer (130), a hole transport layer (140), an emitting layer (150), an electron transport layer (160), and an electron injection layer (170) formed in sequence on the first electrode (120).

Although not shown, the organic electric element according to the present invention may further include a protective layer formed on at least one side of the first and second electrodes, which is a side opposite to the organic material layer.

Otherwise, even if the same core is used, the band gap, the electrical characteristics, the interface characteristics, and the like may vary depending on which substituent is bonded at which position, therefore the choice of core and the combination of sub-substituents associated therewith is also very important, and in particular, when the optimal combination of energy levels and T1 values and unique properties of materials(mobility, interfacial characteristics, etc.) of each organic material layer is achieved, a long life span and high efficiency can be achieved at the same time.

The organic electroluminescent device according to an embodiment of the present invention may be manufactured using a PVD (physical vapor deposition) method. For example, a metal or a metal oxide having conductivity or an alloy thereof is deposited on a substrate to form a cathode, and the organic material layer including the hole injection layer (130), the hole transport layer (140), the emitting layer (150), the electron transport layer (160), and the electron injection layer (170) is formed thereon, and then depositing a material usable as a cathode thereon can manufacture an organic electroluminescent device according to an embodiment of the present invention.

Accordingly, the present invention provides an organic electric element comprising a first electrode; a second electrode; and an organic material layer disposed between the first electrode and the second electrode, wherein the organic material layer contains a compound included in Formula (1).

Also the present invention provides an organic electric element wherein a compound according to Formula (1) may be contained in at least one layer of the hole injection layer, the hole transport layer, the emitting auxiliary layer, the emitting layer, wherein the compound includes a composition in which one or more compounds are mixed.

Further, the present invention includes the compound as a phosphorescent host material of the emitting layer, wherein the phosphorescent host of the emitting layer is used as a red phosphorescent host.

The present invention may further include a light efficiency enhancing layer formed on at least one of the opposite side to the organic material layer among one side of the first electrode, or one of the opposite side to the organic material layer among one side of the second electrode.

Also, in the present invention, the organic material layer is formed by one of a spin coating process, a nozzle printing process, an inkjet printing process, a slot coating process, a dip coating process or a roll-to-roll process, wherein the organic material layer comprises the compound as an electron transport material.

As another specific example, the present invention provides an organic electric element wherein the mixture of the same or different kinds of compounds represented by Formula (1) is used in the organic material layer.

The present invention also provides an electronic device including a display device including the organic electric element; and a control part driving the display apparatus.

According to another aspect, the present invention provides an electronic device wherein the organic electric element is at least one of an OLED, an organic solar cell, an organic photo conductor, an organic transistor and an element for monochromic or white illumination. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint(PMP), a remote controller, a navigation unit, a game player, various kinds of TVs, and various kinds of computers.

Hereinafter, synthesis examples of the compound represented by Formula (1) of the present invention and preparation examples of the organic electric element of the present invention will be described in detail by way of example, but are not limited to the following examples of the invention.

SYNTHESIS EXAMPLE

In Final products according to the present invention, Final product (1) is prepared by reacting Core and Sub 1 as shown in Reaction Scheme 1 below, and as shown in Reaction Scheme 2, the Core or Final Product (1) reacts with Sub 2 to produce Final Product (2), but is not limited thereto.

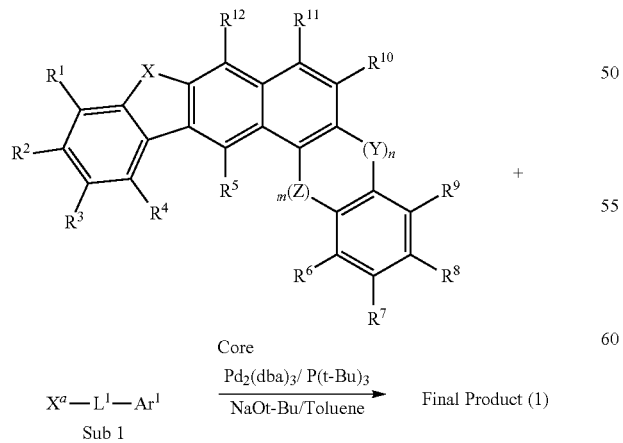

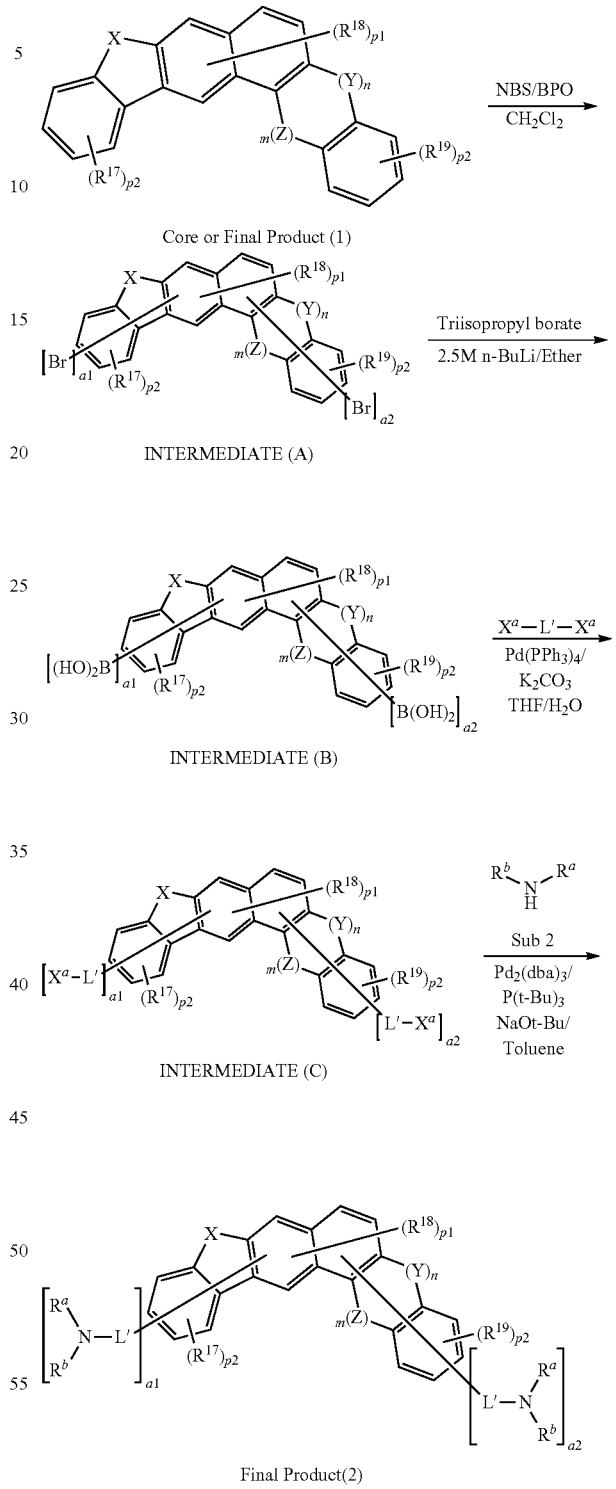

I. Synthesis Example of Core

The Core of the above Reaction Scheme 1 can be synthesized by the reaction path of the following Reaction Schemes 3 to 10, but is not limited thereto.

<Reaction scheme 3>
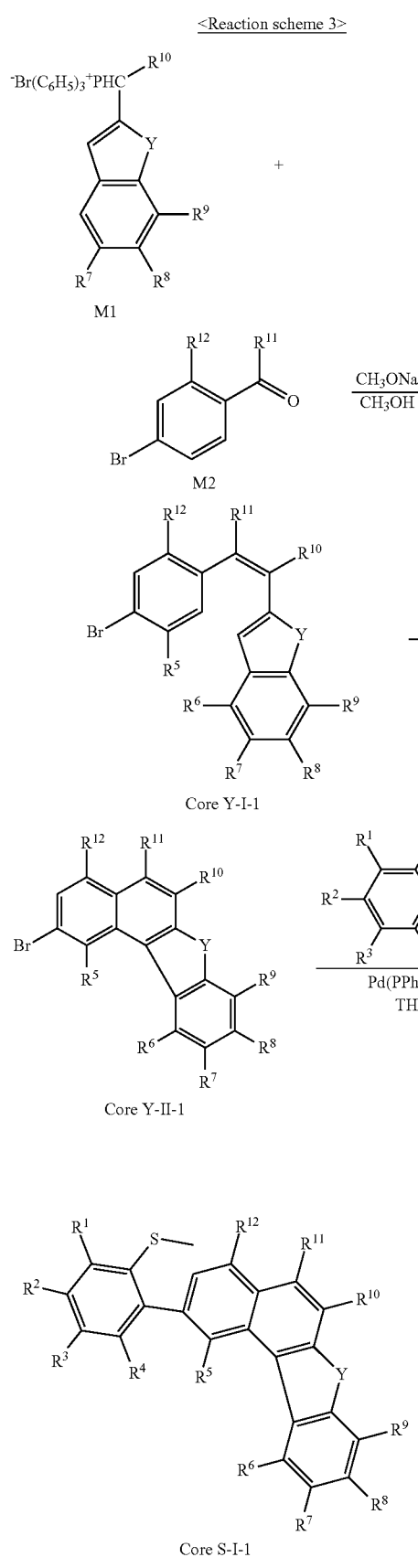
<Reaction scheme 4>
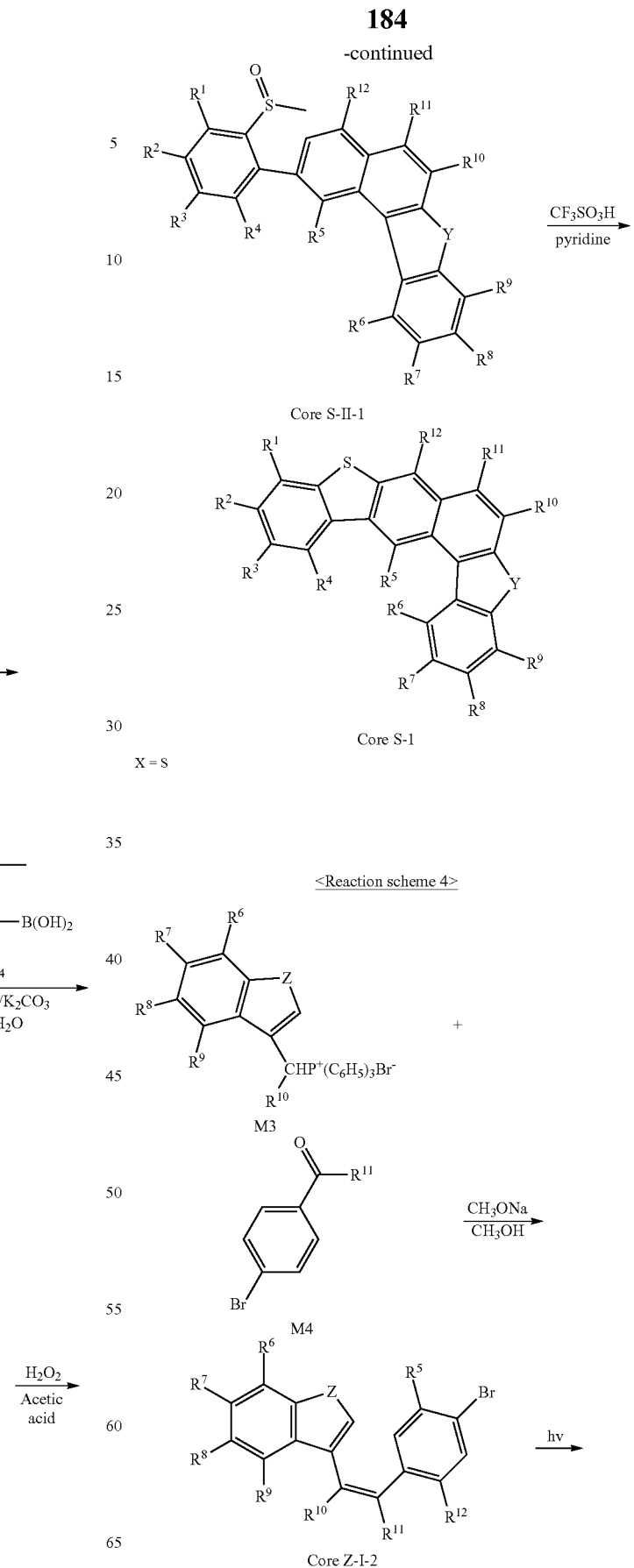

-continued
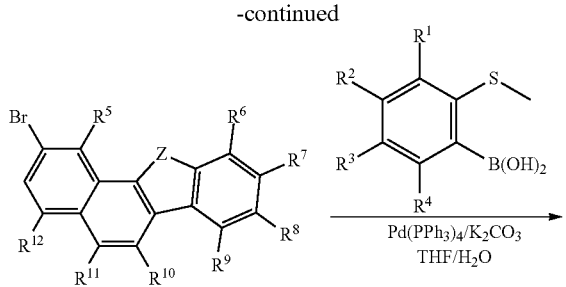
Core Z-II-2
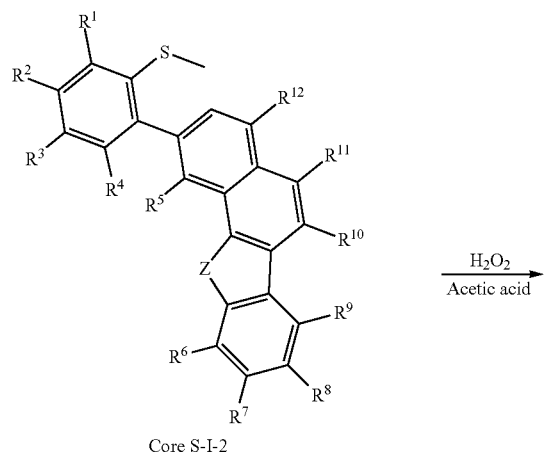
Core S-I-2
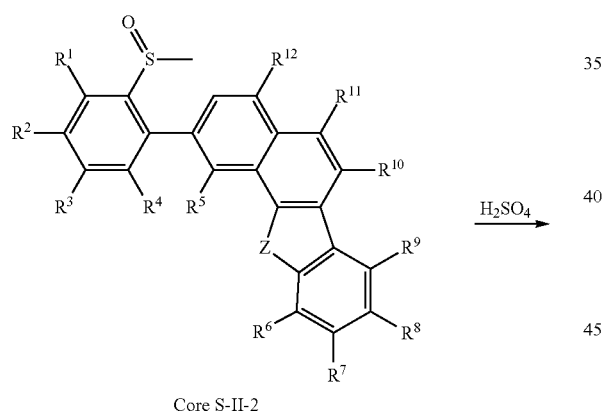
Core S-II-2
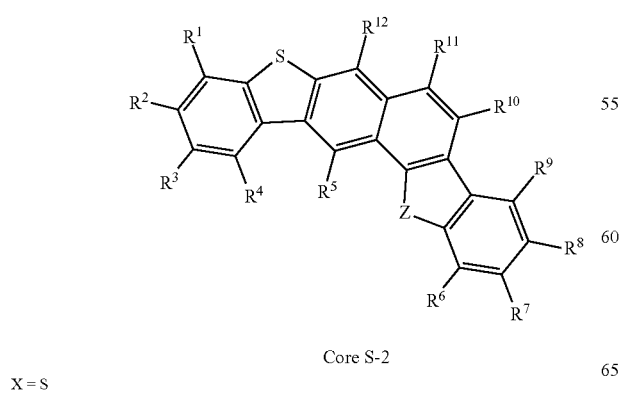
Core S-2
X = S
<Reaction scheme 5>
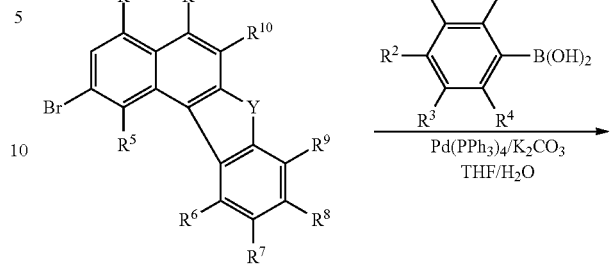
Core Y-II-1
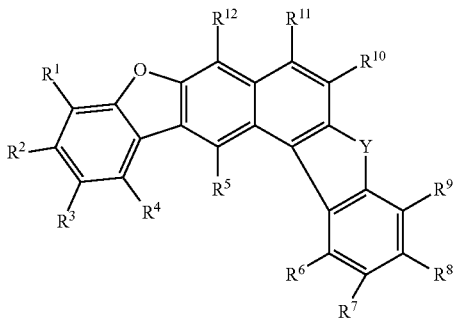
Core O-I-1
Core O-1
X = O
<Reaction scheme 6>
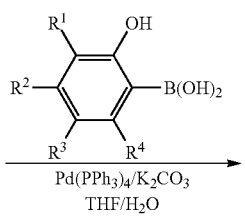
Core Z-II-2

-continued
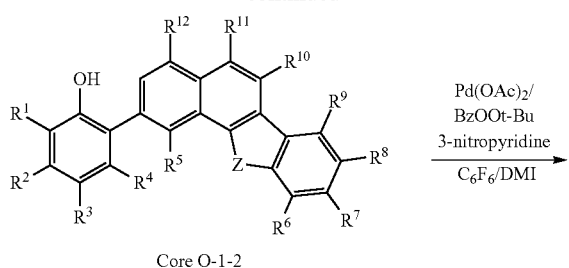
Core O-1-2
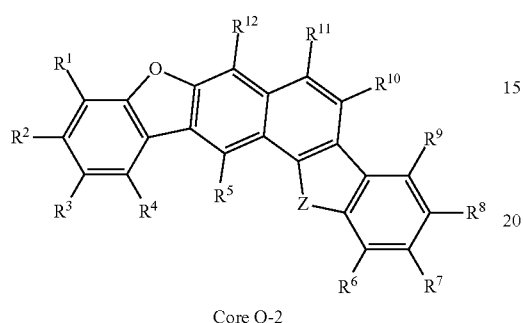
Core O-2
X = O
-continued
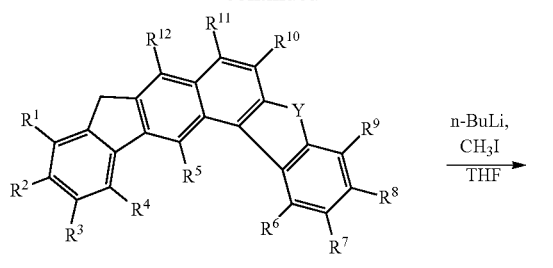
Core C-1-III
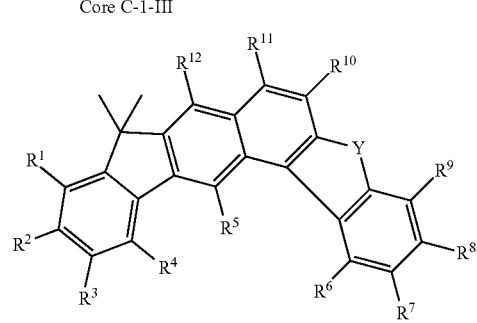
Core C-1
X = O
<Reaction scheme 7>
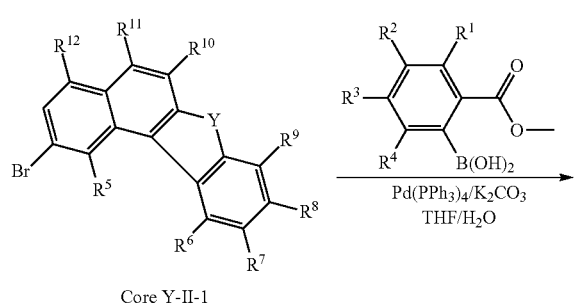
<Reaction scheme 8>
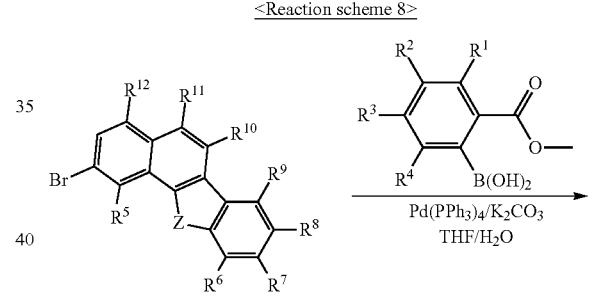
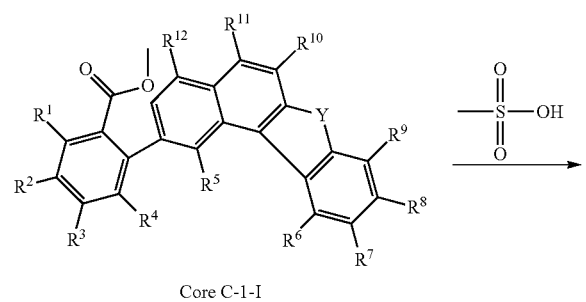
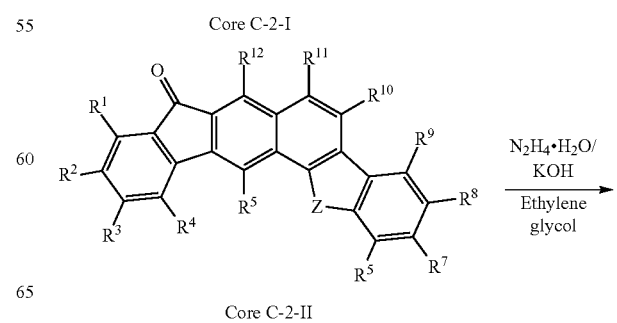

189
-continued
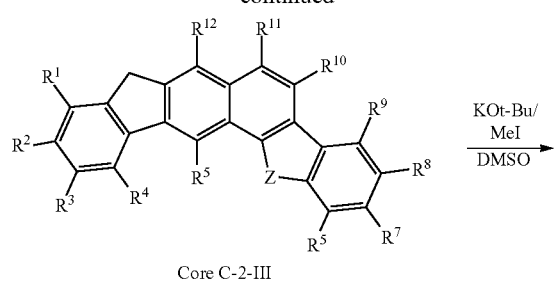
Core C-2-III
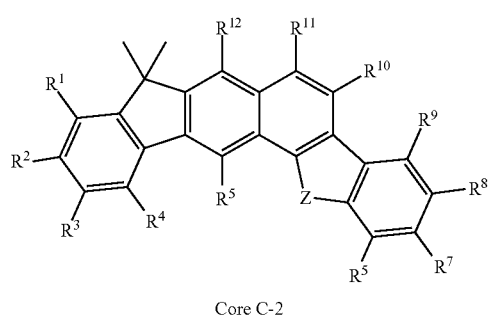
Core C-2
X = C
<Reaction scheme 9>
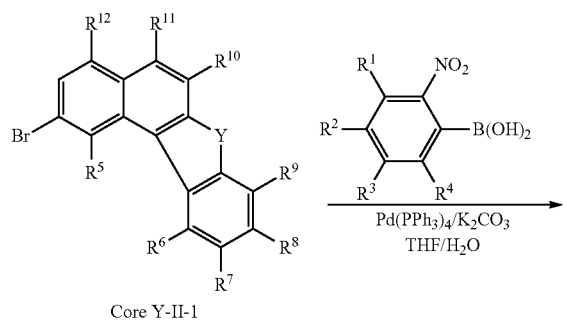
Core Y-II-1
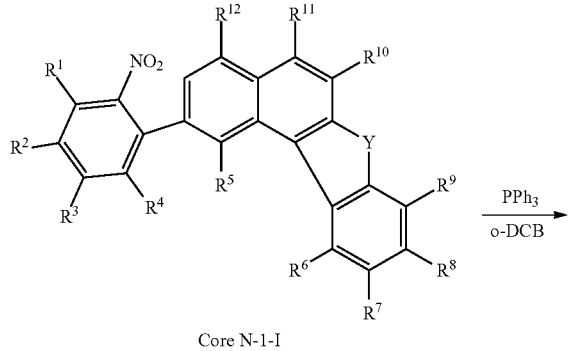
Core N-1-I
190
-continued
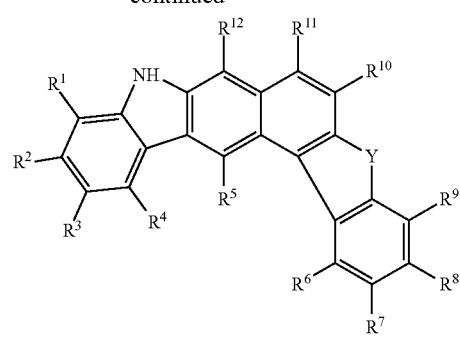
Core N-1
X = N
<Reaction scheme 10>
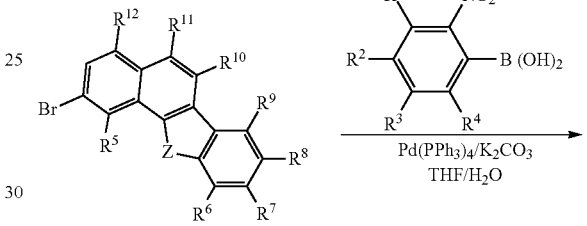
Core Y-II-2
Core N-2-I
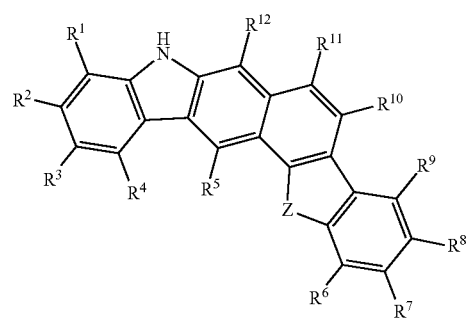
Core N-2
X = N
Synthesis Examples of specific compounds belonging to Core are as follows.

Synthesis Example of Core 1-52

When X=S and Y=N

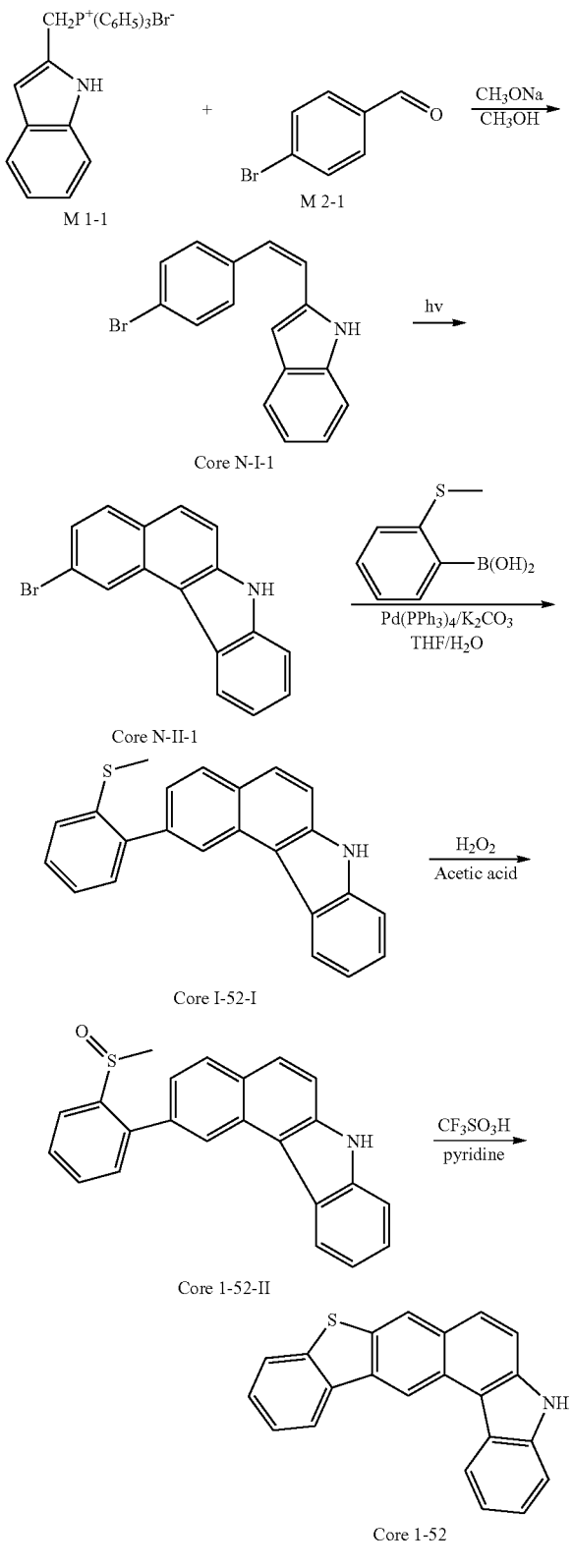

1) Synthesis of Core N-I-1

In a round bottom flask, M 1-1 (200 g, 423.41 mmol) and M 2-1 (78.34 g, 423.41 mmol) were placed in 2540 ml of anhydrous methanol and stirred. To this solution, sodium methoxide (22.87 g, 423.41 mmol) was added and the mixture was stirred and refluxed at 40° C. for 24 hours. After extraction with Dichrolomethane and water, the organic layer was dried and concentrated, and the resulting organic material was separated by silicagel column chromatography and recrystallization to obtain 90.29 g of the product. (yield: 72%)

2) Synthesis of Core N-II-1

In a round bottom flask, Core N-I-1 (90.29 g, 302.80 mmol), iodine (84.54 g, 333.08 mmol) were placed in 1211 m of dry benzene and UV treatment is applied during bubbling of the solution with a UV lamp and monitored by TLC. When the reaction was complete, the solvent was removed under reduced pressure and was recrystallized from ethanol to obtain 37.66 g of the product. (yield: 42%)

3) Synthesis of Core 1-52-I (2-(methylthio)phenyl)boronic acid (21.37 g, 127.16 mmol), Core N-II-1 (37.66 g, 127.16 mmol), tetrakis(triphenylphophine)palladium(0) (4.41 g, 3.82 mmol), $K_2CO_3$ (52.72 g, 381.48 mmol), 560 ml of THF, 280 ml of water were added and stirred at 70° C. When the reaction was complete, the reaction mixture was extracted with $CH_2Cl_2$ and wiped with water, and a small amount of water was removed with anhydrous $MgSO_4$, and after filtration under reduced pressure, the organic solvent was concentrated and the resulting product was recrystallized using $CH_2Cl_2$ and a hexane solvent to obtain 35.83 g of the product. (yield: 83%)

4) Synthesis of Core 1-52-II

Core 1-52-I (35.83 g, 105.55 mmol), $H_2O_2$ (23.35 g, 263.88 mmol), acetic acid (528 ml) were added in a round bottom flask and stirred at room temperature. After the reaction was completed, acetic acid was removed and water was added to obtain a solid, and the solid was dissolved in $CH_2Cl_2$, and was separated by silicagel column chromatography and concentrated to obtain 33.02 g of the product. (yield: 88%)

5) Synthesis of Core 1-52

The resulting Core 1-52-II (33.02 g, 92.89 mmol) was dissolved in an excess amount of $H_2SO_4$ (186 ml) into a round bottom flask and stirred at 40° C. for 3 days. When the reaction was completed, the solution was neutralized to pH 8 to 9 with 0.2 N NaOH aqueous solution. The water was removed by vacuum filtration, and the solution was extracted with $CH_2Cl_2$ and concentrated and was separated by silicagel column chromatography and recrystallization to obtain 25.53 g of the product. (yield: 85%)

Synthesis Example of Core 1-38

When X=S, Z=O

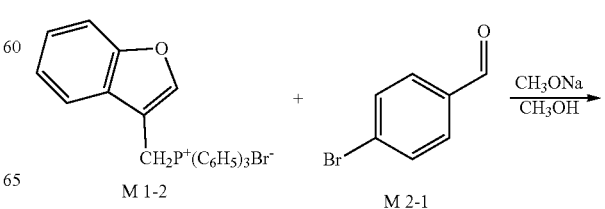

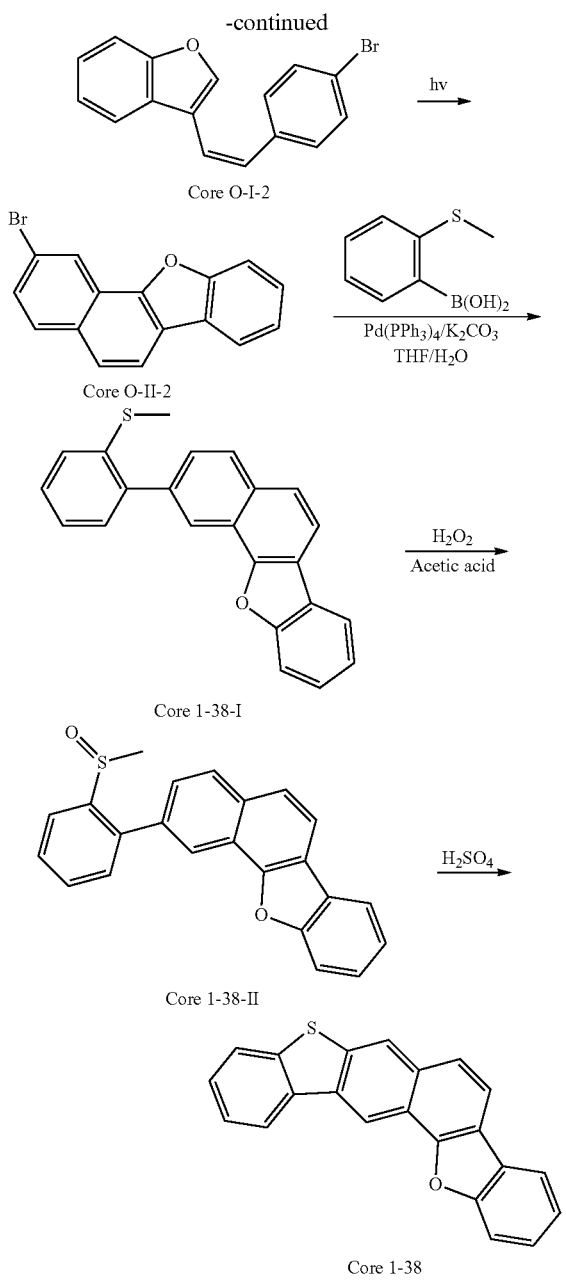

Core O-I-2

Core O-II-2

Core 1-38-I

Core 1-38-II

Core 1-38 were carried out in the same procedure as described in the synthesis method of Core 1-52-I to obtain 36.67 g of the product. (yield: 85%).

4) Synthesis of Core 1-38-II

Core 1-38-I (38.09 g, 111.89 mmol), $H_2O_2$ (24.75 g, 279.71 mmol), acetic acid (559 ml) were carried out in the same procedure as described in the synthesis method of Core 1-52-II to obtain 33.50 g of the product. (yield: 84%).

5) Synthesis of Core 1-38

Core 1-38-II (33.50 g, 93.98 mmol), excess amount of $H_2O_2$ (188 mmol) were carried out in the same procedure as described in the synthesis method of Core 1-52 to obtain 24.70 g of the product. (yield: 81%).

Synthesis Example of Core 1-42

When X=O, Y=N

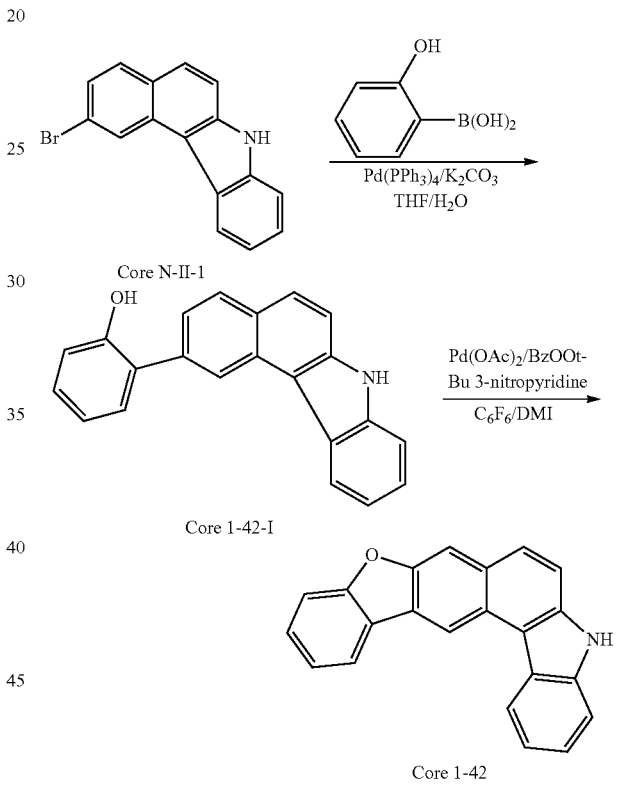

Core N-II-1

Core 1-42-I

Core 1-42

1) Synthesis of Core O-I-2

M 1-2 (200 g, 422.53 mmol), M 2-1 (78.18 g, 422.53 mmol), anhydrous methanol (2535 ml), Sodium methoxide (22.83 g, 422.53 mmol) were carried out in the same procedure as described in the synthesis method of Core N-I-1 to obtain 93.54 g of the product. (yield: 74%).

2) Synthesis of Core O-II-2

Core O-I-2 (93.54 g, 312.68 mmol), iodine (87.30 g, 343.94 mmol) were added in 1251 ml of dry benzene, and the same procedure as described in the synthesis method of Core N-II-1 with a UV lamp was carried out to obtain 38.09 g of the product. (yield: 41%).

3) Synthesis of Core 1-38-I (2-(methylthio)phenyl)boronic acid (21.29 g, 126.74 mmol), Core O-II-2 (37.66 g, 126.74 mmol), tetrakis(triphenylphophine)palladium(0) (4.39 g, 3.80 mmol), $K_2CO_3$ (52.55 g, 380.21 mmol), THF (558 ml) and 279 ml of water 1) Synthesis of Core 1-42-I (2-hydroxyphenyl)boronic acid (13.97 g, 101.3 mol), Core N-II-1 (30.00 g, 101.3 mmol), Pd(PPh$_3$)$_4$ (3.51 g, 3.04 mmol), $K_2CO_3$ (42.00 g, 303.89 mmol), THF (446 ml), water (223 ml) were carried out in the same procedure as described in the synthesis method of Core 1-52-I to obtain 27.26 g of the product. (yield: 87%).

2) Synthesis of Core 1-42

In a round bottom flask, Core 1-42-I (27.26 g, 88.12 mmol), Palladium acetate (0.20 g, 0.88 mmol), 3-nitropyridine (21.87 g, 176.24 mmol) were added and dissolved in solvent 17.62 ml ($C_6H_6$: DMI=3:2), and BzOOt-Bu (0.17 g, 0.88 mmol) was added and stirred at 90° C. for 4 hours. When the reaction was completed, the reaction mixture was extracted with $CH_2Cl_2$ and water. The organic layer was dried over $MgSO_4$ and concentrated. The resulting compound was separated by silicagel column chromatography and recrystallization to obtain 11.37 g of the product (yield: 42%).

Synthesis Example of Core 1-53

When X=O, Y=N

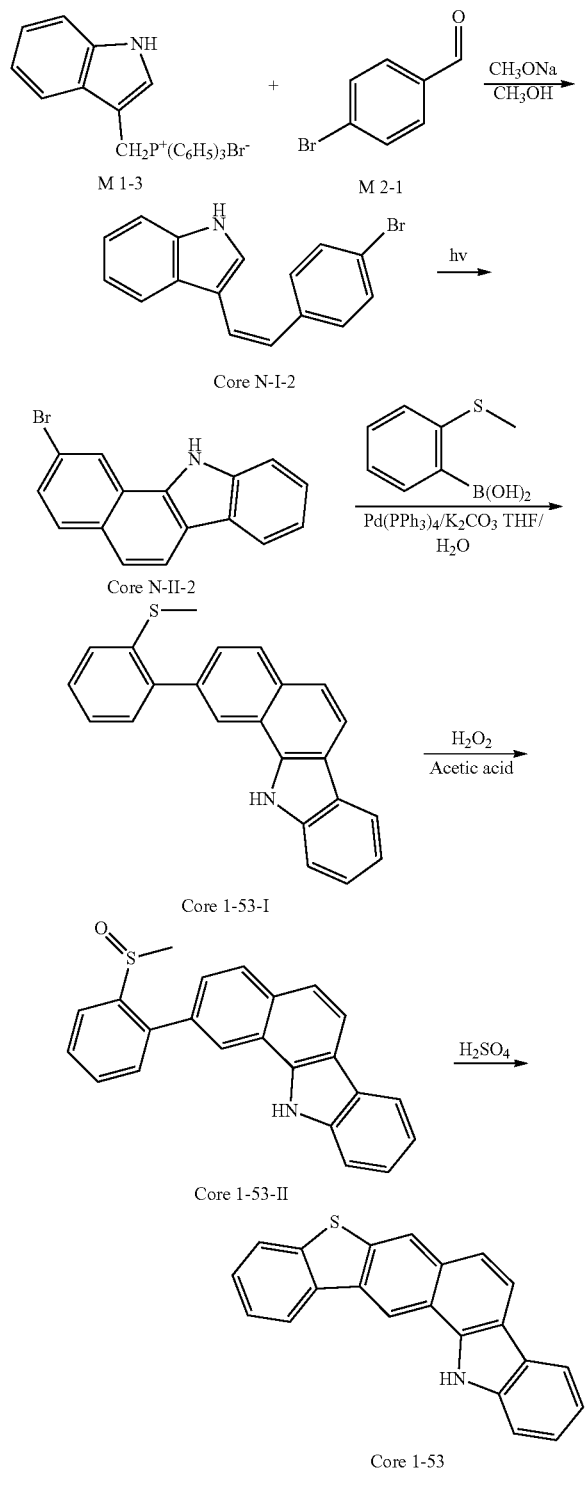

Core N-I-2

Core N-II-2

Core 1-53-I

Core 1-53-II

Core 1-53

1) Synthesis of Core N-I-2

M 1-3 (200 g, 423.41 mmol), M 2-1 (78.34 g, 423.41 mmol), anhydrous methanol (2540 ml), Sodium methoxide (22.87 g, 423.41 mmol) were carried out in the same procedure as described in the synthesis method of Core N-I-1 to obtain 89.64 g of the product. (yield: 71%).

2) Synthesis of Core N-II-2

Core N-I-2 (89.64 g, 300.62 mmol), iodine (83.93 g, 330.69 mmol), dry benzene (1203 ml) were carried out in the same procedure as described in the synthesis method of Core N-II-1 with a UV lamp to obtain 39.31 g of the product. (yield: 44%).

3) Synthesis of Core 1-53-I (2-(methylthio)phenyl)boronic acid (22.30 g, 132.73 mmol), Core N-II-2 (39.31 g, 132.73 mmol), Pd(PPh$_3$)$_4$ (4.60 g, 3.98 mmol), K$_2$CO$_3$ (55.03 g, 398.20 mmol), THF (584 ml), and water (292 ml) were carried out in the same procedure as described in the synthesis method of Core 1-52-I to obtain 39.20 g of the product. (yield: 87%).

4) Synthesis of Core 1-53-II

Core 1-53-I (39.20 g, 115.48 mmol), H$_2$O$_2$ (25.55 g, 288.70 mmol), acetic acid (577 ml) were carried out in the same procedure as described in the synthesis method of Core 1-52-II to obtain 33.25 g of the product. (yield: 81%).

5) Synthesis of Core 1-53

The resulting Core 1-52-II (33.25 g, 93.54 mmol), excess amount of H$_2$SO$_4$ (187 ml) were carried out in the same procedure as described in the synthesis method of Core 1-52 to obtain 23.67 g of the product. (yield: 78%).

Synthesis Example of Core 1-39

When X=O, Y=C

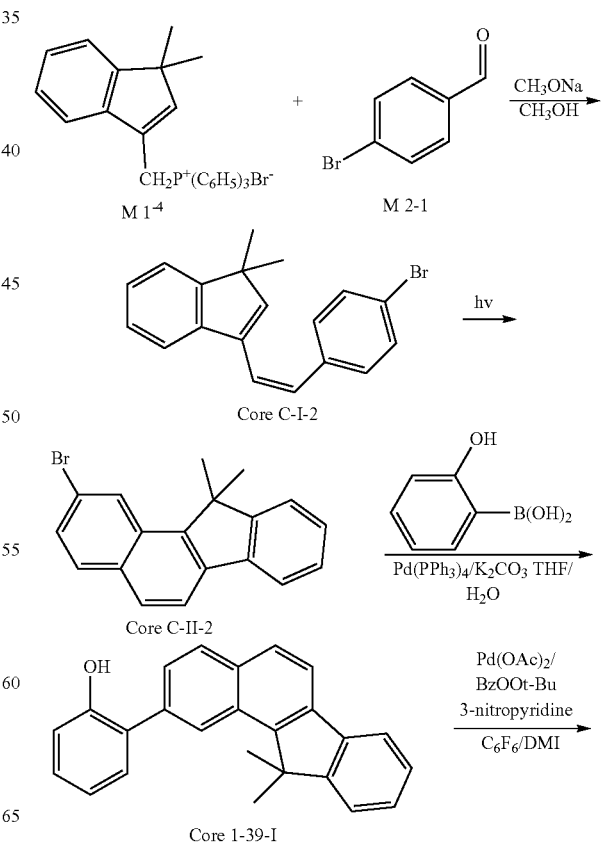

Core C-I-2

Core C-II-2

Core 1-39-I

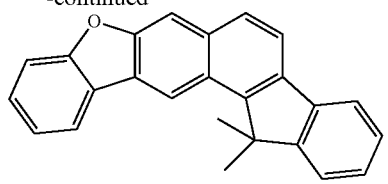

Core 1-39

1) Synthesis of Core C-I-2

M 1-4 (200 g, 400.46 mmol), M 2-1 (74.09 g, 400.46 mmol), anhydrous methanol (2402 ml), sodium methoxide (21.63 g, 400.46 mmol) were carried out in the same procedure as described in the synthesis method of Core N-I-1 to obtain 89.87 g of the product. (yield: 69%).

2) Synthesis of Core C-II-2

Core C-I-2 (89.87 g, 276.32 mmol), iodine (77.15 g, 303.95 mmol), dry benzene (1105 ml) were carried out in the same procedure as described in the synthesis method of Core N-II-1 with a UV lamp to obtain 34.89 g of the product. (yield: 39%).

3) Synthesis of Core 1-39-I (2-hydroxyphenyl)boronic acid (14.89 g, 107.94 mmol), Core C-II-2 (34.89 g, 107.94 mmol), Pd(PPh$_3$)$_4$ (3.74 g, 3.24 mmol), K$_2$CO$_3$ (44.76 g, 323.83 mmol), THF (475 ml) and water (237 ml) were carried out in the same procedure as described in the synthesis method of Core 1-52-I to obtain 31.23 g of the product. (yield: 86%).

4) Synthesis of Core 1-39

Core 1-39-I (31.23 g, 92.83 mmol), Palladium acetate (0.21 g, 0.93 mmol), 3-nitropyridine (23.04 g, 185.66 mmol), solvent 18.57 ml (C$_6$H$_6$: DMI=3:2), BzOOt-Bu (0.18 g, 0.93 mmol) were carried out in the same procedure as described in the synthesis method of Core 1-42 to obtain 12.42 g of the product. (yield: 40%).

Synthesis Example of Core 1-29

When X=C, Y=S

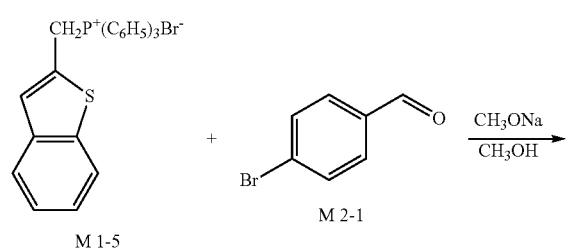

M 1-5     M 2-1

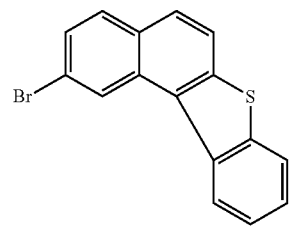

Core S-II-1

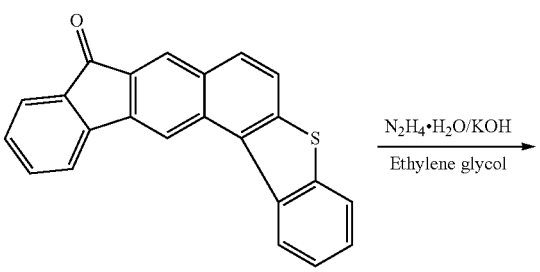

Core S-II-1

Core 1-29-I

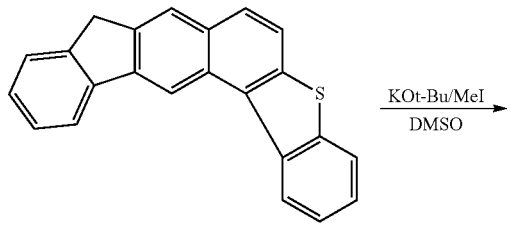

Core 1-29-II

Core 1-29-III

199
-continued

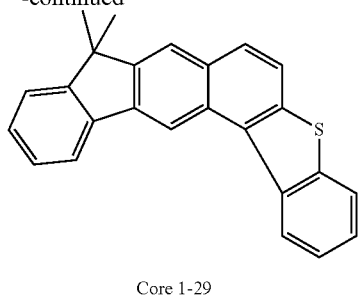

Core 1-29

1) Synthesis of Core S-I-1

M 1-5 (200 g, 408.66 mmol), M 2-1 (75.61 g, 408.66 mmol), anhydrous methanol (2452 ml), sodium methoxide (22.08 g, 408.66 mmol) were carried out in the same procedure as described in the synthesis method of Core N-I-1 to obtain 92.75 g of the product. (yield:72%).

2) Synthesis of Core S-II-1

Core S-I-1 (92.75 g, 294.23 mmol), iodine (82.15 g, 323.65 mmol), dry benzene (1177 ml), were carried out in the same procedure as described in the synthesis method of Core N-II-1 with a UV lamp to obtain 39.63 g of the product. (yield: 43%).

3) Synthesis of Core 1-29-I (2-(methoxycarbonyl)phenyl)boronic acid (22.77 g, 126.53 mmol), Core S-II-1 (39.63 g, 126.53 mmol), Pd(PPh$_3$)$_4$ (4.39 g, 3.8 mmol), K$_2$CO$_3$ (52.46 g, 379.6 mmol), THF (557 ml) and water (278 ml) were carried out in the same procedure as described in the synthesis method of Core 1-52-I to obtain 38.69 g of the product. (yield: 83%).

4) Synthesis of Core 1-29-II

Core 1-29-I (38.69 g, 105 mmol) was dissolved in Methanesulfonic acid (341 ml) and stirred at 50-60° C. When the reaction was completed, the temperature was lowered to 0° C., and water was added, and the solid precipitates are filtered off and washed with a small amount of water and dissolved again in CH$_2$Cl$_2$ and was dried over MgSO$_4$ and concentrated. The resulting compound was separated by silicagel column chromatography and recrystallization to obtain 15.19 g of the product (yield: 43%).

5) Synthesis of Core 1-29-III

The resulting Core 1-29-II (15.19 g, 45.15 mmol) was dissolved in Ethylene glycol (180 mL) and Hydrazine monohydrate (67.81 g, 1354 mmol), KOH (6.33 g, 112.88 mmol) were added and stirred at 185° C. When the reaction was completed, the temperature was lowered to 0° C. and water was added, and the solid precipitates are filtered off and washed with a small amount of water and dissolved again in CH$_2$Cl$_2$ and was dried over MgSO$_4$ and concentrated. The resulting compound was separated by silicagel column chromatography and recrystallization to obtain 13.83 g of the product (yield: 95%).

6) Synthesis of Core 1-29

In a round bottom flask, the resulting Core 1-29-III (13.83 g, 42.89 mmol), KOt-Bu (14.44 g, 128.68 mmol) were dissolved in DMSO (279 ml) and stirred at 0° C. for 5 minutes and then cooled to room temperature and iodomethane (18.27 g, 128.68 mmol) was added. When the reaction was completed, the reaction mixture was extracted with CH$_2$Cl$_2$ and water. The organic layer was dried over MgSO$_4$ and concentrated. The resulting compound was separated by silicagel column chromatography and recrystallization to obtain 13.98 g of the product (yield: 93%).

200
Synthesis Example of Core 1-39

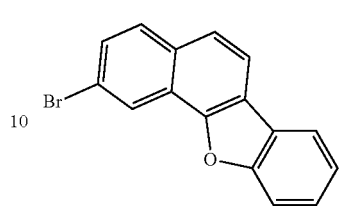

Core O-II-2

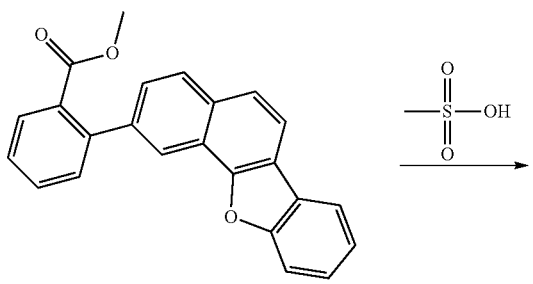

Core 1-39-I

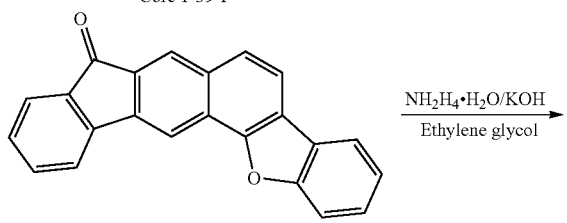

Core 1-39-II

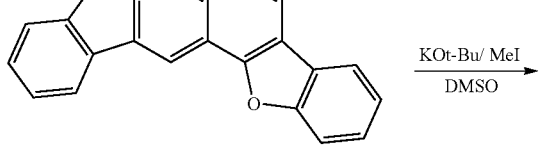

Core 1-39-III

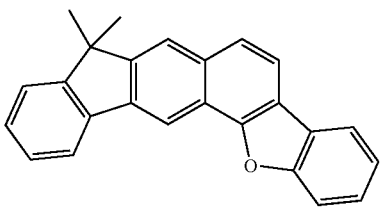

Core 1-39

1) Synthesis of Core 1-39-I (2-(methoxycarbonyl)phenyl)boronic acid (24.23 g, 134.61 mmol), Core O-II-2 (40.00 g, 134.61 mmol), Pd(PPh$_3$)$_4$ (4.67 g, 4.04 mmol), K$_2$CO$_3$ (55.81 g, 403.84 mmol), THF (592 ml) and water (296 ml) were carried out in the same procedure as described in the synthesis method of Core 1-52-I to obtain 40.32 g of the product. (yield: 85%).

2) Synthesis of Core 1-39-II

Core 1-39-I (40.32 g, 114.42 mmol), Methanesulfonic acid (371 ml) were carried out in the same procedure as described in the synthesis method of Core 1-29-II to obtain 16.49 g of the product. (yield: 45%).

3) Synthesis of Core 1-39-III

Core 1-39-II (16.49 g, 51.48 mmol), Ethylene glycol (206 mL), Hydrazine monohydrate (77.31 g, 1544 mmol), KOH (7.22 g, 128.69 mmol) were carried out in the same procedure as described in the synthesis method of Core 1-29-III to obtain 14.67 g of the product. (yield: 93%).

4) Synthesis of Core 1-39

Core 1-39-III (14.67 g, 45.50 mmol), KOt-Bu (15.32 g, 136.50 mmol), DMSO (296 ml), iodomethane (19.37 g, 136.50 mmol) were carried out in the same procedure as described in the synthesis method of Core 1-29 to obtain 15.31 g of the product. (yield: 96%).

Synthesis Example of Core 1-5

1) Synthesis of Core 1-5-I (2-nitro-5-(9-phenyl-9H-carbazol-3-yl)phenyl)boronic acid (26.07 g, 63.86 mmol), Core S-II-1 (20.00 g, 63.86 mmol), Pd(PPh$_3$)$_4$ (2.21 g, 1.92 mmol), K$_2$CO$_3$ (26.48 g, 191.56 mmol), THF (281 ml) and water (140 ml) were carried out in the same procedure as described in the synthesis method of Core 1-52-I to obtain 33.15 g of the product. (yield: 87%).

2) Synthesis of Core 1-5

The resulting Core 1-5-I (33.15 g, 55.56 mmol) and triphenylphosphine (36.43 g, 138.89 mmol) were dissolved in o-dichlorobenzene (222 ml) and stirred for 24 hours. When the reaction was completed, the solvent was removed by distillation under reduced pressure, and the resulting compound was separated by silicagel column chromatography to obtain 13.80 g of the product. (yield: 44%)

Synthesis Example of Core 1-6

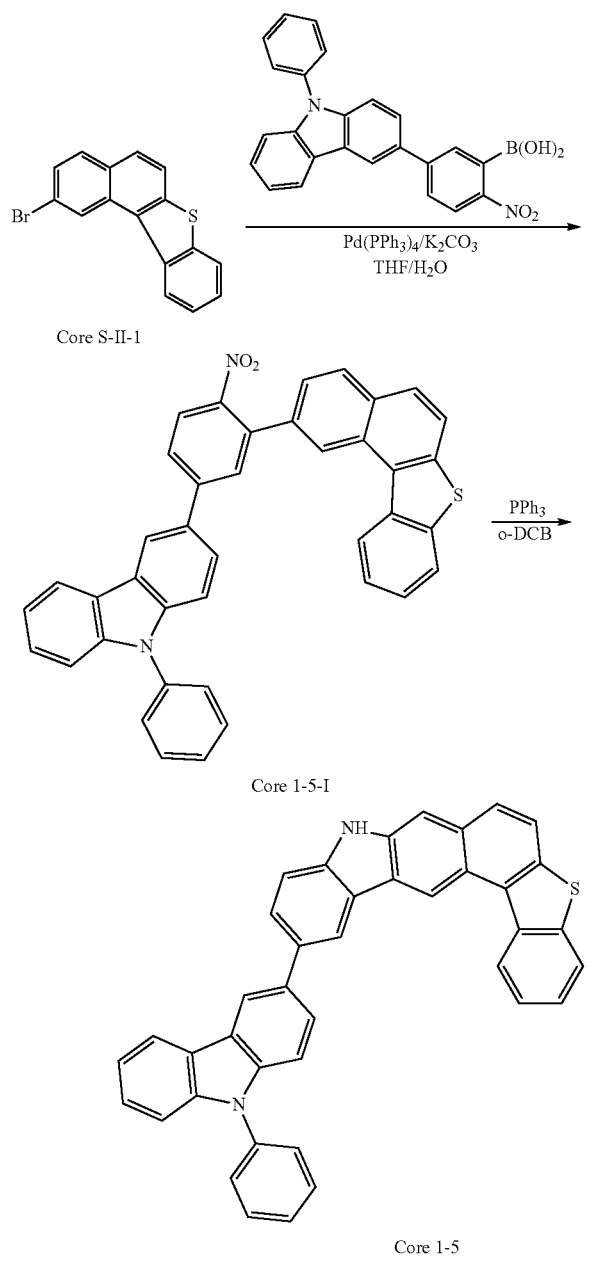

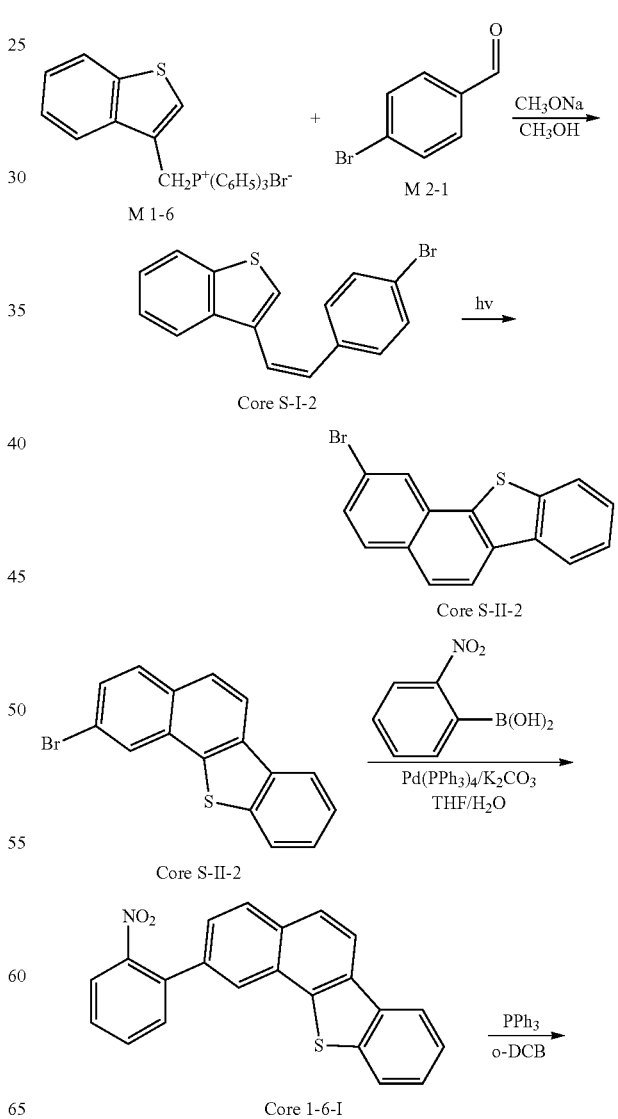

-continued

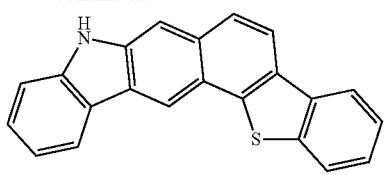

Core 1-6

1) Synthesis of Core S-I-2

M 1-6 (200 g, 408.66 mmol), M 2-1 (75.61 g, 408.66 mmol), anhydrous methanol (2452 ml), and sodium methoxide (22.08 g, 408.66 mmol) were carried out in the same procedure as described in the synthesis method of Core N-I-1 to obtain 94.04 g of the product. (yield: 73%).

2) Synthesis of Core S-II-2

Core S-I-2 (94.04 g, 298.32 mmol), iodine (83.29 g, 328.15 mmol), dry benzene (1193 ml) were carried out in the same procedure as described in the synthesis method of Core N-II-1 with a UV lamp to obtain 39.24 g of the product. (yield: 42%).

3) Synthesis of Core 1-6-I (2-nitrophenyl)boronic acid (20.91 g, 125.28 mmol), Core S-II-2 (39.24 g, 125.28 mmol), Pd(PPh$_3$)$_4$ (4.34 g, 3.76 mmol), K$_2$CO$_3$ (51.95 g, 375.85 mmol), THF (551 ml) and water (276 ml) were carried out in the same procedure as described in the synthesis method of Core 1-52-I to obtain 39.63 g of the product. (yield: 89%).

4) Synthesis of Core 1-6

Core 1-6-I (39.63 g, 111.51 mmol), triphenylphosphine (73.12 g, 278.76 mmol), o-dichlorobenzene (446 ml) were carried out in the same procedure as described in the synthesis method of Core 1-5 to obtain 15.15 g of the product. (yield: 42%).

Synthesis Example of Core 1-7

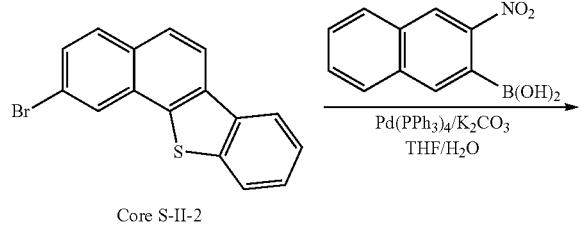

Core S-II-2

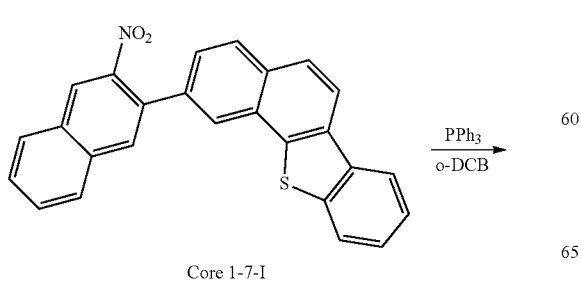

Core 1-7-I

-continued

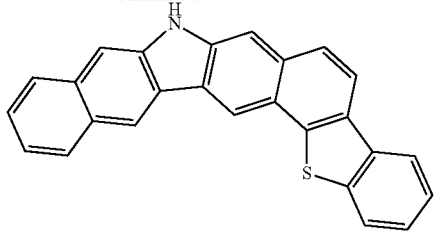

Core 1-7

1) Synthesis of Core 1-7-I (3-nitronaphthalen-2-yl)boronic acid (13.86 g, 63.86 mmol), Core S-II-2 (20.00 g, 63.86 mmol), Pd(PPh$_3$)$_4$ (2.21 g, 1.92 mmol), K$_2$CO$_3$ (26.48 g, 191.56 mmol), THF (281 ml) and water (140 ml) were carried out in the same procedure as described in the synthesis method of Core 1-52-I to obtain 23.04 g of the product. (yield: 89%).

2) Synthesis of Core 1-7

Core 1-7-I (23.04 g, 56.82 mmol), triphenylphosphine (37.26 g, 142.06 mmol), o-dichlorobenzene (227 ml) were carried out in the same procedure as described in the synthesis method of Core 1-5 to obtain 9.34 g of the product. (yield: 44%).

Synthesis Example of Core 1-8

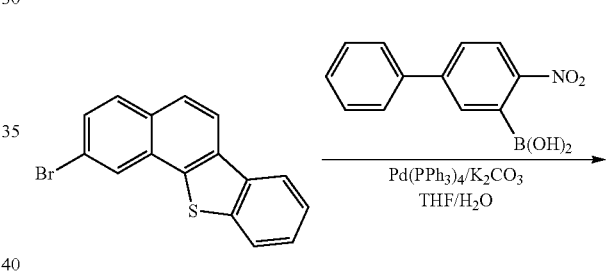

Core S-II-2

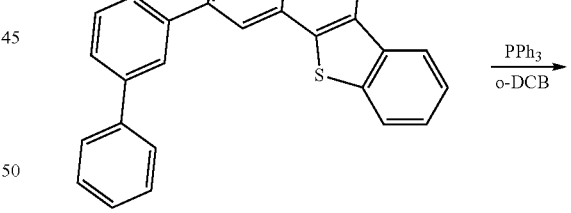

Core 1-8-I

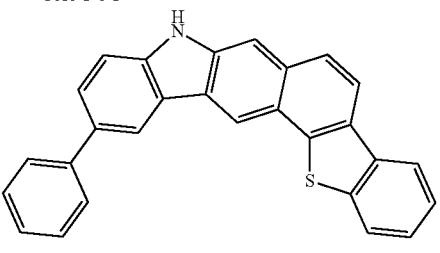

Core 1-8

1) Synthesis of Core 1-8-I (4-nitro-[1,1'-biphenyl]-3-yl)boronic acid (15.52 g, 63.86 mmol), Core S-II-2 (20.00 g, 63.86 mmol), Pd(PPh$_3$)$_4$ (2.21 g, 1.92 mmol), K$_2$CO$_3$ (26.48 g, 191.56 mmol), THF (281 ml) and water (140 ml) were carried out in the same procedure as described in the synthesis method of Core 1-52-I to obtain 23.97 g of the product. (yield: 87%).

2) Synthesis of Core 1-8

Core 1-8-I (23.97 g, 55.55 mmol), triphenylphosphine (36.42 g, 138.87 mmol), o-dichlorobenzene (222 ml) were carried out in the same procedure as described in the synthesis method of Core 1-5 to obtain 9.32 g of the product. (yield: 42%).

Synthesis Example of Core 1-9

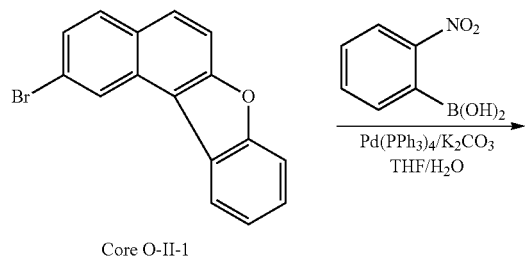

Core O-II-1

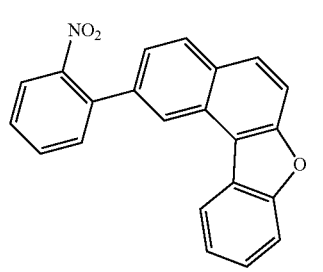

Core 1-9-I

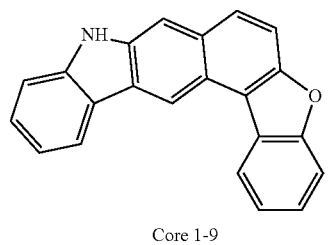

Core 1-9

1) Synthesis of Core 1-9-I (2-nitrophenyl)boronic acid (11.24 g, 67.31 mmol), Core O-II-1 (20.00 g, 67.31 mmol), Pd(PPh$_3$)$_4$ (2.33 g, 2.02 mmol), K$_2$CO$_3$ (27.91 g, 201.92 mmol), THF (296 ml) and water (148 ml) were carried out in the same procedure as described in the synthesis method of Core 1-52-I to obtain 19.41 g of the product. (yield: 85%).

2) Synthesis of Core 1-9

Core 1-9-I (19.41 g, 57.21 mmol), triphenylphosphine (37.51 g, 143.03 mmol), o-dichlorobenzene (229 ml) were carried out in the same procedure as described in the synthesis method of Core 1-5 to obtain 7.91 g of the product. (yield: 45%).

Synthesis Example of Core 1-13

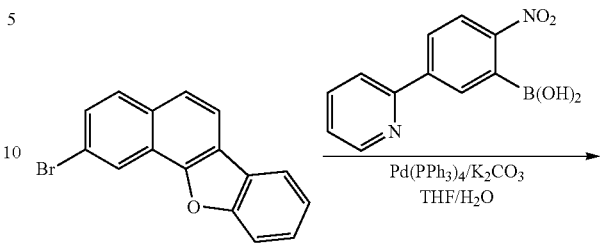

Core O-II-2

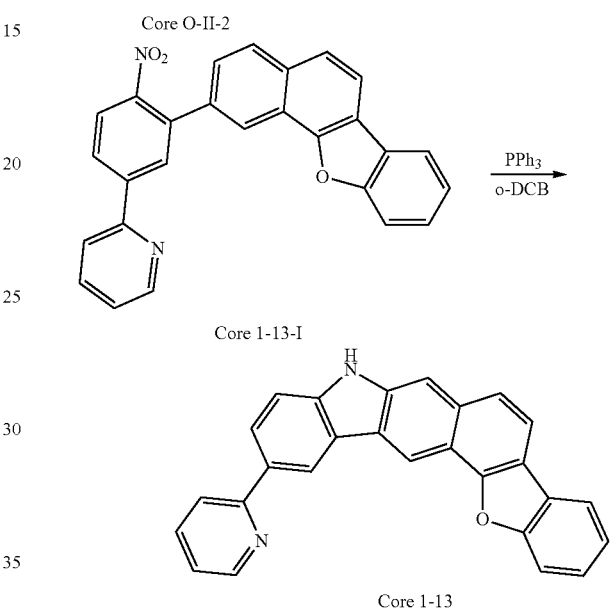

Core 1-13-I

Core 1-13

1) Synthesis of Core 1-13-I (2-nitro-5-(pyridin-2-yl)phenyl)boronic acid (16.42 g, 67.31 mmol), Core O-II-2 (20.00 g, 67.31 mmol), Pd(PPh$_3$)$_4$ (2.33 g, 2.02 mmol), K$_2$CO$_3$ (27.91 g, 201.92 mmol), THF (296 ml) and water (148 ml) were carried out in the same procedure as described in the synthesis method of Core 1-52-I to obtain 22.98 g of the product. (yield: 82%).

2) Synthesis of Core 1-13

Core 1-13-I (22.98 g, 59.79 mmol), triphenylphosphine (39.20 g, 149.46 mmol), o-dichlorobenzene (239 ml) were carried out in the same procedure as described in the synthesis method of Core 1-5 to obtain 7.35 g of the product. (yield: 40%).

Synthesis Example of 1-1-1(C)

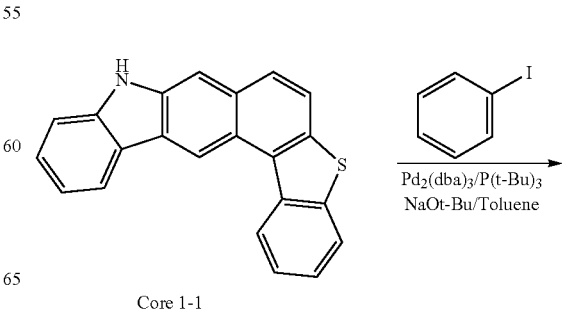

Core 1-1

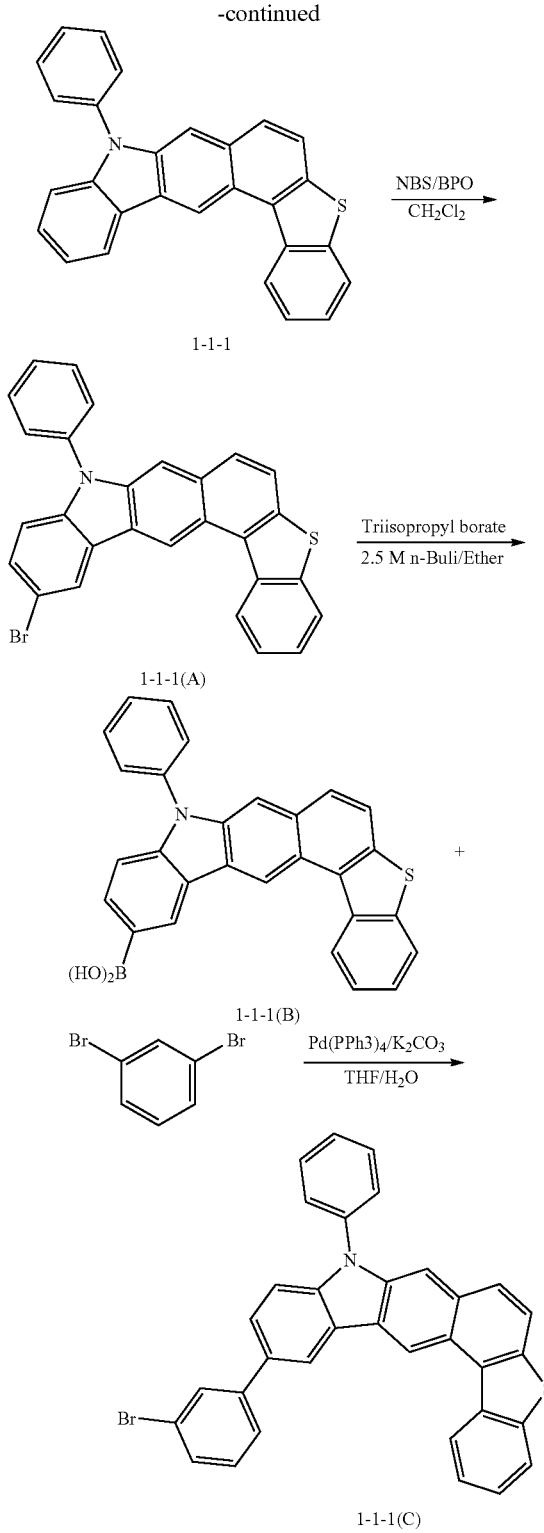

centrated. The resulting compound was separated by silica-gel column chromatography and recrystallization to obtain 108.71 g of the product (yield: 88%).

2) Synthesis of 1-1-1(A)

The compound 1-1-1 (100 g, 250.31 mmol) and NBS (N-bromosuccinimide) (93.6 g, 525.64 mmol), BPO (benzoylperoxide) (6.1 g, 25.03 mmol) were dissolved in $CH_2Cl_2$ (751 ml) and stirred at room temperature for 3 hours. When the reaction was completed, sodium bicarbonate aqueous solution was added, and stirred for 30 minutes, and extracted with $CH_2Cl_2$. The water in the reaction mixture was removed with anhydrous $MgSO_4$, and filtered under reduced pressure, the organic solvent was concentrated and the resulting product was separated by column chromatography to obtain 69.91 g of the product. (yield: 63%)

3) Synthesis of 1-1-1(B)

In a round bottom flask, the resulting 1-1-1(A) (40 g, 83.61 mmol), anhydrous Ether 293 ml were added and all dissolved and the temperature of the reaction product was lowered to −78° C. To this was slowly added dropwise a 2.5 M concentration of n-BuLi (36.8 ml, 92 mmol), followed by stirring at room temperature for an additional 1 hour. After that, the temperature of the reactant was lowered to −78° C. and Tri isopropyl borate was added dropwise. The temperature is gradually raised, stirred at room temperature, diluted by adding water, and stirred with 2 N HCl. When the reaction was completed, the reaction mixture was extracted with ethyl acetate and water. The organic layer was dried over $MgSO_4$ and concentrated. The resulting compound was separated by silicagel column chromatography and recrystallization to obtain 24.38 g of the product (yield: 67%).

4) Synthesis of 1-1-1(C)

Core 1-1-1(B) (25.58 g, 57.70 mmol), THF (254 ml), 1,3-dibromobenzene (13.61 g, 57.70 mmol), Pd(PPh$_3$)$_4$ (2.00 g, 1.73 mmol), K$_2$CO$_3$ (23.92 g, 173.10 mmol), water (127 ml) were carried out in the same procedure as described in the synthesis method of Core 1-52-I to obtain 23.68 g of the product. (yield: 74%).

Synthesis Example of 1-1-1(D)

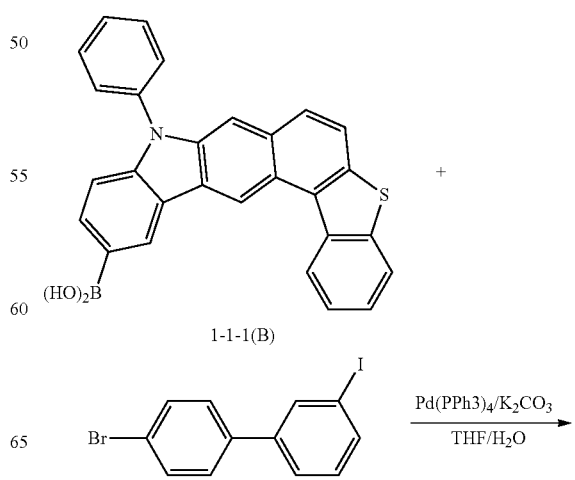

1) Synthesis of 1-1-1

In a round bottom flask, Core 1-1 (100 g, 309.21 mmol), iodobenzene (63.08 g, 309.21 mmol), Pd$_2$(dba)$_3$ (14.16 g, 15.46 mmol), P(t-Bu)$_3$ (6.26 g, 30.92 mmol), NaOt-Bu (44.57 g, 463.81 mmol), toluene (3246 mL) were added and the reaction proceeds at 100° C. When the reaction was completed, the reaction mixture was extracted with ether and water. The organic layer was dried over MgSO$_4$ and con- -continued

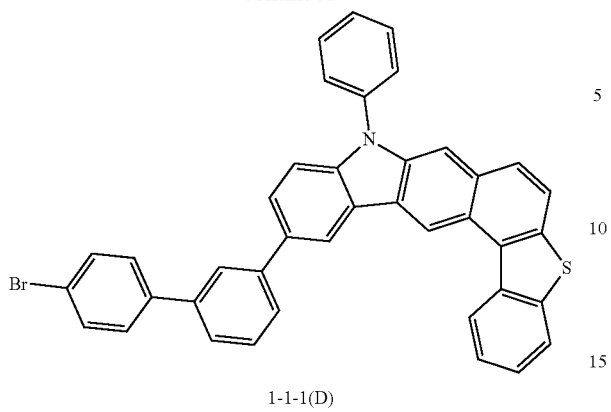

1-1-1(D)

Core 1-1-1(B) (20 g, 45.11 mmol), THF (199 ml), 4'-bromo-3-iodo-1,1'-biphenyl (16.20 g, 45.11 mmol), Pd(PPh₃)₄ (1.56 g, 1.35 mmol), K₂CO₃ (18.71 g, 135.34 mmol), water (99.25 ml) were carried out in the same procedure as described in the synthesis method of Core 1-24-I(1) to obtain 21.34 g of the product. (yield: 75%).

Synthesis Example of 1-2-1(C)

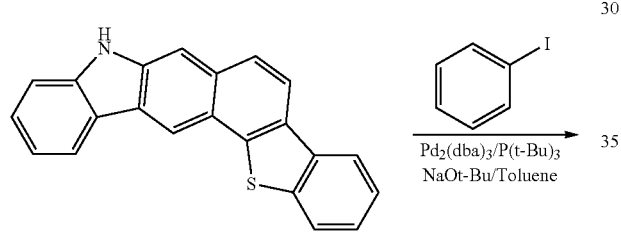

Core 1-6

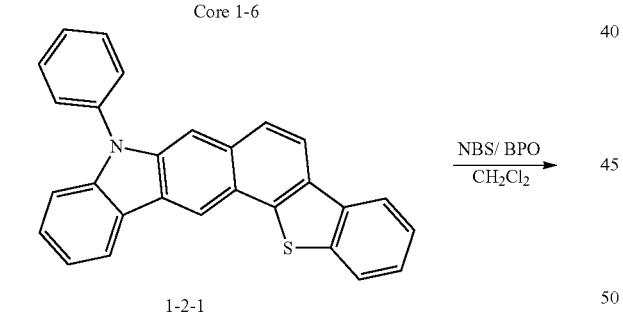

1-2-1

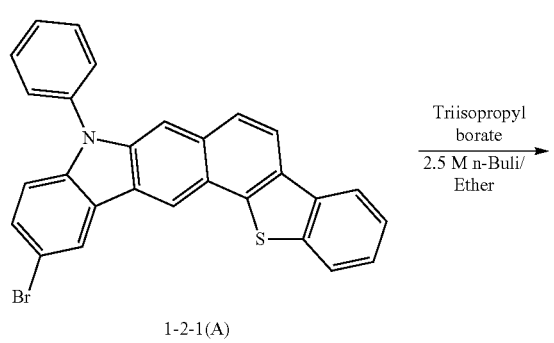

1-2-1(A)

-continued

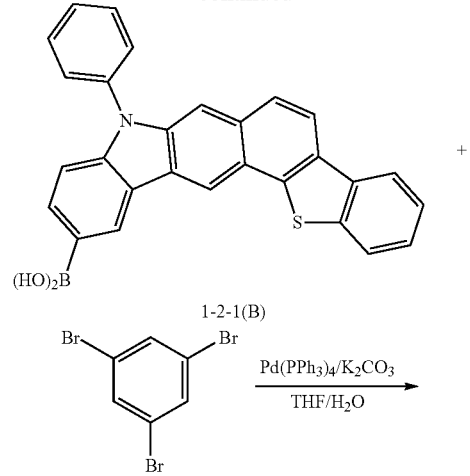

1-2-1(C)

1) Synthesis of 1-2-1

Core 1-6 (100 g, 309.21 mmol), iodobenzene (63.08 g, 309.21 mmol), Pd₂(dba)₃ (14.16 g, 15.46 mmol), P(t-Bu)₃ (6.26 g, 30.92 mmol), NaOt-Bu (44.57 g, 463.81 mmol), toluene (3246 mL) were carried out in the same procedure as described in the synthesis method of 1-1-1 to obtain 106.24 g of the product. (yield: 86%).

2) Synthesis of 1-2-1(A)

The compound 1-2-1 (100 g, 250.31 mmol), NBS (93.55 g, 525.64 mmol), BPO (6.06 g, 25.03 mmol), CH₂Cl₂ (751 ml) were carried out in the same procedure as described in the synthesis method of 1-1-1(A) to obtain 73.05 g of the product. (yield: 62%).

3) Synthesis of 1-2-1(B)

The resulting 1-2-1(A) (73 g, 152.59 mmol), anhydrous Ether 534 ml, 2.5 M concentration n-BuLi (67 ml, 167.85 mmol), Tri isopropyl borate (43.05 g, 228.89 mmol) were carried out in the same procedure as described in the synthesis method of 1-1-1(B) to obtain 45.32 g of the product. (yield: 67%).

4) Synthesis of 1-2-1(C)

1-2-1(B) (45.32 g, 102.23 mmol), THF (225 ml), 1,3,5-tribromobenzene (32.18 g, 102.23 mmol), Pd(PPh₃)₄ (1.18 g, 1.02 mmol), K₂CO₃ (21.19 g, 153.34 mmol), water (225 ml) were carried out in the same procedure as described in the synthesis method of 1-1-1(C) to obtain 40.15 g of the product. (yield: 62%).

Synthesis Example of 2-1-2(B)

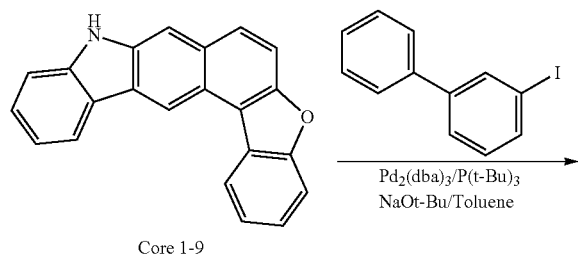

Core 1-9

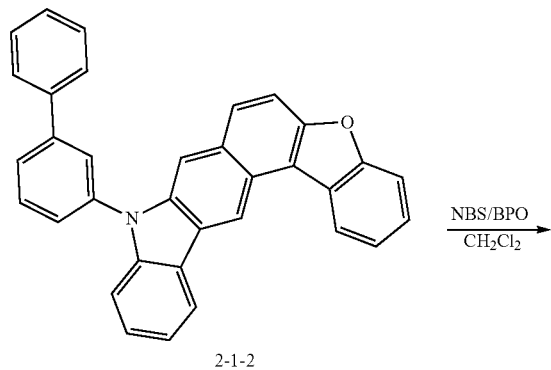

2-1-2

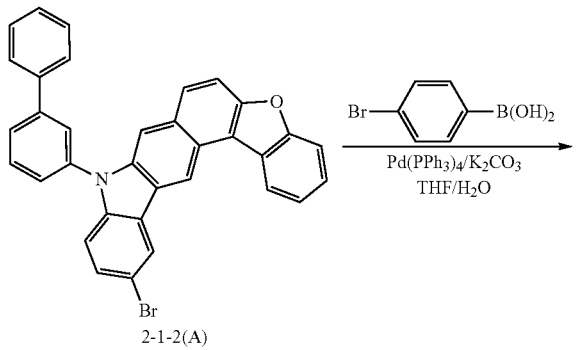

2-1-2(A)

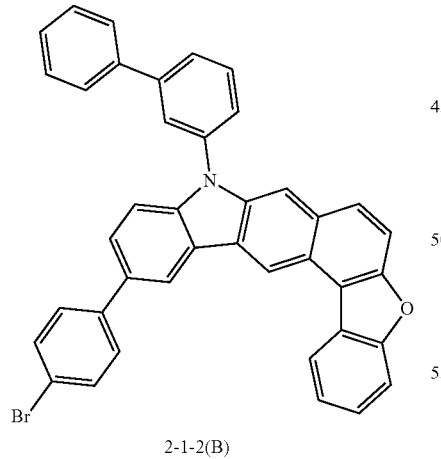

2-1-2(B)

1) Synthesis of 2-1-2

Core 1-9 (100 g, 325.37 mmol), 3-iodo-1,1'-biphenyl (91.14 g, 325.37 mmol), Pd$_2$(dba)$_3$ (14.90 g, 16.27 mmol), P(t-Bu)$_3$ (6.58 g, 32.54 mmol), NaOt-Bu (46.90 g, 488.06 mmol), toluene (3416 mL) were carried out in the same procedure as described in the synthesis method of 1-1-1 to obtain 133.07 g of the product. (yield: 89%).

2) Synthesis of 2-1-2(A)

The compound 2-1-2 (50 g, 108.8 mmol), NBS (40.67 g, 228.49 mmol), BPO (2.64 g, 10.88 mmol), CH$_2$Cl$_2$ (326 ml) were carried out in the same procedure as described in the synthesis method of 1-1-1(A) to obtain 36.32 g of the product. (yield: 62%).

3) Synthesis of 2-1-2(B) 2-1-2(A) (36.32 g, 67.46 mmol), THF (297 ml), (4-bromophenyl)boronic acid (13.55 g, 67.46 mmol), Pd(PPh$_3$)$_4$ (2.34 g, 2.02 mmol), K$_2$CO$_3$ (27.97 g, 202.37 mmol), water (148 ml) were carried out in the same procedure as described in the synthesis method of 1-1-1(C) to obtain 29.43 g of the product. (yield: 71%).

Synthesis Example of 6-1-1(C)

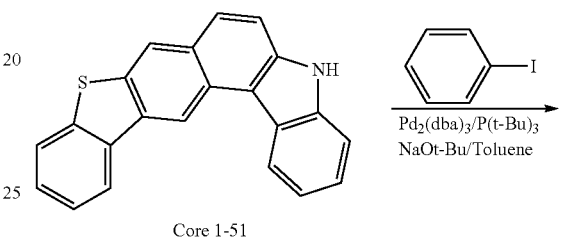

Core 1-51

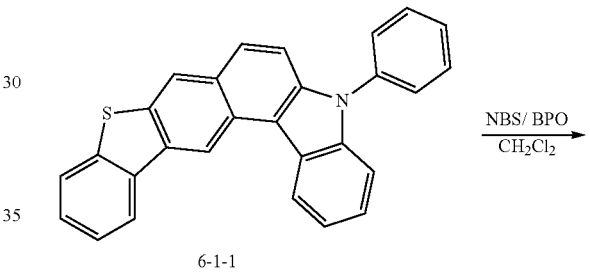

6-1-1

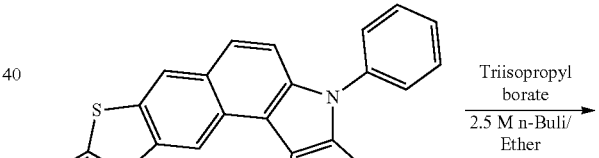

6-1-1(A)

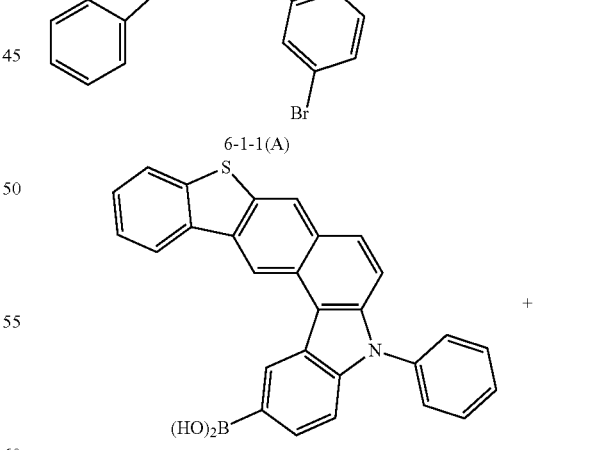

Sub 1-90

-continued

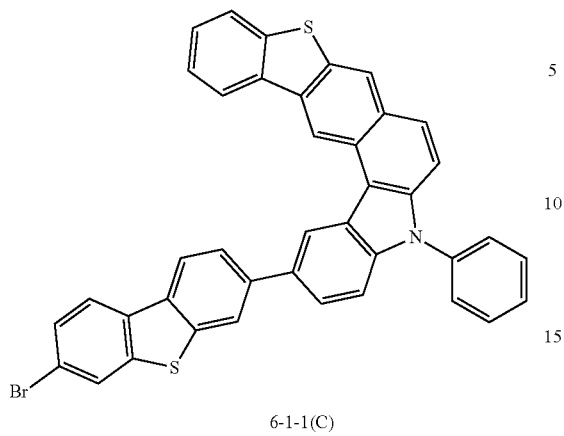

6-1-1(C)

1) Synthesis of 6-1-1

Core 1-51 (100 g, 309.21 mmol), iodobenzne (63.08 g, 309.21 mmol), Pd$_2$(dba)$_3$ (14.16 g, 15.46 mmol), P(t-Bu)$_3$ (6.26 g, 30.92 mmol), NaOt-Bu (89.14 g, 927.62 mmol), toluene (3247 mL) were carried out in the same procedure as described in the synthesis method of 1-1-1 to obtain 109.94 g of the product. (yield: 89%).

2) Synthesis of 6-1-1(A)

The resulting compound 6-1-1 (60 g, 150.18 mmol), NBS (56.13 g, 315.39 mmol), BPO (3.64 g, 15.02 mmol), CH$_2$Cl$_2$ (451 ml) were carried out in the same procedure as described in the synthesis method of 1-1-1(A) to obtain 43.83 g of the product. (yield: 61%).

3) Synthesis of 6-1-1(B)

The resulting 6-1-1(A) (43.83 g, 91.62 mmol), anhydrous Ether (321 ml), 2.5 M concentration n-BuLi (40.31 ml, 100.78 mmol), Tri isopropyl borate (25.85 g, 137.43 mmol) were carried out in the same procedure as described in the synthesis method of 1-1-1(B) to obtain 28.84 g of the product. (yield: 71%).

4) Synthesis of 6-1-1(C)

6-1-1(B) (28.84 g, 65.06 mmol), THF (286 ml), 3,7-dibromodibenzo[b,d]thiophene (22.25 g, 65.06 mmol), Pd(PPh$_3$)$_4$ (11.28 g, 9.76 mmol), K$_2$CO$_3$ (13.49 g, 97.58 mmol), water (143 ml) were carried out in the same procedure as described in the synthesis method of 1-1-1(C) to obtain 27.94 g of the product. (yield: 65%).

<Core Intermediates of FD-MS>

Examples of Core 1

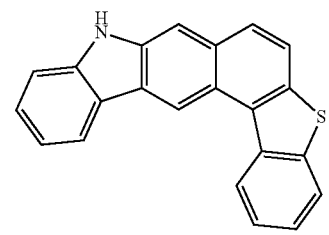

Core 1-1

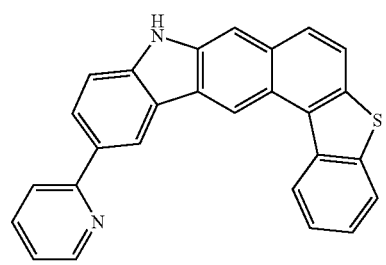

Core 1-2

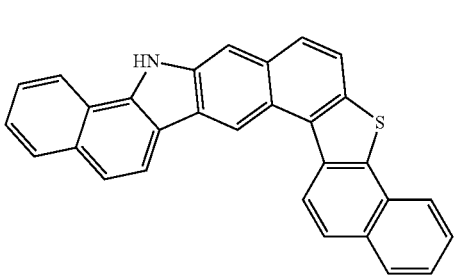

Core 1-3

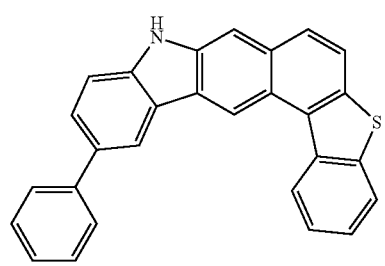

Core-1-4

TABLE 1

| compound | FD-MS | compound | FD-MS |
|---|---|---|---|
| 1-1-1(A) | m/z = 477.02(C$_{28}$H$_{16}$BrNS = 478.40) | 1-1-1(B) | m/z = 443.12(C$_{28}$H$_{18}$BNO$_2$S = 443.32) |
| 1-1-1(C) | m/z = 553.05(C$_{34}$H$_{20}$BrNS = 554.50) | 1-1-1(D) | m/z = 629.08(C$_{40}$H$_{24}$BrNS = 630.59) |
| 1-2-1(A) | m/z = 477.02(C$_{28}$H$_{16}$BrNS = 478.40) | 1-2-1(B) | m/z = 443.12(C$_{28}$H$_{18}$BNO$_2$S = 443.32) |
| 1-2-1(C) | m/z = 630.96(C$_{34}$H$_{19}$Br$_2$NS = 633.39) | 2-1-2(A) | m/z = 537.07(C$_{34}$H$_{20}$BrNO = 538.43) |
| 2-1-2(B) | m/z = 613.10(C$_{40}$H$_{24}$BrNO = 614.53) | 6-1-1(A) | m/z = 477.02(C$_{28}$H$_{16}$BrNS = 478.40) |
| 6-1-1(B) | m/z = 443.12(C$_{28}$H$_{18}$BNO$_2$S = 443.32) | 6-1-1(C) | m/z = 659.04(C$_{40}$H$_{22}$BrNS$_2$ = 660.64) |

Core 1-5
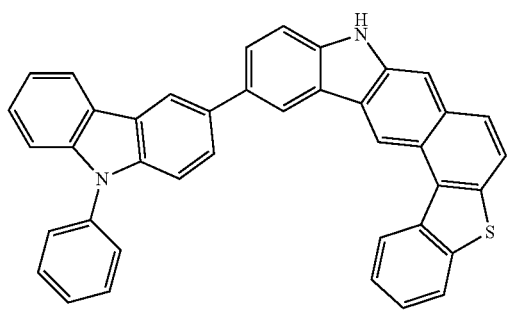
Core 1-6
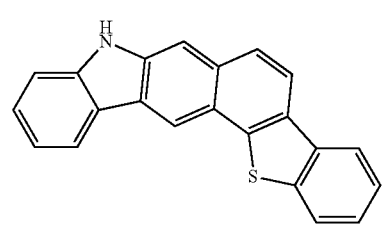
Core 1-7
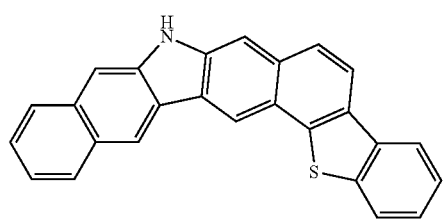
Core 1-8
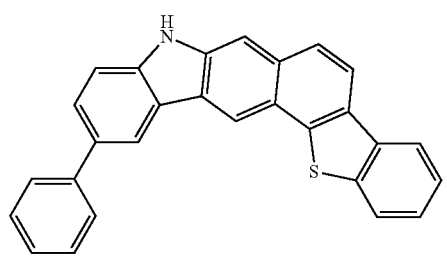
Core 1-9
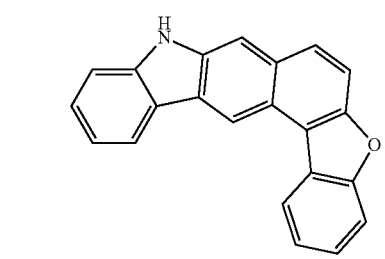
Core 1-10
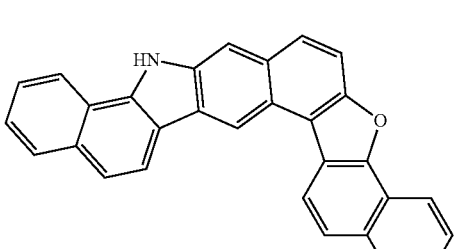
Core 1-11
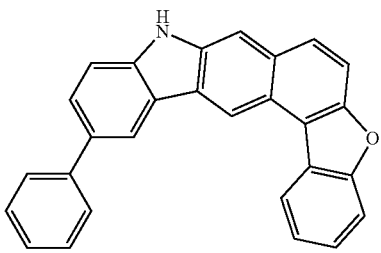
Core 1-12
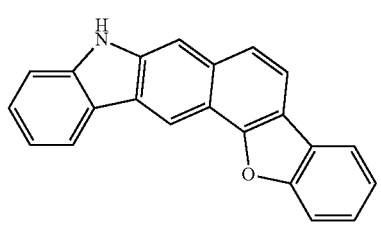
Core 1-13
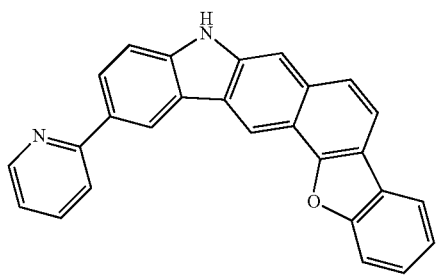
Core 1-14
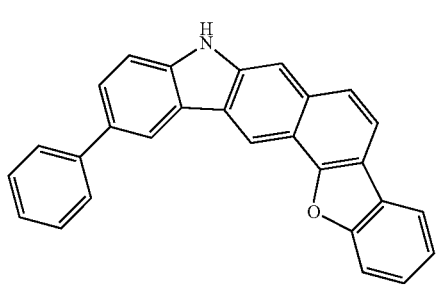
Core 1-15
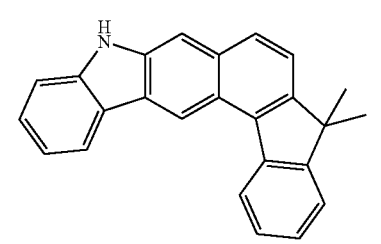
Core 1-16
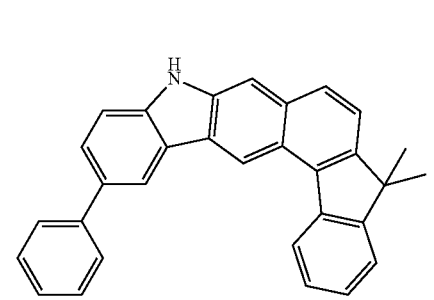

Core 1-17
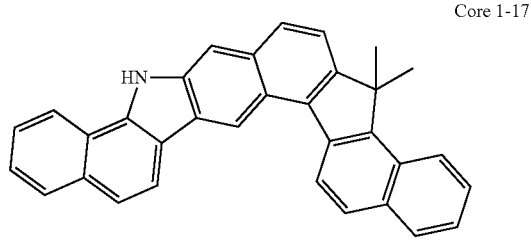
Core 1-18
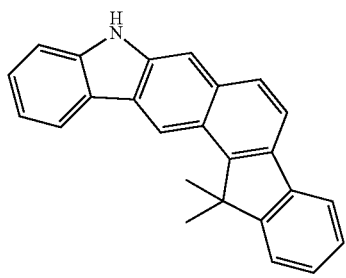
Core 1-19
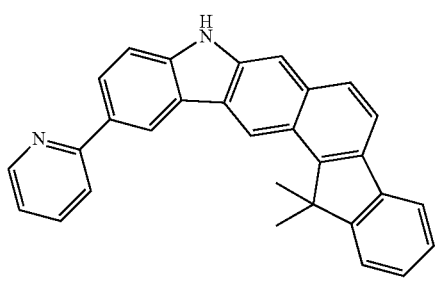
Core 1-20
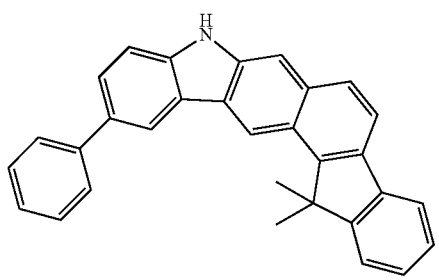
Core 1-21
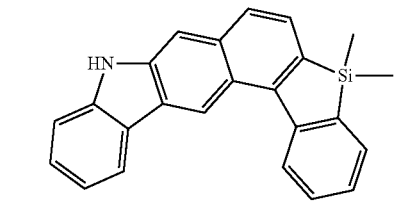
Core 1-22
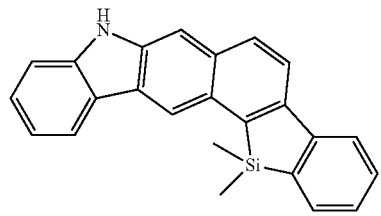
Core 1-23
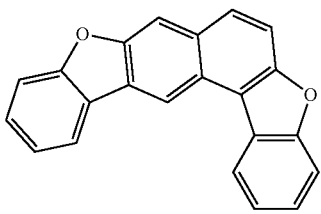
Core 1-24
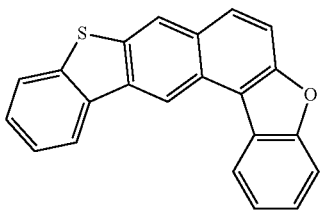
Core 1-25
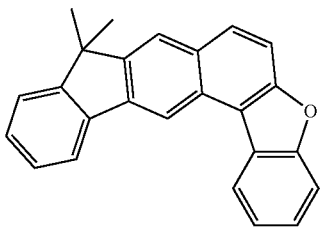
Core 1-26
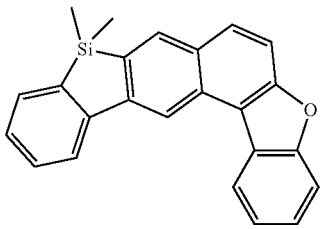
Core 1-27
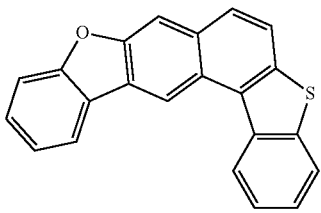
Core 1-28
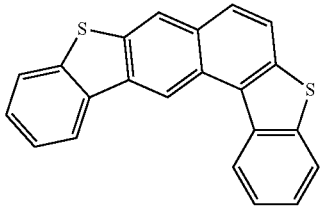
Core 1-29
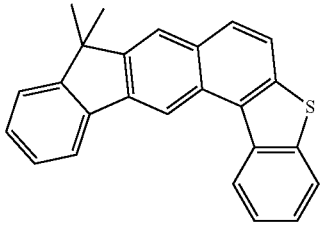

Core 1-30
Core 1-31
Core 1-32
Core 1-33
Core 1-34
Core 1-35
Core 1-36
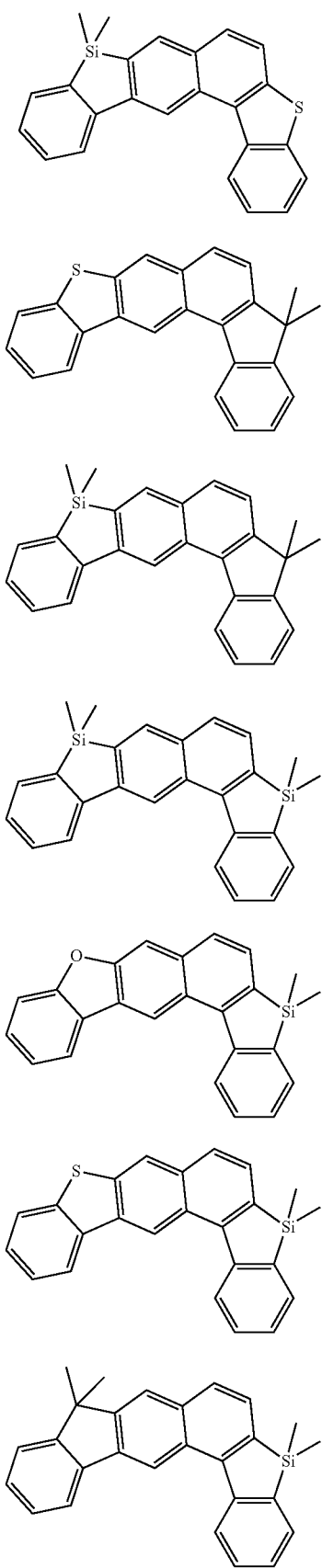
Core 1-37
Core 1-38
Core 1-39
Core 1-40
Core 1-41
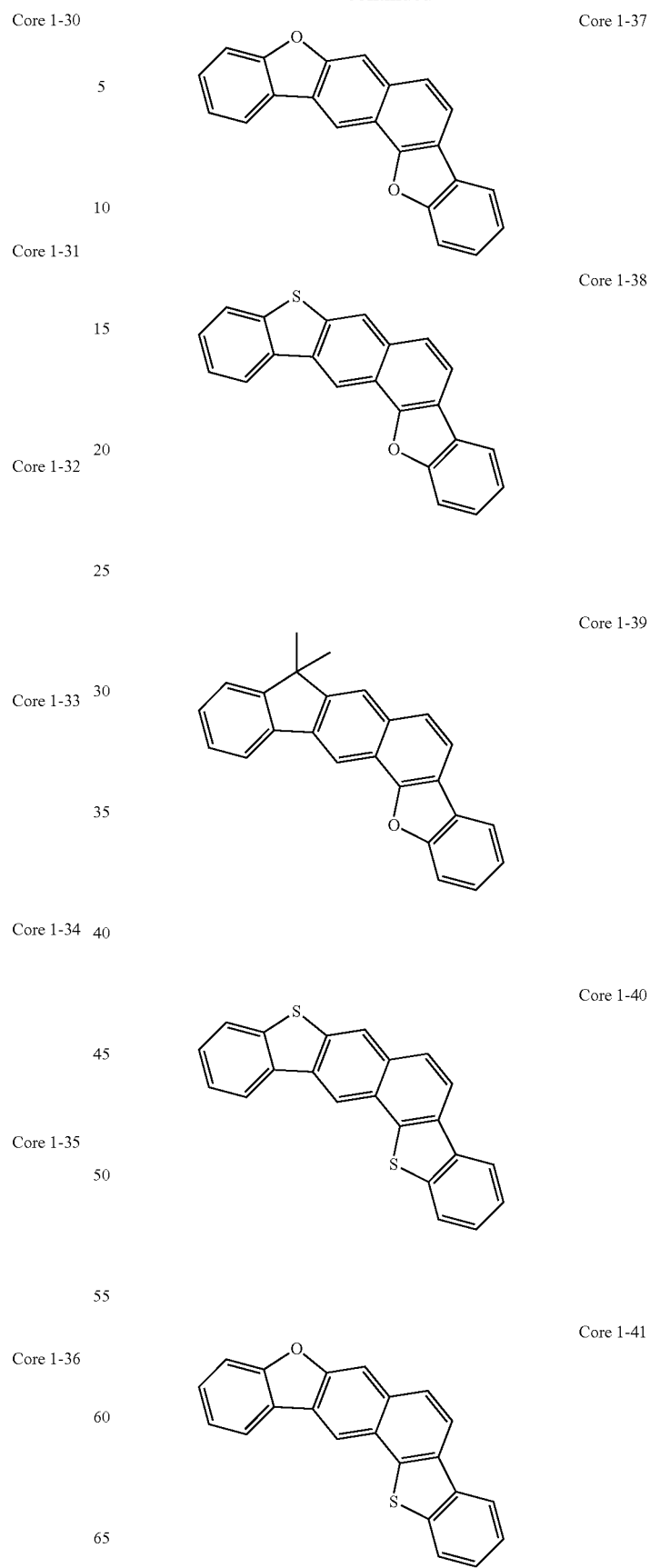

Core 1-42
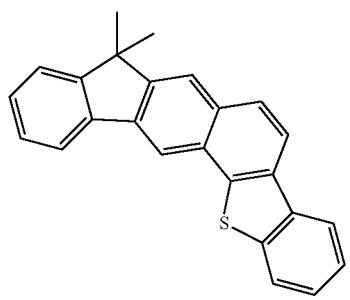
Core 1-43
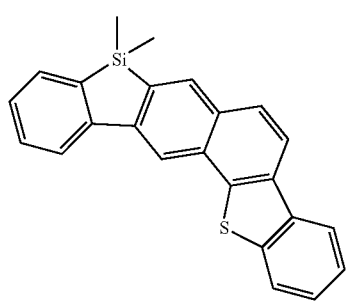
Core 1-44
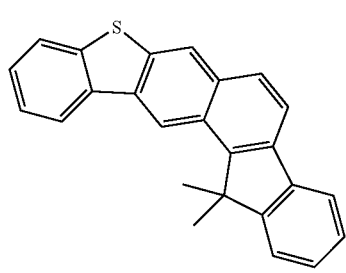
Core 1-45
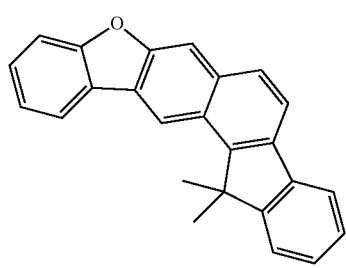
Core 1-46
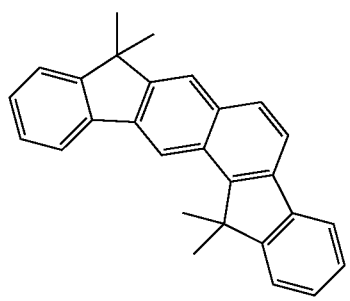
Core 1-47
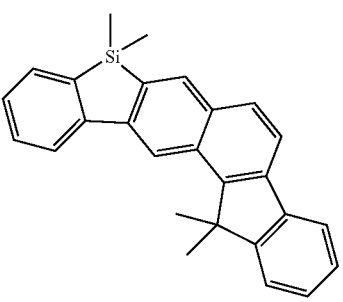
Core 1-48
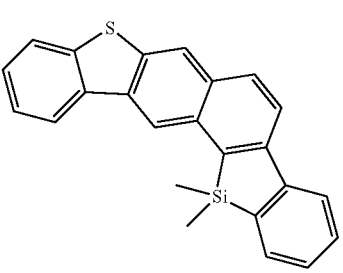
Core 1-49
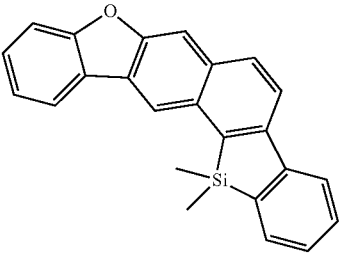
Core 1-50
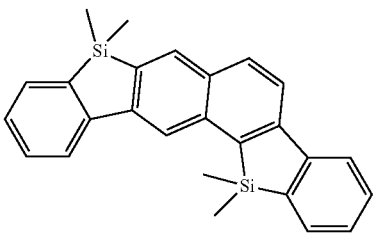
Core 1-51
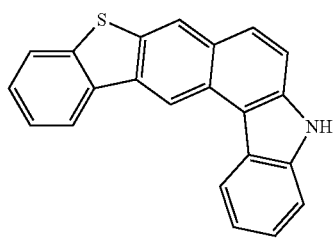
Core 1-52
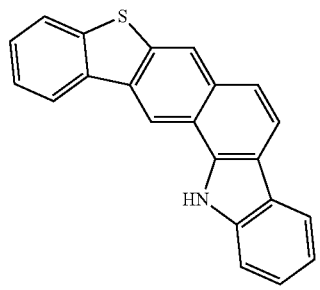

-continued

Core 1-53

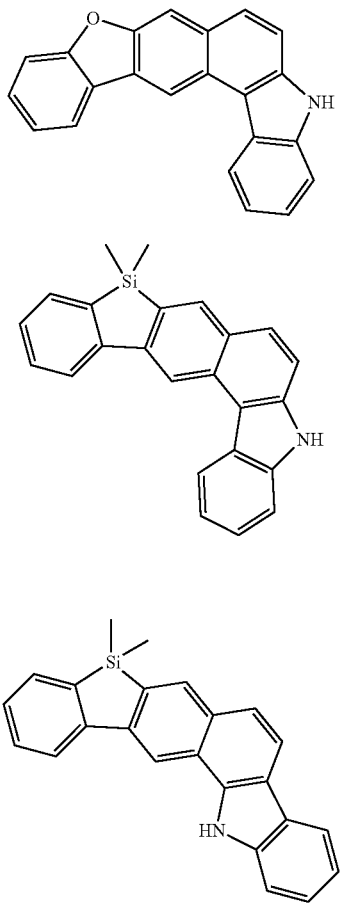

Core 1-54

Core 1-55

<FD-MS of Core Mass Data>

II. Synthesis Example of Sub 1

Synthesis Example of Sub 1-12

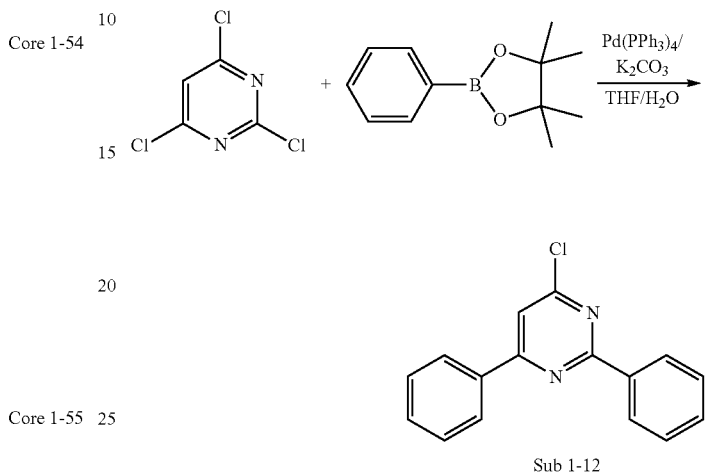

Sub 1-12

Phenylboronic acid pinacol ester (22.3 g, 109 mmol), THF (240 ml), 2,4,6-trichloropyrimidine (10 g, 54.5 mmol), $Pd(PPh_3)_4$ (3.8 g, 3.27 mmol), $K_2CO_3$ (45.2 g, 327 mmol), water (120 ml) were added and stirred at 90° C. When the reaction was completed, the reaction mixture was extracted with $CH_2Cl_2$ and water. The organic layer was dried over $MgSO_4$ and concentrated. The resulting compound was separated by silicagel column chromatography and recrystallization to obtain 9.5 g of the product (yield: 65%).

TABLE 2

| compound | FD-MS | compound | FD-MS |
|---|---|---|---|
| Core 1-1 | m/z = 323.08($C_{22}H_{13}NS$ = 323.41) | Core 1-2 | m/z = 400.10($C_{27}H_{16}N_2S$ = 400.49) |
| Core 1-3 | m/z = 423.11($C_{30}H_{17}NS$ = 423.53) | Core 1-4 | m/z = 399.11($C_{28}H_{17}NS$ = 399.51) |
| Core 1-5 | m/z = 564.17($C_{40}H_{24}N_2S$ = 564.70) | Core 1-6 | m/z = 323.08($C_{22}H_{13}NS$ = 323.41) |
| Core 1-7 | m/z = 373.09($C_{26}H_{15}NS$ = 373.47) | Core 1-8 | m/z = 399.11($C_{28}H_{17}NS$ = 399.51) |
| Core 1-9 | m/z = 307.10($C_{22}H_{13}NO$ = 307.34) | Core 1-10 | m/z = 407.13($C_{30}H_{17}NO$ = 407.46) |
| Core 1-11 | m/z = 383.13($C_{28}H_{17}NO$ = 383.44) | Core 1-12 | m/z = 307.10($C_{22}H_{13}NO$ = 307.34) |
| Core 1-13 | m/z = 384.13($C_{27}H_{16}N_2O$ = 384.43) | Core 1-14 | m/z = 383.13($C_{28}H_{17}NO$ = 383.44) |
| Core 1-15 | m/z = 333.15($C_{25}H_{19}N$ = 333.43) | Core 1-16 | m/z = 409.18($C_{31}H_{23}N$ = 409.52) |
| Core 1-17 | m/z = 433.18($C_{33}H_{23}N$ = 433.54) | Core 1-18 | m/z = 333.15($C_{25}H_{19}N$ = 333.43) |
| Core 1-19 | m/z = 410.18($C_{30}H_{22}N_2$ = 410.51) | Core 1-20 | m/z = 409.18($C_{31}H_{23}N$ = 409.52) |
| Core 1-21 | m/z = 349.13($C_{24}H_{19}NSi$ = 349.50) | Core 1-22 | m/z = 349.13($C_{24}H_{19}NSi$ = 349.50) |
| Core 1-23 | m/z = 308.08($C_{22}H_{12}O_2$ = 308.33) | Core 1-24 | m/z = 324.06($C_{22}H_{12}OS$ = 324.40) |
| Core 1-25 | m/z = 334.14($C_{25}H_{18}O$ = 334.41) | Core 1-26 | m/z = 350.11($C_{24}H_{18}OSi$ = 350.48) |
| Core 1-27 | m/z = 324.06($C_{22}H_{12}OS$ = 324.40) | Core 1-28 | m/z = 340.04($C_{22}H_{12}S_2$ = 340.46) |
| Core 1-29 | m/z = 350.11($C_{25}H_{18}S$ = 350.48) | Core 1-30 | m/z = 366.09($C_{24}H_{18}SSi$ = 366.55) |
| Core 1-31 | m/z = 350.11($C_{25}H_{18}S$ = 350.48) | Core 1-32 | m/z = 376.16($C_{27}H_{24}Si$ = 376.56) |
| Core 1-33 | m/z = 392.14($C_{26}H_{24}Si_2$ = 392.64) | Core 1-34 | m/z = 350.11($C_{24}H_{18}OSi$ = 350.48) |
| Core 1-35 | m/z = 366.09($C_{24}H_{18}SSi$ = 366.55) | Core 1-36 | m/z = 376.16($C_{27}H_{24}Si$ = 376.56) |
| Core 1-37 | m/z = 308.08($C_{22}H_{12}O_2$ = 308.33) | Core 1-38 | m/z = 324.06($C_{22}H_{12}OS$ = 324.40) |
| Core 1-39 | m/z = 334.14($C_{25}H_{18}O$ = 334.41) | Core 1-40 | m/z = 340.04($C_{22}H_{12}S_2$ = 340.46) |
| Core 1-41 | m/z = 324.06($C_{22}H_{12}OS$ = 324.40) | Core 1-42 | m/z = 350.11($C_{25}H_{18}S$ = 350.48) |
| Core 1-43 | m/z = 366.09($C_{24}H_{18}SSi$ = 366.55) | Core 1-44 | m/z = 350.11($C_{25}H_{18}S$ = 350.48) |
| Core 1-45 | m/z = 334.14($C_{25}H_{18}O$ = 334.41) | Core 1-46 | m/z = 360.19($C_{28}H_{14}$ = 360.49) |
| Core 1-47 | m/z = 376.16($C_{27}H_{24}Si$ = 376.56) | Core 1-48 | m/z = 366.09($C_{24}H_{18}SSi$ = 366.55) |
| Core 1-49 | m/z = 350.11($C_{24}H_{18}OSi$ = 350.48) | Core 1-50 | m/z = 392.14($C_{26}H_{24}Si_2$ = 392.64) |
| Core 1-51 | m/z = 323.08($C_{22}H_{13}NS$ = 323.41) | Core 1-52 | m/z = 323.08($C_{22}H_{13}NS$ = 323.41) |
| Core 1-53 | m/z = 307.10($C_{22}H_{13}NO$ = 307.34) | Core 1-54 | m/z = 349.13($C_{24}H_{19}NSi$ = 349.50) |
| Core 1-55 | m/z = 349.13($C_{24}H_{19}NSi$ = 349.50) | | |

Synthesis Example of Sub 1-14

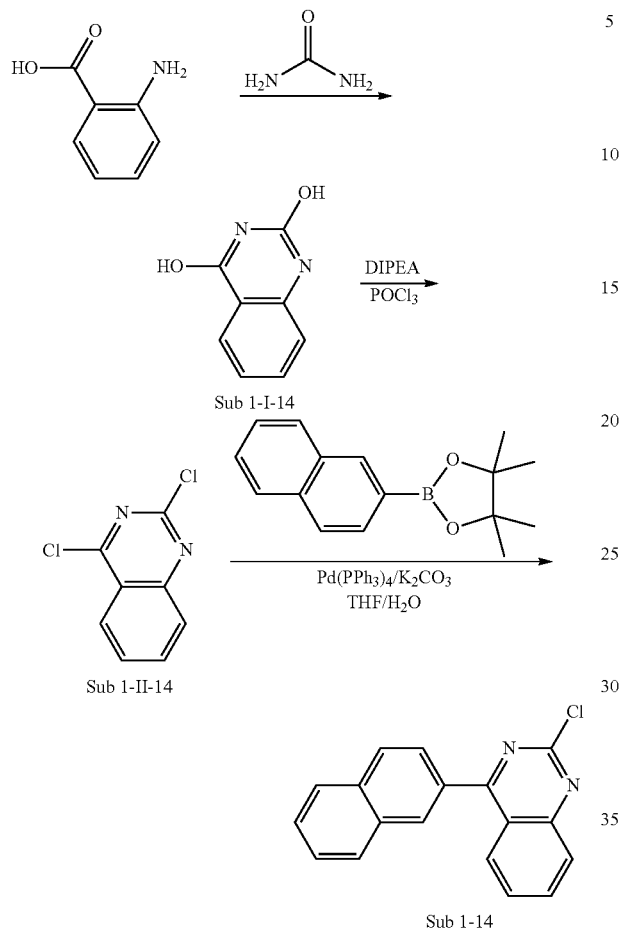

Sub 1-I-14

Sub 1-II-14

Sub 1-14

1) Synthesis of Sub 1-I-14

The starting material, 2-aminobenzoic acid (15.22 g, 111 mmol), was placed in a round bottom flask with urea (46.66 g, 776.9 mmol) and stirred at 160° C. After confirming the reaction by TLC, the reaction mixture was cooled to 100° C., water (55 ml) was added, and the mixture was stirred for 1 hour. When the reaction was completed, the resulting solid was filtered under reduced pressure, washed with water and then dried to obtain 14.58 g of the product (yield: 81%).

2) Synthesis of Sub 1-II-14

In a round bottom flask, the resulting Sub 1-I-14 (14.58 g, 89.9 mmol) and POCl$_3$ (60 ml) were dissolved at room temperature, N,N-Diisopropylethylamine (29.05 g, 224.8 mmol) was added dropwise and stirred at 90° C. When the reaction was completed, the reaction mixture was concentrated, and ice water (120 ml) was added thereto, followed by stirring at room temperature for 1 hour. The resulting solid was filtered under reduced pressure and dried to obtain 15.39 g of the product (yield: 86%).

3) Synthesis of Sub 1-14

Phenylboronic acid pinacol ester (19.2 g, 75.4 mmol), THF (332 ml), 2,4-dichloroquinazoline (15 g, 75.4 mmol), Pd(PPh$_3$)$_4$ (2.6 g, 2.26 mmol), K$_2$CO$_3$ (31.2 g, 226 mmol), water (166 ml) were carried out in the same procedure as described in the synthesis method of Sub 1-51 to obtain 9.64 g of the product. (yield: 49%).

Synthesis Example of Sub 1-24

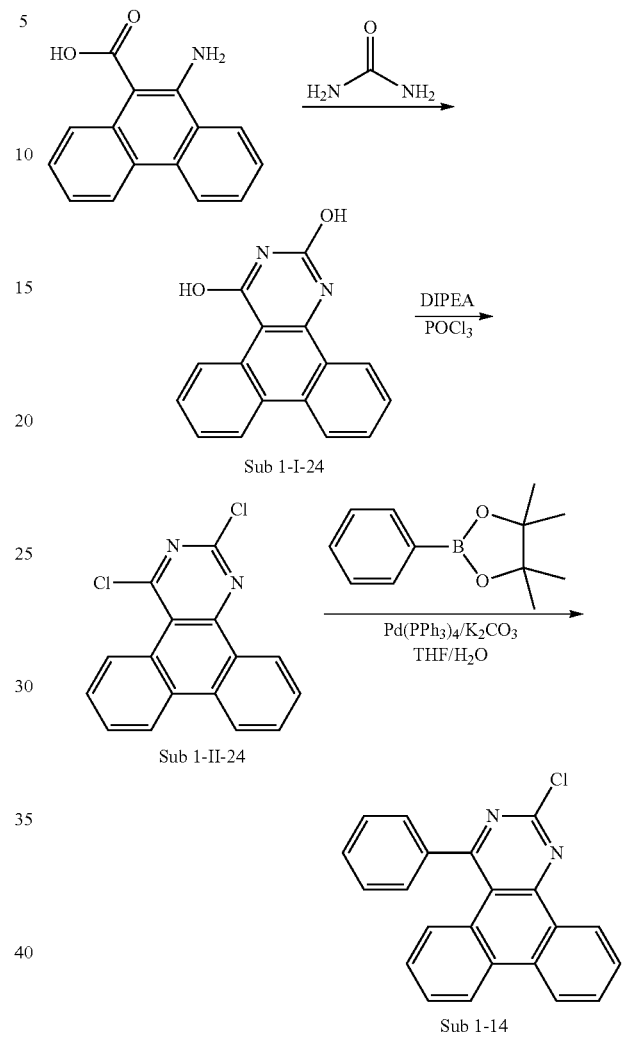

Sub 1-I-24

Sub 1-II-24

Sub 1-14

1) Synthesis of Sub 1-I-24

The starting material 10-aminophenanthrene-9-carboxylic acid (60.22 g, 253.8 mmol), urea (106.71 g, 1776.8 mmol), water (130 ml) were carried out in the same procedure as described in the synthesis method of Sub 1-1-14 to obtain 41.94 g of the product. (yield: 63%).

2) Synthesis of Sub 1-II-24

The resulting Sub 1-I-24 (41.94 g, 159.9 mmol)에 POCl$_3$ (110 ml), N,N-Diisopropylethylamine (51.67 g, 399.8 mmol) were carried out in the same procedure as described in the synthesis method of Sub 1-II-14 to obtain 40.19 g of the product. (yield: 84%).

3) Synthesis of Sub 1-24

The resulting Sub 1-II-24 (40.19 g, 134.3 mmol)에 4,4,5,5-tetramethyl-2-phenyl-1,3,2-dioxaborolane (30.16 g, 147.8 mmol), Pd(PPh$_3$)$_4$ (6.21 g, 5.4 mmol), K$_2$CO$_3$ (55.7 g, 403 mmol), THF, water were carried out in the same procedure as described in the synthesis method of Sub 1-14 to obtain 23.81 g of the product. (yield: 52%).

Synthesis Example of Sub 1-31

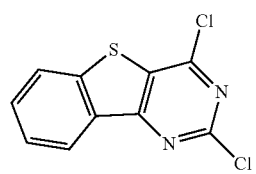

+

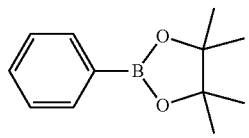

$\xrightarrow{\text{Pd(PPh}_3)_4/\text{K}_2\text{CO}_3}{\text{THF/H}_2\text{O}}$

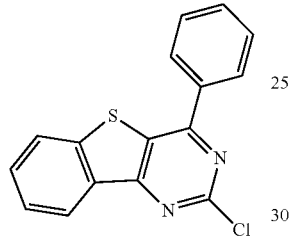

Sub 1-31

Phenylboronic acid pinacol ester (14.4 g, 70.6 mmol), THF (310 ml), 2,4-dichlorobenzo[4,5]thieno[3,2-d]pyrimidine (18 g, 70.6 mmol), Pd(PPh$_3$)$_4$ (2.4 g, 2.1 mmol), K$_2$CO$_3$ (29.3 g, 212 mmol), water (155 ml) were carried out in the same procedure as described in the synthesis method of Sub 1-14 to obtain 9.21 g of the product. (yield: 44%).

TABLE 3

| compound | FD-MS | compound | FD-MS |
|---|---|---|---|
| Sub 1-3 | m/z = 231.99(C$_{12}$H$_9$Br = 233.10) | Sub 1-6 | m/z = 272.02(C$_{15}$H$_{13}$Br = 273.17) |
| Sub 1-11 | m/z = 245.97(C$_{12}$H$_7$BrO = 247.09) | Sub 1-12 | m/z = 266.06(C$_{16}$H$_{11}$ClN$_2$ = 266.72) |
| Sub 1-14 | m/z = 290.06(C$_{18}$H$_{11}$ClN$_2$ = 290.75) | Sub 1-16 | m/z = 290.06(C$_{18}$H$_{11}$ClN$_2$ = 290.75) |
| Sub 1-19 | m/z = 416.11(C$_{28}$H$_{17}$ClN$_2$ = 416.90) | Sub 1-24 | m/z = 340.08(C$_{22}$H$_{13}$ClN$_2$ = 340.81) |
| Sub 1-26 | m/z = 390.09(C$_{26}$H$_{15}$ClN$_2$ = 390.86) | Sub 1-29 | m/z = 446.06(C$_{28}$H$_{15}$ClN$_2$ S = 446.95) |
| Sub 1-31 | m/z = 296.02(C$_{16}$H$_9$Cl$_2$S = 296.77) | Sub 1-34 | m/z = 372.05(C$_{22}$H$_{13}$ClN$_2$S = 372.87) |
| Sub 1-36 | m/z = 422.06(C$_{26}$H$_{15}$ClN$_2$S = 422.93) | Sub 1-41 | m/z = 432.10(C$_{28}$H$_{17}$ClN$_2$O = 432.90) |
| Sub 1-42 | m/z = 406.09(C$_{26}$H$_{15}$ClN$_2$O = 406.86) | Sub 1-51 | m/z = 372.05(C$_{22}$H$_{13}$ClN$_2$S = 372.87) |
| Sub 1-52 | m/z = 280.04(C$_{16}$H$_9$ClN$_2$O = 280.71) | Sub 1-66 | m/z = 402.02(C$_{22}$H$_{13}$BrN$_2$O = 401.26) |
| Sub 1-70 | m/z = 346.03(C$_{20}$H$_{11}$ClN$_2$S = 346.83) | Sub 1-71 | m/z = 356.07(C$_{22}$H$_{13}$ClN$_2$O = 358.80) |
| Sub 1-78 | m/z = 339.86(C$_{12}$H$_6$Br$_2$S = 342.05) | | |

Examples of Sub 1

Sub 1-1

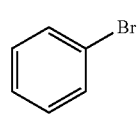

Sub 1-2

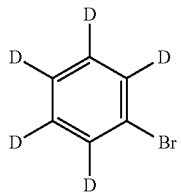

Sub 1-3

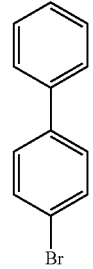

Sub 1-4

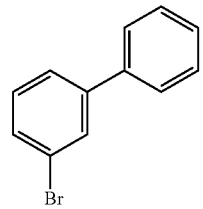

Sub 1-5

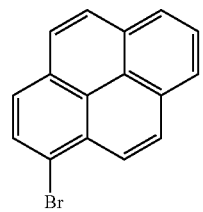

-continued

Sub 1-6

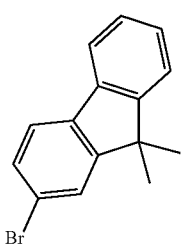

-continued
Sub 1-7
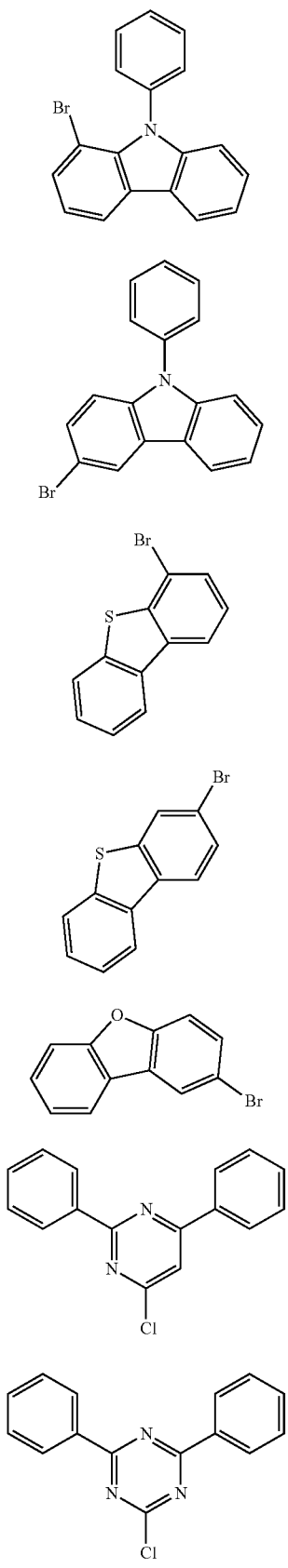
Sub 1-8
Sub 1-9
Sub 1-10
Sub 1-11
Sub 1-12
Sub 1-13
-continued
Sub 1-14
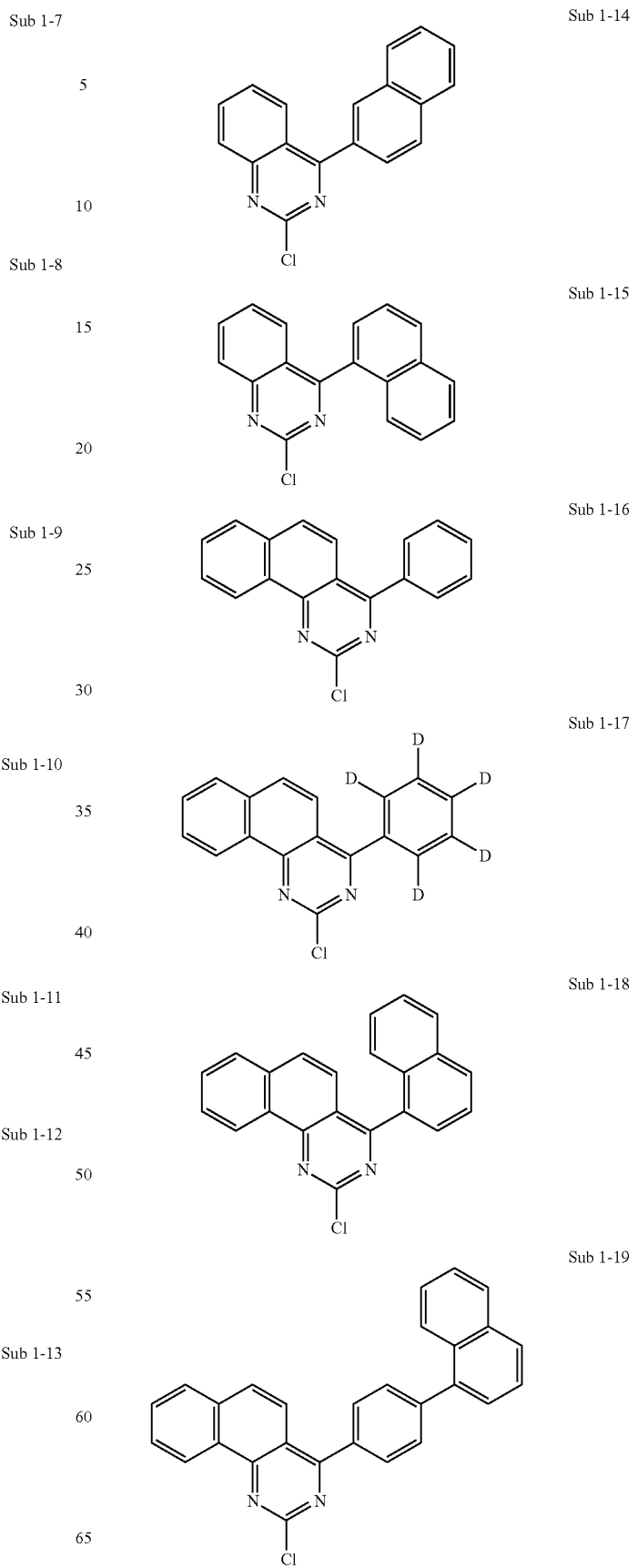
Sub 1-15
Sub 1-16
Sub 1-17
Sub 1-18
Sub 1-19

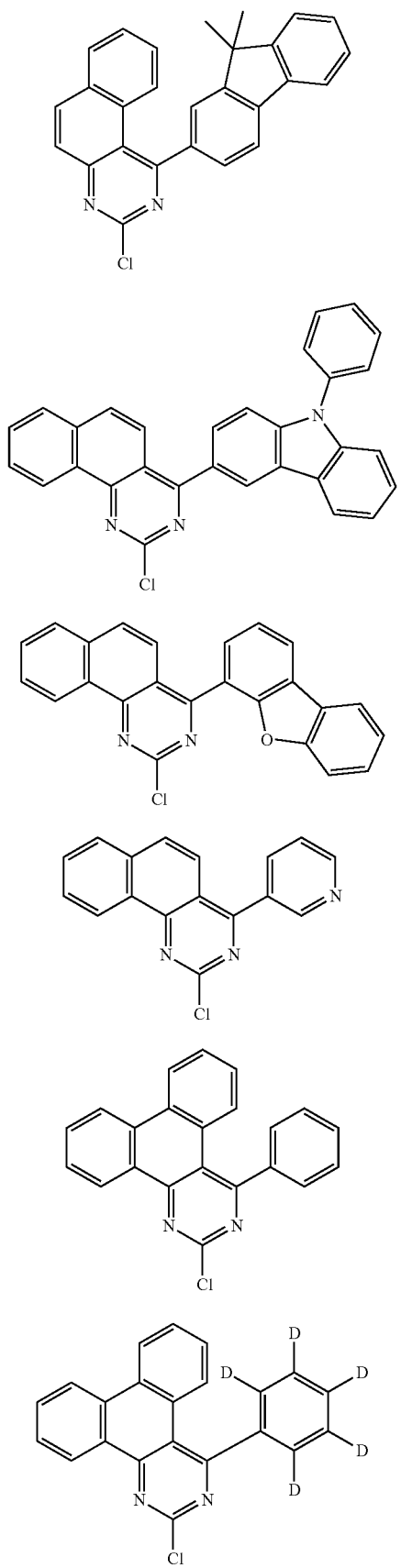
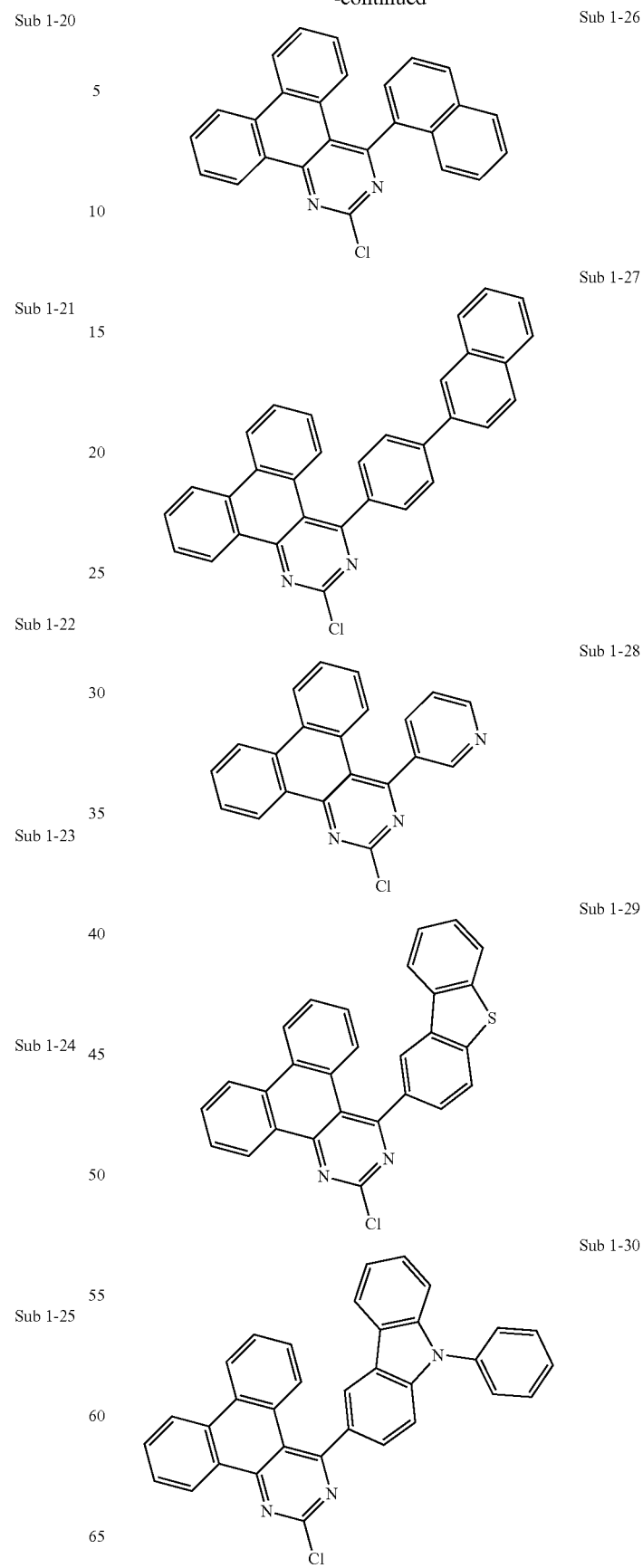

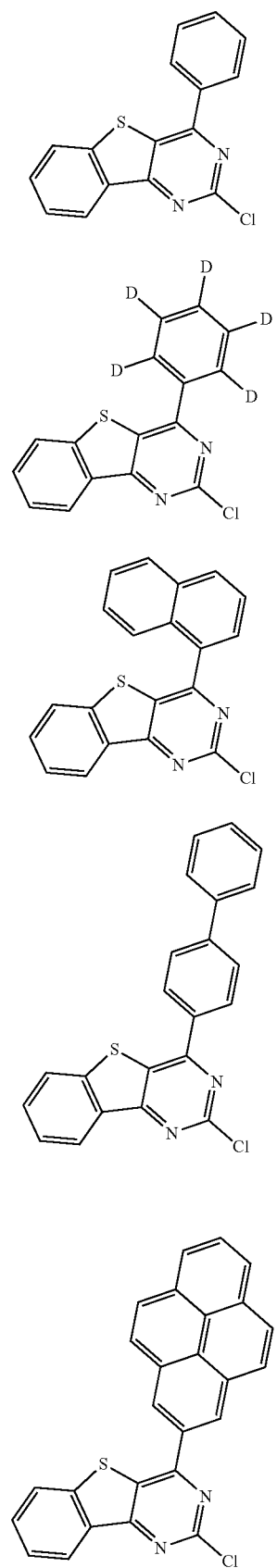
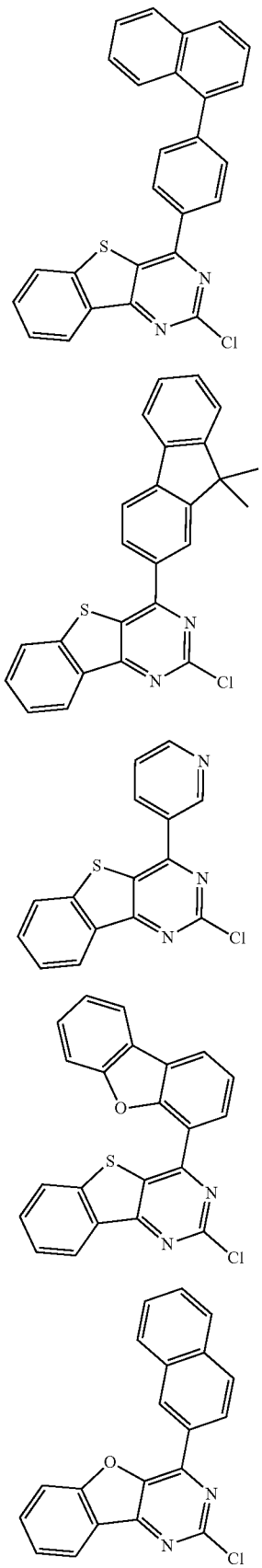
Sub 1-31
Sub 1-32
Sub 1-33
Sub 1-34
Sub 1-35
Sub 1-36
Sub 1-37
Sub 1-38
Sub 1-39
Sub 1-40

-continued
Sub 1-41
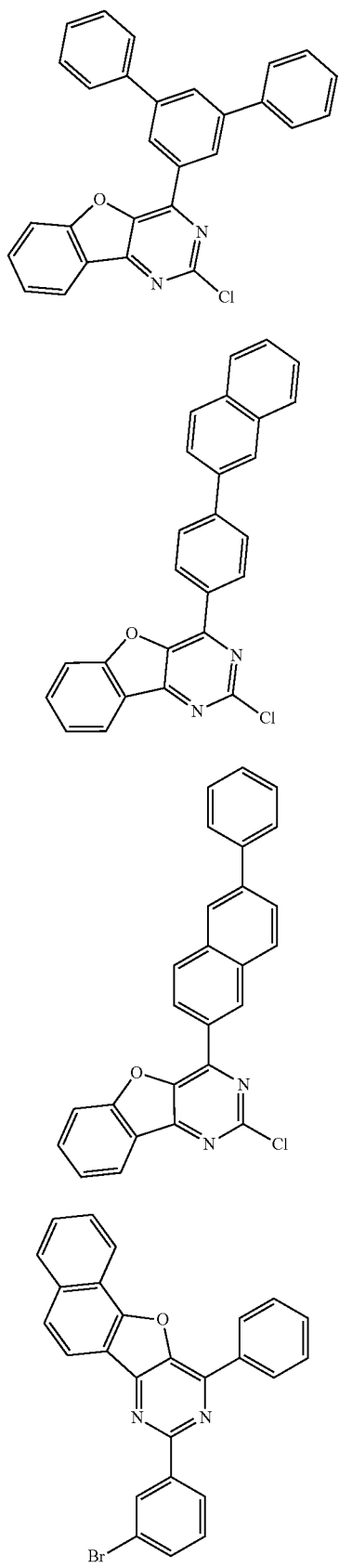
Sub 1-42
Sub 1-43
Sub 1-44
-continued
Sub 1-45
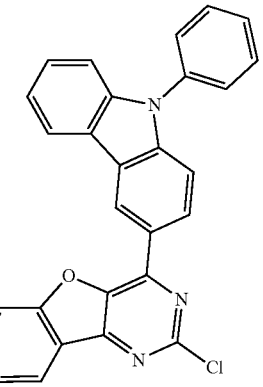
Sub 1-46
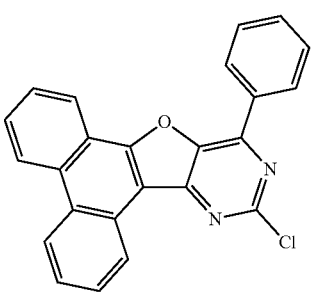
Sub 1-47
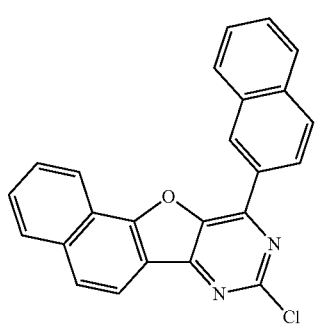
Sub 1-48
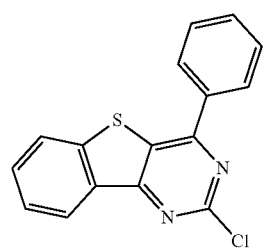
Sub 1-49
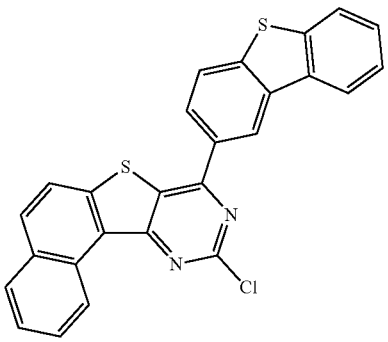

Sub 1-50
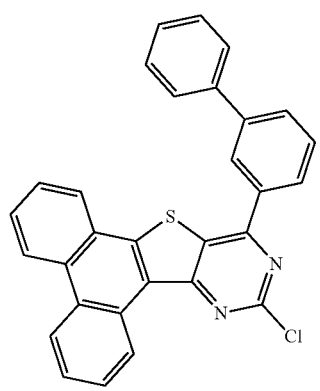
Sub 1-51
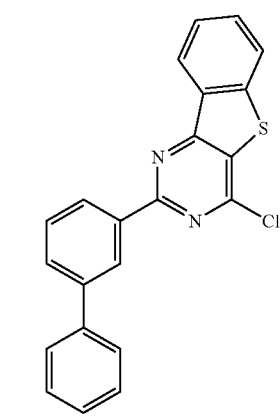
Sub 1-52
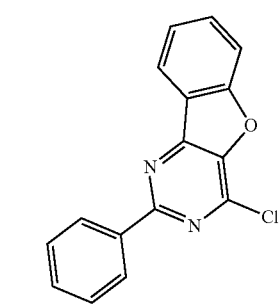
Sub 1-53
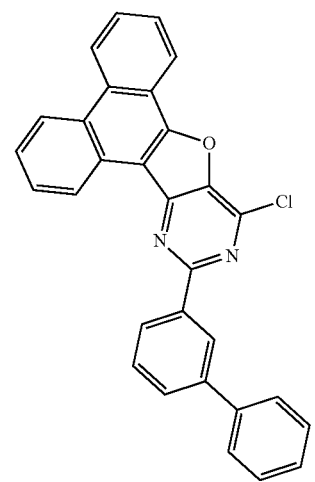
Sub 1-54
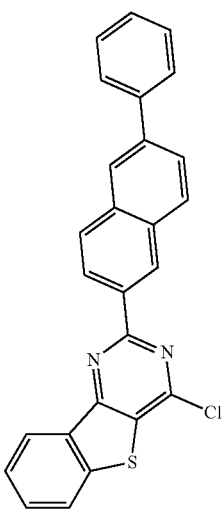
Sub 1-55
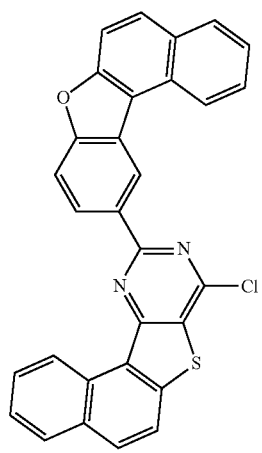
Sub 1-56
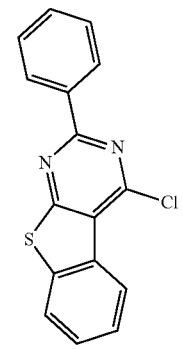

Sub 1-57
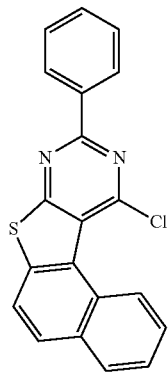
Sub 1-58
Sub 1-59
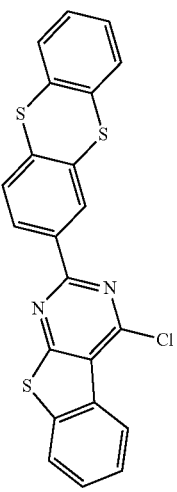
Sub 1-60
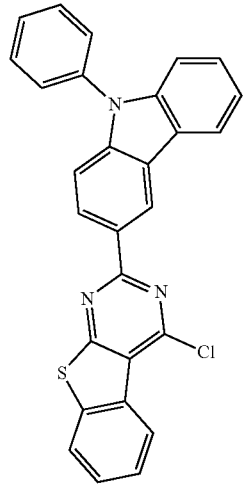
Sub 1-61
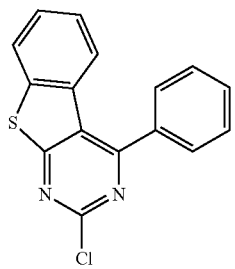
Sub 1-62
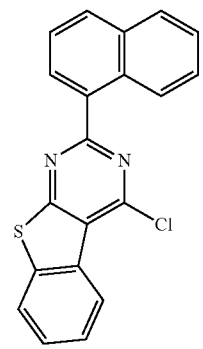
Sub 1-63
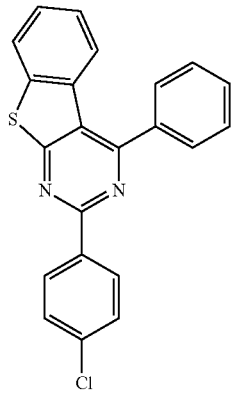

241
-continued
Sub 1-64
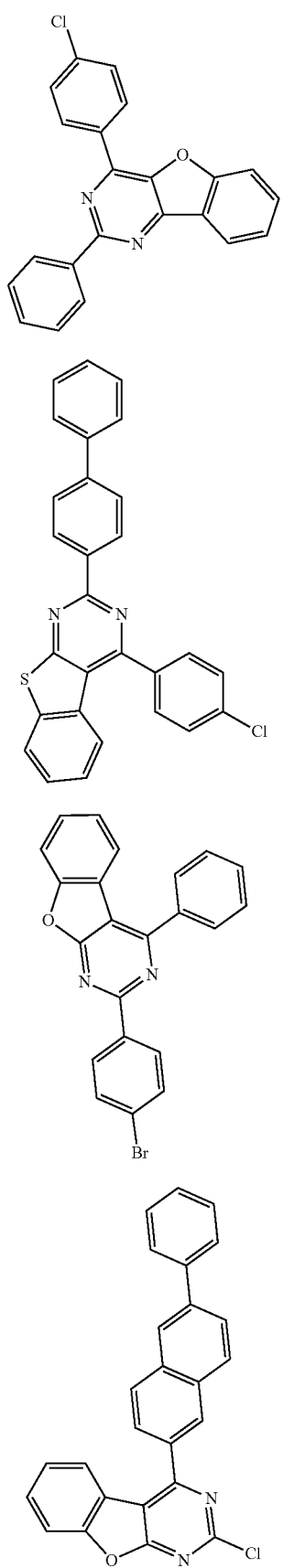
Sub 1-65
Sub 1-66
Sub 1-67
242
-continued
Sub 1-68
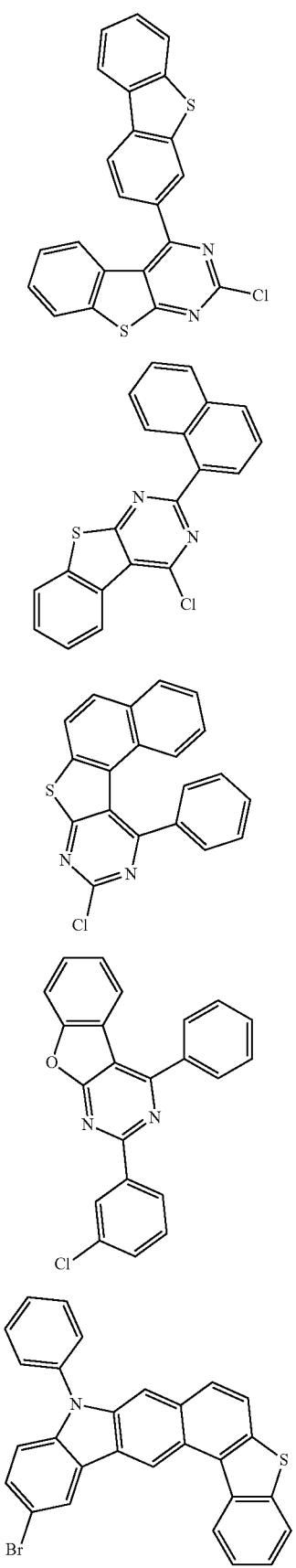
Sub 1-69
Sub 1-70
Sub 1-71
Sub 1-72

-continued

Sub 1-73

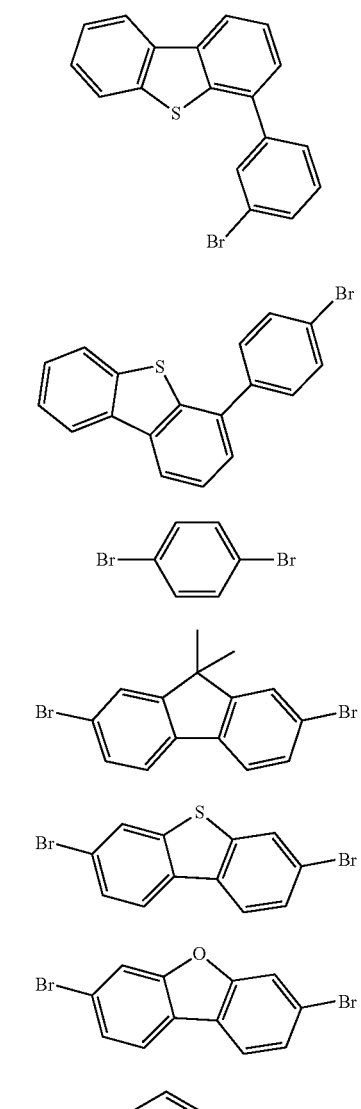

Sub 1-74

Sub 1-75

Sub 1-76

Sub 1-77

Sub 1-78

Sub 1-79

Sub 1-80

III. Synthesis Example of Sub 2

Sub 2 of reaction scheme 1 may be synthesized by the following reaction path, but is not limited thereto.

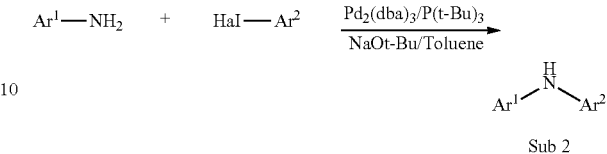

(Wherein Hal is Br or Cl).

Synthesis Example of Sub 2-4

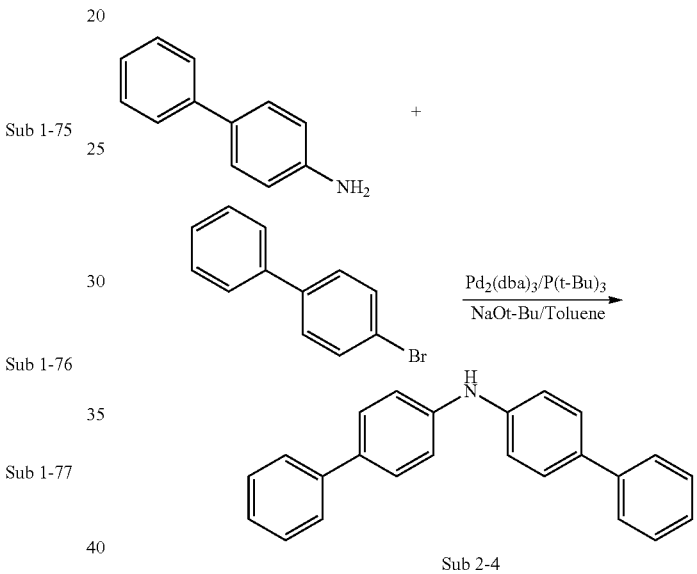

In a round bottom flask, 4-Aminobiphenyl (5.23 g, 30.9 mmol), 4-Bromobiphenyl (7.2 g, 30.9 mmol), $Pd_2(dba)_3$ (1.41 g, 1.54 mmol), $P(t-Bu)_3$ (0.62 g, 3.1 mmol), NaOt-Bu (8.91 g, 92.7 mmol), toluene (324 mL) were added and refluxed with stirring at 100° C. for 24 hours. When the reaction was completed, the reaction mixture was extracted with ether and water. The organic layer was dried over $MgSO_4$ and concentrated. The resulting compound was separated by silicagel column chromatography and recrystallization to obtain 6.75 g of the product (yield: 68%).

Synthesis Example of Sub 2-11

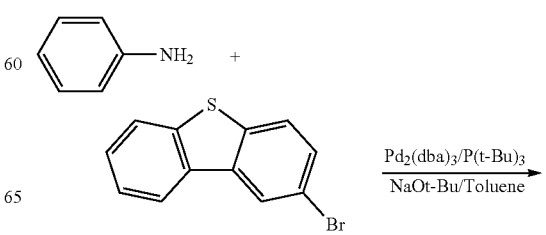

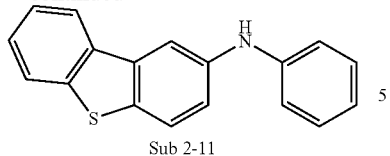
Sub 2-11

2-bromodibenzo[b,d]thiophene (15 g, 57 mmol), aniline (5.31 g, 57 mmol), Pd$_2$(dba)$_3$ (2.61 g, 2.85 mmol), P(t-Bu)$_3$ (1.15 g, 5.7 mmol), NaOt-Bu (16.4 g, 171 mmol), toluene (598 mL) were carried out in the same procedure as described in the synthesis method of Sub 2-4 to obtain 12.1 g of the product. (yield: 77%).

Synthesis Example of Sub 2-16

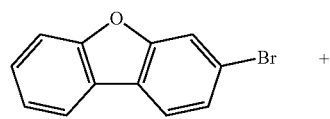

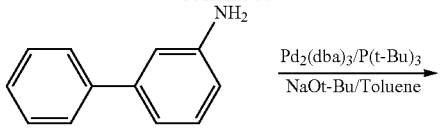

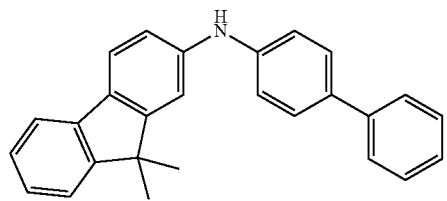
Sub 2-9

The starting material 2-bromo-9,9-dimethyl-9H-fluorene (10.81 g, 39.6 mmol) on [1,1'-biphenyl]-4-amine (13.39 g, 79.1 mmol), Pd$_2$(dba)$_3$ (1.09 g, 1.2 mmol), 50% P(t-Bu)$_3$ (1.5 ml, 3.2 mmol), NaOt-Bu (11.41 g, 118.7 mmol), toluene were carried out in the same procedure as described in the synthesis method of Sub 2-4 to obtain 11.73 g of the product. (yield: 82%).

TABLE 4

| compound | FD-MS | compound | FD-MS |
| --- | --- | --- | --- |
| Sub 2-4 | m/z = 321.15(C$_{24}$H$_{19}$N = 321.41) | Sub 2-6 | m/z = 295.14(C$_{22}$H$_{17}$N = 295.38) |
| Sub 2-9 | m/z = 361.18(C$_{27}$H$_{23}$N = 361.48) | Sub 2-11 | m/z = 275.08(C$_{18}$H$_{13}$NS = 275.37) |
| Sub 2-12 | m/z = 275.08(C$_{18}$H$_{13}$NS = 275.37) | Sub 2-15 | m/z = 259.10(C$_{18}$H$_{13}$NO = 259.30) |
| Sub 2-16 | m/z = 309.12(C$_{22}$H$_{15}$NO = 309.36) | Sub 2-18 | m/z = 385.15(C$_{28}$H$_{19}$NO = 385.46) |
| Sub 2-26 | m/z = 384.16(C$_{28}$H$_{20}$N$_2$ = 384.47) | | |

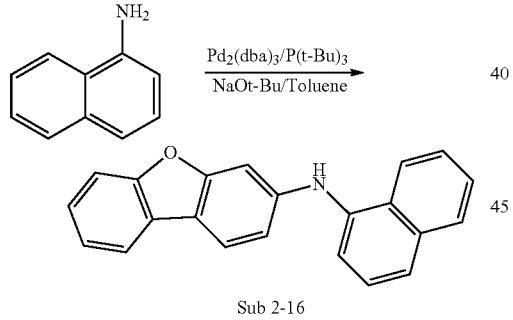
Sub 2-16

The starting material 3-bromodibenzo[b,d]furan (8.06 g, 32.6 mmol) on naphthalen-1-amine (9.34 g, 65.2 mmol), Pd$_2$(dba)$_3$ (0.9 g, 1 mmol), 50% P(t-Bu)$_3$ (1.3 ml, 2.6 mmol), NaOt-Bu (9.41 g, 97.9 mmol), toluene were carried out in the same procedure as described in the synthesis method of Sub 2-4 to obtain 8.07 g of the product. (yield: 80%).

Synthesis Example of Sub 2-9

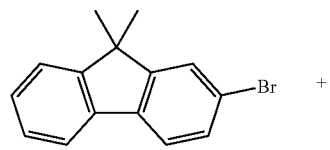

Example of Sub 2

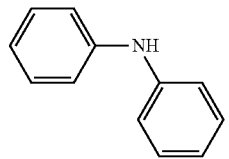
Sub 2-1

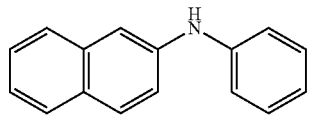
Sub 2-2

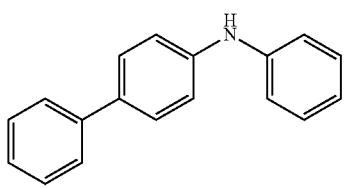
Sub 2-3

-continued
Sub 2-4
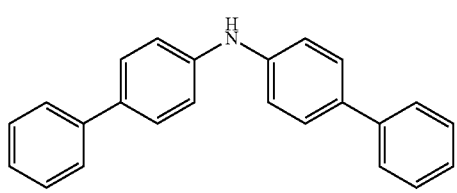
Sub 2-5
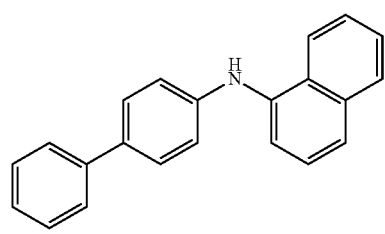
Sub 2-6
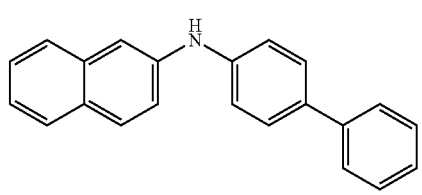
Sub 2-7
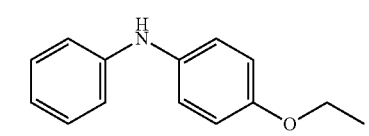
Sub 2-8
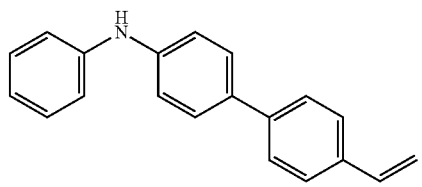
Sub 2-9
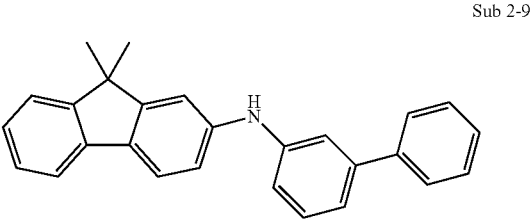
Sub 2-10
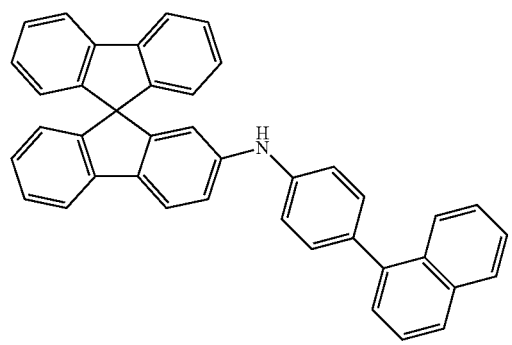
-continued
Sub 2-11
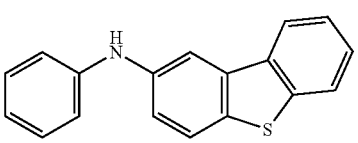
Sub 2-12
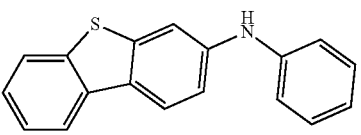
Sub 2-13
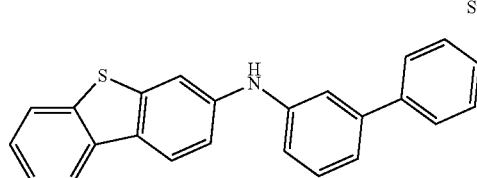
Sub 2-14
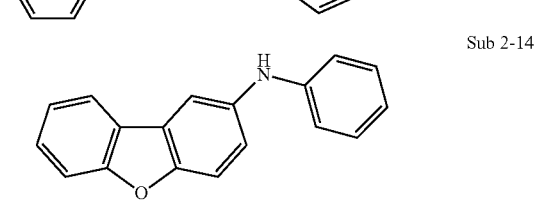
Sub 2-15
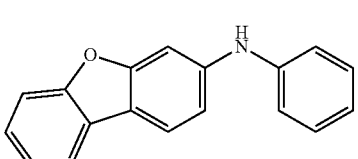
Sub 2-16
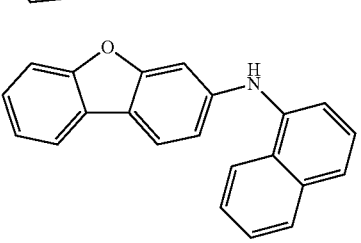
Sub 2-17
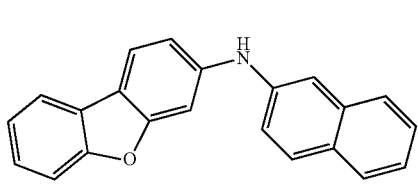
Sub 2-18
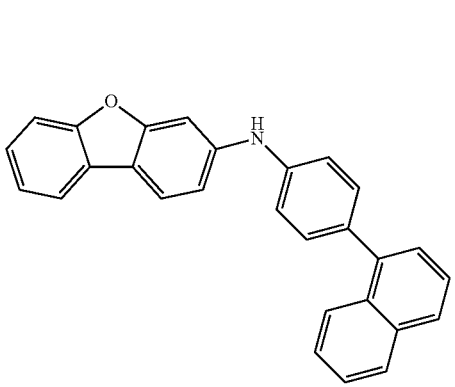

Sub 2-19
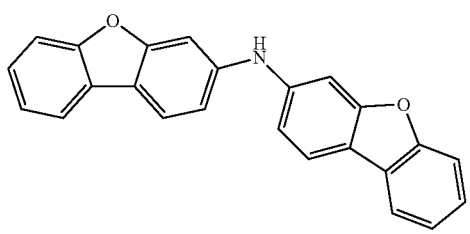
Sub 2-20
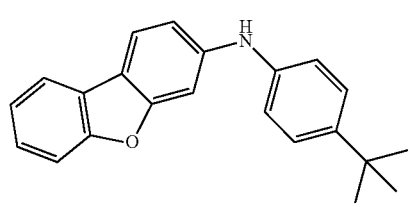
Sub 2-21
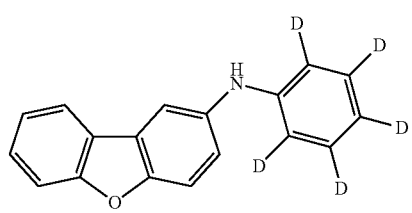
Sub 2-22
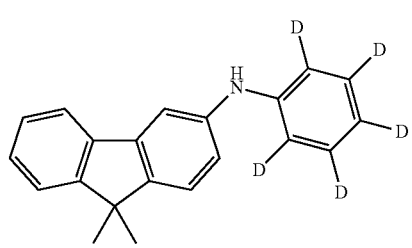
Sub 2-23
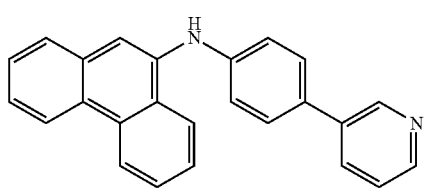
Sub 2-24
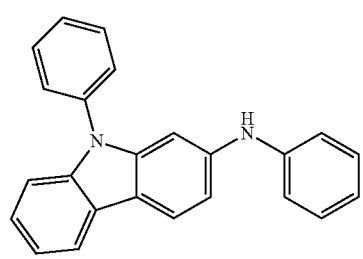
Sub 2-25
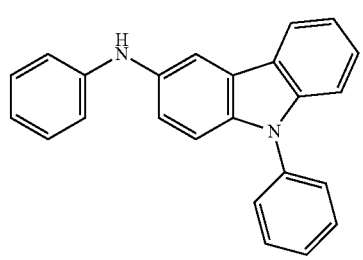
Sub 2-26
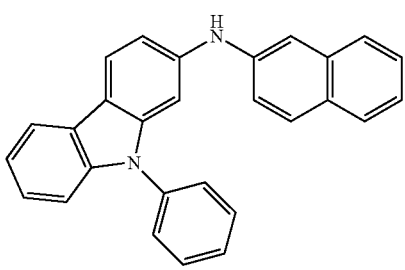
Sub 2-27
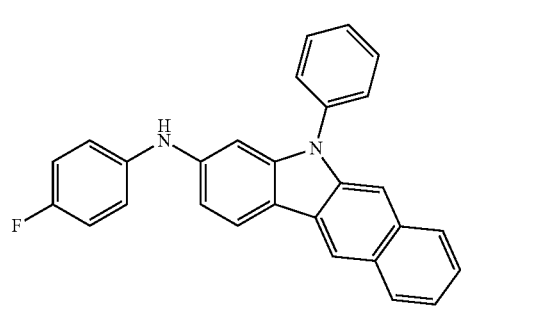
Sub 2-28
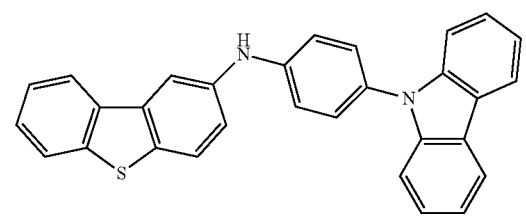
Sub 2-29
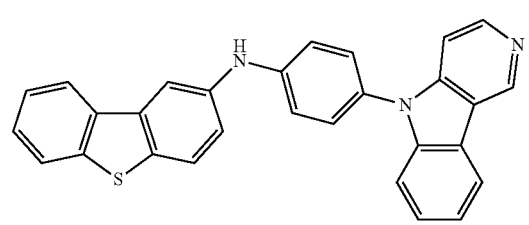
IV. Synthesis Example of Final Product (1)
Synthetic Example of 1-1-5
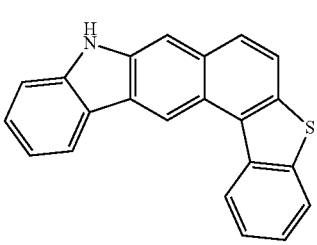
Core 1-1      +

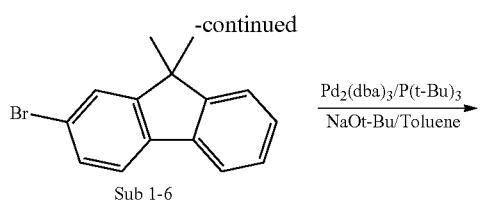

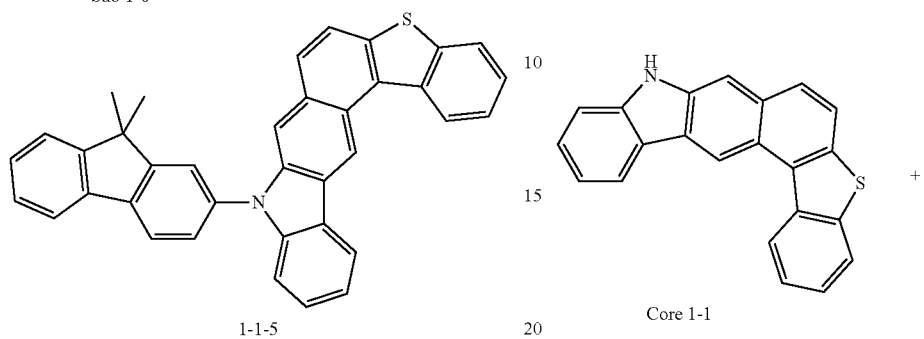

In a round bottom flask, Core 1-1 (5.4 g, 16.7 mmol), Sub 1-6 (4.56 g, 16.7 mmol), Pd$_2$(dba)$_3$ (0.76 g, 0.84 mmol), P(t-Bu)$_3$ (0.34 g, 1.67 mmol), NaOt-Bu (2.41 g, 25.05 mmol), toluene (175 mL) were added and the reaction is carried out at 100° C. When the reaction was completed, the reaction mixture was extracted with ether and water. The organic layer was dried over MgSO$_4$ and concentrated. The resulting compound was separated by silicagel column chromatography and recrystallization to obtain 7.06 g of the product (yield: 82%).

Synthesis Example of 1-1-2

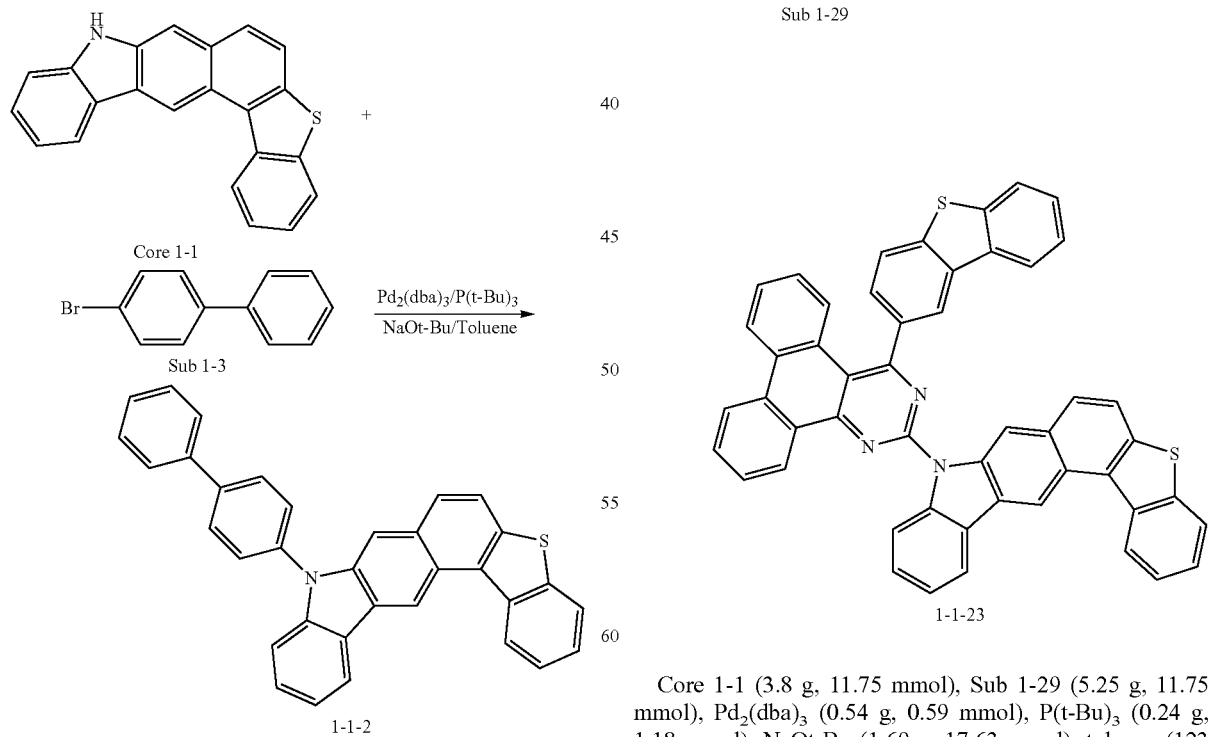

Core 1-1 (5.6 g, 17.32 mmol), Sub 1-3 (4.04 g, 17.32 mmol), Pd$_2$(dba)$_3$ (0.79 g, 0.87 mmol), P(t-Bu)$_3$ (0.35 g, 1.73 mmol), NaOt-Bu (2.50 g, 25.97 mmol), toluene (181 mL) were carried out in the same procedure as described in the synthesis method of 1-1-5 to obtain 7.08 g of the product. (yield: 86%).

Synthesis Example of 1-1-23

Core 1-1 (3.8 g, 11.75 mmol), Sub 1-29 (5.25 g, 11.75 mmol), Pd$_2$(dba)$_3$ (0.54 g, 0.59 mmol), P(t-Bu)$_3$ (0.24 g, 1.18 mmol), NaOt-Bu (1.69 g, 17.63 mmol), toluene (123 mL) were carried out in the same procedure as described in the synthesis method of 1-1-5 to obtain 7.07 g of the product. (yield: 82%).

253
Synthesis Example of 1-1-53

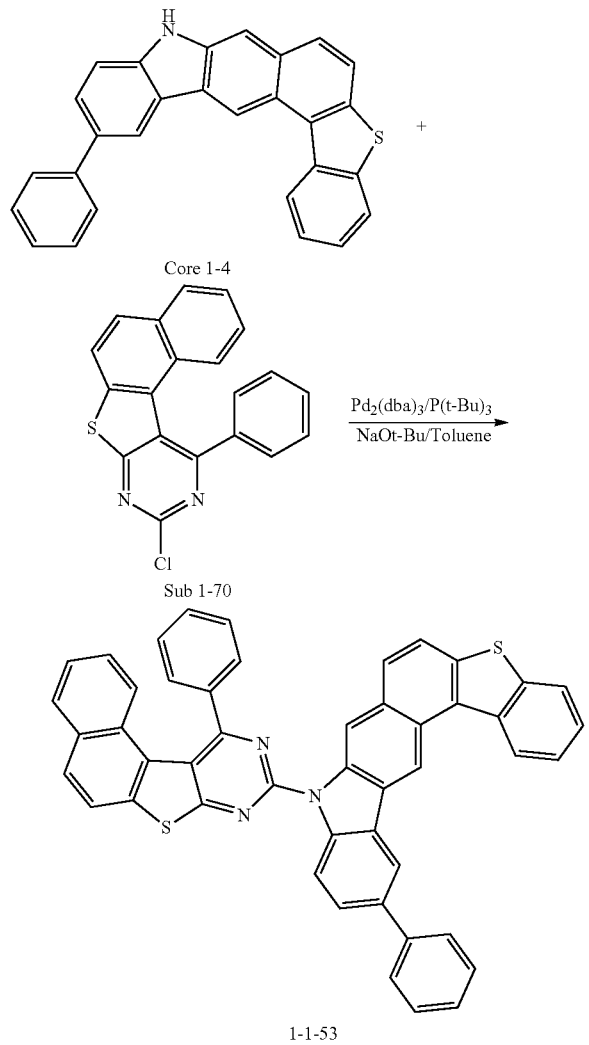

Core 1-4 (4.9 g, 12.27 mmol), Sub 1-70 (4.25 g, 12.27 mmol), Pd$_2$(dba)$_3$ (0.56 g, 0.61 mmol), P(t-Bu)$_3$ (0.25 g, 1.23 mmol), NaOt-Bu (3.54 g, 36.8 mmol), toluene (129 mL) were carried out in the same procedure as described in the synthesis method of 1-1-5 to obtain 7.05 g of the product. (yield: 81%).

254
Synthesis Example of 1-1-51

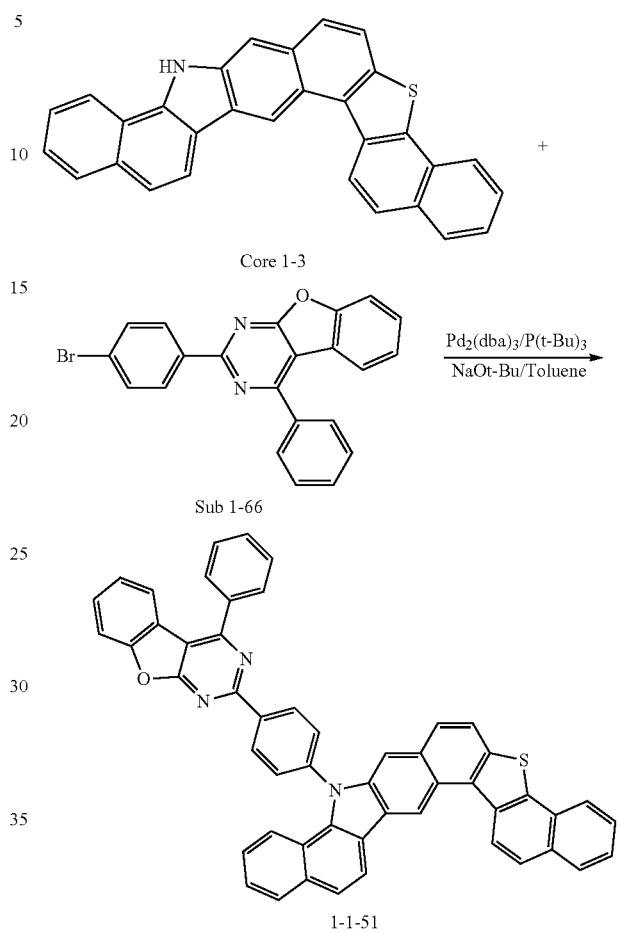

Core 1-3 (5.4 g, 12.75 mmol), Sub 1-66 (5.12 g, 12.75 mmol), Pd$_2$(dba)$_3$ (0.58 g, 0.64 mmol), P(t-Bu)$_3$ (0.26 g, 1.28 mmol), NaOt-Bu (1.84 g, 19.13 mmol), toluene (134 mL) were carried out in the same procedure as described in the synthesis method of 1-1-5 to obtain 7.11 g of the product. (yield: 75%).

Synthesis Example of 1-1-58

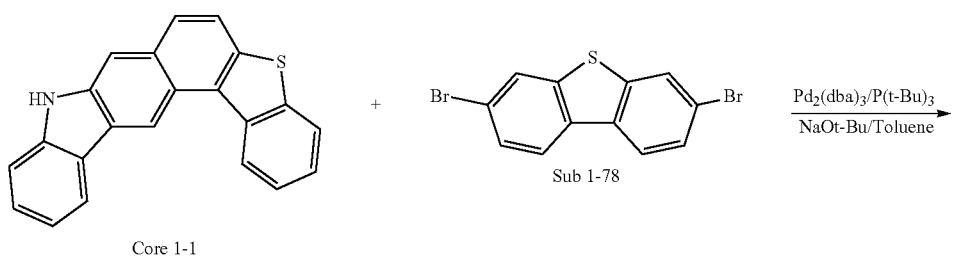

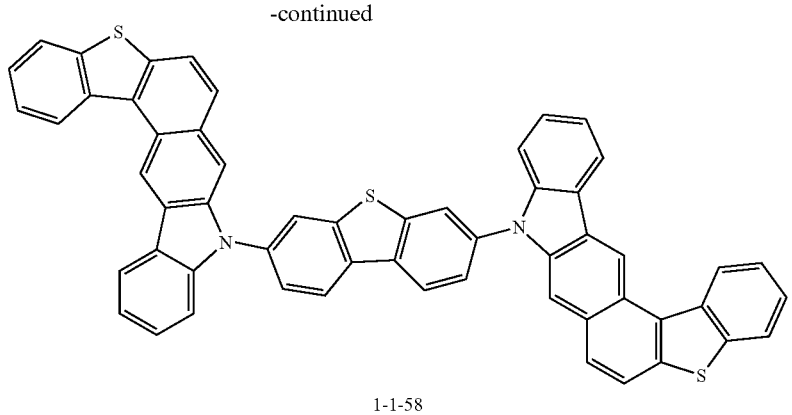

1-1-58

Core 1-1 (7 g, 21.64 mmol), Sub 1-78 (3.7 g, 10.82 mmol), Pd$_2$(dba)$_3$ (0.99 g, 1.08 mmol), P(t-Bu)$_3$ (0.44 g, 2.16 mmol), NaOt-Bu (5.20 g, 54.11 mmol), toluene (227 mL) were carried out in the same procedure as described in the synthesis method of 1-1-5 to obtain 13.43 g of the product. (yield: 75%).

Synthesis Example of 1-2-10

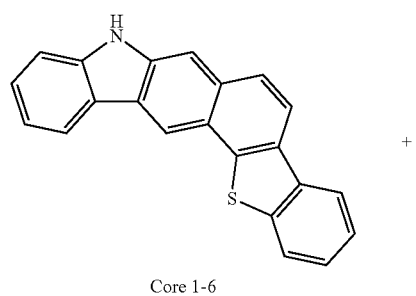

Core 1-6

+

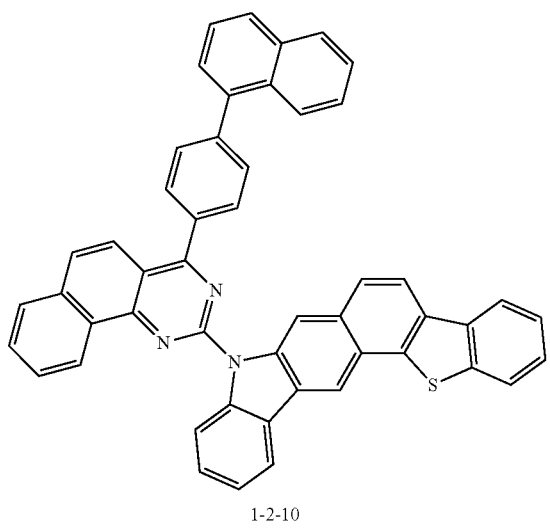

1-2-10

Core 1-6 (4.1 g, 12.68 mmol), Sub 1-19 (5.29 g, 12.68 mmol), Pd$_2$(dba)$_3$ (0.58 g, 0.63 mmol), P(t-Bu)$_3$ (0.26 g, 1.27 mmol), NaOt-Bu (3.65 g, 38.03 mmol), toluene (133 mL) were carried out in the same procedure as described in the synthesis method of 1-1-5 to obtain 7.05 g of the product. (yield: 79%).

Synthesis Example of 1-2-28

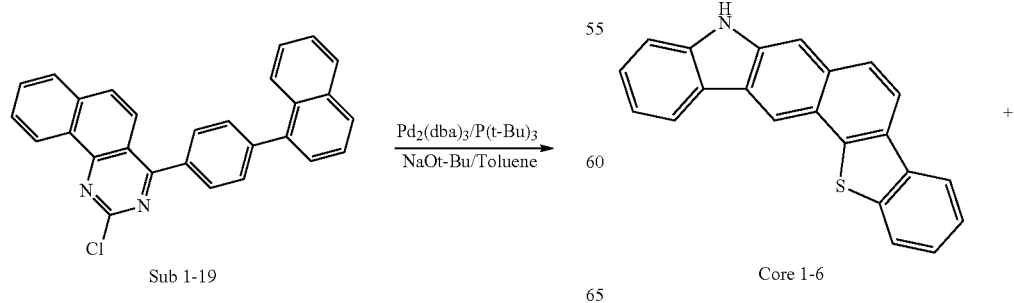

-continued

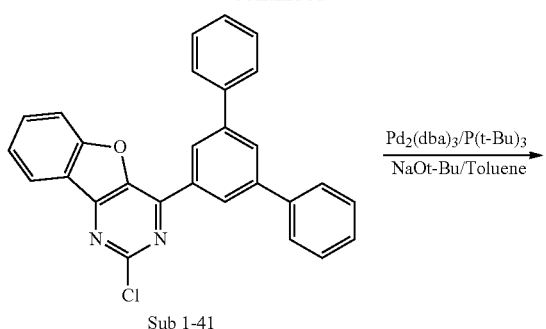
Sub 1-41

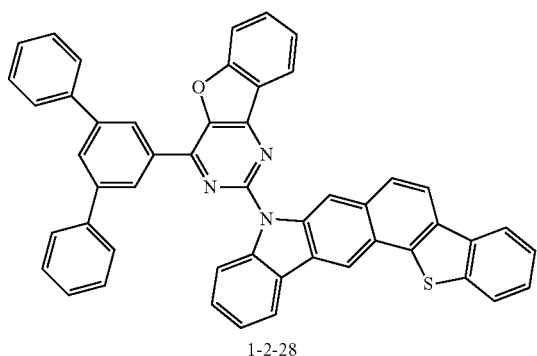
1-2-28

Core 1-6 (4.2 g, 12.99 mmol), Sub 1-41 (5.62 g, 12.99 mmol), Pd₂(dba)₃ (0.59 g, 0.65 mmol), P(t-Bu)₃ (0.26 g, 1.3 mmol), NaOt-Bu (3.74 g, 38.96 mmol), toluene (136 mL) were carried out in the same procedure as described in the synthesis method of 1-1-5 to obtain 7.01 g of the product. (yield: 75%).

Synthesis Example of 2-1-21

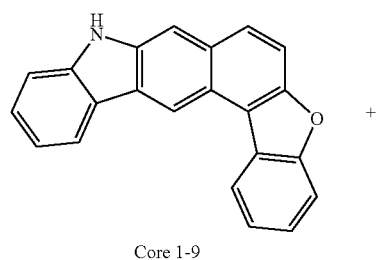
Core 1-9

+

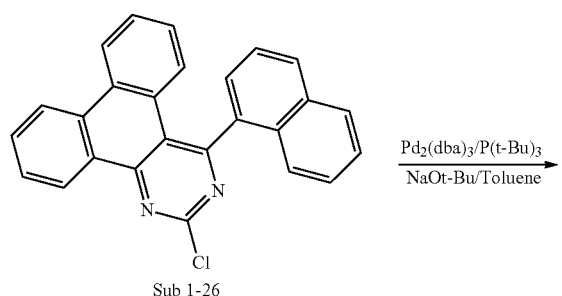
Sub 1-26

-continued

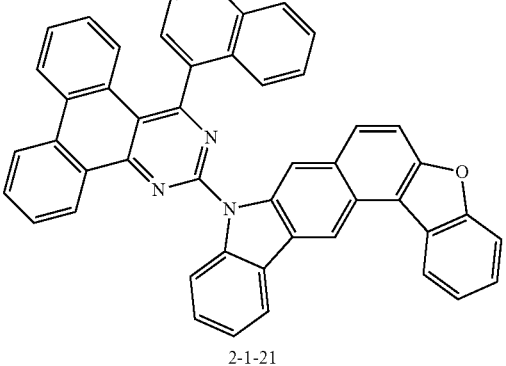
2-1-21

Core 1-9 (4.2 g, 13.67 mmol), Sub 1-26 (5.34 g, 13.67 mmol), Pd₂(dba)₃ (0.63 g, 0.68 mmol), P(t-Bu)₃ (0.28 g, 1.37 mmol), NaOt-Bu (3.94 g, 41 mmol), toluene (143 mL) were carried out in the same procedure as described in the synthesis method of 1-1-5 to obtain 7.05 g of the product. (yield: 78%).

Synthesis Example of 2-2-7

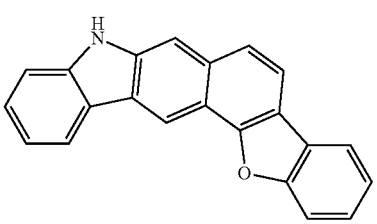
Core 1-12

+

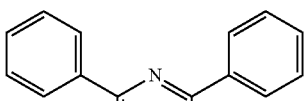
Sub 1-12

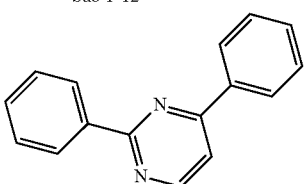
2-2-7

Core 1-12 (5.3 g, 17.25 mmol), Sub 1-12 (4.60 g, 17.25 mmol), Pd₂(dba)₃ (0.79 g, 0.86 mmol), P(t-Bu)₃ (0.35 g, 1.72 mmol), NaOt-Bu (2.49 g, 25.87 mmol), toluene (181 mL) were carried out in the same procedure as described in the synthesis method of 1-1-5 to obtain 7.05 g of the product. (yield: 76%).

Synthesis Example of 2-2-26

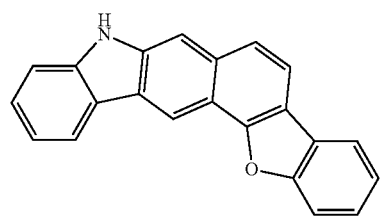

Core 1-12

+

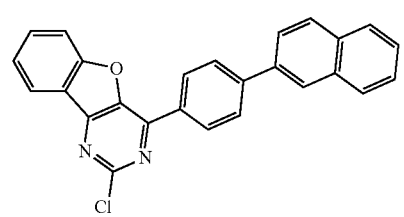

Sub 1-42

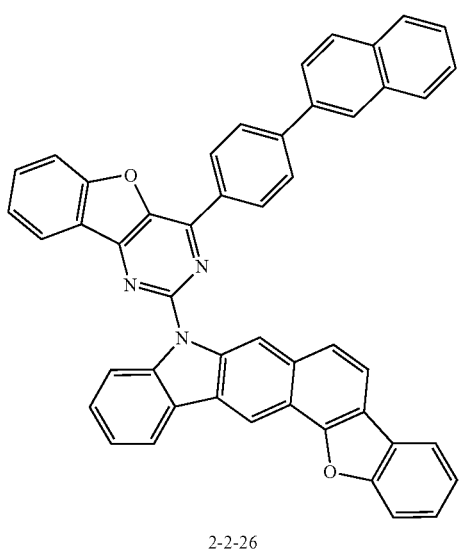

2-2-26

Core 1-12 (4.35 g, 14.15 mmol), Sub 1-42 (5.76 g, 14.15 mmol), Pd$_2$(dba)$_3$ (0.65 g, 0.71 mmol), P(t-Bu)$_3$ (0.29 g, 1.42 mmol), NaOt-Bu (4.08 g, 42.46 mmol), toluene (148 mL) were carried out in the same procedure as described in the synthesis method of 1-1-5 to obtain 7.00 g of the product. (yield: 73%).

Synthesis Example of 3-1-8

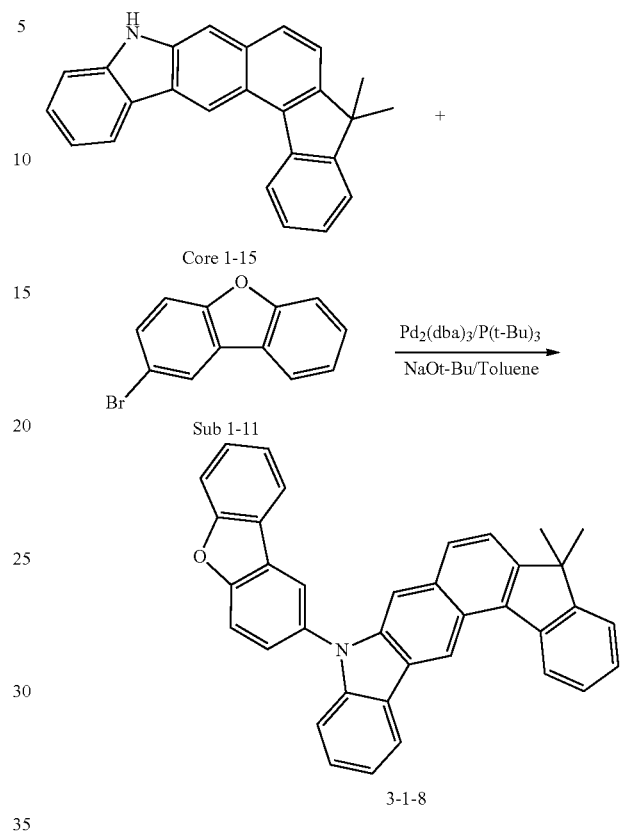

Core 1-15 (6 g, 18 mmol), Sub 1-11 (4.45 g, 18 mmol), Pd$_2$(dba)$_3$ (0.82 g, 0.90 mmol), P(t-Bu)$_3$ (0.36 g, 1.8 mmol), NaOt-Bu (2.59 g, 26.99 mmol), toluene (189 mL) were carried out in the same procedure as described in the synthesis method of 1-1-5 to obtain 7.01 g of the product. (yield: 78%).

Synthesis Example of 3-1-26

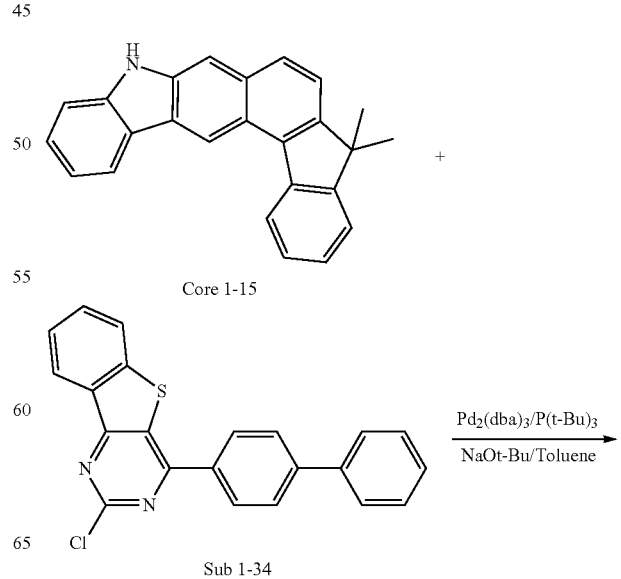

-continued

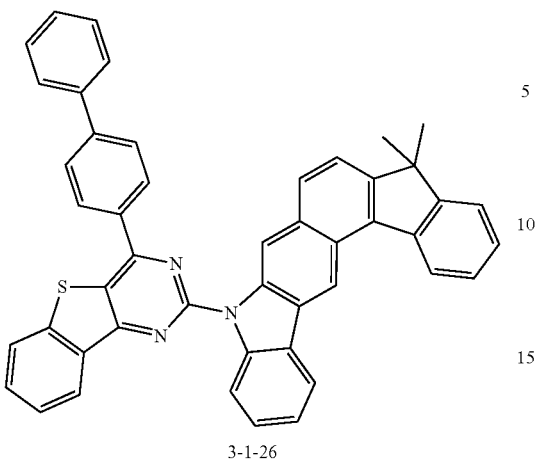

3-1-26

Core 1-15 (4.8 g, 14.4 mmol), Sub 1-34 (5.37 g, 14.4 mmol), Pd$_2$(dba)$_3$ (0.66 g, 0.72 mmol), P(t-Bu)$_3$ (0.29 g, 1.44 mmol), NaOt-Bu (4.15 g, 43.19 mmol), toluene (151 mL) were carried out in the same procedure as described in the synthesis method of 1-1-5 to obtain 7.04 g of the product. (yield: 73%).

Synthesis Example of 3-2-20

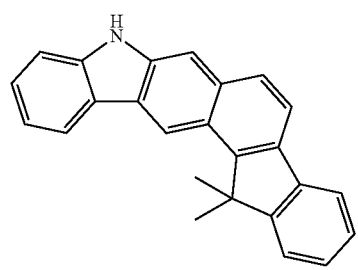

Core 1-18

+

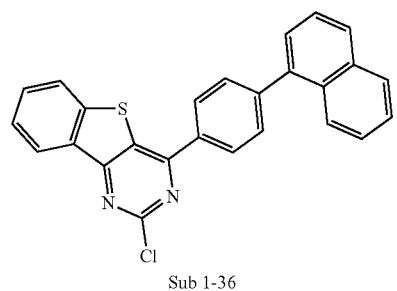

Sub 1-36

Pd$_2$(dba)$_3$/P(t-Bu)$_3$
NaOt-Bu/Toluene →

-continued

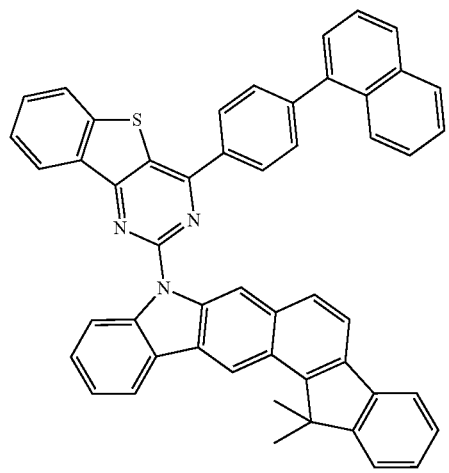

3-2-20

Core 1-18 (4.6 g, 13.8 mmol), Sub 1-36 (5.83 g, 13.8 mmol), Pd$_2$(dba)$_3$ (0.63 g, 0.69 mmol), P(t-Bu)$_3$ (0.28 g, 1.38 mmol), NaOt-Bu (3.98 g, 41.39 mmol), toluene (145 mL) were carried out in the same procedure as described in the synthesis method of 1-1-5 to obtain 7.05 g of the product. (yield: 71%).

Synthesis Example of 3-2-30

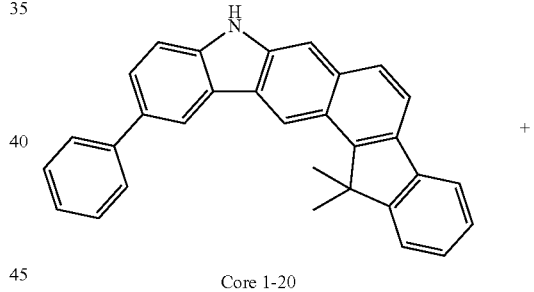

Core 1-20

+

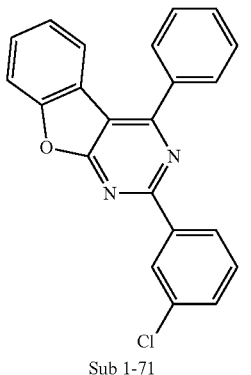

Sub 1-71

Pd$_2$(dba)$_3$/P(t-Bu)$_3$
NaOt-Bu/Toluene →

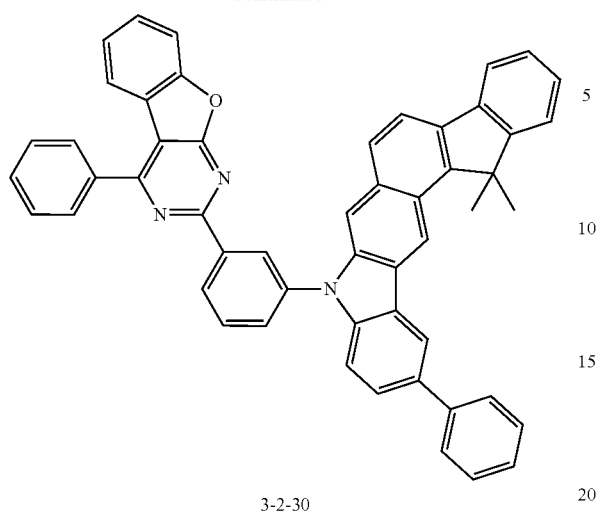

3-2-30

Core 1-20 (5.7 g, 13.92 mmol), Sub 1-71 (4.97 g, 13.92 mmol), Pd$_2$(dba)$_3$ (0.64 g, 0.7 mmol), P(t-Bu)$_3$ (0.28 g, 1.39 mmol), NaOt-Bu (4.01 g, 41.76 mmol), toluene (146 mL) were carried out in the same procedure as described in the synthesis method of 1-1-5 to obtain 7.11 g of the product. (yield: 70%).

Synthesis Example of 6-1-5

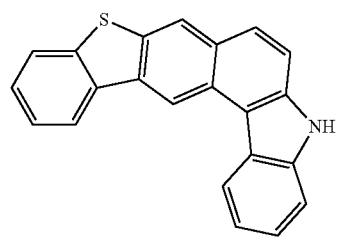

Core 1-51

+

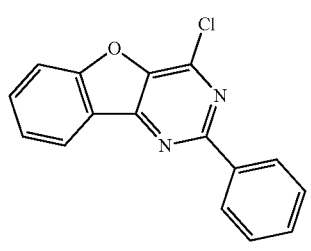

Sub 1-52

$\xrightarrow{\text{Pd}_2(\text{dba})_3/\text{P}(\text{t-Bu})_3}{\text{NaOt-Bu/Toluene}}$

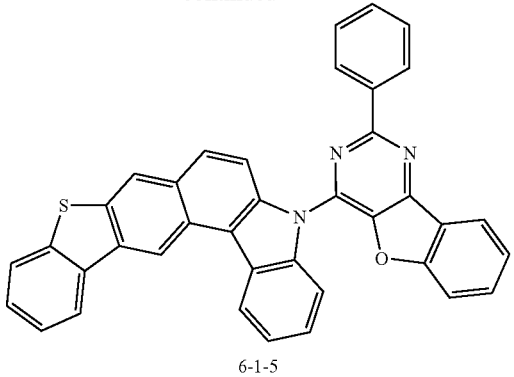

6-1-5

Core 1-51 (5.3 g, 16.39 mmol), Sub 1-52 (4.60 g, 16.39 mmol), Pd$_2$(dba)$_3$ (0.75 g, 0.82 mmol), P(t-Bu)$_3$ (0.33 g, 1.64 mmol), NaOt-Bu (4.72 g, 49.16 mmol), toluene (172 mL) were carried out in the same procedure as described in the synthesis method of 1-1-5 to obtain 7.07 g of the product. (yield: 76%).

Synthesis Example of 7-1-5

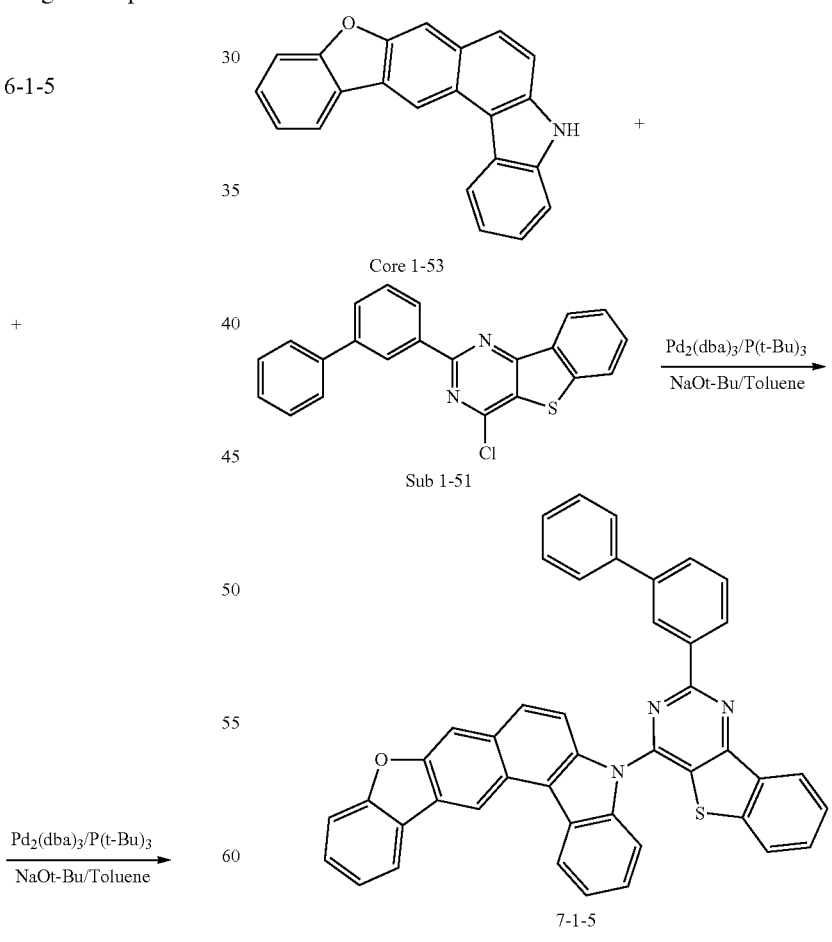

Core 1-53 (4.6 g, 14.97 mmol), Sub 1-51 (5.58 g, 14.97 mmol), Pd$_2$(dba)$_3$ (0.69 g, 0.75 mmol), P(t-Bu)$_3$ (0.30 g, 1.5 mmol), NaOt-Bu (4.32 g, 44.90 mmol), toluene (157 mL)

were carried out in the same procedure as described in the synthesis method of 1-1-5 to obtain 7.03 g of the product. (yield: 73%).

Synthesis Example of 7-2-3

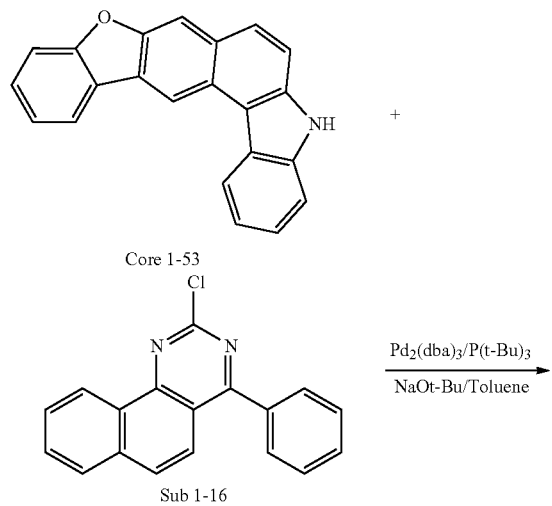

-continued

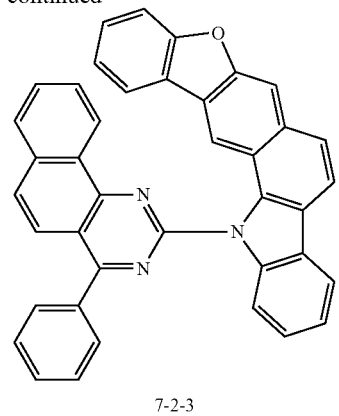

7-2-3

Core 1-53 (5 g, 16.27 mmol), Sub 1-16 (4.73 g, 16.27 mmol), Pd$_2$(dba)$_3$ (0.74 g, 0.81 mmol), P(t-Bu)$_3$ (0.33 g, 1.63 mmol), NaOt-Bu (4.69 g, 48.81 mmol), toluene (170 mL) were carried out in the same procedure as described in the synthesis method of 1-1-5 to obtain 7.04 g of the product. (yield: 77%).

V. Synthesis Example of Final Product (2)

Synthesis Example of A 1-1-1

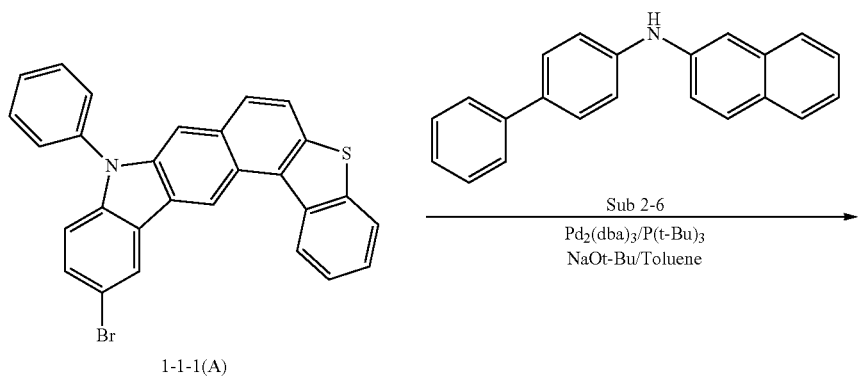

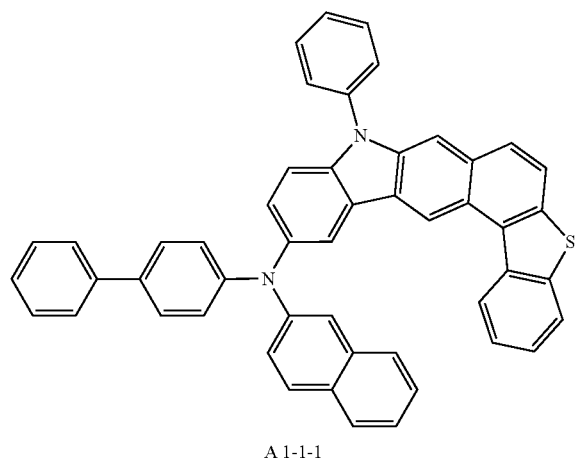

A 1-1-1

In a round bottom flask, 1-1-1(A) (5.9 g, 12.33 mmol), Sub 2-6 (3.64 g, 12.33 mmol), Pd$_2$(dba)$_3$ (0.56 g, 0.62 mmol), P(t-Bu)$_3$ (0.25 g, 1.23 mmol), NaOt-Bu (1.78 g, 18.5 mmol), toluene (129 mL) were added and the reaction is carried out at 100° C. When the reaction was completed, the reaction mixture was extracted with ether and water. The organic layer was dried over MgSO$_4$ and concentrated. The resulting compound was separated by silicagel column chromatography and recrystallization to obtain 7.09 g of the product (yield: 83%).

Synthesis Example of A 1-1-10

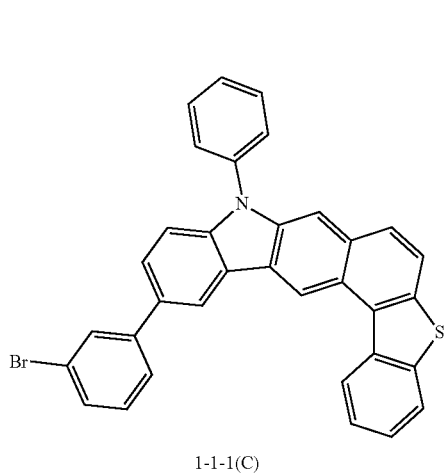

1-1-1(C)

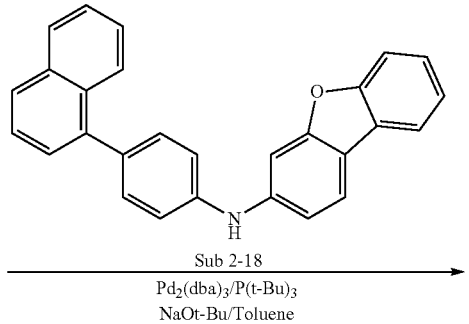

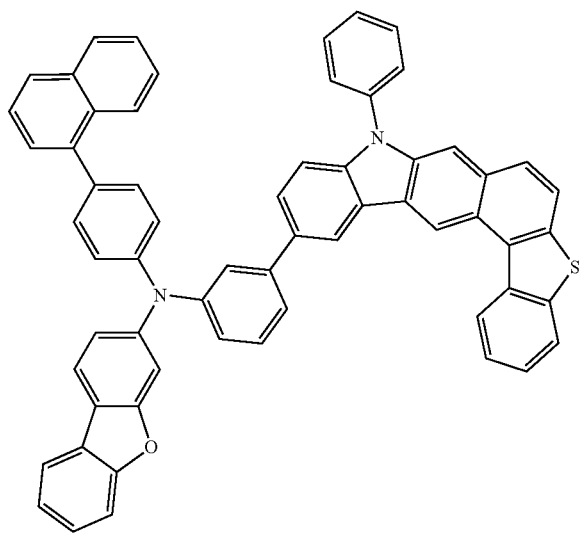

A 1-1-10

1-1-1(C) (5.8 g, 10.46 mmol), Sub 2-18 (4.03 g, 10.46 mmol), Pd$_2$(dba)$_3$ (0.48 g, 0.52 mmol), P(t-Bu)$_3$ (0.21 g, 1.05 mmol), NaOt-Bu (1.51 g, 15.69 mmol), toluene (110 mL) were carried out in the same procedure as described in the synthesis method of A 1-1-1 to obtain 7.10 g of the product. (yield: 79%).

Synthesis Example of A 1-1-19
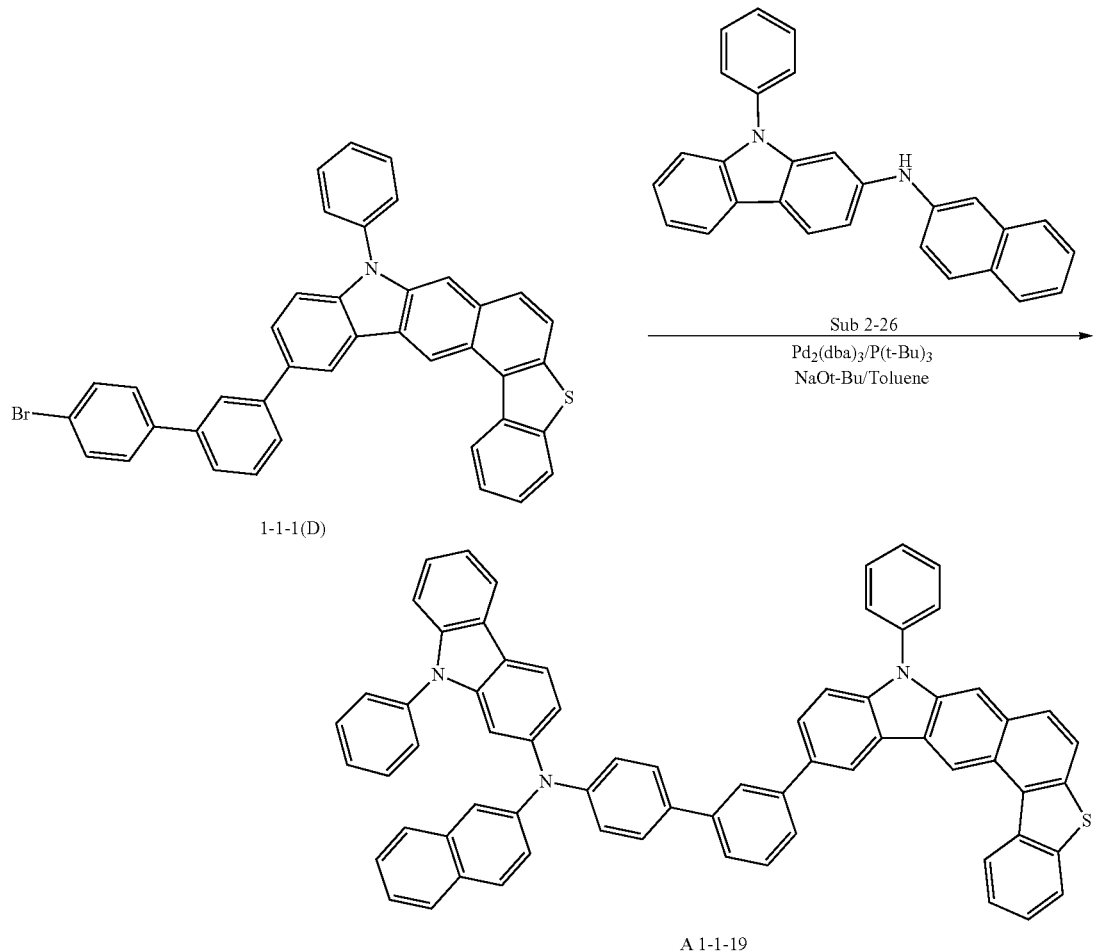
1-1-1(D) (6.2 g, 9.83 mmol), Sub 2-26 (3.78 g, 9.83 mmol), Pd$_2$(dba)$_3$ (0.45 g, 0.49 mmol), P(t-Bu)$_3$ (0.20 g, 0.98 mmol), NaOt-Bu (1.42 g, 14.75 mmol), toluene (103 mL) were carried out in the same procedure as described in the synthesis method of A 1-1-1 to obtain 7.07 g of the product. (yield: 77%).
Synthesis Example of A 1-2-16
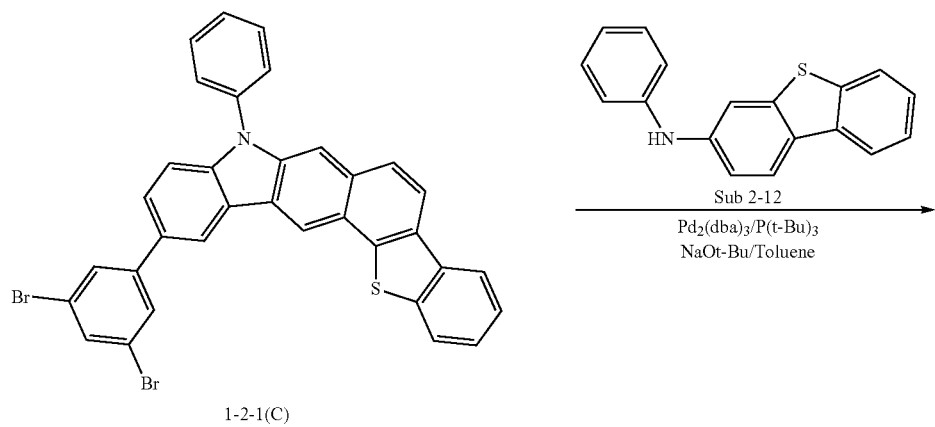

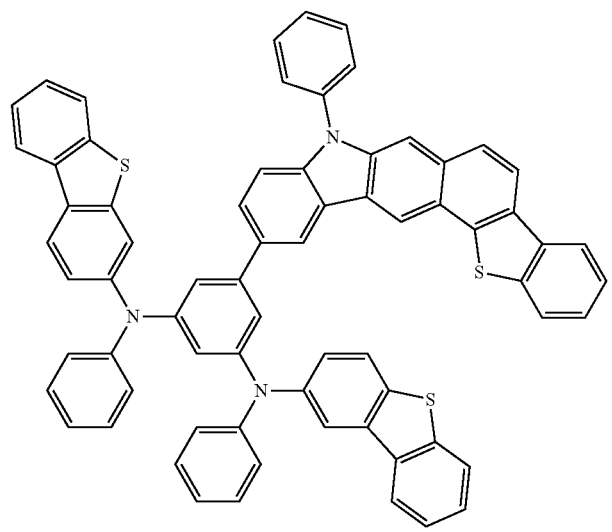
A 1-2-16
1-2-1(C) (5.9 g, 9.32 mmol), Sub 2-12 (5.13 g, 18.63 mmol), Pd$_2$(dba)$_3$ (0.85 g, 0.93 mmol), P(t-Bu)$_3$ (0.38 g, 1.86 mmol), NaOt-Bu (2.69 g, 27.95 mmol), toluene (98 mL) were carried out in the same procedure as described in the synthesis method of A 1-1-1 to obtain 7.05 g of the product. (yield: 74%).
Synthesis Example of A 2-1-7
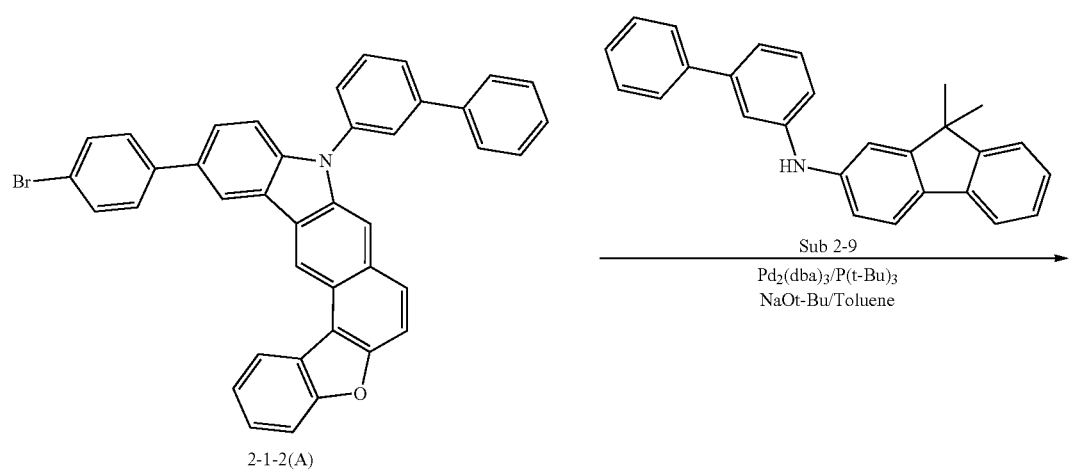
2-1-2(A)

-continued
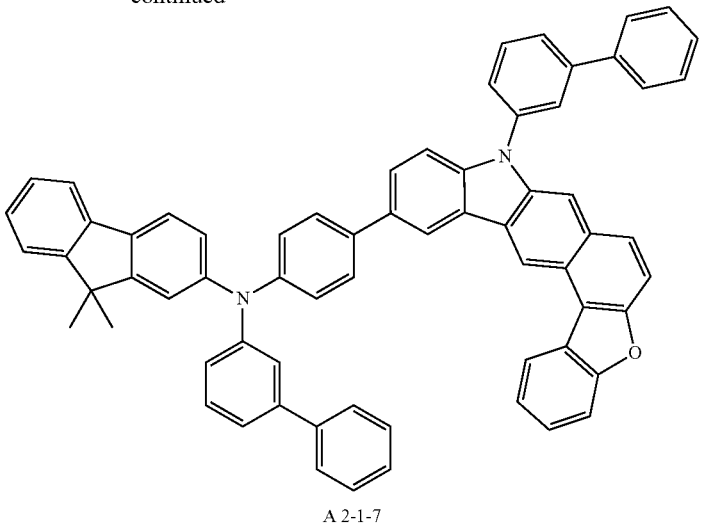
A 2-1-7
2-1-2(A) (6.63 g, 10.79 mmol), Sub 2-9 (3.9 g, 10.79 mmol), Pd$_2$(dba)$_3$ (0.49 g, 0.54 mmol), P(t-Bu)$_3$ (0.22 g, 1.08 mmol), NaOt-Bu (3.11 g, 32.37 mmol), toluene (113 mL) were carried out in the same procedure as described in the synthesis method of A 1-1-1 to obtain 7.05 g of the product. (yield: 73%).
Synthesis Example of A 5-1-13
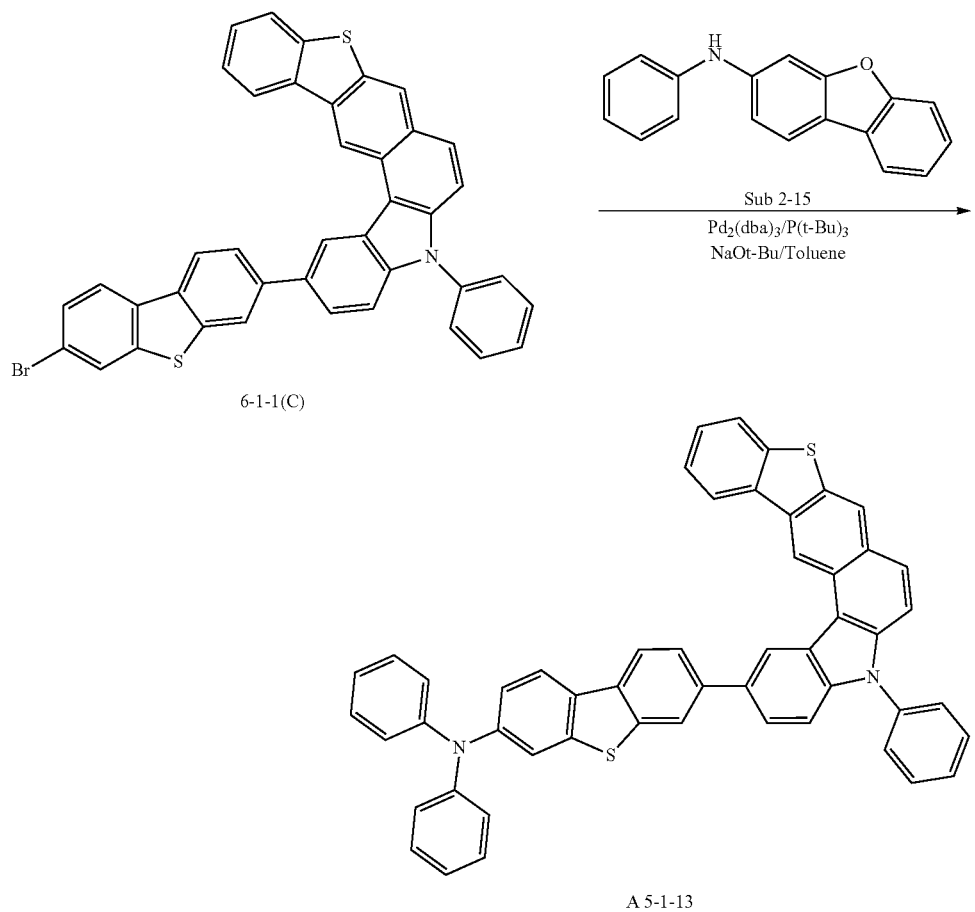
A 5-1-13

6-1-1(C) (8.8 g, 13.32 mmol), Sub 2-15 (3.45 g, 13.32 mmol), Pd$_2$(dba)$_3$ (0.61 g, 0.67 mmol), P(t-Bu)$_3$ (0.27 g, 1.33 mmol), NaOt-Bu (3.84 g, 39.96 mmol), toluene (140 mL) were carried out in the same procedure as described in the synthesis method of A 1-1-1 to obtain 7.08 g of the product. (yield: 71%).

Meanwhile the FD-MS values of the compounds 1-1-5 to 3-2-12 and A 1-1-1 to A 3-1-10 of the present invention prepared according to the above synthesis examples are shown in Tables 5.

TABLE 5

| compound | FD-MS | compound | FD-MS |
|---|---|---|---|
| 1-1-2 | m/z = 475.14($C_{34}H_{21}NS$ = 475.60) | 1-1-5 | m/z = 515.17($C_{37}H_{25}NS$ = 515.67) |
| 1-1-10 | m/z = 577.16($C_{40}H_{23}N_3S$ = 577.70) | 1-1-13 | m/z = 627.18($C_{44}H_{25}N_3S$ = 627.75) |
| 1-1-23 | m/z = 733.16($C_{50}H_{27}N_3S_2$ = 733.90) | 1-1-28 | m/z = 633.13($C_{42}H_{23}N_3S_2$ = 633.78) |
| 1-1-31 | m/z = 709.16($C_{48}H_{27}N_3S_2$ = 709.88) | 1-1-44 | m/z = 743.20($C_{52}H_{29}N_3OS$ = 743.87) |
| 1-1-51 | m/z = 743.20($C_{52}H_{29}N_3OS$ = 743.87) | 1-1-53 | m/z = 709.16($C_{48}H_{27}N_3S_2$ = 709.88) |
| 1-1-58 | m/z = 826.16($C_{56}H_{30}N_2S_3$ = 827.05) | 1-2-1 | m/z = 399.11($C_{28}H_{17}NS$ = 399.51) |
| 1-2-6 | m/z = 505.10($C_{34}H_{19}NS_2$ = 505.65) | 1-2-8 | m/z = 577.16($C_{40}H_{23}N_3S$ = 577.70) |
| 1-2-9 | m/z = 577.16($C_{40}H_{23}N_3S$ = 577.70) | 1-2-10 | m/z = 703.21($C_{50}H_{29}N_3S$ = 703.85) |
| 1-2-14 | m/z = 667.17($C_{46}H_{25}N_3OS$ = 667.78) | 1-2-16 | m/z = 677.19($C_{48}H_{27}N_3S$ = 677.81) |
| 1-2-18 | m/z = 733.16($C_{50}H_{27}N_3S_2$ = 733.90) | 1-2-20 | m/z = 583.12($C_{38}H_{21}N_3S_2$ = 583.72) |
| 1-2-23 | m/z = 709.16($C_{48}H_{27}N_3S_2$ = 709.88) | 1-2-27 | m/z = 617.16($C_{42}H_{23}N_3OS$ = 617.72) |
| 1-2-28 | m/z = 719.20($C_{50}H_{29}N_3OS$ = 719.85) | 1-2-30 | m/z = 732.20($C_{50}H_{28}N_4OS$ = 732.85) |
| 1-2-32 | m/z = 759.18($C_{52}H_{29}N_3S_2$ = 759.94) | 2-1-2 | m/z = 459.16($C_{34}H_{21}NO$ = 459.54) |
| 2-1-21 | m/z = 661.22($C_{48}H_{27}N_{-3}O$ = 661.75) | 2-1-28 | m/z = 617.16($C_{42}H_{23}N_3OS$ = 617.72) |
| 2-1-36 | m/z = 703.23($C_{50}H_{29}N_3O_2$ = 703.78) | 2-2-1 | m/z = 383.13($C_{28}H_{17}NO$ = 383.44) |
| 2-2-7 | m/z = 537.18($C_{38}H_{23}N_3O$ = 537.61) | 2-2-8 | m/z = 561.18($C_{40}H_{23}N_3O$ = 561.63) |
| 2-2-10 | m/z = 687.23($C_{50}H_{29}N_3O$ = 687.78) | 2-2-16 | m/z = 776.26($C_{56}H_{32}N_4O$ = 776.88) |
| 2-2-17 | m/z = 567.14($C_{38}H_{21}N_3OS$ = 567.66) | 2-2-26 | m/z = 677.21($C_{48}H_{27}N_3O_2$ = 677.75) |
| 3-1-1 | m/z = 409.18($C_{31}H_{23}N$ = 409.52) | 3-1-8 | m/z = 499.19($C_{37}H_{25}NO$ = 499.60) |
| 3-1-26 | m/z = 669.22($C_{47}H_{31}N_3S$ = 669.83) | 3-2-1 | m/z = 409.18($C_{31}H_{23}N$ = 409.52) |
| 3-2-17 | m/z = 593.19($C_{41}H_{27}N_3S$ = 593.74) | 3-2-20 | m/z = 719.24($C_{51}H_{33}N_3S$ = 719.89) |
| 3-2-30 | m/z = 729.28($C_{53}H_{35}N_3O$ = 729.86) | 6-1-1 | m/z = 399.11($C_{28}H_{17}NS$ = 399.51) |
| 6-1-4 | m/z = 633.13($C_{42}H_{23}N_3S_2$ = 633.78) | 6-1-5 | m/z = 567.14($C_{38}H_{21}N_3OS$ = 567.66) |
| 6-2-1 | m/z = 551.17($C_{40}H_{25}NS$ = 551.70) | 6-2-4 | m/z = 583.12($C_{38}H_{21}N_3S_2$ = 583.72) |
| 7-1-5 | m/z = 643.17($C_{44}H_{25}N_3OS$ = 643.75) | 7-2-3 | m/z = 561.18($C_{40}H_{23}N_3O$ = 561.63) |
| 7-2-5 | m/z = 627.19($C_{44}H_{25}N_3O_2$ = 627.69) | A 1-1-1 | m/z = 692.23($C_{50}H_{32}N_2S$ = 692.87) |
| A 1-1-2 | m/z = 672.17($C_{46}H_{28}N_2S_2$ = 672.86) | A 1-1-5 | m/z = 768.26($C_{56}H_{36}N_2S$ = 768.96) |
| A 1-1-9 | m/z = 794.28($C_{58}H_{38}N_2S$ = 795.00) | A 1-1-10 | m/z = 858.27($C_{62}H_{38}N_2OS$ = 859.04) |
| A 1-1-15 | m/z = 768.26($C_{56}H_{36}N_2S$ = 768.96) | A 1-1-16 | m/z = 794.28($C_{58}H_{38}N_2S$ = 795.00) |
| A 1-1-19 | m/z = 933.32($C_{68}H_{43}N_3S$ = 934.15) | A 1-1-28 | m/z = 933.32($C_{68}H_{43}N_3S$ = 934.15) |
| A 1-2-1 | m/z = 692.23($C_{50}H_{32}N_2S$ = 692.87) | A 1-2-2 | m/z = 672.17($C_{46}H_{28}N_2S_2$ = 672.86) |
| A 1-2-6 | m/z = 768.26($C_{56}H_{36}N_2S$ = 768.96) | A 1-2-9 | m/z = 718.24($C_{52}H_{34}N_2S$ = 718.90) |
| A 1-2-12 | m/z = 794.28($C_{58}H_{38}N_2S$ = 795.00) | A 1-2-13 | m/z = 794.28($C_{58}H_{38}N_2S$ = 795.00) |
| A 1-2-14 | m/z = 809.29($C_{58}H_{39}N_3S$ = 810.02) | A 1-2-16 | m/z = 1021.26($C_{70}H_{43}N_3S_3$ = 1022.31) |
| A 1-2-26 | m/z = 1021.26($C_{70}H_{43}N_3S_3$ = 1022.31) | A 2-1-1 | m/z = 676.25($C_{50}H_{32}N_2O$ = 676.80) |
| A 2-1-5 | m/z = 752.28($C_{56}H_{36}N_2O$ = 752.90) | A 2-1-7 | m/z = 894.36($C_{67}H_{46}N_2O$ = 895.09) |
| A 2-1-9 | m/z = 778.30($C_{58}H_{38}N_2O$ = 778.94) | A 2-2-1 | m/z = 676.25($C_{50}H_{32}N_2O$ = 676.80) |
| A 2-2-6 | m/z = 752.28($C_{56}H_{36}N_2O$ = 752.90) | A 2-2-9 | m/z = 702.27($C_{52}H_{34}N_2O$ = 702.84) |
| A 3-1-1 | m/z = 702.30($C_{53}H_{38}N_2$ = 702.88) | A 3-1-5 | m/z = 778.33($C_{59}H_{42}N_2$ = 778.98) |
| A 3-1-6 | m/z = 804.35($C_{61}H_{44}N_2$ = 805.02) | A 3-2-1 | m/z = 702.30($C_{53}H_{38}N_2$ = 702.88) |
| A 3-2-5 | m/z = 778.33($C_{59}H_{42}N_2$ = 778.98) | A 3-2-8 | m/z = 804.35($C_{61}H_{44}N_2$ = 805.02) |
| A 5-2-1 | m/z = 616.20($C_{44}H_{28}N_2S$ = 616.77) | A 5-1-13 | m/z = 748.20($C_{52}H_{32}N_2S_2$ = 748.95) |

Otherwise, although the exemplary synthesis example of the present invention represented by Formula (1) has been described above, these are all based on Buchwald-Hartwig cross coupling reactions, Pd(II)-catalyzed oxidative cyclization reactions (*Org. Lett.* 2011, 13, 5504), Miyaura boration reactions and Suzuki cross-coupling reactions, and those skilled in the art will readily understand that the reaction proceeds even if other substituents ($R^1$ to $R^{11}$, $L^1$, $Ar^1$, etc.) as defined in Formula (1) are bonded, in addition to the substituents specified in the specific synthesis example.

Even if substituents not specifically mentioned in these are bonded, the reactions will proceed.

(A method of synthesizing a core containing Si is described in J. AM. CHEM. SOC. 2008, 130, 7670-7685)

Manufacture and Evaluation of Organic Electric Element

[Example 1] Red Organic Electroluminescent Device (Phosphorescent Host)

An organic electroluminescent device was fabricated according to a conventional method using a compound obtained through synthesis as a host material of an emitting layer. First, on an ITO layer (anode) formed on a glass substrate, $N^1$-(naphthalen-2-yl)-$N^4,N^4$-bis(4-(naphthalen-2-yl(phenyl)amino)phenyl)-$N^1$-phenyl benzene-1,4-diamine (hereinafter will be abbreviated as 2-TNATA) was vacuum-deposited to form a hole injection layer with a thickness of 60 nm, and subsequently, on the hole injection layer, NPD layer as a hole transporting compound was vacuum-deposited to form a hole transport layer with a thickness of 60 nm. On the hole transport layer, the inventive compound 1-1-1 were used as a host, and as a dopant material, an emitting layer with a thickness of 30 nm was deposited by doping (piq)$_2$Ir(acac) with a weight of 95:5. As a hole blocking layer, (1,1'-bisphenyl)-4-olato)bis(2-methyl-8-quinolinolato)aluminum (hereinafter abbreviated as BAlq) was vacuum deposited to a thickness of 10 nm, and as an electron transport layer, tris(8-quinolinol)aluminum (hereinafter abbreviated as Alq3) was deposited to a thickness of 40 nm. After that, an alkali metal halide, LiF was vacuum deposited to a thickness of 0.2 nm, and subsequently, Al was deposited to a thickness of 150 nm and the Al/LiF was used as a cathode to produce an organic electroluminescent device.

[Example 2] to [Example 38] Red Organic Light Emitting Device

An organic electric element was manufactured in the same manner as in Example 1, except that the compound of the present invention described in the following Table 4 was used instead of the compound 1-1-1 according to the embodiment of the present invention as the red host material of the emitting layer.

[Comparative Example 1] to [Comparative Example 4]

An organic electric element was manufactured in the same manner as in Example 1, except that one of Comparative compound 1 to Comparative Compound 4 described in the following Table 4 was used instead of the compound 1-1-1 according to the embodiment of the present invention as the host material of the emitting layer comparative compound 1

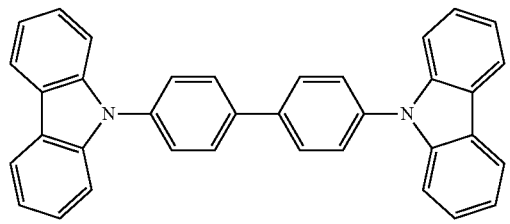

comparative compound 2

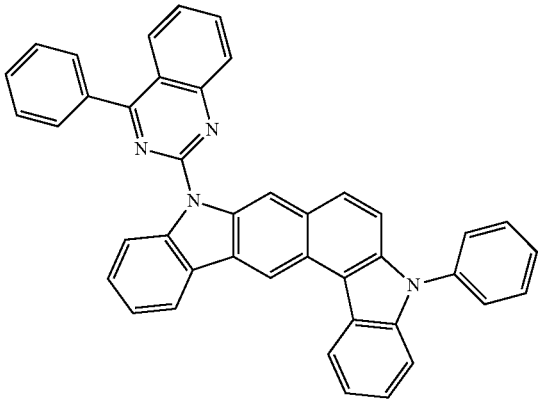

comparative compound 3

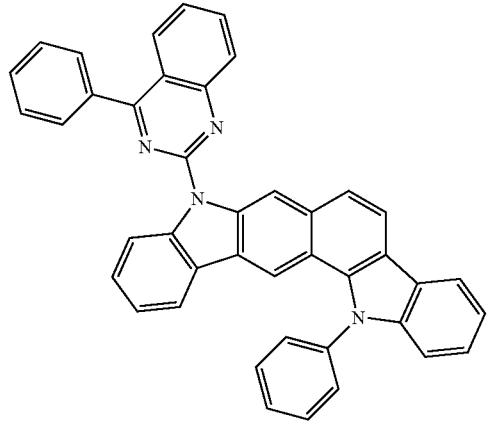

comparative compound 4

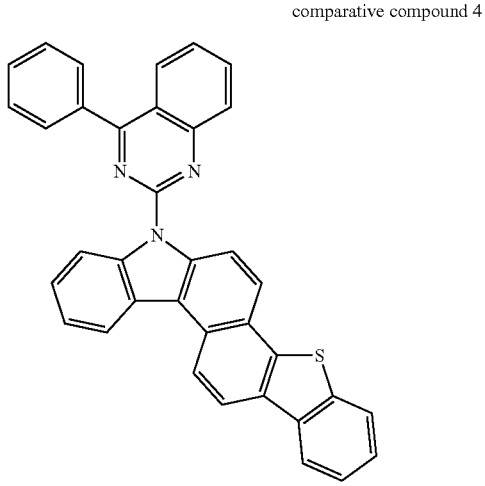

TABLE 6

| | compound | Driving voltage | Current Density (mA/cm$^2$) | Brightness (cd/m$^2$) | Efficiency (cd/A) | T (95) | CIE X | CIE Y |
|---|---|---|---|---|---|---|---|---|
| comparative example (1) | comparative compound 1 | 6.6 | 35.2 | 2500 | 7.1 | 63.3 | 0.65 | 0.31 |
| comparative example (2) | comparative compound 2 | 6.4 | 32.9 | 2500 | 7.6 | 70.5 | 0.66 | 0.32 |
| comparative example (3) | comparative compound 3 | 6.3 | 30.1 | 2500 | 8.3 | 77.8 | 0.65 | 0.32 |
| comparative example (4) | comparative compound 4 | 6.2 | 27.5 | 2500 | 9.1 | 86.2 | 0.65 | 0.31 |
| example (1) | compound 1-1-1 | 5.5 | 18.8 | 2500 | 13.3 | 124.5 | 0.65 | 0.32 |
| example (2) | compound 1-1-10 | 5.5 | 19.1 | 2500 | 13.1 | 122.4 | 0.65 | 0.32 |
| example (3) | compound 1-1-13 | 5.5 | 18.8 | 2500 | 13.3 | 128.8 | 0.65 | 0.31 |
| example (4) | compound 1-1-23 | 5.5 | 18.7 | 2500 | 13.4 | 131.5 | 0.65 | 0.31 |
| example (5) | compound 1-1-28 | 5.4 | 16.1 | 2500 | 15.5 | 146 | 0.65 | 0.32 |
| example (6) | compound 1-1-31 | 5.4 | 16.6 | 2500 | 15.1 | 143.3 | 0.66 | 0.31 |
| example (7) | compound 1-1-44 | 5.4 | 16.3 | 2500 | 15.3 | 140.4 | 0.65 | 0.32 |

TABLE 6-continued

| | compound | Driving voltage | Current Density (mA/cm$^2$) | Brightness (cd/m$^2$) | Efficiency (cd/A) | T (95) | CIE X | CIE Y |
|---|---|---|---|---|---|---|---|---|
| example (8) | compound 1-2-1 | 5.3 | 18.8 | 2500 | 13.3 | 130.7 | 0.66 | 0.31 |
| example (9) | compound 1-2-6 | 5.3 | 18.8 | 2500 | 13.3 | 133.1 | 0.65 | 0.31 |
| example (10) | compound 1-2-8 | 5.3 | 18.8 | 2500 | 13.3 | 127.8 | 0.65 | 0.31 |
| example (11) | compound 1-2-9 | 5.3 | 18.8 | 2500 | 13.3 | 133 | 0.65 | 0.32 |
| example (12) | compound 1-2-14 | 5.3 | 18.7 | 2500 | 13.4 | 131.9 | 0.66 | 0.32 |
| example (13) | compound 1-2-16 | 5.3 | 18.9 | 2500 | 13.2 | 135.6 | 0.66 | 0.31 |
| example (14) | compound 1-2-18 | 5.3 | 18.9 | 2500 | 13.2 | 139.9 | 0.66 | 0.31 |
| example (15) | compound 1-2-20 | 5.2 | 13.4 | 2500 | 18.7 | 158.6 | 0.65 | 0.32 |
| example (16) | compound 1-2-23 | 5.2 | 13.7 | 2500 | 18.3 | 153.4 | 0.66 | 0.32 |
| example (17) | compound 1-2-27 | 5.2 | 14.0 | 2500 | 17.8 | 151.8 | 0.66 | 0.32 |
| example (18) | compound 1-2-30 | 5.2 | 15.0 | 2500 | 16.7 | 150.6 | 0.66 | 0.31 |
| example (19) | compound 1-2-32 | 5.2 | 13.8 | 2500 | 18.1 | 154.3 | 0.65 | 0.32 |
| example (20) | compound 2-1-2 | 5.6 | 22.1 | 2500 | 11.3 | 126.4 | 0.66 | 0.32 |
| example (21) | compound 2-1-28 | 5.4 | 18.0 | 2500 | 13.9 | 141.5 | 0.65 | 0.32 |
| example (22) | compound 2-1-36 | 5.5 | 18.9 | 2500 | 13.2 | 138.9 | 0.65 | 0.32 |
| example (23) | compound 2-2-1 | 5.5 | 20.3 | 2500 | 12.3 | 126.4 | 0.65 | 0.31 |
| example (24) | compound 2-2-8 | 5.5 | 20.7 | 2500 | 12.1 | 123.7 | 0.65 | 0.32 |
| example (25) | compound 2-2-10 | 5.4 | 19.7 | 2500 | 12.7 | 131 | 0.65 | 0.32 |
| example (26) | compound 2-2-16 | 5.4 | 19.4 | 2500 | 12.9 | 135.4 | 0.65 | 0.32 |
| example (27) | compound 2-2-17 | 5.3 | 17.0 | 2500 | 14.7 | 145.3 | 0.65 | 0.32 |
| example (28) | compound 2-2-26 | 5.3 | 17.7 | 2500 | 14.1 | 141.7 | 0.66 | 0.31 |
| example (29) | compound 3-1-1 | 5.6 | 24.3 | 2500 | 10.3 | 118.1 | 0.65 | 0.32 |
| example (30) | compound 3-1-26 | 5.6 | 20.2 | 2500 | 12.4 | 131.4 | 0.65 | 0.31 |
| example (31) | compound 3-2-1 | 5.5 | 20.7 | 2500 | 12.1 | 125.2 | 0.65 | 0.32 |
| example (32) | compound 3-2-17 | 5.5 | 17.5 | 2500 | 14.3 | 139.5 | 0.66 | 0.32 |
| example (33) | compound 6-1-1 | 5.5 | 19.8 | 2500 | 12.6 | 121.2 | 0.65 | 0.32 |
| example (34) | compound 6-1-4 | 5.3 | 15.0 | 2500 | 16.7 | 143.6 | 0.66 | 0.31 |
| example (35) | compound 6-2-1 | 5.4 | 19.1 | 2500 | 13.1 | 128.4 | 0.65 | 0.31 |
| example (36) | compound 6-2-4 | 5.2 | 14.5 | 2500 | 17.3 | 151.2 | 0.65 | 0.32 |
| example (37) | compound 7-1-5 | 5.4 | 18.5 | 2500 | 13.5 | 137.7 | 0.66 | 0.32 |
| example (38) | compound 7-2-5 | 5.3 | 19.1 | 2500 | 13.1 | 134.5 | 0.65 | 0.32 |

1) Comparison of Heteroatoms in 6 Cyclic Compounds (Comparative Compound 2 to 3)

Compounds of the present invention having heterozygous atoms of unequal type of N—S, N—O, N—CR'R" and N—SiR'R" than N—N type comparative compounds 2 to 3 have higher efficiency and significantly higher lifetime.

Generally, when molecules are stacked, they have strong electrical interactions as the number of adjacent π-electrons increases, which is closely related to the charge carrier mobility.

In the case of the N—N type 6 cyclic compound of Comparative Compounds 2 to 3, when the molecules are stacked, since they are N—N type homo-heterocyclic core, the arrangement order of molecules has an edge-to-face morphology, which is considered to cause low charge carrier mobility and low oxidation stability.

Since the 6-membered cyclic compound of the present invention has a heterodimeric heterocyclic core in which hetero atoms in the cyclic compound are different from each other, it has an antiparallelcofacial π-stacking structure in which the packing structure of the molecules is in the opposite direction. This makes the arrangement order of the molecules face-to-face, and the steric effect of Ar1 of the asymmetrically arranged hetero atom N, which is the cause of the lamination structure, results in remarkably high carrier mobility and is considered to have a high efficiency and to increase the lifetime remarkably because it has a high oxidation stability.

Further, in the case of Comparative Compounds 2 to 3 having same condensation position but opposite cores, Comparative Compound 3 shows better performance than Comparative Compound 2 which looks in the same direction. This is, in the case of comparative compound 2 which looks in the same direction to each other, because it has relatively non-linear structure than comparative compound 3, as a result, the charge transfer from the host to the dopant is not smooth as the difference in T1 value between host and dopant increases.

2) Performance Difference According to Fused Position (Comparative Compound 4)

Comparing the compound of the present invention with the comparative compound 4 having the N—S type in the 6 cyclic compound, which is similar but the fused position of the carbazole core is different, when the fused bond position of the 6 cyclic compound is changed, T1 and energy band gap vary depending on the degree of twist of the molecule. The core of the inventive compound is structurally less folded, therefore as the T 1 value is relatively low, the charge transfer from the host to the dopant becomes smooth, so that the efficiency is increased by reducing the number of excess polaron generated in the emitting layer.

Particularly, compounds having specific substituent groups such as benzothienopyrimidine or benzofuropyrimidine among the compounds of the present invention exhibit the most superior device results than general aryl groups and general heterocyclic groups. By introducing two nitrogen atoms (N) into the core (dibenzothiophene, dibenzofuran) having a strong hole characteristic, a structure suitable for accommodating both holes and electrons is obtained, as a result, it is considered that charge balance of the holes and electrons is facilitated, and the light emission is efficiently performed in the emitting layer.

From the results shown in Table 4, it is suggested that the efficiency and lifetime may vary depending on the type of heteroatom contained in the 6 cyclic compound, it can be seen that the band gap, electrical characteristics, interface characteristics, and the like can be largely changed depending on which substituent is bonded at which position.

Particularly, in the case of a phosphorescent host, it is necessary to grasp the correlation with the hole transport layer and the dopant and even with similar cores, it would be very difficult to deduce the excellent electrical properties that the compounds of the present invention exhibit in the phosphorescent host.

[Example 39] Green Organic Electroluminescent Device (Hole Transport Layer)

An organic electroluminescent device was fabricated according to a conventional method using the compound of the present invention as a hole transport layer material. First, on an ITO layer (anode) formed on a glass substrate, 2-TNATA was vacuum-deposited with a thickness of 60 nm to form a hole injection layer, and on the hole injection layer, the compound of the present invention, A 1-1-1 was vacuum-deposited to form a hole transport layer with a thickness of 60 nm. On the hole transport layer, 4,4'-N,N'-dicarbazole-biphenyl (CBP) was used as a host, tris(2-phenylpyridine)-iridium (Ir(ppy)$_3$) was used as a dopant, and an emitting layer was vacuum deposited with a thickness of 30 nm by doping with a weight of 90:10 weight ratio. And on the emitting layer, BAlq was vacuum deposited with a thickness of 10 nm to form a hole blocking layer, and on the hole blocking layer, Alq3 was vacuum deposited with a thickness of 40 nm to form an electron transport layer. After that, an alkali metal halide, LiF was vacuum deposited to form an electron injection layer with a thickness of 0.2 nm, and Al was deposited to a thickness of 150 nm to form a cathode to manufacture an OLED.

[Examples 40 to 64] A Green Organic Electroluminescent Device (Hole Transport Layer)

An organic electroluminescent device was manufactured in the same manner as in Example 37, except that Compound A 1-1-2 to A 5-2-1 of the present invention described in Table 5 below were used instead of Compound A 1-1-1 of the present invention as the hole transport layer material

[Comparative Example 5] to [Comparative Example 7]

In Comparative Example 5, an organic electroluminescent device was fabricated in the same manner as in Example 37 except that the Comparative Compound 6 was used instead of the compound A 1-1-1 of the present invention as a hole transport layer material.

In Comparative Example 6, an organic electroluminescent device was fabricated in the same manner as in Example 37 except that the Comparative Compound 7 was used instead of the compound A 1-1-1 of the present invention as a hole transport layer material.

In Comparative Example 7, an organic electroluminescent device was fabricated in the same manner as in Example 37 except that the Comparative Compound 8 was used instead of the compound A 1-1-1 of the present invention as a hole transport layer material.

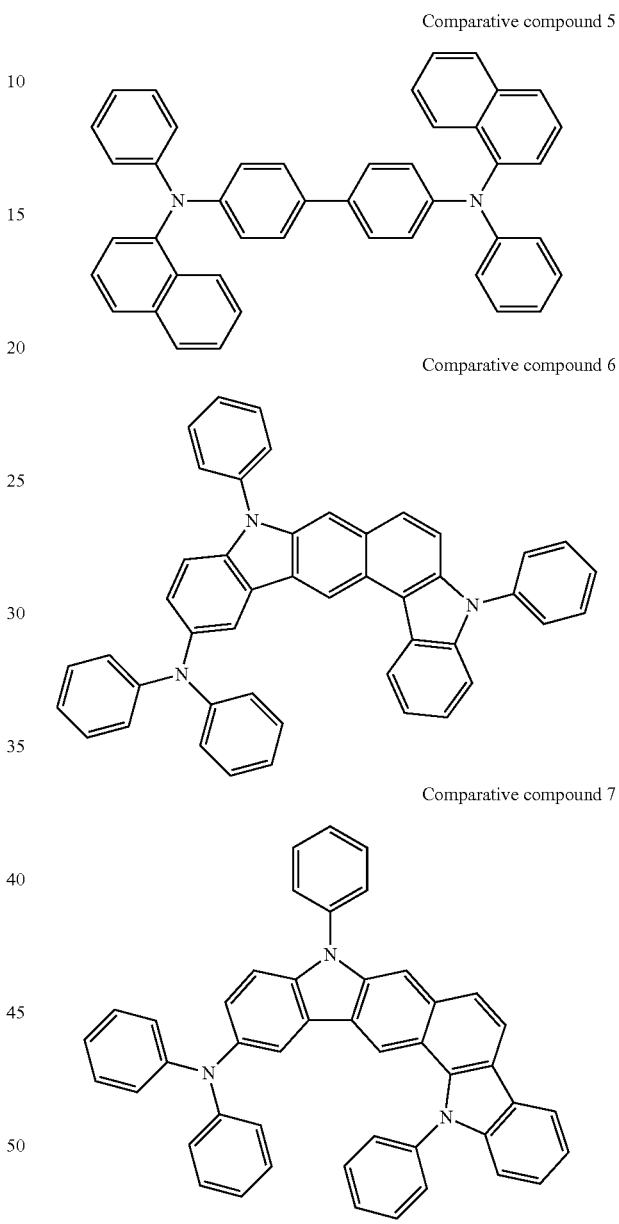

Comparative compound 5

Comparative compound 6

Comparative compound 7

TABLE 7

| | compound | Voltage | Current density (mA/cm$^2$) | Brightness (cd/m$^2$) | Efficiency (cd/A) | T (95) | CIE x | y |
|---|---|---|---|---|---|---|---|---|
| Comparative Example (5) | Comparative compound 5 | 5.8 | 21.7 | 5000 | 23 | 59.6 | 0.33 | 0.62 |
| Comparative Example (6) | Comparative compound 6 | 5.7 | 19.5 | 5000 | 25.7 | 77 | 0.33 | 0.62 |
| Comparative Example (7) | Comparative compound 7 | 5.5 | 17.9 | 5000 | 28.0 | 89.2 | 0.32 | 0.62 |

TABLE 7-continued

| | compound | Voltage | Current density (mA/cm$^2$) | Brightness (cd/m$^2$) | Efficiency (cd/A) | T (95) | CIE x | CIE y |
|---|---|---|---|---|---|---|---|---|
| Example (39) | compound A 1-1-1 | 5.4 | 12.8 | 5000.0 | 39.2 | 136.3 | 0.33 | 0.62 |
| Example (40) | compound A 1-1-2 | 5.5 | 12.3 | 5000.0 | 40.5 | 139.4 | 0.33 | 0.61 |
| Example (41) | compound A 1-1-5 | 5.5 | 11.4 | 5000.0 | 43.9 | 141.8 | 0.33 | 0.61 |
| Example (42) | compound A 1-1-9 | 5.3 | 11.0 | 5000.0 | 45.5 | 146.8 | 0.33 | 0.61 |
| Example (43) | compound A 1-1-15 | 5.4 | 12.0 | 5000.0 | 41.7 | 137.6 | 0.33 | 0.61 |
| Example (44) | compound A 1-1-16 | 5.3 | 11.1 | 5000.0 | 44.9 | 144.1 | 0.33 | 0.61 |
| Example (45) | compound A 1-2-1 | 5.2 | 11.7 | 5000.0 | 42.7 | 146.5 | 0.32 | 0.61 |
| Example (46) | compound A 1-2-2 | 5.2 | 11.5 | 5000.0 | 43.4 | 148.3 | 0.32 | 0.61 |
| Example (47) | compound A 1-2-6 | 5.2 | 11.1 | 5000.0 | 44.9 | 151.6 | 0.33 | 0.62 |
| Example (48) | compound A 1-2-9 | 5.1 | 10.3 | 5000.0 | 48.7 | 156.6 | 0.33 | 0.62 |
| Example (49) | compound A 1-2-12 | 5.1 | 10.9 | 5000.0 | 46.0 | 152.6 | 0.33 | 0.62 |
| Example (50) | compound A 1-2-13 | 5.0 | 10.0 | 5000.0 | 50.1 | 154.6 | 0.32 | 0.62 |
| Example (51) | compound A 1-2-14 | 5.2 | 12.0 | 5000.0 | 41.6 | 148.6 | 0.33 | 0.62 |
| Example (52) | compound A 2-1-1 | 5.4 | 14.7 | 5000.0 | 33.9 | 123.7 | 0.33 | 0.61 |
| Example (53) | compound A 2-1-5 | 5.4 | 14.0 | 5000.0 | 35.8 | 129.0 | 0.33 | 0.61 |
| Example (54) | compound A 2-1-9 | 5.3 | 12.7 | 5000.0 | 39.3 | 132.6 | 0.32 | 0.62 |
| Example (55) | compound A 2-2-1 | 5.3 | 13.6 | 5000.0 | 36.8 | 127.8 | 0.32 | 0.62 |
| Example (56) | compound A 2-2-6 | 5.3 | 12.9 | 5000.0 | 38.8 | 133.5 | 0.32 | 0.62 |
| Example (57) | compound A 2-2-9 | 5.2 | 11.9 | 5000.0 | 42.1 | 135.7 | 0.33 | 0.61 |
| Example (58) | compound A 3-1-1 | 5.5 | 17.3 | 5000.0 | 28.9 | 119.6 | 0.32 | 0.61 |
| Example (59) | compound A 3-1-5 | 5.5 | 15.8 | 5000.0 | 31.7 | 124.3 | 0.33 | 0.62 |
| Example (60) | compound A 3-1-6 | 5.5 | 14.2 | 5000.0 | 35.2 | 129.7 | 0.33 | 0.61 |
| Example (61) | compound A 3-2-1 | 5.5 | 16.1 | 5000.0 | 31 | 121.6 | 0.33 | 0.62 |
| Example (62) | compound A 3-2-5 | 5.5 | 14.9 | 5000.0 | 33.5 | 126.3 | 0.32 | 0.61 |
| Example (63) | compound A 3-2-8 | 5.5 | 13.3 | 5000.0 | 37.7 | 131.5 | 0.32 | 0.61 |
| Example (64) | compound A 5-2-1 | 5.3 | 12.6 | 5000.0 | 39.6 | 139.7 | 0.32 | 0.62 |

As can be seen from the results of the element measurement in Table 5, it was confirmed that the device using the compound of the present invention as the hole transport layer exhibited higher efficiency and longer lifetime than the device using Comparative Compounds 5 to 7 as the hole transport layer material.

By applying —N(R$^a$)(R$^b$) to a 6-ring heterocyclic core, it can be used as a hole transport layer, and the intrinsic properties of the compounds of the present invention, the deep HOMO energy level increase the charge balance in the emitting layer, thereby reducing the surplus polaron in the emitting layer and reducing the interface deterioration and dopant quenching due to the surplus polaron.

The NN-type 6 cyclic compound of Comparative Compound 6 has an edge-to-face morphology because of the NN type and homo heterocyclic core when the molecules are stacked, which is believed to result in low charge carrier mobility and low oxidation stability.

Since the 6 cyclic compound of the present invention has a heterodimeric heterocyclic core in which hetero atoms in the cyclic compound are different from each other, the packing structure of the molecules has an antiparallel cofacial π-stacking structure facing in the opposite direction. This makes the arrangement order of the molecules face-to-face, and due to the steric effect of Ar$^1$ of the asymmetrically arranged heteroatom N which is the cause of this lamination structure, it is judged to have a high efficiency by causing a remarkably high carrier mobility, and it is presumed that the lifetime is remarkably increased because it has a high oxidation stability.

Among the compounds of the present invention, the non-linear type bonded to the ortho or meta position showed better performance than the linker-amine group bonded to L1 and L' to para. It is considered that the coupling angle is reduced and high T1 value is obtained and the electronic blocking ability is improved.

It was confirmed that when the compound of the present invention was used as a hole transport layer material, the lifetime was remarkably improved as well as the low driving voltage and high luminous efficiency.

As can be seen from the results of Table 5, it is considered that the efficiency and lifetime due to the difference in fused position and heteroatom type and arrangement in 6 cyclic compounds are difficult to be easily deduced.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis of the accompanying claims, and it shall be construed that all of the technical ideas included within the scope equivalent to the claims belong to the present invention.

What is claimed is:

1. A compound represented by Formula (1):

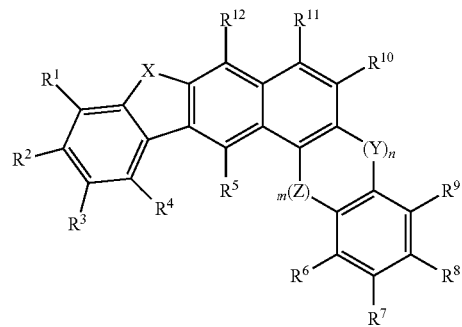

wherein:
1) X, Y and Z are each independently selected from the group consisting of N-L¹-Ar¹, O, S, CR¹³R¹⁴, SiR¹⁵R¹⁶, with the proviso that both X and Y, or both X and Z are not N-L¹-Ar¹ at the same time, and with the proviso that where Z and Y are both CR¹³R¹⁴, the R¹³ and R¹⁴ in either of Z and Y are not equally hydrogen
2) m and n are each independently 0 or 1, and m+n is 1 or 2, and when m or n is 0, Z or Y is a single bond,
3) R¹, R², R³, R⁴, R⁵, R⁶, R⁷, R⁸, R⁹, R¹⁰, R¹¹, R¹², R¹³, R¹⁴, R¹⁵, and R¹⁶ are each independently selected from the group consisting of hydrogen; deuterium; halogen; a $C_6$-$C_{60}$ aryl group; a fluorenyl group; a $C_2$-$C_{60}$ heterocyclic group including at least one heteroatom of O, N, S, Si or P; a $C_1$-$C_{50}$ alkyl group; a fused ring group of a $C_3$-$C_{60}$ aliphatic ring and a $C_6$-$C_{60}$ aromatic ring; a $C_2$-$C_{20}$ alkenyl group; a $C_1$-$C_{30}$ alkoxyl group; a $C_6$-$C_{30}$ aryloxy group; and -L'-N(R$^a$)(R$^b$);
and R¹, R², R³, R⁴, R⁵, R⁶, R⁷, R⁸, R⁹, R¹⁰, R¹¹, and/or R¹² may form a ring together with neighboring groups wherein the ring does not include a heterocyclic group, and R¹³, R¹⁴, R¹⁵, R¹⁶ may be bonded to each other to form a spiro compound together with C or Si to which they are bonded,
4) L¹ is selected from the group consisting of a single bond, a $C_6$-$C_{60}$ arylene group, a fluorenylene group, and a $C_2$-$C_{60}$ heteroarylene group including at least one heteroatom selected from O, N, S, Si or P,
5) Ar¹ is a $C_{10}$-$C_{60}$ heterocyclic group including at least one heteroatom of O, N, S, Si or P, or -L'-N(R$^a$)(R$^b$), wherein the heterocyclic group includes 4 to 6 fused rings or a benzothieno- or benzofuro-pyrimidine moiety,
6) L' is selected from the group consisting of a single bond; a $C_6$-$C_{60}$ arylene group; a fluorenylene group; a fused ring group of a $C_3$-$C_{60}$ aliphatic ring and a $C_6$-$C_{60}$ aromatic ring; a $C_2$-$C_{60}$ heterocyclic group including at least one heteroatom selected from O, N, S, Si or P, and
7) R$^a$ and R$^b$ are independently selected from the group consisting of a $C_6$-$C_{60}$ aryl group; a fluorenyl group; a fused ring group of a $C_3$-$C_{60}$ aliphatic ring and a $C_6$-$C_{60}$ aromatic ring; and a $C_2$-$C_{60}$ heterocyclic group containing at least one hetero atom of O, N, S, Si, and P,
wherein, the aryl group, heteroaryl group, fluorenyl group, arylene group, heterocyclic group, fused ring group may be substituted with one or more substituents selected from the group consisting of deuterium; halogen; silane group; siloxane group; boron group; germanium group; cyano group; nitro group; -L'-N(R$^a$)(R$^b$); $C_1$-$C_{20}$ alkylthio group; $C_1$-$C_{20}$ alkoxyl group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$-$C_{20}$ heterocyclic group; $C_3$-$C_{20}$ cycloalkyl group; $C_7$-$C_{20}$ arylalkyl group and $C_8$-$C_{20}$ arylalkenyl group, wherein the substituents may combine each other and form a ring, wherein the term 'ring' means a $C_3$-$C_{60}$ aliphatic ring or a $C_6$-$C_{60}$ aromatic ring or a $C_2$-$C_{60}$ heterocyclic ring or a fused ring formed by the combination thereof and comprises a saturated or unsaturated ring.
2. An organic electric element comprising a first electrode; a second electrode; and an organic material layer positioned between the first electrode and the second electrode; wherein the organic material layer comprises a compound according to claim 1.
3. The organic electric element of claim 2, wherein the compound may be contained in at least one of a hole injection layer, a hole transport layer, a emitting auxiliary layer, and an emitting layer of the organic material layer and is comprised of a single compound or two or more compounds.

4. The organic electric element of claim 2, wherein the compound is used as a phosphorescent host material of an emitting layer.

5. The organic electric element of claim 4, wherein the phosphorescent host of the emitting layer is used as a red phosphorescent host.

6. The organic electric element of claim 2, further comprising a light efficiency enhancing layer formed on at least one side opposite to the organic material layer among one side of the first electrode and the second electrode.

7. The organic electric element of claim 2, wherein the organic material layer is formed by a spin coating process, a nozzle printing process, an inkjet printing process, a slot coating process, a dip coating process or a roll-to-roll process.

8. An electronic device comprising a display device comprising the organic electric element of claim 2; and a control part driving the display device.

9. The electronic device of claim 8, wherein the organic electric element is an OLED, an organic solar cell, an organic photo conductor(OPC), organic transistor(organic TFT), or an element for monochromic or white illumination.

10. A compound represented by one of Formula (2) to (5):

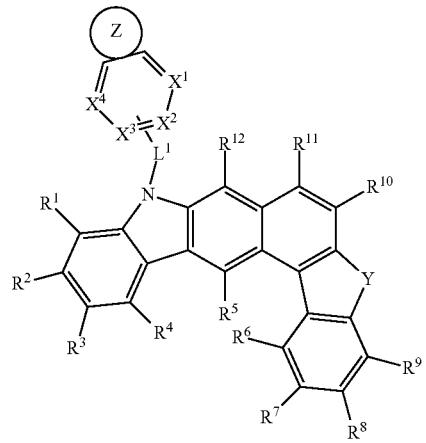

<Formula (2)>

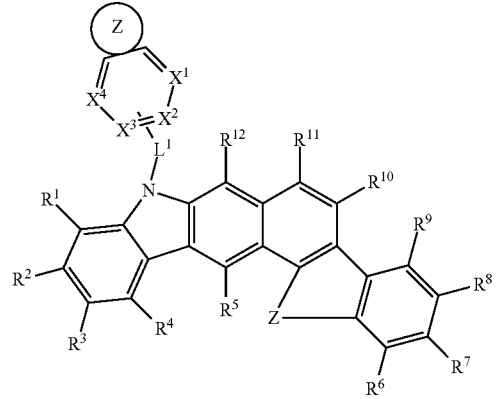

<Formula (3)>

<Formula (4)>

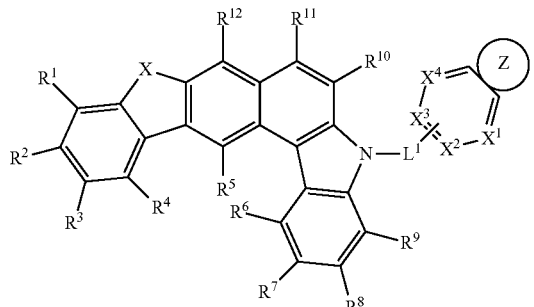

<Formula (5)>

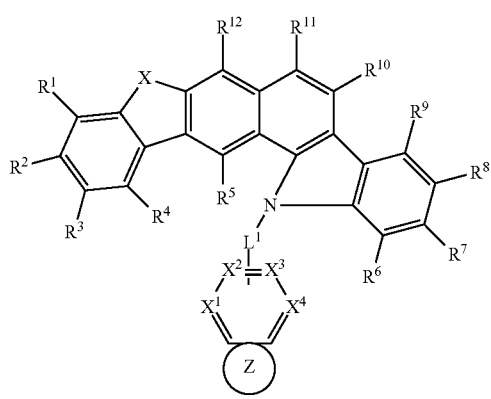

wherein,
1)

is selected from the group consisting of a $C_{10}$ to $C_{60}$ aromatic group and a $C_{10}$ to $C_{60}$ heterocyclic group containing at least one hetero atom of O, N, S, Si, or P, 2) $X^1$, $X^2$, $X^3$, and $X^4$ are independently $CR^{17}$, N, or $L^1$, wherein at least one of $X^1$, $X^2$, $X^3$, and $X^4$ is N, and one of the remaining $X^1$, $X^2$, $X^3$, and $X^4$ is a carbon atom bonded to $L^1$, 3) X, Y and Z are each independently selected from the group consisting of O, S, $CR^{13}R^{14}$, $SiR^{15}R^{16}$, 4) $R^1$ to $R^{17}$ are each independently selected from the group consisting of hydrogen; deuterium; halogen; a $C_6$-$C_{60}$ aryl group; a fluorenyl group; a $C_2$-$C_{60}$ heterocyclic group including at least one heteroatom of O, N, S, Si or P; a $C_1$-$C_{50}$ alkyl group; a fused ring group of a $C_3$-$C_{60}$ aliphatic ring and a $C_6$-$C_{60}$ aromatic ring; a $C_2$-$C_{20}$ alkenyl group; a $C_1$-$C_{30}$ alkoxyl group; a $C_6$-$C_{30}$ aryloxy group; and -L'-N($R^a$)($R^b$), and $R^1$, $R^2$, $R^3$, $R^4$, $R^5$, $R^6$, $R^7$, $R^8$, $R^9$, $R^{10}$, $R^{11}$, and/or $R^{12}$ may form an aryl ring together with neighboring groups, and $R^{13}$, $R^{14}$, $R^{15}$, $R^{16}$ may be bonded to each other to form a spiro compound together with C or Si to which they are bonded, 5) $L^1$ is selected from the group consisting of a single bond, a $C_6$-$C_{60}$ arylene group, a fluorenylene group, a $C_2$-$C_{60}$ heteroarylene group including at least one heteroatom selected from O, N, S, Si or P.

11. The compound of claim 10, wherein

is represented by one of formulas Z-4 to Z-9:

<Z-4>

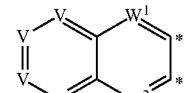

<Z-5>

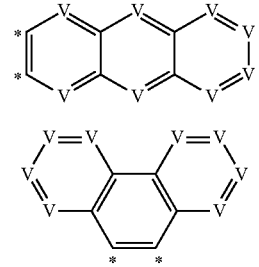

<Z-6>

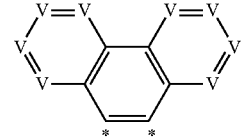

<Z-7>

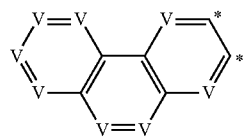

<Z-8>

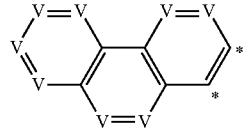

<Z-9>

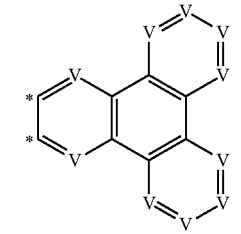

wherein:
1) * represents the corresponding adjacent group in Formulas (2) to (3),
2) V is $CR^{18}$ or N,
3) $W^1$ and $W^2$ are each independently a single bond, $CR^{19}R^{20}$, $NAr^4$, O, S or $SiR^{21}R^{22}$,
4) $R^{18}$ to $R^{22}$ is the same as $R^1$ to $R^{12}$ defined in claim 10,
5) $Ar^4$ is the same as $Ar^1$ defined in claim 10,
6) $R^{18}$, $R^{19}$, $R^{20}$, $R^{21}$, and $R^{22}$ may be bonded to each other to form a spiro bonded with C or Si to be bonded.

12. An organic electric element comprising a first electrode; a second electrode; and an organic material layer positioned between the first electrode and the second electrode, wherein the organic material layer comprises a compound according to claim 10.

13. An electronic device comprising a display device comprising the organic electric element of claim 12, and a control part driving the display device.

14. The compound of claim 10, wherein
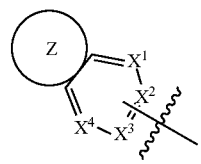
is represented by one of Formulas Z-12 to Z-31:
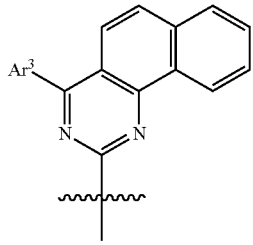
<Z-12>
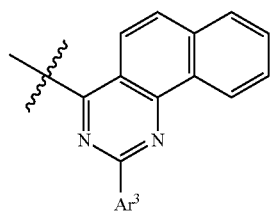
<Z-13>
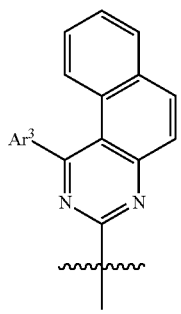
<Z-14>
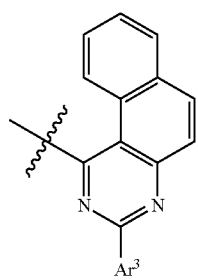
<Z-15>
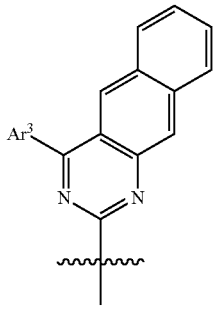
<Z-16>
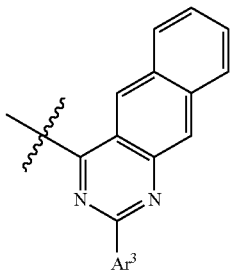
<Z-17>
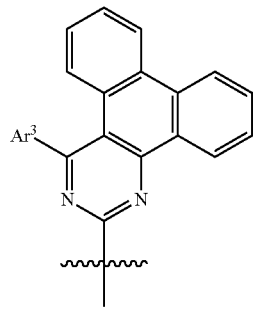
<Z-18>
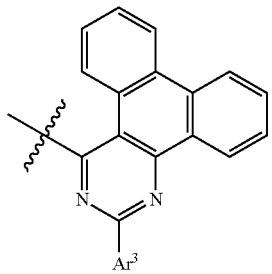
<Z-19>
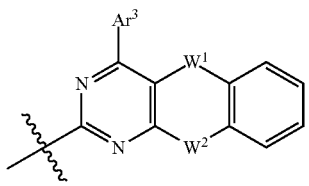
<Z-20>
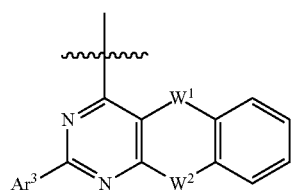
<Z-21>

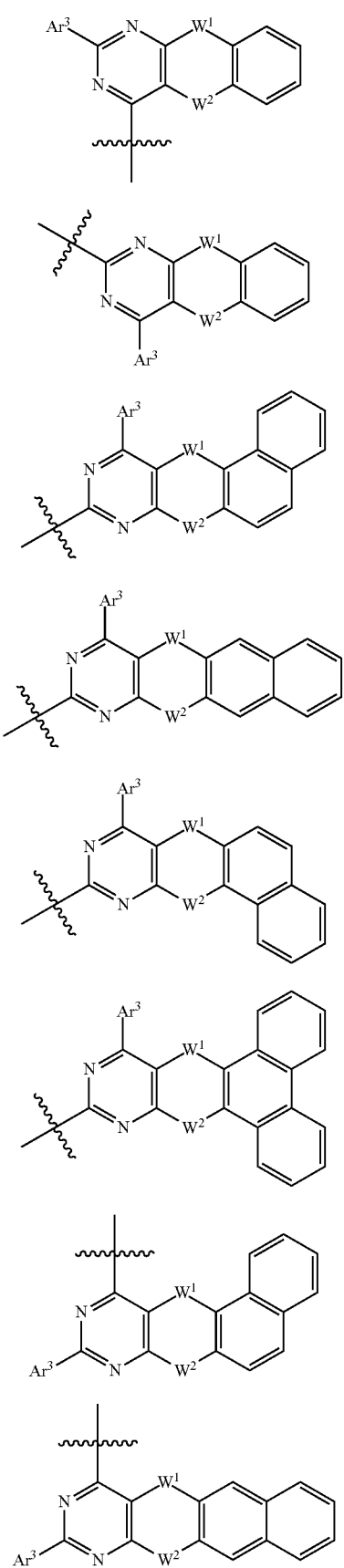

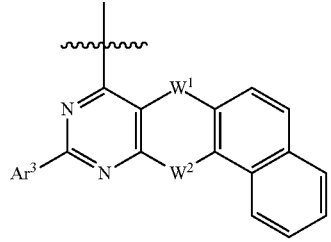

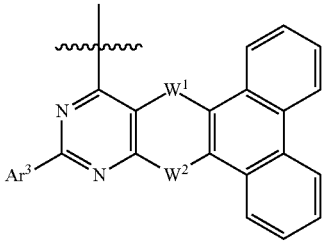

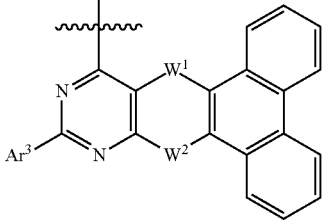

wherein Ara is selected from the group consisting of a $C_6$-$C_{30}$ aryl group, a fluorenyl group, a fused ring group of a $C_3$-$C_{30}$ aliphatic ring and a $C_6$-$C_{30}$ aromatic ring, and a $C_2$-$C_{30}$ heterocyclic group including at least one heteroatom of O, N, S, Si or P, and $W^1$ and $W^2$ are each independently a single bond, $CR^{19}R^{20}$, $NAr^4$, O, S or $SiR^{21}R^{22}$.

15. A compound represented by Formula (10):

<Formula 10>

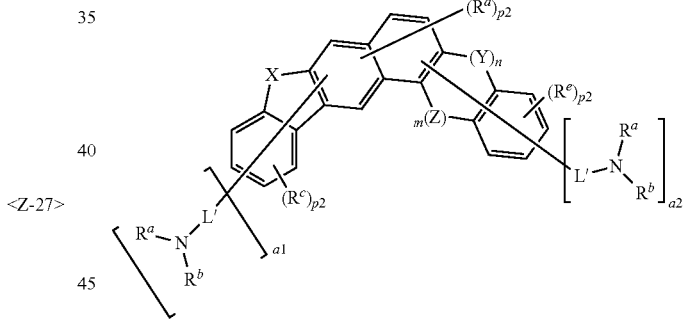

wherein:
1) X, Y and Z are each independently selected from the group consisting of N-$L^1$-$Ar^1$, O, S, $CR^{13}R^{14}$, $SiR^{15}R^{16}$, with the proviso that both X and Y, or both X and Z are not N-$L^1$-$Ar^1$ at the same time,
2) m and n are each independently 0 or 1, and m+n is 1 or 2, and when m or n is 0, Z or Y is a single bond,
3) $R^c$, $R^d$, $R^e$, $R^{13}$, $R^{14}$, $R^{15}$ and $R^{16}$ are each independently selected from the group consisting of hydrogen; deuterium; halogen; a $C_6$-$C_{60}$ aryl group; a fluorenyl group; a $C_2$-$C_{60}$ heterocyclic group including at least one heteroatom of O, N, S, Si or P; a $C_1$-$C_{50}$ alkyl group; a fused ring group of a $C_3$-$C_{60}$ aliphatic ring and a $C_6$-$C_{60}$ aromatic ring; a $C_2$-$C_{20}$ alkenyl group; a $C_1$-$C_{30}$ alkoxyl group; a $C_6$-$C_{30}$ aryloxy group; and -$L'$-N($R^a$)($R^b$); and $R^c$, $R^d$ and/or $R^e$ may form an aryl ring together with neighboring groups, and $R^{13}$, $R^{14}$, $R^{15}$, $R^{16}$ may be bonded to each other to form a spiro compound together with C or Si to which they are bonded, 4) $L^1$ is selected from the group consisting of a single bond, a $C_6$-$C_{60}$ arylene group, a fluorenylene group, and a $C_2$-$C_{60}$ heteroarylene group including at least one heteroatom selected from O, N, S, Si or P, 5) $Ar^1$ is selected from the group consisting of a $C_6$-$C_{60}$ aryl group, a fluorenyl group, a fused ring group of a $C_3$-$C_{60}$ aliphatic ring and a $C_6$-$C_{60}$ aromatic ring, a $C_2$-$C_{60}$ heterocyclic group including at least one heteroatom of O, N, S, Si or P, and -L'-N($R^a$)($R^b$), 6) L' is selected from the group consisting of a single bond, a $C_6$-$C_{60}$ arylene group, a fluorenylene group, a fused ring group of a $C_3$-$C_{60}$ aliphatic ring and a $C_6$-$C_{60}$ aromatic ring, and a $C_2$-$C_{60}$ heterocyclic group including at least one heteroatom selected from O, N, S, Si or P, 7) $R^a$ and $R^b$ are independently selected from the group consisting of a $C_6$-$C_{60}$ aryl group, a fluorenyl group, a fused ring group of a $C_3$-$C_{60}$ aliphatic ring and a $C_6$-$C_{60}$ aromatic ring, and a $C_2$-$C_{60}$ heterocyclic group containing at least one hetero atom of O, N, S, Si, and P, 8) a1 and a2 are each independently integer of 0 to 1, and the sum of a1 and a2 is 1 or 2, and 9) p2 is an integer of 0 to 4, wherein, the aryl group, heteroaryl group, fluorenyl group, arylene group, heterocyclic group, fused ring group may be substituted with one or more substituents selected from the group consisting of deuterium; halogen; silane group; siloxane group; boron group; germanium group; cyano group; nitro group; -L'-N($R^a$) ($R^b$); $C_1$-$C_{20}$ alkylthio group; $C_1$-$C_{20}$ alkoxyl group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$-$C_{20}$ heterocyclic group; $C_3$-$C_{20}$ cycloalkyl group; $C_7$-$C_{20}$ arylalkyl group and $C_8$-$C_{20}$ arylalkenyl group, wherein the substituents may combine each other and form a ring, wherein the term 'ring' means a $C_3$-$C_{60}$ aliphatic ring or a $C_6$-$C_{60}$ aromatic ring or a $C_2$-$C_{60}$ heterocyclic ring or a fused ring formed by the combination thereof and comprises a saturated or unsaturated ring.

16. An organic electric element comprising a first electrode; a second electrode; and an organic material layer positioned between the first electrode and the second electrode, wherein the organic material layer comprises a compound according to claim 15.

17. An electronic device comprising a display device comprising the organic electric element of claim 16, and a control part driving the display device.

* * * * *

UNITED STATES PATENT AND TRADEMARK OFFICE
CERTIFICATE OF CORRECTION

PATENT NO. : 10,934,308 B2  
APPLICATION NO. : 15/760004  
DATED : March 2, 2021  
INVENTOR(S) : Mun et al.

Page 1 of 1

It is certified that error appears in the above-identified patent and that said Letters Patent is hereby corrected as shown below:

In the Claims

Claim 14, Column 292, Line 23:  
Please delete "wherein Ara is selected"  
And replace with -- wherein $Ar^3$ is selected --

Signed and Sealed this  
Thirteenth Day of April, 2021

Drew Hirshfeld  
*Performing the Functions and Duties of the*  
*Under Secretary of Commerce for Intellectual Property and*  
*Director of the United States Patent and Trademark Office*